US008524248B2

(12) United States Patent
Moore et al.

(10) Patent No.: US 8,524,248 B2
(45) Date of Patent: Sep. 3, 2013

(54) METHODS TO DIAGNOSE AND IMMUNIZE AGAINST THE VIRUS CAUSING HUMAN MERKEL CELL CARCINOMA

(75) Inventors: Patrick S. Moore, Pittsburgh, PA (US); Yuan Chang, Pittsburgh, PA (US); Huichen Feng, Pittsburgh, PA (US); Christopher Brian Buck, Adelphi, MD (US); Diana V. Pastrana, McLean, VA (US)

(73) Assignees: University of Pittsburgh—Of the Commonwealth System of Higher Education, Pittsburgh, PA (US); The United States of America, as represented by the Secretary, Department of Health and Human Services, Washington, DC (US)

( * ) Notice: Subject to any disclaimer, the term of this patent is extended or adjusted under 35 U.S.C. 154(b) by 226 days.

(21) Appl. No.: 12/808,042

(22) PCT Filed: Dec. 15, 2008

(86) PCT No.: PCT/US2008/086895
§ 371 (c)(1),
(2), (4) Date: Jan. 21, 2011

(87) PCT Pub. No.: WO2009/079481
PCT Pub. Date: Jun. 25, 2009

(65) Prior Publication Data
US 2011/0135598 A1 Jun. 9, 2011

Related U.S. Application Data

(60) Provisional application No. 61/013,772, filed on Dec. 14, 2007.

(51) Int. Cl.
| | | |
|---|---|---|
| A61K 39/275 | (2006.01) | |
| A61K 35/12 | (2006.01) | |
| A61K 31/675 | (2006.01) | |
| A61K 31/7076 | (2006.01) | |
| A61K 38/21 | (2006.01) | |
| A61K 31/436 | (2006.01) | |
| A61K 31/7088 | (2006.01) | |
| A61K 38/16 | (2006.01) | |
| C12Q 1/70 | (2006.01) | |
| C12Q 1/68 | (2006.01) | |
| C07H 21/00 | (2006.01) | |
| C07K 14/065 | (2006.01) | |
| C40B 40/10 | (2006.01) | |
| A61P 31/20 | (2006.01) | |
| A61P 35/00 | (2006.01) | |
| A61P 37/04 | (2006.01) | |

(52) U.S. Cl.
USPC ............ 424/232.1; 424/186.1; 424/139.1; 424/85.4; 424/184.1; 424/93.71; 435/5; 435/320.1; 435/6.13; 536/23.72; 530/387.9; 530/350; 514/86; 514/46; 514/291; 514/1.1

(58) Field of Classification Search
None
See application file for complete search history.

(56) References Cited

U.S. PATENT DOCUMENTS

| | | | |
|---|---|---|---|
| 2011/0135711 A1* | 6/2011 | Huang et al. | 424/450 |
| 2011/0182901 A1* | 7/2011 | Peter et al. | 424/139.1 |
| 2012/0164104 A1* | 6/2012 | Lanier et al. | 424/85.5 |
| 2012/0258126 A1* | 10/2012 | Scholler et al. | 424/186.1 |

FOREIGN PATENT DOCUMENTS

WO    WO 2012056440 A1 * 5/2012

OTHER PUBLICATIONS

Durand JM, Weiller C, Richard MA, Portal I, Mongin M. Treatment of Merkel cell tumor with interferon-alpha-2b. Br J Dermatol. May 1991;124(5):509.*
Boratyńska M, Watorek E, Smolska D, Patrzalek D, Klinger M. Anticancer effect of sirolimus in renal allograft recipients with de novo malignancies. Transplant Proc. Nov. 2007;39(9):2736-9.*
Siray H, Ozel M, Jandrig B, Voronkova T, Jia W, Zocher R, Arnold W, Scherneck S, Krüger DH, Ulrich R. Capsid protein-encoding genes of hamster polyomavirus and properties of the viral capsid. Virus Genes. 1999;18(1):39-47.).*
Viscidi RP, Shah KV. Cancer. A skin cancer virus? Science. Feb. 22, 2008;319(5866):1049-50.*
Feng H, Shuda M, Chang Y, Moore PS. Clonal integration of a polyomavirus in human Merkel cell carcinoma. Science. Feb. 22, 2008;319(5866):1096-100. Epub Jan. 17, 2008.*
Allander T, Andreasson K, Gupta S, Bjerkner A, Bogdanovic G, Persson MA, Dalianis T, Ramqvist T, Andersson B. Identification of a third human polyomavirus. J Virol. Apr. 2007;81(8):4130-6. Epub Feb. 7, 2007.*
Schrama D and Becker JC. "Merkel cell polyomavirus". In: Cancer Associated Viruses. Robertson ES, ed. pp. 449-462. 2012.*
Kanitakis J, Euvrard S, Chouvet B, Butnaru AC, Claudy A. Merkel cell carcinoma in organ-transplant recipients: report of two cases with unusual histological features and literature review. J Cutan Pathol. 2006: 33: 686-694.*
Tolstov YL, Pastrana DV, Feng H, Becker JC, Jenkins FJ, Moschos S, Chang Y, Buck CB, Moore PS. Human Merkel cell polyomavirus infection II. MCV is a common human infection that can be detected by conformational capsid epitope immunoassays. Int J Cancer. Sep. 15, 2009;125(6):1250-6.*

(Continued)

*Primary Examiner* — Benjamin P Blumel
*Assistant Examiner* — Rachel Gill
(74) *Attorney, Agent, or Firm* — Leydig, Voit & Mayer, Ltd.

(57) ABSTRACT

The present invention provides isolated or substantially purified polypeptides, nucleic acids, and virus-like particles (VLPs) derived from a Merkel cell carcinoma virus (MCV), which is a newly-discovered virus. The invention further provides monoclonal antibody molecules that bind to MCV polypeptides. The invention further provides diagnostic, prophylactic, and therapeutic methods relating to the identification, prevention, and treatment of MCV-related diseases.

25 Claims, 29 Drawing Sheets

(56) References Cited

OTHER PUBLICATIONS

Figure 1A:
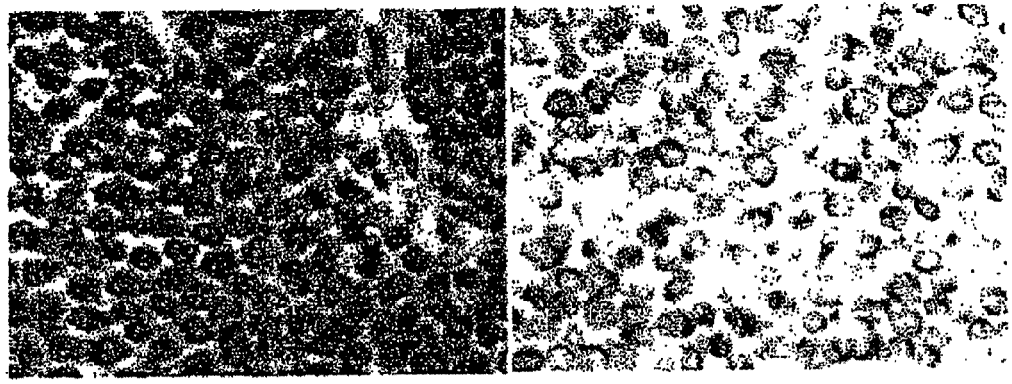

Shuda M, Arora R, Kwun HJ, Feng H, Sarid R, Fernández-Figueras MT, Tolstoy Y, Gjoerup O, Mansukhani MM, Swerdlow SH, Chaudhary PM, Kirkwood JM, Nalesnik MA, Kant JA, Weiss LM, Moore PS, Chang Y. Human Merkel cell polyomavirus infection I. MCV T antigen expression in Merkel cell carcinoma, lymphoid tissues and lymphoid tumors. Int J Cancer. Sep. 2009.*

Ahuja et al., "SV40 large T antigen targets multiple cellular pathways to elicit cellular transformation," *Oncogene*, 24: 7729-7745 (2005).

Allander et al., "Identification of a Third Human Polyomavirus," *Journal of Virology*, 81(8): 4130-4136 (Apr. 2007).

Becker et al., "MC Polyomavirus Is Frequently Present in Merkel Cell Carcinoma of European Patients," *Journal of Investigative Dermatology*, 129: 248-250 (2009).

Brade et al., "B-Lymphotropic Papovavirus and Possibility of Infections in Humans," *Journal of Medical Virology*, 6(4): 301-308 (1980).

Campbell et al., "DnaJ/hsp40 chaperone domain of SV40 large T antigen promotes efficient viral DNA replication," *Genes and Development*, 11: 1098-1110 (1997).

Chang et al., "Identification of Herpesvirus-Like DNA Sequences in AIDS-Associated Kaposi's Sarcoma," *Science*, 266(5192): 1865-1869 (Dec. 16, 1994).

Chou et al., "DNA sequence quality trimming and vector removal," *Bioinformatics*, 17(12): 1093-1104 (Dec. 2001).

Cotsiki et al., "Simian virus 40 large T antigen targets the spindle assembly checkpoint protein Bib1," *Proc. Natl., Acad Sci. USA*, 101(4): 947-952 (Jan. 27, 2004).

Crandall et al., "Phylogenomics and Molecular Evolution of Polyomaviruses," *Adv. Exp. Med. Biol.* 577: 46-59 (2006).

Decaprio et al., "SV40 Large Tumor Antigen Forms a Specific Complex with the Product of the Retinoblastoma Susceptibility Gene," *Cell*, 54: 275-283 (Jul. 15, 1988).

Diamandopoulos, "Leukemia, Lymphoma, and Osteosarcoma Induced in the Syrian Golden Hamster by Simian Virus 40," *Science*, 176(4031): 173-175 (Apr. 14, 1972).

Dilworth, "Polyoma virus middle T antigen and its role in identifying cancer-related molecules," *Nature Reviews Cancer*, 2: 951-956 (2002).

Dorries et al., "Infection of Human Polyomaviruses JC and BK in Peripheral Blood Leukocytes from Immunocompetent Individuals," *Virology*, 198: 59-70 (1994).

Dürst et al., "The Physical State of Human Papillomavirus Type 16 DNA in Benign and Malignant Genital Tumours," *Journal of General Virology*, 66: 1515-1522 (1985).

Engels et al., Merkel cell carcinoma and HIV infection, *The Lancet*, 359: 497-498 (Feb. 9, 2002).

Feng et al., "Human Transcriptome Subtraction by Using Short Sequence Tags to Search for Tumor Viruses in Conjunctival Carcinoma," *Journal of Virology*, 81(20): 11332-11340 (Oct. 2007).

Feng et al., "Clonal Integration of a Polyomavirus in Human Merkel Cell Carcinoma," *Science*, 319: 1096-1100 (Feb. 22, 2008).

Fernández-Figueras et al., "Expression profiles associated with aggressive behavior in Merkel cell carcinoma," *Modern Pathology*, 20: 90-101 (2007).

Fu et al., "Induction and Persistence of a Cytotoxic T Lymphocyte (CTL) Response against a Herpes Simples Virus-Specific CTL Epitope Expressed in a Cellular Protein," *Virology*, 222: 269-274 (1996).

Gannon et al., "Interactions Between SV40 T Antigen and DNA Polymerase α," *The New Biologist*, 2(1): 84-92 (Jan. 1990).

Gaynor et al., "Identification of a Novel Polyomavirus from Patients with Acute Respiratory Tract Infections," *PLoS Pathogens*, 3(5): 0595-0604 (May 2007).

Goldmann et al., "Molecular Cloning and Expression of Major Structural Protein VP1 of the Human Polyomavirus JC Virus: Formation of Virus-Like Particles Useful for Immunological and Therapeutic Studies," *Journal of Virology*, 73(5): 4465-4469 (May 1999).

Goldmann et al., "Packaging of small molecules into VP1-virus-like particles of the human polyomavirus JC virus," *Journal of Virological Methods*, 90: 85-90 (2000).

Gross, "A Filterable Agent, Recovered from Ak Leukemic Extracts, Causing Salivary Gland Carcinomas in C3H Mice," *Proceedings of the Society for Experimental Biology and Medicine*, 83(2): 414-421 (1953).

Gurney et al., "Antigenic Binding Sites of Monoclonal Antibodies Specific for Simian Virus 40 Large T Antigen," *Journal of Virology*, 57(3): 1168-1172 (Mar. 1986).

Harlow et al., "Monoclonal Antibodies Specific for Simian Virus 40 Tumor Antigens," *Journal of Virology*, 39(3): 861-869 (Sep. 1981).

Havre et al., "Targeted Mutagenesis of Simian Virus 40 DNA Mediated by a Triple Helix-Forming Oligonucleotide," *Journal of Virology*, 67(12): 7324-7331 (Dec. 1993).

Hildesheim et al., "Effect of Human Papillomavirus 16/18 L1 Virus-like Particle Vaccine Among Young Women With Preexisting Infection," *The Journal of the American Medical Association*, 298(7): 743-753 (Aug. 15, 2007).

Holländerova et al., "Interference of mouse polyomavirus with the c-myc gene and its product in mouse mammary adenocarcinomas," *International Journal of Oncology*, 23: 333-341 (2003).

Howard et al., "Merkel Cell Carcinoma and Multiple Primary Cancers," *Cancer Epidemiology, Biomarkers & Prevention*, 15(8): 1545-1549 (Aug. 2006).

Howley et al., "Cloned Human Polyomavirus JC DNA Can Transform Human Amnion Cells," *Journal of Virology*, 36(3): 878-882 (Dec. 1980).

Johne et al., "Novel Polyomavirus Detected in the Feces of a Chimpanzee by Nested Broad-Spectrum PCR," *Journal of Virology*, 79(6): 3883-3887 (Mar. 2005).

June, "Adoptive T cell therapy for cancer in the clinic," *The Journal of Clinical Investigation*, 117(6): 1466-1476 (Jun. 2007).

Kaplan et al., "Mechanisms of transformation by polyoma virus middle T antigen," *Biochimica et Biophysica Acta*, 948(3): 345-364 (Feb. 1988).

Karjalainen et al., "Abrogation of Simian Virus 40 DNA-Mediated Transformation of Primary C57BL/6 Mouse Embryo Fibroblasts by Exposure to a Simian Virus 40-Specific Cytotoxic T-Lymphocyte Clone," *Journal of Virology*, 56(2): 373-377 (Nov. 1985).

Kassem et al., "Frequent Detection of Merkel Cell Polyomavirus in Human Merkel Cell Carcinomas and Identification of a Unique Deletion in the VP1 Gene," *Cancer Research*, 68(13): 5009-5013 (Jul. 1, 2008).

Kosukegawa et al., "Purification and characterization of virus-like particles and pentamers produced by the expression of SV40 capsid proteins in insect cells," *Biochimica et Biophysica Acta*, 1290(1): 37-45 (May 21, 1996).

Kwun et al., "Kaposi's Sarcoma-Associated Herpesvirus Latency-Associated Nuclear Antigen 1 Mimics Epstein-Barr Virus EBNA1 Immune Evasion through Central Repeat Domain Effects on Protein Processing," *Journal of Virology*, 81(15): 8225-8235 (Aug. 2007).

Lane et al., "T antigen is bound to a host protein in SV40-transformed cells," *Nature*, 278: 261-263 (Mar. 15, 1979).

Laney et al., "Use of a Multiantigen Detection Algorithm for Diagnosis of Kaposi's Sarcoma-Associated Herpesvirus Infection," *Journal of Clinical Microbiology*, 44(10): 3734-3741 (Oct. 2006).

Lemos et al., "Merkel Cell Carcinoma: More Deaths but Still No Pathway to Blame," *Journal of Investigative Dermatology*, 127: 2100-2103 (2007).

Leonard et al., "Characterization of Cell Lines Established From Merkel-Cell ('Small-Cell') Carcinoma of the Skin," *International Journal of Cancer*, 55: 803-810 (1993).

Linzer et al., "Characterization of a 54K Dalton Cellular SV40 Tumor Antigen Present in SV40-Transformed Cells and Uninfected Embryonal Carcinoma Cells," *Cell*, 17: 43-52 (May 1979).

Livolsi et al., "The Cooperative Human Tissue Network," *Cancer*, 71(4): 1391-1394 (Feb. 15, 1993).

Lundstig et al., "Serological Diagnosis of Human Polyomavirus Infection," *Adv. Exp. Med. Biol.*, 577: 96-101 (2006).

Margulies et al., "Genome sequencing in microfabricated high-density picolitre reactors," *Nature*, 437: 376-380 (Sep. 15, 2005).

Mole et al., "Structure and function of SV40 large-T antigen," *Phil. Trans. R. Soc. Lond. B*, 317: 455-469 (1987).

Moll et al., "Identification of Protein IT of the Intestinal Cytoskeleton as a Novel Type I Cytokeratin with Unusual Properties and Expression Patterns," *The Journal of Cell Biology*, 111: 567-580 (Aug. 1990).

Moll et al., "Cytokeratin 20 in Human Carcinomas, A New Histodiagnostic Marker Detected by Monoclonal Antibodies," *American Journal of Pathology*, 140(2): 427-447 (Feb. 1992).

Moore et al., "Kaposi's sarcoma-associated herpesvirus infection prior to onset of Kaposi's sarcoma," *AIDS*, 10(2): 175-180 (1996).

Moore et al., "Kaposi's Sarcoma-Associated Herpesvirus Immunoevasion and Tumorigenesis: Two Sides of the Same Coin," *Annual Review of Microbiology*, 57: 609-639 (2003).

Pallas et al., "Polyoma Small and Middle T Antigens and SV40 Small t Antigen Form Stable Complexes with Protein Phosphatase 2A," *Cell*, 60: 167-176 (Jan. 12, 1990).

Parsonnet "Introduction," *Microbes and Malignancy, Infection as a Cause of Human Cancers*, (Parsonnet ed.) 3-15 (Oxford University Press, New York, NY, 1999).

Pawlita et al., "Complete DNA Sequence of Lymphotropic Papovavirus: Prototype of a New Species of the Polyomavirus Genus," *Virology*, 143(1): 196-211 (May 1985).

Pipas, "Common and Unique Features of T Antigens Encoded by the Polyomavirus Group," *Journal of Virology*, 66(7): 3979-3985 (Jul. 1992).

Pitterle et al., "Hot Spots for Molecular Genetic Alterations in Lung Cancer," In Vivo, 12: 643-658 (1998).

Pope et al., "Detection of Specific Antigen in SV40-Transformed Cells by Immunofluorescence," *The Journal of Experimental Medicine*, 120: 121-128 (1964).

Poulin et al., "p53 Targets Simian Virus 40 Large T Antigen for Acetylation by CBP," *Journal of Virology*, 78(15): 8245-8253 (Aug. 2004).

Poulin et al., "Is There a Role for Sv-40 in Human Cancer," *Journal of Clinical Oncology*, 24(26): 4356-4365 (Sep. 10, 2006).

Quaglino et al., "Association between chronic lymphocytic leukaemia and secondary tumours: Unusual occurrence of a neuroendocrine (Merkell cell) carcinoma," *European Review for Medical and Pharmacological Sciences*, 1: 11-16 (1997).

Schell et al., "Cytotoxic T-Lymphocyte Epitope Immunodominance in the Control of Choroid Plexus Tumors in Simian Virus 40 Large T Antigen Transgenic Mice," *Journal of Virology*, 73(7): 5981-5993 (Jul. 1999).

Seif et al., "The Genome of Human Papovavirus BKV," *Cell*, 18: 963-977 (Dec. 1979).

Shuda et al., "T antigen mutations are a human tumor-specific signature for Merkel cell polyomavirus," *Proc. Natl. Acad. Sci. USA*, 105(42): 16272-16277 (Oct. 21, 2008).

Soulier et al., "Kaposi's Sarcoma-Associated Herpesvirus-Like DNA Sequences in Multicentric Castleman's Disease," *Blood*, 86(4): 1276-1280 (Aug. 15, 1995).

Stolt et al., "Seroepidemiology of the human polyomaviruses," *Journal of General Virology*, 84: 1499-1504 (2003).

Tack et al., "Alterations in the Structure of New and Old Forms of Simian Virus 40 Large T Antigen (T) Defined by Age-Dependent Epitope Changes: New T Is the Same as ATPase-Active T," *Journal of Virology*, 63(5): 2352-2356 (May 1989).

Tegerstedt et al., "A Single Vaccination with Polyomavirus VP1/VP2Her2 Virus-Like Particles Prevents Outgrowth of HER-2/neu-Expressing Tumors," *Cancer Research*, 65(13): 5953-5957 (Jul. 1, 2005).

Tegerstedt et al., "Murine Polyomavirus Virus-like Particles (VLPs) as Vectors for Gene and Immune Therapy and Vaccines against Viral Infections and Cancer," *Anticancer Research*, 25(4): 2601-2608 (Jul.-Aug. 2005).

Tegerstedt et al., "Dendritic cells loaded with polyomavirus VP1/VP2Her2 virus-like particles efficiently prevent outgrowth of a Her2/neu expressing tumor," *Cancer Immunol. Immunother.*, 56(9): 1335-1344 (Sep. 2007).

Thompson et al., "Dissociation of Rb-Binding and Anchorage-Independent Growth from Immortalization and Tumorigenicity Using SV40 Mutants Producing N-Terminally Truncated Large T Antigens," *Virology*, 178: 15-34 (1990).

Van Gele et al., "Gene-expression profiling reveals distinct expression patterns for Classic versus Variant Merkel cell phenotypes and new classifier genes to distinguish Merkel cell from small-cell lung carcinoma," *Oncogene*, 23(15): 2732-2742 (2004).

Viscidi et al., "Serological Cross-Reactivities between Antibodies to Simian Virus 40, BK Virus, and JC Virus Assessed by Virus-Like-Particle-Based Enzyme Immunoassays," *Clinical and Diagnostic Laboratory Immunology*, 10(2): 278-285 (Mar. 2003).

Viscidi et al., "Serological Cross Reactivity between Polyomavirus Capsids," *Adv. Exp. Med. Biol.*, 577: 73-84 (2006).

Whitby et al., "Detection of Kaposi sarcoma associated herpesvirus in peripheral blood of HIV-infected individuals and progression to Kaposi's sarcoma," *The Lancet*, 346: 799-802 (Sep. 23, 1995).

Xu et al., "Pathogen discovery from human tissue by sequence-based computational subtraction," *Genomics*, 81: 329-335 (2003).

Yin et al., "Self-Inhibition of Synthesis and Antigen Presentation by Epstein-Barr Virus-Encoded EBNA1," *Science*, 301: 1371-1374 (Sep. 5, 2003).

Yokoyama et al., "Mutational Analysis of the Carboxyl-terminal Region of the SV40 Major Capsid Protein VP1," *J. Biochem*, 141(2): 279-286 (Feb. 2007).

Zerrahn et al., "Independent expression of the transforming amino-terminal domain of SV40 large T antigen from an alternatively spliced third SV40 early mRNA," *The EMBO Journal*, 12(12): 4739-4746 (1993).

Zielonka et al., "Generation of virus-like particles consisting of the major capsid protein VP1 of goose hemorrhagic polyomavirus and their application in serological tests," *Virus Research*, 120(1-2): 128-137 (Sep. 2006).

Zur Hausen et al., "Lymphotropic Papovaviruses Isolated from African Green Monkey and Human Cells," *Med. Microbiol. Immunol.*, 167: 137-153 (1979).

\* cited by examiner

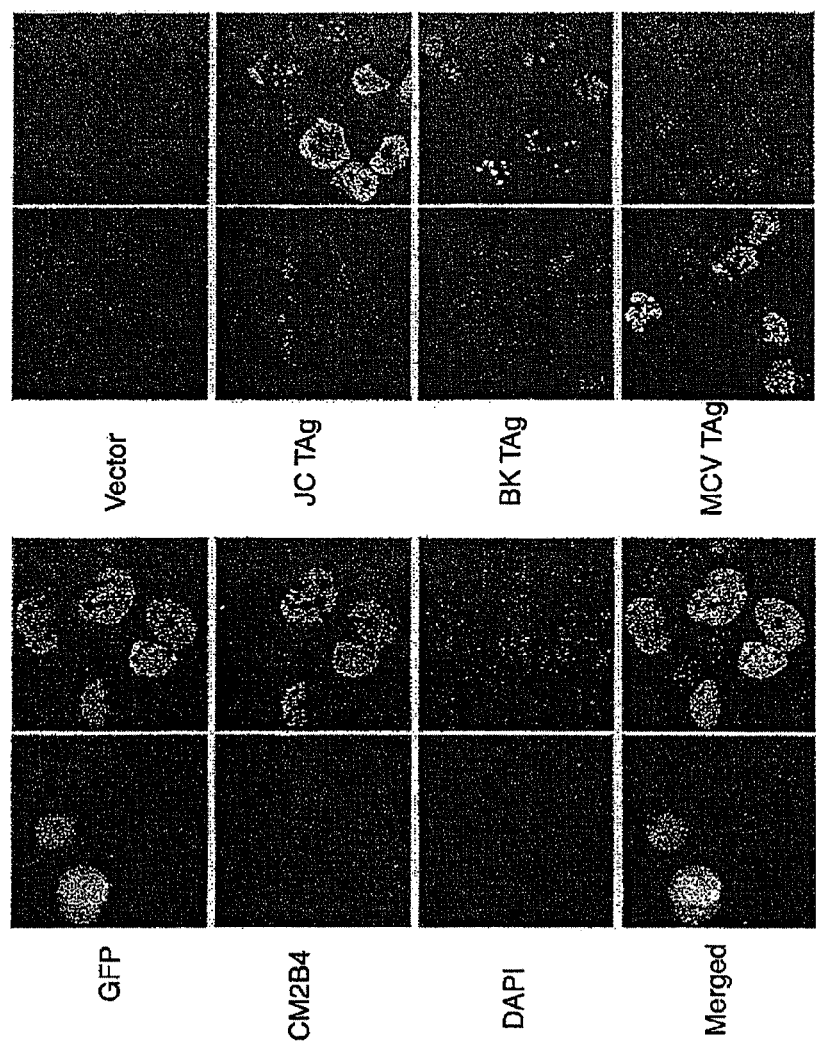

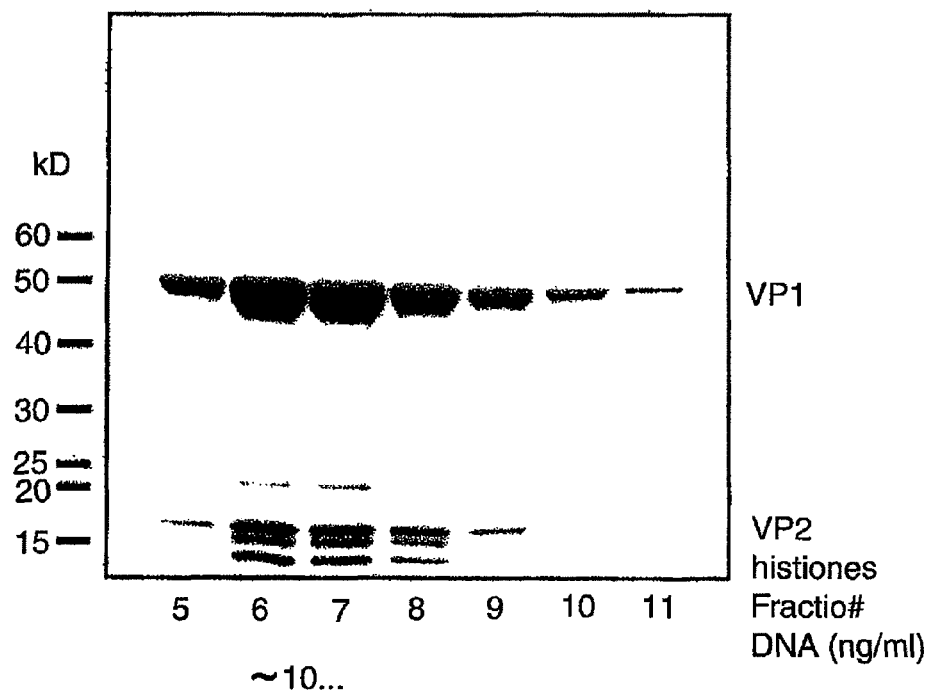

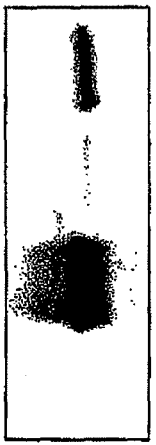
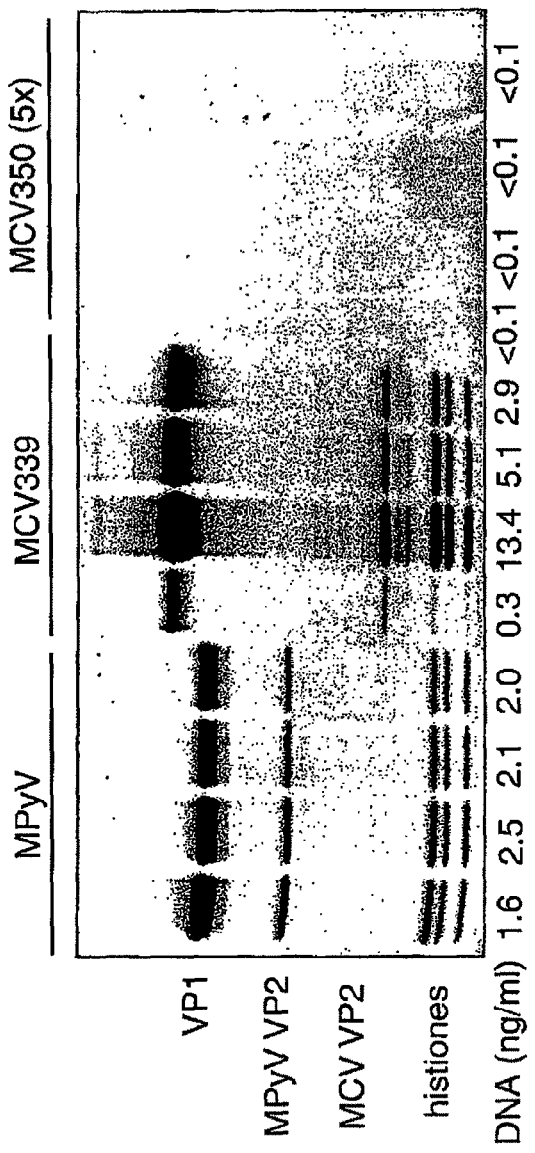
FIG. 12
VLP production

FIGURE 23: SEQUENCES

Outline

1. MCV sequences (1). 4 MCV genome sequences (MCV 350, MCV 339, MCV 352 and MCV MKL1). SEQ ID NOS:1-4.

(2). Putative transcripts and predicted amino acid sequences for proteins from MCV 350). SEQ ID NOs5-20.

2. SCLC sequences (1). 15 preliminary reads from NCI-H69 cells. SEQ ID NOs:21-35.

(2). 10 preliminary reads from NCI-H146 cells. SEQ ID NOs:36-45.

1. MCV sequences
(1). 4 MCV genome sequences

>MCV_350 5387bp (SEQ ID NO:1)
```
GGGGCTCCTAGCCTCCGAGGCCTCTGGAAAAAAAAGAGAGAGGACTCTGAGGCTTAAGAGGCTTAATTAGCAAAAAAGGCAGTATCT
AAGGGCAGATCCCAAGGGCGGGAAACTGCAGTATAAAAACCACTCCTTAGTGAGGTAGCTCATTTGCTCCTCTGCTGTTTCTGCAAA
CTCCTTCTGCATATAGACAAGATGGATTTAGTCCTAAATAGGAAAGAAAGAGAGGCTCTGTGCAAGCTTTTGGAGATTGCTCCTAAT
TGTTATGGCAACATCCCTCTGATGAAAGCTGCTTTCAAAAGAAGCTGCTTAAAGCATCACCCTGATAAAGGGGGAAATCCTGTTATA
ATGATGGAATTGAACACCCTTTGGAGCAAATTCCAGCAAAATATCCACAAGCTCAGAAGTGACTTCTCTATGTTTGATGAGGTTAGT
ACAAAATTTCCTTGGGAAGAATATGGAACTTTAAAGGATTATATGCAAAGTGGATATAATGCTAGATTTTGCAGAGGTCCTGGGTGC
ATGCTTAAGCAACTTAGAGATTCTAAGTGCGCTTGTATTAGCTGTAAGTTGTCTCGCCAGCATTGTAGTCTAAAAACTTTAAAGCAA
AAAAACTGTCTGACGTGGGGAGAGTGTTTTTGCTATCAGTGCTTTATTCTTTGGTTTGGATTTCCTCCTACTTGGGAAAGTTTTGAC
TGGTGGCAAAAAACTTTAGAAGAAACTGACTACTGCTTACTGCATCTGCACCTTTTCTAGACTCCTACTTCCTTCCTCTGTAAGTAT
TAGATATGGAAAAGTCTATAAGGCAAAATATCAAAGAAAGGTTATTTATGACAGATTTTGTGTACTTTCCCATCTAGGTTGACGAGG
CCCCTATATATGGGACCACTAAATTCAAAGAATGGTGGAGATCAGGAGGATTCAGCTTCGGGAAGGCATACGAATATGGGCCCAATC
CACACGGGGCCAACTCAAGATCCAGAAAGCCTTCCTCCAATGCATCCAGGGGAGCCCCCAGTGGAAGCTCACCACCCCACAGCCAGA
GCTCTTCCTCTGGGTATGGGTCCTTCTCAGCGTCCCAGGCTTCAGACTCCCAGTCCAGAGGACCCGATATACCTCCCGAACACCATG
AGGAACCCACCTCATCCTCTGGATCCAGTAGCAGAGAGGAGACCACCAATTCAGGAAGAGAATCCAGCACACCCAATGGAACCAGTG
TACCTAGAAATTCTTCCAGAACGTATGGCACCTGGGAGGATCTCTTCTGCGATGAATCACTTTCCTCCCCTGAGCCTCCCTCGTCCT
CTGAGGAGCCTGAGGAGCCCCCCTCCTCAAGAAGCTCGCCCCGGCAGCCCCCGTGTTCCTCTGCCGAGGAGGCCTCGTCATCTCAGT
TTACAGATTAGGAATACATATCCTCCTCCTTCACCACCCCGAAGACCCCTCCTCCATTCTCAAGAAAGCGAAAATTTGGGGGTCCC
GAAGCTCTGCAAGCTCTGCTAGTTCAGCAAGTTTTACAAGCACTCCACCAAAGCTAAAAAACAACAGAGAAACTCCTGTTCCTACTA
ATTTTCCTATTGATGTTTCTGATTATCTTAGCCATGCTGTATATAGTAATAAAACAGTAAGTTGTTTTGCCATTTATACTACTTCTG
ATAAAGCTATAGAGTTATATGATAAGATTGAGAAATTTAAAGTTGATTTTAAAAGCAGGCATGCCTGTGAATTAGGATGTATTTTAT
TGTTTATAACTTTATCAAAGCATAGAGTATTTGCTATTAAGAATTTTTGCTCTACCTTCTGCACTATAAGCTTTTTAATTTGTAAAG
GAGTGAATAAGATGCCTGAAATGTATAATAATTTATGCAAGCCCCCTTACAAATTACTGCAAGAGAATAAGCCACTGCTCAATTATG
AATTTCAAGAAAAAGAAAAAGAGGCCAGCTGTAATTGGAATTTAGTTGCTGAATTTGCTTGTGAATATGAGCTAGACGACCACTTTA
TTATCTTAGCCCATTATCTAGACTTTGCAAAACCATTTCCTTGCCAAAAGTGTGAAAACAGATCTCGCCTCAAACCTCACAAGGCTC
ATGAGGCTCATCATTCTAATGCTAAGCTATTTTTATGAATCTAAATCTCAGAAAACCATTTGCCAACAAGCCGCAGACACTGTTCTAG
CCAAAAGGAGGTTAGAGATGCTGGAAATGACCAGGACAGAAATGCTATGTAAGAAGTTTAAGAAGCACCTAGAGAGATTAAGAGATT
TAGATACAATAGATCTACTGTATTATATGGGTGGTGTGGCCCTGGTACTGCTGCTTATTTGAAGAGTTTGAAAAGAAGCTGCAGAAAA
TTATTCAATTATTAACAGAGAATATACCTAAGTATAGAAACATTTGGTTTAAAGGGCCTATTAACAGTGGAAAAACAAGCTTTGCTG
CAGCCTTAATAGATTTGCTAGAAGGGAAGGCCTTGAATATAAACTGTCCATCTGATAAACTGCCTTTTGAACTAGGATGTGCTTTGG
ATAAATTTATGGTTGTTTTTGAGGATGTGAAAGGGCAAAATAGCCTAAATAAAGATCTGCAACCAGGGCAAGGAATAAATAACCTTG
ATAACTTAAGAGATCATCTAGATGGTGCTGTAGCTGTGAGCTTAGAGAAGAAGCATGTGAATAAAAAGCATCAGATTTTTCCTCCTT
GTATTGTTACTGCTAATGATTATTTTATTCCCAAAACATTAATAGCAAGATTTAGTTATACTTTACACTTTTTCCCAAAGGCAAATC
TAAGAGATTCCCTGGATCAGACATCAGAAATAAGAAAAAGAAGAATTCTTCAAAGTGGAACCACTTTATTGCTTTGTCTTATTTGGT
GCTTGCCTGATACAACCTTTAAGCCTTGCTTACAAGAAGAAATTAAAAACTGGAAGCAAATTTTACAGAGTGAAATATCATATGGTA
AATTTTGTCAAATGATAGAAAATGTAGAAGCTGGTCAGGACCCTCTGCTCAATATTCTTATTGAGGAAGAGGGCCCTGAGGAAACTG
AGGAAACCCAAGATTCTGGTACTTTTTCTCAATAAAGGCATCTGCTTCATATTTCCTGTGTTTGTTTTCTGGGGCCTACTTAACTG
AATAGGAATGCATGAAATAATTCTCATAATTGTTGTGTTTGGCTTTCTTTTTGAGAGGCCTTTTGAGGTCCTTTCAGTGGCGCCTTG
CCCTTATCCTGCTGATTACTTTGGAATGTTACTGCTGCTGGGGCAACAGAGGGCTTTGGGTAAACAGTTTTCTCCTGCCCAAATTTA
TCTAAAAATCTGACAATATCAGGATTACCAGGTAATTGTTCTGACCCCTCATATATTCTGACCTCTTCTACCTGATTATCTTTTCCT
TCCATAGGTTGGCCTGACACTTTTGGCATTAAGTTGCTGAAGAGTCAGTTTATTAAATTAACTACTGGGTAGGGGTTTTTCACCCAT
```

FIGURE 23A

ATTTTTCTCAAAGTAACATTAAAATATCTAGGCAACCCATGAAGAGCCATTTTTCCACTGGTTTTAAACAGAAACCCCACTATGTGT
GCACAGCTAATAAATAGGCCATCTCCTTTGCATAGAGGGCCCACTCCATTCTCATCTAAAAGGACAGTAGTTAGAGTATTACTAAAT
TGAAGAACTGTAGGAGTCTGAGAGCCTGTCTGAATAGACCCATAGTATCTACTGTTTTCATTTTTAGAAGGATCAGGACACCATACT
TCTATAGGATAATTTCCATCTTTATCTAATTTTGCTTTAGCTTGTGGATCTAGGCCCTGATTTTTAGGTGTCATTTTTCTTCCTAAT
ACAGTTTCAATTGTAATAGGCCCACCATTTGTAGTTTTTGGATACTCAGTCTGGTAATCTAAAACTAGGCCTTGCAAATCCAGAGGT
TCTCCCCCAATGGCAAACATATGGTAATTTACCCCTGACACAGGAATACCAGCACCATAATCATGAACTCTTTTCATGTCCCAATAA
TGAACATTAATTAAAGAACTTATTCCAACTACTTCTGTTTTAACAGATATTGCCTCCCACATCTGCAATGTGTCACAGGTAATATCC
TCATTTAGCATTGGCAGAGACACTCTTGCCACACTGTAAGCTGGCAAATTTTCCTTGATGGGCTGATCTGGAGATGATCCCTTTGGC
TGCAGGTCATAAGTATAAGTATACCAGTTTGAAGTAGTAGGAAGATCAGGGGAATTAACTCCCATTCTTGGATTCAAATACAACTCA
ATTTGGGTAATGCTATCTTCTCCAGTAACCACAGATAATACTTCCACTCCTCCTTTAACAAGCAGTTTTGGAACTGAGGCAACATTA
GGGCAGCATCCCGGCTTAGGTATACATTGCCTTTTGGGTGTTTTACAGGTGGATGATGCTTTTCTTTTTGGTGCCATCTTCAATTAC
TTGTAATTCAGGAGAAATATATCCACTAAGGCCTAGTACCAGAGGAAGAAGCCAATCTGGAGTTTGCTGCTGCAGAGTTCCTCCTAT
ATGTTCAGGAATTAATATAGCCTCCTGATAAAAGGCCCTGATTCTGAGAAGCAGTTGTCTGAAAGACCCACCGGCTATTTAGTAT
CAGATTCACTAGGTTTGATTGTATCTGCAGCCTAGAGGTAGGAGATAAAGAATTAAAAATATTTTGCCCCACAGAATGCAGCAAGCT
ATTTTCCCACTGCAGAGGATCTAGGCTAAAGGCCATAAGTGCATGCCTCAAAACCTCATTACTACCTACCCACGAAACATCCCTGTT
TACAAGTGACACTTGCTCGCGTGACAACCTCACCCCCACAGTTATTAGAGAGCCTATACCACTAACAGTTTGGAGAATGAAGCCATA
AGTTAAACCTTGGTTAACCAAAGAAGCCACTAATGAGAAATTTGAAAACTGTTCAGCTGTGAACCCAAGTTGAGCTAAAGCCTCAAT
GCCAGAAATACCCTCAATTGTCATTAAACTGGAGATGTCTGCTTCCAAAGCTGCTAAAGCTTCTCCTGTAAGAATAGCTTCCAAAGT
TACTCCTGTGGTGGCACTTAGTTCAGTAGCAATTTCACCAATATTGGCCAGCAGTGTGATGATGCCCCCATCCTGAAAAATAAATA
AGGATACTTACTCTTTTAATGTCCTCCTCCCTTTGTAAGAGAAAAAAAAGCCTCCGGGCCTCCCTTGTTGAAAAAAAGTTAAGAGTT
TTCCGTCTCCCTCCCAAACAGAAAGAAAAAAAGTTTTGTTTATCAGTCAAACTCCGCCTCTCCAGGAAATGAGTCAATGCCAGAAAC
CCTGCAGCAATAAAAGTTCAATCATGTAACCACAACTTGGCTGCCTAGGTGACTTTTTTTTTTCAAGTTGGCAGAGGCTT

>MCV_339 5201bp (SEQ ID NO:2)
GGGGCTCCTAGCCTCCGAGGCCTCTGGAAAAAAAGAGAGAGGCCTCTGAGGCTTAAGAGGCTTAATTAGCAAAAAAGGCAGTATCT
AAGGGCAGATCCCAAGGGCGGGAAACTGCAGTATAAAAACCACTCCTTAGTGAGGTAGCTCATTTGCTCCTCTGCTCTTTCTGCAAA
CTCCTTCTGCATATAGACAAGATGGATTTAGTCCTAAACAGGAAAGAAAGAGAGGCTCTCTGCAAGCTTTTAGAGATTGCTCCTAAT
TGTTATGGCAACATCCCTCTGATGAAAGCTGCTTTCAAAAGAAGCTGCTTAAAGCATCACCCTGATAAAGGGGGAAATCCTGTTATA
ATGATGGAATTGAACACCCTTTGGAGCAAATTCCAGCAAAATATCCACAAGCTCAGAAGTGACTTCTCTATGTTTGATGAGGTCAGT
ACAAAATTTCCTTGGGAAGAATATGGAACTTTAAAGGATTATATGCAAAGTGGATATAATGCTAGATTTTGCAGAGGTCCTGGGTGC
ATGCTTAAGCAACTTAGAGATTCTAAGTGCGCTTGTATTAGCTGGTTGTCTCGCCAGCATTGTAGTCTAAAAACTTTAAAGCAA
AAAAACTGTCTGACGTGGGGAGAGTGTTTTTGCTATCAGTGCTTTATTCTTTGGTTTGGATTTCCTCCTACTTGGGAAAGTTTTGAC
TGGTGGCAAAAAACTTTAGAAGAAACTGACTACTGCTTACTGCATCTGCACCTTTTCTAGACTCCTACTTCCTTCCTCTGTAAGTAT
TAGATATGGAAAAGTCTATAAGGCAAAATATCAAAGAAAGGTTATTTATGACAGATTTTCTGTACTTTCCCATCTAGGTTGACGAGG
CCCCTATATATGGGACCACTAAATTCAAAGAATGGTGGAGATCAGGAGGATTCAGCTTCGGGAAGGCATACGAATATGGGCCCAATC
CACACGGGACCAACTCAAGATCCAGAAAGCCTTCCTCCAATGCATCCAGGGGAGCCCCAGTGGAAGTCACCACCCCACAGCCAGA
GCTCTTCCTCTGGGTATGGGTCCTTCTCAGCGTCCCAGGCTTCAGACTCCCAGTCCAGAGGACCCGATATACCTCCCGAACACCATG
AGGAACCCACCTCATCCTCTGGATCCAGTAGCAGAGAGGAGACCACCAATTCAGGAAGAGAATCCAGCACACCAAATGGAACCAGTG
TACCTAGAAATTCTTCCAGAACTGATGGCACCTGGGAGGATCTCTTCTGCGATGAATCACTTTCCTCCCCTGAGCCTCCCTCGTCCT
CTGAGGAGCCTGAGGAGCCCCCCTCCTCAAGAAGCTCGCCCCGGCAGCCCCGTCTTCCTCTGCCGAGGAGGCCTCGTCATCTCAGT
TTACAGATGAGGAATACAGATCCTCCTCCTTCACCCACCCCGAAGACCCCTCCTCCATTCTCAAGAAAGCGAAAATTTGGGGGGTCC
GAAGCTCTGCAAGCTCTGCTAGTTCAGCAAGTTTTACAAGCACTCCACCAAAGCCAAAAAAGAACAGAGAAACTCCTGTTCCTACTG
ATTTTCCTATTGATCTTTCTGATTATCTTAGCCATGCTGTATATAGTAATAAAACAGTAAGTTGTTTTGCCATTTATACTACTTCTG
ATAAAGCTATAGAGTTATATGATAAGATTGAGAAATTTAAAGTTGATTTTAAAAGCAGGCATGCCTGTGAATTAGGATGTATTTTAT
TGTTTATAACTTTATCAAAGCATAGAGTATCTGCTATTAAGAATTTCTGCTCTACCTTCTGCACTATAAGCTTTTTAATTTGTAAAG
GAGTGAATAAGATGCCTGAAATGTATAATAATTTATGCAAGCCCCTTACAAATTACTGCAAGAGAATAAGCCACTGCTCAATTATG
AATTTCAAGAAAAGAAAAGAGGCCAGCTGCAATTGGAATTTAGTTGCTGAATTTGCTTGTGAATATGAGCTAGACGAGGTTAGAG
ATGCTGGAAATGACCAGGACAGAAATGCTATGTAAGAAGTTTAAGAAGCACCTAGAGAGATTAAGAGATTTAGATACAATAGATCTA
CTGTATTATATGGGTGGTGTGGCCTGGTACTGCTGCTTATTTGAAGAGTTTGAAAAGAAGCTGCAGAAAATTATTCAATTATTAACA
GAGAATATACCTAAGTATAGAAACATTTGGTTTAAAGGGCCTATTAACAGTGGAAAAACAAGCTTTGCTGCAGCCTTAATAGATTTG
CTGGAAGGGAAGGCCTTGAATATAAACTGTCCATCTGATAAACTACCTTTTGAACTAGGATGTGCTTTGGATAAATTTATGGTTGTT
TTTGAGGATGTGAAAGGGCAAAATAGCCTAAATAAAGATCTGCAACCAGGGCAAGGAATAAATAACCTTGATAACTAAGAGATCAT
CTAGATGGTGCTGTAGCTGTAAGCTTAGAGAAGAAGCATGTGAATAAAAAGCATCAGATTTTTCCTCCTTGTATTGTTACTGCTAAT
GATTATTTATTCCCAAAACATTAATAGCAAGATTTAGTTATACTTTACACTTTTCCCCAAAGGCAAATCTAAGAGATTCCCTGGAT
CAGAACATGGAAATAAGAAAAAGAGAATTCTTCAAAGTGGAAACCACTTTATTGCTTTGTCTTTATTTGGTGCTTGCCTGATACAACC
TTTAAGCCTTGCTTACAAGAAGAAATTAAAAACTGGAAGCAAATTTTACAGAGTGAAATATCATATGGTAAATTTTGTCAAATGATA
GAAAATGTAGAAGCTGGTCAGGACCCTCTGCTCAATATTCTTATTGAGGAAGAGGGCCCTGAGGAAACTGAAGAAACCCAAGATTCT
GGTACTTTTTCTCAATAAAGACATCTGCTTCATATTTCCTGTGTTTGTTTTCTGGGGCCTACTTAACTGAATAGGAATGCATGAAA
TAATTCTCATAATTCTTGTGTTTGGCTTTCTTTTTGAGAGGCCTTTTGAGGTCCTTTCAGTGGCGCCTTGCCCTTATCCTGCTGATT
ACTTTGGAATGTTACTGCTGCTGGGGCAACAGAGGGCTTTGGGTAAACAGTTTTCTCCTGCCCAAATTTATCTAAAAATCTGACAAT
ATCAGGATCACCAGGTAATTGTTCTGACCCCTCATATATTCTAACCTCTTCTACCTGATTATCTTTTCCTTCCATAGGTTGGCCTGA

FIGURE 23B

CACTTTTGGCATTAAGTTGCTAAAGAGTGAGTTTATTAAATTAACTACTGGGTAGGGGTTTTTCACCCATCTTTTTCTCAAAGTAAC
ATTAAAATATCTAGGCAACCCATGAAGAGCCATTTTTCCACTGGTTTTAAACAGAAACCCCACTATGTCTGCACAGCTAATAAATAG
GCCGTCTCCTTTGCATAGAGGGCCCACTCCATTCTCATCTAAAAGGACAGTAGTTAGAGTATTACTAAATTGAAGAACTGTAGGAGT
CTGAGAGCCTGTCTGAATAGACCCATAGTATCTACTGTTTTCATTTTTAGAAGGATCAGGACACCCATACTTCTATAGGATAATTTCC
ATCTTTATCTAATTTTGCTTTAGCTTGTGGATCTAGGCCCTGATTTTTAGGTGTCATTTTTCTTCCCAATACAGTTTCAATTGTAAT
AGGCCCACCATTTGTAGTTTTTGGATACTGAGTCTGGTAATCTAAAACTAGGCCTTGCAAATCTAGAGGTTCTCCCCCAATGGCAAA
CATATGGTAATTTACCCCTGACACAGGAATACCAGCACCATAATCATGAACTCTTTTCATGTCCCAATAATGAACATTAATTAAAGA
ACTAATTCCAACTACTTCTGTTTTAACAGATATTGCCTCCCACATCTGCAATGTGTCACAGGTAATATCCTCATTTAGCATTGGCAG
AGACACTCTTGCCACACTGTAAGCTGGCAAATTTTCCTTGATGGGCTGATCTGGAGATGATCCCTTTGGCTGCAGGTCATAAGTATA
AGTATACCAGTTGAAGTAGTAGGAAGATCAGGGGAATTAACTCCCATTCTTGGATTCAAATACAACTCAATTTGGGTAATGCTATC
TTCTCCAGTAACCACAGATAATACTTCCACTCCTCCTTTAACAAGCAGTTTTGGAACTGAGGCAACATTAGGGCAGCATCCCGGCTT
AGGTATACATTGCCTTTTGGGTGTTTTACAGGTGGATGATGCTTTTCTTTTTGGTGCCATCTTCAATTACTTGTAATTCAGGAGAAA
TATATCCACTAAGGCCTAGTACCAGAGGAAGAAGCCAATCTGGAGTTTGCTGCTGCAGAGTTCCTCCTATATGTTCAGGAATTAATA
TAGCCTCTCCTGATAAAAGGCCCTGATTCTGAGAAGCAGTTGTCTGAAAGACCCACCGGCTATTTAGTATCAGATTCACTAGGTTTG
ATTGTATCTGCAGCCTAGAGGTAGGAGATAAAGAATTAAAAATATCTTGCCCCACAGAATGCAGCAAGCTATTTTCCCACTGCAGAG
GATCTAGGCTAAAGGCCATAAGTGCATGCCTCAAAACCTCATTACTACCTACCCACGAAACATCCCTCTTTACAAGTGACACTTGCT
CGCGTGACAACCTCACCCCCACAGTTATTAGAGAGCCTATACCACTAACAGTTTGGAGAATGAAGCCATAAGTTAAACCTTGGTTAA
CCAAAGAAGCCACTAATGAGAAATTTGAAAACTGTTCAGCTGTGAACCCAAGTTGAGCTAAAGCCTCAATGCCAGAAATACCCTCAA
TTGTCATTAAACTGGAGATCTCTGCTTCCAAAGCTGCTAAAGCTTCTCCTGTAAGTATAGCTTCCAAAGTTACTCCTGTGGTGGCAC
TTAGTTCAGTAGCAATTTCACCAATATTGGCCAGCAGTGTGCCCCCATCCTGAAAAATAAATAGGAATACTTACTCTTTT
AATGTCCTCCTCCCTTTGTAAGAGAAAAAAAAGCCTCCGGGCCTCCCTTGTTGAAAAAAAGTTGAGTTAAGAGTCTTCCGTCTCCCT
CCCAAACAGAAAGAAAAAAAGTTTTGTTTATCAGTCAAACTCCGCCTCTCCAGGAAATGAGTCAATGCCAGAAACCCTGCAGCAATA
AAAGTTCAATCATGTAACCACAACTTGGCTGCCTAGGTGACTTTTTTTTTTCAAGTTGGCAGAGGCTT

>MCV_352 5185bp (SEQ ID NO: 3)
GGGGCTCCTAGCCTCCGAGGCCTCTGGAAAAAAAGAGAGAGGCCTCTGAGGCTTAAGAGGCTTAATTAGCAAAAAAGGCAGTATCT
AAGGGCAGATCCCAAGGGCGGGAAACTGCAGTATAAAAACCACTCCTTAGTGAGGTAGCTCATTTGCTCCTCTGCTCTTTCTGCAAA
CTCCTTCTGCATATAGACAAGATGGATTTAGTCCTAAATAGGAAAGAAAGAGAGGCTCTCTGCAAGCTTTTAGAGATTGCTCCTAAT
TGTTATGGCAACATCCCTCTGATGAAAGCTGCTTTCAAAAGAAGCTGCTTAAAGCATCACCCTGATAAAGGGGGAAATCCTGTTATA
ATGATGGAATTGAACACCCTTTGGAGCAAATTCCAGCAAATATCCACAAGCTCAGAAGTGACTTCTCTATGTTTGATGAGGTCAGT
ACAAAATTTCCTTGGGAAGAATATGGAACTTTAAAGGATTATATGCAAAGTGGATATAATGCTAGATTTTGCAGAGGTCCTGGGTGC
ATGCTTAAGCAACTTAGAGATTCTAAGTGCGCTTGTATTAGCTGTAAGTTGTCTCGCCAGCATTGTAGTCTAAAAACTTTAAAGCAA
AAAAACTGTCTGACGTGGGCAGAGTGTTTTTGCTATCAGTGCTTTATTCTTTGGTTTGGATTTCCTCCTACTTGGGAAAGTTTTGAC
TGGTGGCAAAAAACTTTAGAAGAAACTGACTACTGCTTACTGCATCTGCACCTTTTCTAGACTCCTACTTCCTTCCTCTGTAAGTAT
TAGATATGGAAAAGTCTATAAGGCAAAATATCAAAGAAAGGTTATTTATGACAGATTTTCTGTACTTTCCCATCTAGGTTGACGAGG
CCCCTATATATGGGACCCACTAAATTCAAAGAATGGTGGAGATCAGGAGGATTCAGCTTCGGGAAGGCATACGAATATGGCCCAATC
CACACGGGACCAACTCAAGATCCAGAAAGCCTTCCTCCAATGCATCCAGGGGAGCCCCCAGTGGAAGCTCACCACCCCACAGCCAGA
GCTCTTCCTCTGGGTATGGGTCCTTCTCAGCGTCCCAGGCTTCAGACTCCCAGTCCAGAGGACCCGATATACCTCCCGAACACCATG
AGGAACCCACCTCATCCTCTGGATCCAGTAGCAGAGAGGAGACCACCAATTCAGGAAGAGAATCCAGCACACCCAATGGAACCAGTC
TACCTAGAAATTCTTCCAGAACGGATGGCACCTGGGAGGATCTCTTCTGCGATGAATCACTTTCCTCCCCTGAGCCTCCCTCGTCTC
CTGAGGAGCCTGAGGAGCCCCCCTGCTCAAGAAGCTCGCCCCGGCAGCCCCCGTCTTCCTCTGCGCCGAGGAGGCCTCGTCATCTCAGT
TTACAGATGAGGAATACAGATCCTCCTCCTTCACCACCCCGAAGACCCCTCCTCCATTCTCAAGAAAGCGAAAATTTGGGGGTGCC
GAAGCTCTGCAAGCTCTGCTAGTTGAGCAAGTTTTACAAGCACTCCACCAAAGCCAAAAAAGAACAGAGAAACTCCTGTTCCTACTG
ATTTTCCTATTGATCTTTCTGATTATCTTAGCCATGCTGTATATAGTAATAAAACAGTAAGTTGTTTTGCCATTTATACTACTTCTG
ATAAAGCTATAGAGTTATATGATAAGATTGAGAAATTTAAAGTTGATTTTAAAAGCAGGCATGCCTGTGAATTAGGATGTATTTAT
TGTTTATAACTTTATGAAAGCATAGAGTATCTGCTATTAAGAATTTTTGCTCTACCTTCTGCACTATAAGCTTTTAATTTGTAAAG
GAGTGAATAAGATGCCTGAAATGTATAATAATTTATGCAAGCCCCCTTACAAATTACTGCAAGAGAATAAGCCACTGCTCAATATG
AATTTCAAGAAAAAGAAAAAGAGGCCAGCCTGTAATTGGATTTAGTTGCTGAATTTGCTTGTGAATATGAGCTAGACGACCACTTTA
TTATCTTAGCCCATTATCTAGACTTTGCAAAACCATTTCCTTGCCAAAAGTGTGAAAACAGATCTCGCCTCAAACCTCACAAGGCTC
ATGAGGCTCATCATTCTAATGCTAAGCTATTTTATGAATCTAAATCTCAGAAAACCATTTGCCAACAAGCCGCAGACACTGTTCTAG
CCAAAAGGAGGTTAGAGATGCTGGAAATGACCAGGACAGAAATGCTATGTAAGAAGTTTAAGAAGCACCTAGAGAGATTAAGAGATT
TAGATACAATAGATCTACTGTATTATATGGGTGGTGTGGCCTGGTACTGCTGCTTATTTGAAGAGTTTGAAAAGAAGCTGCAGAAAA
TTATTCAATTATTAACAGAGAATATACCTAAGTATAGAAACATCTGGTTTAAAGGGCCTATTAACAGTGGAAAAACAAGCTTTGCTG
CAGCCTTAATAGATTTGCTAGAAGGGAAGGCCTTGAATATAAACTGTCCATCTGATAAACTGCCTTTTGAAGTAGGATGTGCTTTGG
ATAAATTTATGGTTGTTTTTGAGGATGTGAAAGGGCAAAATAGCCTAAATAAAGATCTGCAACCAGGGCAAGGAATAAATAACCTTG
ATAACTTAAGAGATCATCTAGATGGTGCTGTAGCTGTAAGCTGTAAGAAGCATGTGAATAAAAAGCATTAGATTTTTCCTCCTT
GTATTGTTACTGCTAATGATTATTTTATTCCCAAAACATTAATAGCAAGATTTAGTTATACTTTACACTTTTCCCCAAAGGCAAATC
TAAGAGATTCCCTGGATCAGAACATGGAAATAAGAAAAAGAAGAATTCTTCAAAGTGGAACCACTTTATTGCTTTGTCTTATTTGGT
GCTTGCCTGATACAACCTTTAAGCCTTGCTTACAAGAAGAAATTAAAAACTGGAAGCAAATTTTACAGAGTGAAATATCATATGGTA
AATTTTGTCAAATGATAGAAAATGTAGAAGCTGGTCAGGACCCTCTGCTCAATATTCTTATTGAGGAAGAGGGCCCTGAGGAAACTG
AAGAAACCCAAGATTCTGGTACTTTTTCTCAATAAAGGCATCTGCTTCATATTTCCTGTGTTTGTTTTTCTGGGGCCTACTTAACTG

```
AATAGGAATGCATGAAATAATTCTCATAATTCTTGTGTTTGGCTTTCTTTTTGAGAGGCCTTTTGAGGTCCTTTCAGTGGCGCCTTG
CCCCTTATCCTGCTGATTACTTTGGAATGTTACTGCTGCTGGGGCAACAGAGGGCTTTGGGTAAACAGTTTTCTCCTGCCCAAATTTA
TCTAAAAATCTGACAATATCAGGATCACCAGGTAATTGTTCTGACCCCTCATATATTCTAACCTCTTCTACCTGATTATCTTTTCCT
TCCATAGGTTGGCCTGACACTTTTGGCATTAAGTTGCTGTAGTTAGAGTATTACTAAATTGAAGAACTGTAGGAGTCTGAGAGCCTG
TCTGAATAGACCCATAGTATCTACTGTTTTCATTTTTAGAAGGATCAGGACACCATACTTCTATAGGATAATTTCCATCTTTATCTA
ATTTTGCTTTAGCTTGTGGATCTAGGCCCTGATTTTTAGGTGTCATTTTTCTTCCCAATACAGTTTCAATTGTAATAGGCCCACCAT
TTGTAGTTTTTGGATACTCAGTCTGGTAATCTAAAACTAGGCCTTGCAAATCCAGAGGTTCTCCCCCAATGGCAAACATATGGTAAT
TTACCCCTGACACAGGAATACCAGCACCATAATCATGAACTCTTTTCATGTCCCAATAATGAACATTAATTAAAGAACTTATTCCAA
CTACTTCTGTTTTAACAGATATTGCCTCCCACATCTGCAATGTGTCACAGGTAATATCCTCATTTAGCATTGGCAGAGACACTCTTG
CCACACTGTAAGCTGGCAAATTTTCCTTGATGGGCTGATCTGGAGATGATCCCTTTGGCTGCAGGTCATAAGTATAAGTATACCAGT
TTGAAGTAGTAGGAAGATCAGGGGAATTAACTCCCATTCTTGGATTCAAATACAACTCAATTTGGGTAATGCTATCTTCTCCAGTAA
CCACAGATAATACTTCCACTCCTCCTTTAACAAGCAGTTTTGGAACTGAGGCAACATTAGGGCAGCATCCCGGCTTAGGTATACATT
GCCTTTTGGGTGTTTTACAGGTGGATGATGCTTTCTTTTTGGTGCCATCTTCAATTACTTGTAATTCAGGAGAAATATATCCACTA
AGGCCTAGTACCAGAGGAAGAAGCCAATCTGGAGTTTGCTGCTGCAGAGTTCCTCCTATATGTTCAGGAATTAATATAGCCTCTCCT
GATAAAAGGCCCTGATTCTGAGAAGCAGTTGTCTGAAAGACCCACCGGCTATTTAGTATCAGATTCACTAGGTTTGATTGTATCTGC
AGCCTAGAGGTAGGAGATAAAGAATTAAAAATATCTTGCCCCACAGAATGCAGCAAGCTATTTTCCCACTGCAGAGGATCTAGGCTA
AAGGCCATAAGTGCATGCCTCAAAACCTCATTACTACCTACCCACGAAACATCCCTCTTTACAAGTGACACTTGCTCGCGTGACAAC
CTCACCCCCACAGTTATTAGAGAGCCTATACCACTAACAGTTTGGAGAATGAAGCCATAAGTTAAACCTTGGTTAACCAAAGAAGCC
ACTAATGAGAAATTTGAAAACTGTTCAGCTGTGAACCCAAGTTGAGCTAAAGCCTCAATGCCAGAAATACCCTCAATTGTCATTAAA
CTGGAGATCTCTGCTTCCAAAGCTGCTAAAGCTTCTCCTGTAAGAATAGCTTCCAAAGTTACTCCTGTGGTGGCACTTAGTTCAGTA
GCAATTTCACCAATATTGGCCAGCAGTGTGATGATGCCCCCCATCCTGAAAAATAAATAAGGATACTTACTCTTTTAATGTCCTCCT
CCCTTTGTAAGAGAAAAAAAAGCCTCCGGGCCTCCCTTGTTGAAAAAAAGTTAAGAGTCTTCCGTCTCCCTCCCAAACAGAAAGAAA
AAAAGTTTTGTTTATCAGTCAAACTCCGCCTCTCCAGGAAATGAGTCAATGCCAGAAACCCTGCAGCAATAAAAGTTCAATCATGTA
ACCACAACTTGGCTGCCTAGGTGACTTTTTTTTTTCAAGTTGGCAGAGGCTT

>MCV_MKL1 5341bp (SEQ ID NO:4)
GGGGCTCCTAGCCTCCGAGGCCTCTGGAAAAAAAGAGAGAGGCCTCTGAGGCTTAAGAGGCTTAATTAGCAAAAAGGCAGTATCT
AAGGGCAGATCCCAAGGGCGGGAAACTGCAGTATAAAAACCACTCCTTAGTGAGGTGGCTCATTTGCTCCTCTGCTCTTTCTGCAAA
CTCCTTCTGCATATAGACAAGATGGATTTAGTCCTAAATAGGAAAGAAAGAGAGGCTCTCTGCAAGCTTTTAGAGATTGCTCCTAAT
TGTTATGGCAACATCCCTCTGATGAAAGCTGCTTTCAAAAGAAGCTGCTTAAAGCATCACCCTGATAAAGGGGGAAATCCTGTTATA
ATGATGGAATTGAACACCCTTTGGAGCAAATTCCAGCAAAATATCCACAAGCTCAGAAGTGACTTCTCTATGTTTGATGAGGTCAGT
ACAAAATTTCCTTGGGAAGAATATGGAACTTTAAAGGATTATATGCAAAGTGGATATAATGCTAGATTTTGCAGAGGTCCTGGGTGC
ATGCTTAAGCAACTTAGAGATTCTAAGTGCGCTTGTATTAGCTGTAAGTTGTCTCGCCAGCATTGTAGTCTAAAAACTTTAAAGCAA
AAAAACTGTCTGACGTGGGGAGAGTGTTTTTGCTATCAGTGCTTTATTCTTTGGTTTGGATTTCCTCCTACTTGGGAAAGTTTTGAC
TGGTGGCAAAAAACTTTAGAAGAAACTGACTACTGCTTACTGCATCTGCACCTTTTCTAGACTCCTACTTCCTTCCTCTGTAAGTAT
TAGATATGGAAAAGTCTATAAGGCAAAATATCAAAGAAAGGTTATTTTATGACAGATTTTCTGTACTTTCCCATCTAGGTTGACGAGG
CCCCTATATATGGGACCACTAAATTCAAAGAATGGTGGAGATCAGGAGGATTCAGCTTCGGGAAGGCATACAATACGAATATGGGCCCAATC
CACACGGGACCAACTCAAGATCCAGAAAGCCTTCCTCCAATGCATCCAGGGGGAGCCCCCAGTGGAAGCTCACCACCCCACAGCCAGA
GCTCTTCCTCTGGGTATGGGTCCTTCTCAGCGTCCCAGGCTTCGAGACTCCCAGTCCAGAGGACCCGATATACCTCCCGAACACCATG
AGGAACCCACCTCATCCTCTGGATCCAGTAGCAGAGAGGAGACCACCAATTCAGGAAGAGAATCCAGCACACCCAATGGAACCAGTG
TACCTAGAAATTCTTCCAGAACGGATGGCACCTGGGAGGATCTCTTCTGCGATGAATCACTTTCCTCCCCTGAGCCTCCCTCGTCCT
CTGAGGAGCCTGAGGAGCCCCCCTCCTCAAGAAGCTCGCCCCGGCAGCCCCCCGTCTTCCTCTGCCGAGGAGGCCTCGTCATCTCAGT
TTACAGATGAGGAATAAGATCCTCCTCCTTCACCACCCCGAAGACCCCTCCTCCATTCTCAAGAAAGCGAAAATTTGGGGGGTCCC
GAAGCTCTGCAAGCTCTGCTAGTTCAGCAAGTTTTACAAGCACTCCACCAAAGCCAAAAAAGAACAGAGAAACTCCTGTTCCTACTG
ATTTTCCTATTGATCTTTCTGATTATCTTAGCCATGCTGTATATAAGCTATAGAGTTATATGATAAGATTGAGAAATTTAAAGTTGA
TTTTAAAAGCAGGCATGCCTGTGAATTAGGATGTATTTTATTGTTTATAACTTTATCAAAGCATAGAGTATCTGCTATTAAGAATTT
TTGCTCTACCTTCTGCACTATAAGCTTTTTAATTTGTAAAGGAGTGAATAAGATGCCTGAAATGTATAATAATTTATGCAAGCCCCC
TTACAAATTACTGCAAGAGAATAAGCCACTGCTCAATTATGAATTTCAAGAAAAGAAAAAGAGGCCAGCTGTAATTGGAATTTAGT
TGCTGAATTTGCTTGTGAATATGAGCTAGACGACCACTTTATTATCTTAGCCCATTATCTAGACTTTGCAAAACCATTTCCTTGCCA
AAAGTGTGAAAACAGATCTCGCCTCAAACCTCACAAGGCTCATGAGGCTCATCATTCTAATGCTAAGCTATTTTATGAATCTAAATC
TCAGAAAACCATTTGCCAACAAGCCGCAGACACTGTTCTAGCCAAAAGGAGGTTAGAGATGCTGGAAATGACCAGGACAGAAATGCT
ATGTAAGAAGTTTAAGAAGCACCTAGAGAGATTAAGAGATTTAGATACAATAGATCTACTGTATTATATGGGTGGTGTGGCCTGGTA
CTGCTGCTTATTTGAAGAGTTTGAAAAGAAGCTGCAGAAAATTATTCAATTATTAACAGAGAATATACCTAAGTATAGAAACATTTG
GTTTAAAGGGCCTATTAACAGTGGAAAAACAAGCTTTGCTGCAGCCTTAATAGATTTGCTAGAAGGGAAGGCCTTGAATATAAACTG
TCCATCTGATAAACTGCCTTTTGAACTAGGATGTGCTCTGATAAATTTATGGTTGTTTTTGAGGATGTGAAAGGCAAAATAGCCT
AAATAAAGATCTGCAACCAGGGCAAGGAATAAATAACCTTGATAACTTAAGAGATCATCTAGATGGTGCTGTAGCTGTAAGCTTAGA
GAAGAAGCATGTGAATAAAAAGCATCAGATTTTTCCTCCTTGTATTGTTACTGCTAATGATTATTTTATTCCCAAACATTAATAGC
AAGATTTAGTTATACTTTACACTTTTCCCCAAAGGCAAATCTAAGAGATTCCCTGGATCAGAACATGGAAATAAGAAAAGAAGAAT
TCTTCAAAGTGGAACCACTTTATTGCTTTGTCTTATTTGGTGCTTGCCTGATACAACCTTTAAGCCTTGCTTACAAGAAGAAATTAA
AAACTGGAAGCAAATTTTACAGAGTGAAATATCATATGGTAAATTTTGTCAAATGATAGAAATGTAGAAGCTGGTCAGGACCCTCT
GCTCAATATTCTTATTGAGGAAGAGGGCCCTGAGGAAACTGAAGAAACCCAAGATTCTGGTACTTTTTCTCAATAAAGGCATCTGCT
```

FIGURE 23D

```
TCATATTTCCTGTGTTTGTTTTTCTGGGGCCTACTTAACTGAATAGGAATGCATGAAATAATTCTCATAATTCTTGTGTTTGGCTTT
CTTTTTGAGAGGCCTTTTGAGGTCCTTTCAGTGGCGCCTTGCCCTTATCCTGCTGATTACTTTGGAATGTTACTGCTGCTGGGGCAA
CAGAGGGCTTTGGGTAAACAGTTTTCTCCTGCCCAAATTTATCTAAAAATCTGACAATATCAGGATCACCAGGTAATTGTTCTGACC
CCTCATATATTCTAACCTCTTCTACCTGATTATCTTTTCCTTCCATAGGTTGGCCTGACACTTTTGGCATTAAGTTGCTGAAGAGTG
AGTTTATTAAATTAACTACTGGGTAGGGGTTTTTCACCCATCTTTTTCTCAAAGTAACATTAAAATATCTAGGCAACCCATGAAGAG
CCATTTTTCCACTGGTTTTAAACAGAAACCCCACTATGTCTGCACAGCTAATAAATAGGCCATCTCCTTTGCATAGAGGGCCCACTC
CATTCTCATCTAAAAGGACAGTAGTTAGAGTATTACTAAATTGAAGAACTGTAGGAGTCTGAGAGCCTGTCTGAATAGACCCATAGT
ATCTACTGTTTTCATTTTTAGAAGGATCAGGACACCATACTTCTATAGGATAATTTCCATCTTTATCTAATTTTGCTTTAGCTTGTG
GATCTAGGCCCTGATTTTTAGGTGTCATTTTTCTTCCCAATACAGTTTCAATTGTAATAGGCCCACCATTTGTAGTTTTTGGATACT
CAGTCTGGTAATCTAAAACTAGGCCTTGCAAATCCAGAGGTTCTCCCCCAATGGCAAACATATGGTAATTTACTCCTGACACAGGAA
TACCAGCACCATAATCATGAACTCTTTTCATGTCCCAATAATGAACATTAATTAAAGAACTTATTCCAACTACTTCTGTTTTAACAG
ATATTGCCTCCCACATCTGCAATGTGTCACAGGTAATATCCTCATTTAGCATTGGCAGAGACACTCTTGCCACACTGTAAGCTGGCA
AATTTTCCTTGATGGGCTGATCTGGAGATGATCCCTTTGGCTGCAGGTCATAAGTATAAGTATACCAGTTTGAAGTAGTAGGAAGAT
CAGGGGAATTAACTCCCATTCTTGGATTCAAATACAACTCAATTTGGGTAATGCTATCTTCTCCAGTAACCACAGATAATACTTCCA
CTCCTCCTTTAACAAGCAGTTTTGGAACTGAGGCAACATTAGGGCAGCATCCCGGCTTAGGTATACATTGCCTTTTGGGTGTTTTAC
AGGTGGATGATGCTTTTCTTTTTGGTGCCATCTTCAATTACTTGTAATTCAGGAGAAATATATCCACTAAGGCCTAGTACCAGAGGA
AGAAGCCAATCTGGAGTTTGCTGCTGCAGAGTTCCTCCTATATGTTCAGGAATTAATATAGCCTCTCCTGATAAAAGGCCCTGATTC
TGAGAAGCAGTTGTCTGAAAGACCCACCGGCTATTTAGTATCAGATTCACTAGGTTTGATTGTATCTGCAGCCTAGAGGTAGGAGAT
AAAGAATTAAAAATATCTTCCCCCACAGAATGCAGCAAGCTATTTTCCCACTGCAGAGGATCTAGGCTAAAGGCCATAAGTGCATGC
CTCAAAACCTCATTACTACCTACCCACGAACATCCCTCTTTACAAGTGACACTTGCTCGCGTGACAACCTCACCCCCACAGTTATT
AGAGAGCTATACCACTAACAGTTTGGAGAATGAAGCCATAAGTTAAACCTTGGTTAACCAAAGAAGCCACTAATGAGAAATTTGAA
AACTGTTCAGCTGTGAACCCAAGTTGAGCTAAAGCCTCAATGCCAGAAATACCCTCAATTGTCATTAAACTGGAGATCTCTGCTTCC
AAAGCTGCTAAAGCTTCTCCTGTAAGAATAGCTTCCAAAGTTACTCCTGTGGTGGCACTTAGTTCAGTAGCAATTTCACCAATATTG
GCCAGCAGTGTGATGATGCCCCCCATCCTGAAAAATAAATAAGGATACTTACTCTTTTAATGTCCTCCTCCCTTTGTAAGAGAAAAA
AAAGCCTCCGGGCCTCCCTTGTTGAAAAAAAGTTAAGAGTCTTCCGTCTCCCTCCCAAACAGAAAGAAAAAAAGTTTTGTTTATCAG
TCAAACTCCGCCTCTCCAGGAAATGAGTCAATGCCAGAAACCCTGCAGCAATAAAAGTTCAATCATGTAACCACAACTTGGCTGCCT
AGGTGACTTTTTTTTTTCAAGTTGGCAGAGGCTT
```

(2). Putative coding transcripts and predicted amino acid (based on MCV_350 genome, % marks site of tumor-derived stop codon that is absent in wild-type virus)

>VP1 (4427-3156) (SEQ ID NO:5)
```
ATGGCACCAAAAAGAAAAGCATCATCCACCTGTAAAACACCCAAAAGGCAATGTATACCCTAAGCCGGGATGCTGCCCTAATGTTGCC
TCAGTTCCAAAAGTGCTTGTTAAAGGAGGAGTGGAAGTATTATCTGTGGTTACTGGAGAAGATAGCATTACCCAAATTGAGTTGTAT
TTGAATCCAAGAATGGGAGTTAATTCCCCTGATCTTCCTACTACTTCAAACTGGTATACTTATACTTATGACCTGCAGCCAAAGGGA
TCATCTCCAGATCAGCCCATCAAGGAAAATTTGCCAGCTTACAGTGTGGCAAGAGTGTCTCTGCCAATGCTAAATGAGGATATTACC
TGTGACACATTGCAGATGTGGGAGGCAATATCTGTTAAAACAGAAGTAGTTGGAATAAGTTCTTTAATTAATGTTCATTATTGGGAC
ATGAAAAGAGTTCATGATTATGGTGCTGGTATTCCTGTGTCAGGGGTGAATTACCATATGTTTGCCATTGGGGGAGAACCTCTGGAT
TTGCAAGGCCTAGTTTTAGATTACCAGACTGAGTATCCAAAAACTACAAATGGTGGGCCTATTACAATTGAAACTGTATTAGGAAGA
AAAATGACACCTAAAAATCAGGGCCTAGATCCACAAGCTAAAGCAAAATTAGATAAAGATGGAAATTATCCTATAGAAGTATGGTGT
CCTGATCCTTCTAAAAATGAAAACAGTAGAGATACTATGGGTCTATTCAGACAGGCTCTCAGACTCCTACAGTTCTTCAATTTAGTAAT
ACTCTAACTACTGTCCTTTTAGATGAGAATGGAGTGGGCCCTCTATGCAAAGGAGATGGCCTATTTATTAGCTGTGCACACATAGTG
GGGTTTCTGTTTAAAACCAGTGGAAAAATGGCTCTTCATGGGTTGCCTAGATATTTTAATGTTACTTTGAGAAAAATATGGGTGAAA
AACCCCTACCCAGTAGTTAATTTAATAAACTCACTCTTCAGCAACTTAATGCCAAAAGTGTCAGGCCAACCTATGGAAGGAAAAGAT
AATCAGGTAGAAGAGGTCAGAATATATGAGGGGTCAGAACAATTACCTGGTAATCCTGATATTGTCAGATTTTTAGATAAATTTGGG
CAGGAGAAAACTGTTTACCCAAAGCCCTCTGTTGCCCCAGCAGCAGTAACATTCCAAAGTAATCAGCAGGATAAGGGCAAGGCGCCA
CTGAAAGGACCTCAAAAGGCCTCTCAAAAAGAAAGCCAAACACAACAATTATGA
```

>VP1 protein (4427-3156) (SEQ ID NO:6)

MAPKRKASSTCKTPKRQCIPKPGCCPNVASVPKLLVKGGVEVLSVVTGEDSITQIELYLNPRMGVNSPDLPTTSNWYTYTYDLQPKG
SSPDQPIKENLPAYSVARVSLPMLNEDITCDTLQMWEAISVKTEVVGISSLINVHYWDMKRVHDYGAGIPVSGVNYHMFAIGGEPLD
LQGLVLDYQTEYPKTTNGGPITIETVLGRKMTPKNQGLDPQAKAKLDKDGNYPIEVWCPDPSKNENSRYYGSIQTGSQTPTVLQFSN
TLTTVLLDENGVGPLCKGDGLFISCAHIVGFLFKTSGKMALHGLPRYFNVTLRKIWVKNPYPVVNLINSLFSNLMPKVSGQPMEGKD
NQVEEVRIYEGSEQLPGNPDIVRFLDKFGQEKTVYPKPSVAPAAVTFQSNQQDKGKAPLKGPQKASQKESQTQQL*

>VP2 (5118-4393) (SEQ ID NO:7)
```
ATGGGGGGCATCATCACACTGCTGGCCAATATTGGTGAAATTGCTACTGAACTAAGTGCCACCACAGGAGTAACTTTGGAAGCTATT
CTTACAGGAGAAGCTTTAGCAGCTTTGGAAGCAGACATCTCCAGTTAATGACAATTGAGGGTATTTCTGGCATTGAGGCTTTAGCT
CAACTTGGGTTCACAGCTGAACAGTTTTCAAATTTCTCATTAGTGGCTTCTTTGGTTAACCAAGGTTTAACTTATGCCTTCATTCTC
CAAACTGTTAGTGGTATAGGCTCTCTAATAACTGTGGGGGTGAGGTTGTCACGCGAGCAAGTGTCACTTGTAAACAGGGATGTTTCG
```

```
TGGGTAGGTAGTAATGAGGTTTTGAGGCATGCACTTATGGCCTTTAGCCTAGATCCTCTGCAGTGGGAAAATAGCTTGCTGCATTCT
GTGGGGCAAAATATTTTTAATTCTTTATCTCCTACCTCTAGGCTGCAGATACAATCAAACCTAGTGAATCTGATACTAAATAGCCGG
TGGGTCTTTCAGACAACTGCTTCTCAGAATCAGGGCCTTTTATCAGGAGAGGCTATATTAATTCCTGAACATATAGGAGGAACTCTG
CAGCAGCAAACTCCAGATTGGCTTCTTCCTCTGGTACTAGGCCTTAGTGGATATATTTCTCCTGAATTACAAGTAATTGAAGATGGC
ACCAAAAAGAAAAGCATCATCCACCTGTAA
```

>VP2 protein(5118-4393) (SEQ ID NO:8)
```
MGGIITLLANIGEIATELSATTGVTLEAILTGEALAALEADISSLMTIEGISGIEALAQLGFTAEQFSNFSLVASLVNQGLTYGFIL
QTVSGIGSLITVGVRLSREQVSLVNRDVSWVGSNEVLRHALMAFSLDPLQWENSLLHSVGQNIFNSLSPTSRLQIQSNLVNLILNSR
WVFQTTASQNQGLLSGEAILIPEHIGGTLQQQTPDWLLPLVLGLSGYISPELQVIEDGTKKKSIIHL*
```

>VP3 (4983-4393) (SEQ ID NO:9)
```
ATGACAATTGAGGGTATTTCTGGCATTGAGGCTTTAGCTCAACTTGGGTTCACAGCTGAACAGTTTTCAAATTTCTCATTAGTGGCT
TCTTTGGTTAACCAAGGTTTAACTTATGGCTTCATTCTCCAAACTGTTAGTGGTATAGGCTCTCTAATAACTGTGGGGGTGAGGTTG
TCACGCGAGCAAGTGTCACTTGTAAACAGGGATGTTTCGTGGGTAGGTAGTAATGAGGTTTTGAGGCATGCACTTATGGCCTTTAGC
CTAGATCCTCTGCAGTGGGAAAATAGCTTGCTGCATTCTGTGGGGCAAAATATTTTTAATTCTTTATCTCCTACCTCTAGGCTGCAG
ATACAATCAAACCTAGTGAATCTGATACTAAATAGCCGGTGGGTCTTTCAGACAACTGCTTCTCAGAATCAGGGCCTTTTATCAGGA
GAGGCTATATTAATTCCTGAACATATAGGAGGAACTCTGCAGCAGCAAACTCCAGATTGGCTTCTTCCTCTGGTACTAGGCCTTAGT
GGATATATTTCTCCTGAATTACAAGTAATTGAAGATGGCACCAAAAAGAAAAGCATCATCCACCTGTAA
```

>VP3 protein(4983-4393) (SEQ ID NO:10)
```
MTIEGISGIEALAQLGFTAEQFSNFSLVASLVNQGLTYGFILQTVSGIGSLITVGVRLSREQVSLVNRDVSWVGSNEVLRHALMAFS
LDPLQWENSLLHSVGQNIFNSLSPTSRLQIQSNLVNLILNSRWVFQTTASQNQGLLSGEAILIPEHIGGTLQQQTPDWLLPLVLGLS
GYISPELQVIEDGTKKKSIIHL*
```

>T-1 (196-429, 861-3080) (SEQ ID NO:11)
```
ATGGATTTAGTCCTAAATAGGAAAGAAAGAGAGGCTCTGTGCAAGCTTTTGGAGATTGCTCCTAATTGTTATGGCAACATCCCTCTG
ATGAAAGCTGCTTTCAAAAGAAGCTGCTTAAAGCATCACCCTGATAAAGGGGGAAATCCTGTTATAATGATGGAATTGAACACCCTT
TGGAGCAAATTCCAGCAAAATATCCACAAGCTCAGAAGTGCTTCTCTATGTTTGATGAGGTTGACGAGGCCCCTATATATGGGACC
ACTAAATTCAAAGAATGGTGGAGATCAGGAGGATTCAGCTTCGGGAAGGCATACGAATATGGGCCCAATCCACACGGGGCCAACTCA
AGATCCAGAAAGCCTTCCTCCAATGCATCCAGGGGAGCCCCCAGTGGAAGCTCACCACCCCACAGCCAGAGCTCTTCCTCTGGGTAT
GGGTCCTTCTCAGCGTCCCAGGCTTCAGACTCCCAGTCCAGAGGACCCGATATACCTCCCGAACACCATGAGGAACCCACCTCATCC
TCTGGATCCAGTAGCAGAGAGGAGACCACCAATTCAGGAAGAGAATCCAGCACACCCAATGGAACCAGTGTACCTAGAAATTCTTCC
AGAACGTATGCCACCTGGGAGGATCTCTTCTGCGATGAATCACTTTCCTCCCCTGAGCCTCCCTCGTCCTCTGAGGAGCCTGAGGAG
CCCCCCCTCCTCAAGAAGCTCGCCCCGGCAGCCCCCGTGTTCCTCTGCCGAGGAGGCCTCGTCATCTCAGTTTACAGATAGGAATAC
ATATCCTCCTCCTTCACCACCCCGAAGACCCCTCCTCCATTCTCAAGAAAGCGAAAATTTGGGGGGTCCCGAAGCTCTGCAAGCTCT
GCTAGTTCAGCAAGTTTTACAAGCACTCCACCAAAAGCTAAAAAACAACAGAGAAACTCCTGTTCCTACTAATTTTCCTATTGATGTT
TCTGATTATCTTAGCCATGCTGTATATAGTAATAAAACAGTAAGTTGTTTTGCCCATTTATACTACTTCTGATAAAGCTATAGAGTTA
TATGATAAGATTGAGAAATTTAAAGTTGATTTTAAAAGCAGGCATGCCTGTGAATTAGGATGTATTTTATTGTTTATAACTTTATCA
AAGCATAGAGTATTTGCTATTAAGAATTTTTGCTCTACCTTCTGCACTATAAGCTTTTTAATTTGTAAAGGAGTGAATAAGATGCCT
GAAATGTATAATAATTTATGCAAGCCCCCTTACAAATTACTGCAAGAGAATAAGCCACTGCTCAATTATGAATTTCAAGAAAAAGAA
AAAGAGGCCAGCTGTAATTGGAATTTAGTTGCTGAATTTGCTTGTGAATATGAGCTAGACGACCACTTTATTATCTTAGCCCATTAT
CTAGACTTTGCAAAACCATTTCCTTGCCAAAAGTGTGAAAACAGATCTCGCCTCAAACCTCACAAGGCTCATGAGGCTCATCATTCT
AATGCTAAGCTATTTTATGAATCTAAATCTCAGAAAACCATTTGCCAACAAGCCGCAGACACTGTTCTAGCCAAAAGGAGGTTAGAG
ATGCTGGAAATGACCAGGACAGAAATGCTATGTAAGAAGTTTAAGAAGCACCTAGAGAGATTAAGAGATTTAGATACAATAGATCTA
CTGTATTATATGGGTGGTGTGGCCTGGTACTGCTGCTTATTTGAAGAGTTTGAAAAGAAGCTGCAGAAAATTATTCAATTATTAACA
GAGAATATACCTAAGTATAGAAACATTTGGTTTAAAGGGCCTATTAACAGTGGAAAACAAGCTTTGCTGCAGCCTTAATAGATTTG
CTAGAAGGGAAGGCCTTGAATATAAACTGTCCATCTGATAAACTGCCTTTTGAACTAGGATGTGCTTTGGATAAATTTATGGTTGTT
TTTGAGGATGTGAAAGGGCAAAATAGCCTAAATAAAGATCTGCAACCAGGGCAAGGAATAAATAACCTTGATAACTTAAGAGATCAT
CTAGATGGTGCTGTAGCTGTGAGCTTAGAGAAGAAGCATGTGAATAAAAAGCATCAGATTTTTCCTCCTTGTATTGTTACTGCTAAT
GATTATTTTATTCCCAAAACATTAATAGCAAGATTTAGTTTATACTTTACACTTTTTCCCAAAGGCAAATCTAAGAGATTCCCTGGAT
CAGAACATGGAAATAAGAAAAAGAAGAATTCTTCAAAGTGGAACCACTTTATTGCTTTGTCTTATTTGGTGCTTGCCTGATACAACC
TTTAAGCCTTGCTTACAAGAAGAAATTAAAAACTGGAAGCAAATTTTACAGAGTGAAATATCATATGGTAAATTTTGTCAAATGATA
GAAAATGTAGAAGCTGGTCAGGACCCTCTGCTCAATATTCTTATTGAGGAAGAGGGCCCTGAGGAAACTGAGGAAACCCAAGATTCT
GGTACTTTTTCTCAATAA
```

>T-1 protein (196-429, 861-3080) (SEQ ID NO:12)
```
MDLVLNRKEREALCKLLEIAPNCYGNIPLMKAAFKRSCLKHHPDKGGNPVIMMELNTLWSKFQQNIHKLRSDFSMFDEVDEAPIYGT
TKFKEWWRSGGFSFGKAYEYGPNPHGANSRSRKPSSNASRGAPSGSSPPHSQSSSGYGSFSASQASDSQSRGPDIPPEHHEEPTSS
SGSSSREETTNSGRESSTPNGTSVPRNSSRTYGTWEDLFCDESLSSPEPPSSSEEPEEPPSSRSSPRQPPCSSAEEASSSQFTDKEY
```

FIGURE 23F

ISSSFTTPKTPPPFSRKRKFGGSRSSASSASSASFTSTPPKLKNNRETPVPTNFPIDVSDYLSHAVYSNKTVSCFAIYTTSDKAIEL
YDKIEKFKVDFKSRHACELGCILLFITLSKHRVFAIKNFCSTFCTISFLICKGVNKMPEMYNNLCKPPYKLLQENKPLLNYEFQEKE
KEASCNWNLVAEFACEYELDDHFIILAHYLDFAKPFPCQKCENRSRLKPHKAHEAHHSNAKLFYESKSQKTICQQAADTVLAKRRLE
MLEMTRTEMLCKKFKKHLERLRDLDTIDLLYYMGGVAWYCCLFEEFEKKLQKIIQLLTENIPKYRNIWFKGPINSGKTSFAAALIDL
LEGKALNINCPSDKLPFELGCALDKFMVVFEDVKGQNSLNKDLQPGQGINNLDNLRDHLDGAVAVSLEKKHVNKKHQIFPPCIVTAN
DYFIPKTLIARFSYTLHFFPKANLRDSLDQNMEIRKRRILQSGTTLLLCLIWCLPDTTFKPCLQEEIKNWKQILQSEISYGKFCQMI
ENVEAGQDPLLNILIEEEGPEETEETQDSGTFSQ*

>T-2 (196-777, 861-1622, 2778-3080) (SEQ ID NO:13)
ATGGATTTAGTCCTAAATAGGAAAGAAAGAGAGGCTCTGTGCAAGCTTTTGGAGATTGCTCCTAATTGTTATGGCAACATCCCTCTG
ATGAAAGCTGCTTTCAAAAGAAGCTGCTTAAAGCATCACCCTGATAAAGGGGGAAATCCTGTTATAATGATGGAATTGAACACCCTT
TGGAGCAAATTCCAGCAAAATATCCACAAGCTCAGAAGTGACTTCTCTATGTTTGATGAGGTTAGTACAAAATTTCCTTGGGAAGAA
TATGGAACTTTAAAGGATTATATGCAAAGTGGATATAATGCTAGATTTTGCAGAGGTCCTGGGTGCATGCTTAAGCAACTTAGAGAT
TCTAAGTGCGCTTGTATTAGCTGTAAGTTGTCTCGCCAGCATTGTAGTCTAAAAACTTTAAAGCAAAAAAACTGTCTGACGTGGGGA
GAGTGTTTTTGCTATCAGTGCTTTATTCTTTGGTTTGGATTTCCTCCTACTTGGGAAAGTTTTGACTGGTGGCAAAAAACTTTAGAA
GAAACTGACTACTGCTACTGCATCTGCACCTTTTCTAGACTCCTACTTCCTTCCTCTGTGTTGACGAGGCCCCTATATATGGGACC
ACTAAATTCAAAGAATGGTGGAGATCAGGAGGATTCAGCTTCGGGAAGGCATACGAATATGGGCCCAATCCACACGGGGCCAACTCA
AGATCCAGAAAGCCTTCCTCCAATGCATCCAGGGGAGCCCCCAGTGGAAGCTCACCACCCCACAGCCAGAGCTCTTCCTCTGGGTAT
GGGTCCTTCTCAGCGTCCCAGGCTTCAGACTCCCAGTCCAGAGGACCCGATATACCTCCCGAACACCATGAGGAACCCACCTCATCC
TCTGGATCCAGTAGCAGAGAGGAGACCACCAATTCAGGAAGAGAATCCAGCACACCCAATGGAACCAGTGTACCTAGAAATTCTTCC
AGAACGTATGGCACCTGGGAGGATCTCTTCTGCGATGAATCACTTTCCTCCCCTGAGCCTCCCTCGTCCTCTGAGGAGCCTGAGGAG
CCCCCCTCCTCAAGAAGCTCGCCCCGGCAGCCCCCGTGTTCCTCTGCCGAGGAGGCCTCGTCATCTCAGTTTACAGATTAGGAATAC
ATATCCTCCTCCTTCACCACCCCGAAGACCCCTCCTCCATTCTCAAGAAAGCGAAAATTTGGGGGGTCCCGAAGCTCTGCAAGCTCT
GCTAGTTCAGCAAGTTTTACAAGCACTCCACCAAAGCTAAAAAACAACAGAGAAACTCCTGTTCCTACTAATTTTCCTATTGATGTT
TCTGATTATCTTAGCCATGCTGTATATAGTAATAAAACAGCAAATCTAAGAGATTCCCTGGATCAGAACATGGAAATAAGAAAAAGA
AGAATTCTTCAAAGTGGAACCACTTTATTGCTTTGTCTTATTTGGTGCTTGCCTGATACAACCTTTAAGCCTTGCTTACAAGAAGAA
ATTAAAAACTGGAAGCAAATTTTACAGAGTGAAATATCATATGGTAAATTTTGTCAAATGATAGAAAATGTAGAAGCTGGTCAGGAC
CCTCTGCTCAATATTCTTATTGAGGAAGAGGGCCCTGAGGAAACTGAGGAAACCCAAGATTCTGGTACTTTTTCTCAATAA

>T-2 protein (196-777, 861-1622, 2778-3080) (SEQ ID NO:14)

MDLVLNRKEREALCKLLEIAPNCYGNIPLMKAAFKRSCLKHHPDKGGNPVIMMELNTLWSKFQQNIHKLRSDFSMFDEVSTKFPWEE
YGTLKDYMQSGYNARFCRGPGCMLKQLRDSKCACISCKLSRQHCSLKTLKQKNCLTWGECFCYQCFILWFGFPPTWESFDWWQKTLE
ETDYCLLHLHLFXTPTSFLCVDEAPIYGTTKFKEWWRSGGFSFGKAYEYGPNPHGANSRSRKPSSNASRGAPSGSSPPHSQSSSSGY
GSFSASQASDSQSRGPDIPPEHHEEPTSSSGSSSREETTNSGRESSTPNGTSVPRNSSRTYGTWEDLFCDESLSSPEPPSSSEEPEE
PPSSRSSPRQPPCSSAEEASSSQFTDXEYISSSFTTPKTPPPFSRKRKFGGSRSSASSASSASFTSTPPKLKNNRETPVPTNFPIDV
SDYLSHAVYSNKTANLRDSLDQNMEIRKRRILQSGTTLLLCLIWCLPDTTFKPCLQEEIKNWKQILQSEISYGKFCQMIENVEAGQD
PLLNILIEEEGPEETEETQDSGTFSQ*

>T-3 (196-429, 861-1622, 2778-3080) (SEQ ID NO:15)
ATGGATTTAGTCCTAAATAGGAAAGAAAGAGAGGCTCTGTGCAAGCTTTTGGAGATTGCTCCTAATTGTTATGGCAACATCCCTCTG
ATGAAAGCTGCTTTCAAAAGAAGCTGCTTAAAGCATCACCCTGATAAAGGGGGAAATCCTGTTATAATGATGGAATTGAACACCCTT
TGGAGCAAATTCCAGCAAAATATCCACAAGCTCAGAAGTGACTTCTCTATGTTTGATGAGGTTGACGAGGCCCCTATATATGGGACC
ACTAAATTCAAAGAATGGTGGAGATCAGGAGGATTCAGCTTCGGGAAGGCATACGAATATGGGCCCAATCCACACGGGGCCAACTCA
AGATCCAGAAAGCCTTCCTCCAATGCATCCAGGGGAGCCCCCAGTGGAAGCTCACCACCCCACAGCCAGAGCTCTTCCTCTGGGTAT
GGGTCCTTCTCAGCGTCCCAGGCTTCAGACTCCCAGTCCAGAGGACCCGATATACCTCCCGAACACCATGAGGAACCCACCTCATCC
TCTGGATCCAGTAGCAGAGAGGAGACCACCAATTCAGGAAGAGAATCCAGCACACCCAATGGAACCAGTGTACCTAGAAATTCTTCC
AGAACGTATGGCACCTGGGAGGATCTCTTCTGCGATGAATCACTTTCCTCCCCTGAGCCTCCCTCGTCCTCTGAGGAGCCTGAGGAG
CCCCCCTCCTCAAGAAGCTCGCCCCGGCAGCCCCCGTGTTCCTCTGCCGAGGAGGCCTCGTCATCTCAGTTTACAGATTAGGAATAC
ATATCCTCCTCCTTCACCACCCCGAAGACCCCTCCTCCATTCTCAAGAAAGCGAAAATTTGGGGGGTCCCGAAGCTCTGCAAGCTCT
GCTAGTTCAGCAAGTTTTACAAGCACTCCACCAAAGCTAAAAAACAACAGAGAAACTCCTGTTCCTACTAATTTTCCTATTGATGTT
TCTGATTATCTTAGCCATGCTGTATATAGTAATAAAACAGCAAATCTAAGAGATTCCCTGGATCAGAACATGGAAATAAGAAAAAGA
AGAATTCTTCAAAGTGGAACCACTTTATTGCTTTGTCTTATTTGGTGCTTGCCTGATACAACCTTTAAGCCTTGCTTACAAGAAGAA
ATTAAAAACTGGAAGCAAATTTTACAGAGTGAAATATCATATGGTAAATTTTGTCAAATGATAGAAAATGTAGAAGCTGGTCAGGAC
CCTCTGCTCAATATTCTTATTGAGGAAGAGGGCCCTGAGGAAACTGAGGAAACCCAAGATTCTGGTACTTTTTCTCAATAA

>T-3 protein (196-429, 861-1622, 2778-3080) (SEQ ID NO:16)
MDLVLNRKEREALCKLLEIAPNCYGNIPLMKAAFKRSCLKHHPDKGGNPVIMMELNTLWSKFQQNIHKLRSDFSMFDEVDEAPIYGT
TKFKEWWRSGGFSFGKAYEYGPNPHGANSRSRKPSSNASRGAPSGSSPPHSQSSSSGYGSFSASQASDSQSRGPDIPPEHHEEPTSS
SGSSSREETTNSGRESSTPNGTSVPRNSSRTYGTWEDLFCDESLSSPEPPSSSEEPEEPPSSRSSPRQPPCSSAEEASSSQFTDXEY

FIGURE 23G

ISSSFTTPKTPPPFSRKRKFGGSRSSASSASSASFTSTPPKLKNNRETPVPTNFPIDVSDYLSHAVYSNKTANLRDSLDQNMEIRKR
RILQSGTTLLLCLIWCLPDTTFKPCLQEEIKNWKQILQSEISYGKFCQMIENVEAGQDPLLNILEEEGPEETEETQDSGTFSQ'

>T-4 (196-429, 2778-3080) (SEQ ID NO:17)
ATGGATTTAGTCCTAAATAGGAAAGAAAGAGAGGCTCTGTGCAAGCTTTTGGAGATTGCTCCTAATTGTTATGGCAACATCCCTCTG
ATGAAAGCTGCTTTCAAAAGAAGCTGCTTAAAGCATCACCCTGATAAAGGGGGAAATCCTGTTATAATGATGGAATTGAACACCCTT
TGGAGCAAATTCCAGCAAAATATCCACAAGCTCAGAAGTGACTTCTCTATGTTTGATGAGGCAAATCTAAGAGATTCCCTGGATCAG
AACATGGAAATAAGAAAAAGAAGAATTCTTCAAAGTGGAACCACTTTATTGCTTTGTCTTATTTGGTGCTTGCCTGATACAACCTTT
AAGCCTTGCTTACAAGAAGAAATTAAAAACTGGAAGCAAATTTTACAGAGTGAAATATCATATGGTAAATTTTGTCAAATGATAGAA
AATGTAGAAGCTGGTCAGGACCCTCTGCTCAATATTCTTATTGAGGAAGAGGGCCCTGAGGAAACTGAGGAAACCCAAGATTCTGGT
ACTTTTTCTCAATAA

>T-4 protein (196-429, 2778-3080) (SEQ ID NO:18)
MDLVLNRKEREALCKLLEIAPNCYGNIPLMKAAFKRSCLKHHPDKGGNPVIMMELNTLWSKFQQNIHKLRSDFSMEDEANLRDSLDQ
NMEIRKRRILQSGTTLLLCLIWCLPDTTFKPCLQEEIKNWKQILQSEISYGKFCQMIENVEAGQDPLLNILEEEGPEETEETQDSG
TFSQ*

>T-5 (997-1665) similar to middle T pattern (SEQ ID NO:19)
ATGCATCCAGGGGAGCCCCCAGTGGAAGCTCACCACCCCACAGCCAGAGCTCTTCCTCTGGGTATGGGTCCTTCTCAGCGTCCCAGG
CTTCAGACTCCCAGTCCAGAGGACCCGATATACCTCCCGAACACCATGAGGAACCCACCTCATCCTCTGGATCCAGTAGCAGAGAGG
AGACCACCAATTCAGGAAGAGAATCCAGCACACCCAATGGAACCAGTGTACCTAGAAATTCTTCCAGAACGTATGGCACCTGGGAGG
ATCTCTTCTGCCATGAATCACTTTCCTCCCCTGAGCCTCCCTCGTCCTCTGAGGAGCCTGAGGAGCCCCCCTCCTCAAGAAGCTCGC
CCCGGCAGCCCCCGTGTTCCTCTGCCGAGGAGGCCTCGTCATCTCAGTTTACAGATTAGGAATACATATCCTCCTCCTTCACCACCC
CGAAGACCCCTCCTCCATTCTCAAGAAAGCGAAAATTTGGGGGGTCCCGAAGCTCTGCAAGCTCTGCTAGTTCAGCAAGTTTTACAA
GCACTCCACCAAAGCTAAAAAACAACAGAGAAACTCCTGTTCCTACTAATTTTCCTATTGATGTTTCTGATTATCTTAGCCATGCTG
TATATAGTAATAAAAACAGTAAGTTGTTTTGCCATTTATACTACTTCTGATAAAGCTATAG >T-5 protein(997-1665) similar to middle T pattern(SEQ ID NO:20)

MHPGEPPVEAHHPTARALPLGMGPSQRPRLQTPSPEDPIYLPNTMRNPPHPLDPVAERRPPIQEENPAHPMEPVYLEILPERMAPGR
ISSAMNHFPPLSLPRPLRSLRSPPPQEARPGSPRVPLPRRPRHLSLQIRNTYPPPSPPRRPLLHSQESENLGGPEALQALLVQQVLQ
ALHQSXKTTEKLLFLLIFLLMFLIILAMLYIVIKQ XVVLPFILLLIKL*

2. Small Cell Lung Cancer cell line sequences
(1). 15 preliminary reads from NCI-H69 cells >H69-PCR4-4F_052.ab1 (SEQ ID NO:21)
atTCagGaaGAGAATCCagcaCACCAAATGGAACCAGTGTACCTAGAAattCTTCcaGAACTGATGGCACCTGGGAGGATCTCTTCT
GCGATGAATCACTTTCCTCCCCTGAGCCTCCCTCGTCCTCTGAGGAGCCTGAGGAGCCCCCCTCCTCAAGAAGCTCGCCCCCGGCAGC
CCCCGTCTTCCTCTGCCGAGGAGGCCTCGTCATCTCAGTTTACAGATGAGGAATACAGATCCTCCTCCTTCACCACCCCGAAGACCC
CTCCTCCATTCTCAAGAAAGCGAAAATTTGGGGGGTCCCGAAGCTCTGCAAGCTCTGCTAGTTCAGCAAGTTTTACAAGCACTCCAC
CAAAGCCAAAAAAGAACAGAGAAACTCCTGTTCCTACTGATTTTCCTATTGATCTTTCTGATTATCTTAGCCATGCTGTATATAGTA
ATAAAACAGTAAGTTGTTTTGCcattt >H69-PCR4-4R_050.ab1 (SEQ ID NO:22)
ataatCagaAAGatCaATAGGAAAATCAGTAGGAACAGGAGTTTCTCTGTTCTTTTTTGGCTTTGGTGGAGTGCTTGTAAAACTTGC
TGAACTAGCAGAGCTTGCAGAGCTTCGGGACCCCCCAAATTTTCGCTTTCTTGAACTAGCAGAGCTTGCAGAGCTTCGGGACCCCCAA
GGAGGATCTGTATTCCTCATCTGTAAACTGAGATGACGAGGCCTCCTCGGCAGAGGAAGACGGGGGCTGCCGGGGCGAGCTTCTTGA
GGAGGGGGCTCCTCAGGCTCCTCAGAGGACGAGGGAGGCTCAGGGGAGGAAAGTGATTCATCGCAGAAGAGATCCTCCCAGGTGCC
ATCAGTTCTGGAAGAATTTCTAGGTACACTGGTTCCATTTGGTGTGCTGGATTCTCTTCCTGAATTGGTGGTCTCCTCTCTGCTACT
GGATCCAGAGGATGAGGTGGGTTCCT >H69-PCR4-2_M13R_061.ab1 (SEQ ID NO:23)
AAATGGCAAAACAACTTACTGTTTTATTACTATATACAGCATGGCTAAGATAATCAGAAAGATCAATAGGAAAATCAGTAGGAACAG
GAGTTTCTCTGTTCTTTTTTGGCTTTGGTGGAGTGCTTGTAAAACTTGCTGAACTAGCAGAGCTTGCAGAGCTTCGGGACCCCCCAA
ATTTTCGCTTTCTTGAGAATGGAGGAGGGGTCTTCGGGGTGGTGAAGGAGGAGGATCTGTATTCCTCATCTGTAAACTGAGATGACG
AGGCCTCCTCGGCAGAGGAAGACGGGGGCTGCCGGGGCGAGCTTCTTGAGGAGGGGGCTCCTCAGGCTCCTCAGAGGACGAGGGAG
GCTCAGGGGAGGAAAGTGATTCATCGCAGAAGAGATCCTCCCAGGTGCCATCAGTTCTGGAAGAATTTCTAGGTACACTGGTTCCAT
TTGGTGTGCTGGATTCTCTTCCTGAATTGGTGGTCTCCTCTCTGCTACTGGATCCAGAGGATGAGGTGGGTTCCT

FIGURE 23H

>H69-PCR4-1_M13R_063.ab1 (SEQ ID NO:24)
AATGGCAAAACAACTTACTGTTTTATTACTATATACAGCATGGCTAAGATAATCAGAAAGATCAATAGGAAAATCAGTAGGAACAGG
AGTTTCTCTGTTCTTTTTTGGCTTTGGTGGAGTGCTTGTAAAACTTGCTGAACTAGCAGAGCTTGCAGAGCTTCGGGACCCCCAAA
TTTTCGCTTTCTTGAGAATGGAGGAGGGGTCTTCGGGGTGGTGAAGGAGGAGGATCTGTATTCCTCATCTGTAAACTGAGATGACGA
GGCCTCCTCGGCAGAGGAAGACGGGGGCTGCCGGGGCGAGCTTCTTGAGGAGGGGGGCTCCTCAGGCTCCTCAGAGGACGAGGGAGG
CTCAGGGGAGGAAAGTGATTCATCGCAGAAGAGATCCTCCCAGGTGCCATCAGTTCTGGAAGAATTTCTAGGTACACTGGTTCCATT
TGGTGTGCTGGATTCTCTTCCTGAATTGGTGGTCTCCTCTCTGCTACTGGATCCAGAGGATGAGGTGGGTTCCT

>H69-PCR6-6R_077.ab1 (SEQ ID NO:25)
TaTaCTtAgGTaTATTCTCTGTTAATAATTGAATAATTTTCTGCACCTTcTTtTCAAACTCTTCAAATAAGCAGCAGTACCAGGCCA
CACCACCCATATAATACAGTAGATCTATTGTATCTAAATCTCTTAATCTCTCTAGGTGCTTCTTAAACTTCTTACATAGCATTTCTG
TCCTGGTCATTTCCAGCATCTCTAACCTCGTCTAGCTCATATTCACAAGCAAATTCAGCAACTAAAT
TCCAATTACAGCTGGCCTCT

>H69-PCR6-2_M13R_057.ab1 (SEQ ID NO:26)
GCAGCAAAGCTTGTTTTTCCACTGTTAATAGGCCCTTTAAACCAAATGTTTCTATACTTAGGTATATTCTCTGTTAATAATTGAATA
ATTTTCTGCAGCTTCTTTTCAAACTCTTCAAATAAGCAGCAGTACCAGGCCACACCACCCATATAATACAGTAGATCTATTGTATCT
AAATCTCTTAATCTCTCTAGGTGCTTCTTAAACTTCTTACATAGCATTTCTGTCCTGGTCATTTCCAGCATCTCTAACCTCGTCTAG
CTCATATTCACAAGCAAATTCAGCAACTAAATTCCAATTACAGCTGGCCTCT

>H69-PCR6-1_M13R_059.ab1 (SEQ ID NO:27)
CAGCAAAGCTTGTTTTTCCACTGTTAATAGGCCCTTTAAACCAAATGTTTCTATACTTAGGTATATTCTCTGTTAATAATTGAATAA
TTTTCTGCAGCTTCTTTTCAAACTCTTCAAATAAGCAGCAGTACCAGGCCACACCACCCATATAATACAGTAGATCTATTGTATCTA
AATCTCTTAATCTCTCTAGGTGCTTCTTAAACTTCTTACATAGCATTTCTGTCCTGGTCATTTCCAGCATCTCTAACCTCGTCTAGC
TCATATTCACAAGCAAATTCAGCAACTAAATTCCAATTACAGCTGGCCTCT

>H69-PCR9-9R_073.ab1 (SEQ ID NO:28)
tCTaaCTACTGTCCTTTTAGATGAGAATGGAGTGGGCCCTCTATGCAAAgGAgAcaGcCTATTTATTAGCTGTGCASACATAGTGGG
GTTTCTGTTTAAAACCAGTGGAAAAATGGCTCTTCATGGGTTGCCTAGATATTTTAATGTTACTTTGAGAAAAATATGGGTGAAAAA
CCCCTACCCAGTAGTTAATTTAATAAACTCACTCTTYAGCAACTTAATGCCAAAAGTGTCAGGCCAACCTATGGAAGGAAAAGATAA
TCAGGTAGAAGAGGTTAGAATATATGAGGGGTCAGAACAATTACCTGGTGATCCTGATATTGTCAGATTTTTAGATAAATTTGGGCA
GGAGAAAACTGTTTACCCAAAGCCCTCTGTTGCCCCAGCAGCAGTAACATTCCAAAGTAATCAGCAGGATAAGGGCAAGGCGCCACT
GAAAGGACCTCAAAAGGCCTC

>H69-PCR9-9F_075.ab1 (SEQ ID NO:29)
cTGCTGAtTACTTTGGaATGtTACTGCTGCTGGGGCAACAGAGGGCTTTGGGTAAACAGTTTTCTCCTGCCCAAATTTATCTAAAAA
TCTGACAATATCAGGATCACCAGGTAATTGTTCTGACCCCTCATATATTCTAACCTCTTCTACCTGATTATCTTTTCCTTCCATAGG
TTGGCCTGACACTTTTGGCATTAAGTTGCTRAAGAGTGAGTTTATTAAATTAACTACTGGGTAGGGGTTTTTCACCCATMTTTTTCT
CAAAGTAACATTAAAATATCTAGGCAACCCATGAAGAGCCATTTTTCCACTGGTTTTAAACAGAAACCCCACTATGTSTGCACAGCT
AATAAATAGGCCGTCTCCTTTGCATAGAGGGCCCACTCCATTCTCATCTAAAAGGACAGTAGTTAGAGTATTACTAAATTGAAGAAC
TGTAGGAGTCTGAGAGCCTGTCTGA

>H69-PCR9-1_M13R_055.ab1 (SEQ ID NO:30)
GAGGCCTTTTGAGGTCCTTTCAGTGGCGCCTTGCCCTTATCCTGCTGATTACTTTGGAATGTTACTGCTGCTGGGGCAACAGAGGGC
TTTGGGTAAACAGTTTTCTCCTGCCCAAATTTATCTAAAAATCTGACAATATCAGGATCACCAGGTAATTGTTCTGACCCCTCATAT
ATTCTAACCTCTTCTACCTGATTATCTTTTCCTTCCATAGGTTGGCCTGACACTTTTGGCATTAAGTTGCTGAAGAGTGAGTTTATT
AAATTAACTACTGGGTAGGGGTTTTTCACCCATCTTTTTCTCAAAGTAACATTAAAATATCTAGGCAACCCATGAAGAGCCATTTTT
CCACTGGTTTTAAACAGAAACCCCACTATGTCTGCACAGCTAATAAATAGGCCGTCTCCTTTGCATAGAGGGCCCACTCCATTCTCA
TCTAAAAGGACAGTAGTTAGAGTATTACTAAATTGAAGAACTGTAGGAGTCTGAGAGCCTGTCT

>H69-PCR9-2_M13R_053.ab1 (SEQ ID NO:31)
GACGCCTTTTGAGGTCCTTTCAGTGGCGCCTTGCCCTTATCCTGCTGATTACTTTGGAATGTTACTGCTGCTGGGGCAACAGAGGGC
TTTGGGTAAACAGTTTTCTCCTGCCCAAATTTATCTAAAAATCTGACAATATCAGGATTACCAGGTAATTGTTCTGACCCCTCATAT
ATTCTGACCTCTTCTACCTGATTATCTTTTCCTTCCATAGGTTGGCCTGACACTTTTGGCATTAAGTTGCTGAAGAGTGAGTTTATT
AAATTAACTACTGGGTAGGGGTTTTTCACCCATATTTTTCTCAAAGTAACATTAAAATATCTAGGCAACCCATGAAGAGCCATTTTT
CCACTGGTTTTAAACAGAAACCCCACTATGTGTGCACAGCTAATAAATAGGCCATCTCCTTTGCATAGAGGGCCCACTCCATTCTCA
TCTAAAAGGACAGTAGTTAGAGTATTACTAAATTGAAGAACTGTAGGAGTCTGAGAGCCTGTCT

FIGURE 23I

>H69-PCR10-10R_069.abl (SEQ ID NO:32)
gqGAgGcAATATCTGTTaaaaCAGAAGTAGTTGGAATAAGTTCTTTAATTAATGTTCATTATTGGGACATGAAAAGAGTTCATGATT
ATGGTGCTGGTATTCCTGTGTCAGGGGTAAATTACCATATGTTTGCCATTGGGGGAGAACCTCTGGATTTGCAAGGCCTAGTTTTAG
ATTACCAGACTSAgTATCCAAAAACTACAAATGGTGGGCCTATTACAATTGAAACTGTATTGGGAAGAAAAATGACACCTAAAAATC
AGGGCCTAGATCCACAAGCTAAAGCAAAATTAGATAAAGATGSAAATTATCCTATAGAAGTATGGTGTCCTGATCCTTCTAAAAATG
AAAACAGTAGATACTATGGGTCTATTCAGACAGGCTCTCAGACTCCTACAGTTCTTCAATTTAGTAATACTCTAACTACTGTCCTTT
TAGATGAGAATGGAGTGGGCCCTCTAT >H69-PCR10-10F_071.abl (SEQ ID NO:33)
AGTAtTACTAAATTGAAGAACTGTAGGAGTCTGAGAGCCTGTCTGAATAGACCCatagTATCTACTGTTTTCATTTTTAGAAGGATC
AGGACACCATACTTCTATAGGATAATTTSCATCTTTATCTAATTTTGCTTTAGCTTGTGGATCTAGGCCCTGATTTTTAGGTGTCAT
TTTTCTTCCCAATACAGTTTCAATTGTAATAGGCCCACCATTTGTAGTTTTTGGATACTSAgTCTGGTAATCTAAAACTAGGCCTTG
CAAATCCAGAGGTTCTCCCCCAATGGCAAACATATGGTAATTTACCCCTGACACAGGAATACCAGCACCATAATCATGAACTCTTTT
CATGTCCCAATAATGAACATTAATTAAAGAACTTATTCCAACTACTTCTGTTTTAACAGATATTGCCTCCCACATCTGCAATGTGTC
ACAGGTAATATCCTCATTTAGCATTGGCAGA >H69-PCR10-1_M13R_051.abl (SEQ ID NO:34)
ATAGAGGGCCCACTCCATTCTCATCTAAAAGGACAGTAGTTAGAGTATTACTAAATTGAAGAACTGTAGGAGTCTGAGAGCCTGTCT
GAATAGACCCATAGTATCTACTGTTTTCATTTTTAGAAGGATCAGGACACCATACTTCTATAGGATAATTTGCATCTTTATCTAATT
TTGCTTTAGCTTGTGGATCTAGGCCCTGATTTTTAGGTGTCATTTTTCTTCCCAATACAGTTTCAATTGTAATAGGCCCACCATTTG
TAGTTTTTGGATACTCAGTCTGGTAATCTAAAACTAGGCCTTGCAAATCCAGAGGTTCTCCCCCAATGGCAAACATATGGTAATTTA
CCCGTGACACAGGAATACCAGCACCATAATCATGAACTCTTTTCATGTCCCAATAATGAACATTAATTAAAGAACTTATTCCAACTA
CTTCTGTTTTAACAGATATTGCCTCCCACATCTGCAATGTGTCACAGGTAATATCCTCATTTAGCATTGGCAGA >H69-PCR10-2_M13R_049.abl (SEQ ID NO:35)
ATAGAGGGCCCACTCCATTCTCATCTAAAAGGACAGTAGTTAGAGTATTACTAAATTGAAGAACTGTAGGAGTCTGAGAGCCTGTCT
GAATAGACCCATAGTATCTACTGTTTTCATTTTTAGAAGGATCAGGACACCATACTTCTATAGGATAATTTCCATCTTTATCTAATT
TTGCTTTAGCTTGTGGATCTAGGCCCTGATTTTTAGGTGTCATTTTTCTTCCCAATACAGTTTCAATTGTAATAGGCCCACCATTTG
TAGTTTTTGGATACTGAGTCTGGTAATCTAAAACTAGGCCTTGCAAATCCAGAGGTTCTCCCCCAATGGCAAACATATGGTAATTTA
CCCCTGACACAGGAATACCAGCACCATAATCATGAACTCTTTTCATGTCCCAATAATGAACATTAATTAAAGAACTTATTCCAACTA
CTTCTGTTTTAACAGATATTGCCTCCCACATCTGCAATGTGTCACAGGTAATATCCTCATTTAGCATTGGCAGA (2). 10 preliminary reads from NCI-H146 cells >H146-PCR4-2_M13R_058.abl (SEQ ID NO:36)
AGGAACCCACCTCATCCTCTGGATCCAGTAGCAGAGAGGAGACCACCAATTCAGGAAGAGAATCCAGCACACCCAATGGAACCAGTG
TACCTAGAAATTCTTCCAGAACGTATGGCACCTGGGAGGATCTCTTCTGCGATGAATCACTTTCCTCCCCTGAGCCTCCCTCGTCCT
CTGAGGAGCCTGAGGAGCCCCCCTCCTCAAGAAGCTCGCCCCGGCAGCCCCCGTGTTCCTCTGCCGAGGAGGCCTCGTCATCTCAGT
TTACAGATTAGGAATACATATCCTCCTCCTTCACCACCCGAAGACCCCTCCTCCATTCTCAAGAAAGCGAAATTTGGGGGGTCCC
GAAGCTCTGCAAGCTCTGCTAGTTCAGCAAGTTTTACAAGCACTCCACCAAAGCCAAAAAACAACAGAGAAACTCCTGTTCCTACTA
ATTTTCCTGTTGATGTTTCTGATTATCTTAGCCATGCTGTATATAGTAATAAAACAGTAAGTTGTTTTGCCATTT >H146-PCR4-1_M13R_060.abl (SEQ ID NO:37)
AAATGGCaaaacaacTTACTGTTTTATTACTATATACAGCATGGCTAAGATAATCAGAAAGATCAATAGGAAAATCAGTAGGAACAG
GAGTTTCTCTGTTCTTTTTTGGCTTTGGTGGAGTGCTTGTAAAACTTGCTGAACTAGCAGAGCTTGCAGAGCTTCGGGACCCCCCAA
ATTTTCGCTTTCTTGAGAATGGAGGAGGGGTCTTCGGGGTGGTGAAGGAGGAGGATCTGTATTCCTCATCTGTAAACTGAGATGACA
AGGCCTCCTCGGCAGAGGAAGACGGGGGCTGCCGGGGCGAGCTTCTTGAGGAGGGGGGCTCCTCAGGCTCCTCAGAGGACGAGGGAG
GCTCAGGGGAGGAAAGTGATTCATCGCAGAAGAGATCCTCCCAGGTGCCATCAGTTCTGGAAGAATTTCTAGGTACACTGGTTCCAT
TTGGTGTGCTGGATTCTCTTCCTGAATTGGTGGTCTCCTCTCTGCTACTGGATCCAGAGGATGAGGTGGGTTCCT >H146-PCR6-2_M13R_054.abl (SEQ ID NO:38)
GCAGCAaAGCTTGTTTTTCCACTGTTAATAGGCCCTTTAAACCAAATGTTTCTATACTTAGGTATATTCTCTGTTAATAATTGAATA
ATTTTCTGCAGCTTCTTTTCAAACTCTTCAAATAAGCAGCAGTACCAGGCCACACCACCCATATAATACAGTAGATCTATTGTATCT
AAATCTCTTAATCTCTCTAGGTGCTTCTTAAACTTCTTACATAGCATTTCTGTCCTGGTCATTTCCAGCATCTCTAACCTCGTCTAG
CTCATATTCACAAGCAAATTCAGCAACTAAATTCCAATTACAGCTGGCCTCT >H146-PCR6-1_M13R_056.abl (SEQ ID NO:39)
GCAGCAaAGCTTGTTTTTCCACTGTTAATAGGCCCTTTAAACCAAATGTTTCTATACTTAGGTATATTCTCTGTTAATAATTGAATA
ATTTTCTGCAGCTTCTTTTCAAACTCTTCAAATAAGCAGCAGTACCAGGCCACACCACCCATATAATACAGTAGATCTATTGTATCT
AAATCTCTTAATCTCTCTAGGTGCTTCTTAAACTTCTTACATAGCATTTCTGTCCTGGTCATTTCCAGCATCTCTAACCTCGTCTAG
CTCATATTCACAAGCAAATTCAGCAACTAAATTCCAATTACAGCTGGCCTCT

FIGURE 23J

>H146-PCR9-9F_060.ab1 (SEQ ID NO:40)
TGGATGtTACTGCTGCTGGGGCAACAGAGGGCTTTGGgTAaacagttttTCTCCTGCCCAAATTTATCTAAAAATCTGACAATATCag
GATTACCAGGTAATTGTTCTGACCCCTCATATATTCTGACCTCTTCTACCTGATTATCTTTTCCTTCCATAGGTTGGCCTGACACCT
TTGGCATTAAGTTGCTGAAGAGTGAGTTTATTAAATTAACTACTGGGTAGGGGTTTTTCACCCATATTTTTCTCAAAGTAACATTAA
AATATCTAGGCAACCCATGAAGAGCCATTTTTCCACTGGTTTTAAACAGAAACCCCACTATGTGTGCACAGCTAATAAATAGGCCAT
CTCCTTTGCATAGAGGGCCCACTCCATTCTCATCTAAAAGGACAGTAGTTAGAGTATTACTAAATTGAAGAACTGTAGGAGTCTCAG
AGCCTGTCTG >H146-PCR9-9R_058.ab1 (SEQ ID NO:41)
actctaaCTACTGTCCTTTTAGATGAGAATGGAGTGGGCCCTCTATGCAAAggagatggcctATTTATTTAGCTGTGCACACATAGTG
GGGTTTCTGTTTAAAACCAGTGGAAAAATGGCTCTTCATGGGTTGCCTAGATATTTTAATGTTACTTTGAGAAAAATATGGGTGAAA
AACCCCTACCCAGTAGTTAATTTAATAAACTCACTCTTCAGCAACTTAATGCCAAAGGTGTCAGGCCAACCTATGGAAGGAAAGAT
AATCAGGTAGAAGAGGTCAGAATATATGAGGGGTCAGAACAATTACCTGGtAATCCTGATATTGTCAGATTTTTAGATAAATTTGGG
CAGGAGAAAACTGTTTACCCAAAGCCCTCTGTTGCCCCAGCAGCAgtAACaTTCCAAAGtAATCAGCAGGATAAGGGCAAGGCGCCA
CTGAAAGGACCCTCaAAAGGCCTC >H146-PCR9-2_M13R_050.ab1 (SEQ ID NO:42)
TCAGACAGGCTCTCAGACTCCTACAGTTCTTCAATTTAGTAATACTCTAACTACTGTCCTTTTAGATGAGAATGGAGTGGGCCCTCT
ATGCAAAGGAGATGGCCTATTTATTAGCTGTGCACACATAGTGGGGTTTCTGTTTAAAACCAGTGGAAAAATGGCTCTTCATGGGTT
GCCTAGATATTTTAATGTTACTTTGAGAAAAATATGGGTGAAAAACCCCTACCCAGTAGTTAATTTAATAAACTCACTCTTCAGCAA
CTTAATGCCAAAGGTGTCAGGCCAACCTATGGAAGGAAAAGATAATCAGGTAGAAGAGGTCAGAATATATGAGGGTCAGAACAATT
ACCTGGTAATCCTGATATTGTCAGATTTTTAGATAAATTTGGGCAGGAGAAAACTGTTTACCCAAAGCCCTCTGTTGCCCCAGCAGC
AGTAACATTCCAAAGTAATCAGCAGGATAAGGGCAAGGCGCCACTGAAAGGACCCTCAAAAGGCCTC >H146-PCR9-1_M13R_052.ab1 (SEQ ID NO:43)
CAGACAGGCTCTCAGACTCCTACAGTTCTTCAATTTAGTAATACTCTAACTACTGTCCTTTTAGATGAGAATGGAGTGGGCCCTCTA
TGCAAAGGAGATGGCCTATTTATTAGCTGTGCACACATAGTGGGGTTTCTGTTTAAAACCAGTGGAAAAATGGCTCTTCATGGGTTG
CCTAGATATTTTAATGTTACTTTGAGAAAAATATGGGTGAAAAACCCCTACCCAGTAGTTAATTTAATAAACTCACTCTTCAGCAAC
TTAATGCCAAAGGTGTCAGGCCAACCTATGGAAGGAAAAGATAATCAGGTAGAAGAGGTCAGAATATATGAGGGGTCAGAACAATTA
CCTGGTAATCCTGATATTGTCAGATTTTTAGATAAATTTGGGCAGGAGAAAACTGTTTACCCAAAGCCCTCTGTTGCCCCAGCAGCA
GTAACATTCCAAAGTAATCAGCAGGATAAGGGCAAGGCGCCACTGAAAGGACCCTCAAAAGGCCT >H146-PCR10-10R_054.ab1 (SEQ ID NO:44)
ggAGGcAaTAtCTGTTaaaacaGAAgTAGTTGGAATAAGTTCTTTAAttaatgttcattaTTGGGACATGAAAAGAGTTCATGATTA
tggtgctgGTATTCCTGTGTCAGGGGTAAATTACCATATGTTTGCCATTGGGGGAGAACCTCtGGAtttGcaAGCCCTAGTTTTAGA
TTACCAGACTGAATATCCAAAAACTACAAATGGTGGGCCTATTACAATTGAAACAGTATTGGGAAGAAAAATGACACCTAAAAATCA
GGGCCTAGATCCACAAGCTAAAGCAAAATTAGATAAAGATGGAAATTATCCTATAgAAGTATGGTGTCCTGATCCTTCTAAAAATGA
AAACAGTAgATACTATGGGTCTATTCAGACAGGTTCTCagACTCCTACAGTTCTtCAaTTCAgtAATACTTtAACTACTGTCCTTTT
agAtKAgAATGGAGTGGGCCCTCtat >H146-PCR10-10F_056.ab1 (SEQ ID NO:45)
gAATTgaagAACTGTagGAGTCTGAGAACCTGTCTGAATAGACCcatagtatctacTGTTTTCATTTTTAGAAGGATCAGGACACCa
TacttcTATAGGATAATTTCCATCTTTATCTAATTTTGCTTTAGCTTGTGGATCTAGGCCCTGATTTTTAgGTGTCATTTTTCTTCC
CAATACTGTTTCAATTGGCCCACCATTTGTAGTTTTTGGATATTCAGTCTGGTAATCTAAAACTAGGCCTTGCAAATCCAG
AGGTTCTCCCCCAATGGCAAACATATGGTAATTTACCCCTGACACAGGAATACCAGCACCATAATCATGAACTCTTTTCATGTCCCA
ATAATGAACATTAATTAAAGAACTTATTCCAACTACTTCTGTTTTAACAGATATTGCCTCCCACATCTGCAATGTGTCACAGGTAAT
ATCCTCATTTAgCATTGGCAGa

FIGURE 23K

SEQUENCE LISTING

```
<160> NUMBER OF SEQ ID NOS: 134

<210> SEQ ID NO 1
<211> LENGTH: 5387
<212> TYPE: DNA
<213> ORGANISM: Merkel Cell Carcinoma Virus
<220> FEATURE:
<221> NAME/KEY: misc_feature
<222> LOCATION: (1)..(5387)
<223> OTHER INFORMATION: MCV_350 Genome

<400> SEQUENCE: 1
ggggctccta gcctccgagg cctctggaaa aaaaagagag aggactctga ggcttaagag        60
gcttaattag caaaaaaggc agtatctaag ggcagatccc aagggcggga aactgcagta       120
taaaaaccac tccttagtga ggtagctcat ttgctcctct gctgtttctg caaactcctt       180
ctgcatatag acaagatgga tttagtccta aataggaaag aaagagaggc tctgtgcaag       240
cttttggaga ttgctcctaa ttgttatggc aacatccctc tgatgaaagc tgctttcaaa       300
agaagctgct taaagcatca ccctgataaa gggggaaatc ctgttataat gatggaattg       360
aacacccttt ggagcaaatt ccagcaaaat atccacaagc tcagaagtga cttctctatg       420
tttgatgagg ttagtacaaa atttccttgg gaagaatatg gaacttttaaa ggattatatg       480 caaagtggat ataatgctag attttgcaga ggtcctgggt gcatgcttaa gcaacttaga       540
gattctaagt gcgcttgtat tagctgtaag ttgtctcgcc agcattgtag tctaaaaact       600
ttaaagcaaa aaaactgtct gacgtgggga gagtgttttt gctatcagtg ctttattctt       660
```

```
tggtttggat ttcctcctac ttgggaaagt tttgactggt ggcaaaaaac tttagaagaa      720
actgactact gcttactgca tctgcacctt ttctagactc ctacttcctt cctctgtaag      780
tattagatat ggaaaagtct ataaggcaaa atatcaaaga aaggttattt atgacagatt      840
ttgtgtactt tcccatctag gttgacgagg cccctatata tgggaccact aaattcaaag      900
aatggtggag atcaggagga ttcagcttcg ggaaggcata cgaatatggg cccaatccac      960
acggggccaa ctcaagatcc agaaagcctt cctccaatgc atccagggga gccccagtg     1020 gaagctcacc accccacagc cagagctctt cctctgggta tgggtccttc tcagcgtccc     1080
aggcttcaga ctcccagtcc agaggacccg atataccctcc cgaacaccat gaggaaccca     1140
cctcatcctc tggatccagt agcagagagg agaccaccaa ttcaggaaga gaatccagca     1200
cacccaatgg aaccagtgta cctagaaatt cttccagaac gtatggcacc tgggaggatc     1260
tcttctgcga tgaatcactt tcctcccctg agcctccctc gtcctctgag gagcctgagg     1320
agcccccctc ctcaagaagc tcgccccggc agccccgtg ttcctctgcc gagaggcct      1380 cgtcatctca gtttacagat taggaataca tatcctcctc cttcaccacc ccgaagaccc     1440
ctcctccatt ctcaagaaag cgaaaatttg ggggtcccg aagctctgca agctctgcta     1500
gttcagcaag ttttacaagc actccaccaa agctaaaaaa caacagagaa actcctgttc     1560
ctactaattt tcctattgat gtttctgatt atcttagcca tgctgtatat agtaataaaa     1620
cagtaagttg ttttgccatt tatactactt ctgataaagc tatagagtta tatgataaga     1680
ttgagaaatt taaagttgat tttaaaagca ggcatgcctg tgaattagga tgtattttat     1740
tgtttataac tttatcaaag catagagtat ttgctattaa gaattttgc tctaccttct     1800 gcactataag cttttaatt tgtaaaggag tgaataagat gcctgaaatg tataataatt     1860
tatgcaagcc cccttacaaa ttactgcaag agaataagcc actgctcaat tatgaatttc     1920
aagaaaaaga aaagaggcc agctgtaatt ggaattagt tgctgaattt gcttgtgaat     1980
atgagctaga cgaccacttt attatcttag cccattatct agactttgca aaaccattc     2040 cttgccaaaa gtgtgaaaac agatctcgcc tcaaacctca caaggctcat gaggctcatc     2100
attctaatgc taagctattt tatgaatcta aatctcagaa aaccatttgc caacaagccg     2160
cagacactgt tctagccaaa aggaggttag agatgctgga aatgaccagg acagaaatgc     2220
tatgtaagaa gtttaagaag cacctagaga gattaagaga tttagataca atagatctac     2280
tgtattatat gggtggtgtg gcctggtact gctgcttatt tgaagagttt gaaaagaagc     2340
tgcagaaaat tattcaatta ttaacagaga atatacctaa gtatagaaac atttggttta     2400
aagggcctat taacagtgga aaaacaagct ttgctgcagc cttaatagat ttgctagaag     2460
ggaaggcctt gaatataaac tgtccatctg ataaactgcc ttttgaacta ggatgtgctt     2520
tggataaatt tatggttgtt tttgaggatg tgaaagggca aaatagccta aataaagatc     2580
tgcaaccagg gcaaggaata ataaaccttg ataacttaag agatcatcta gatggtgctg     2640
tagctgtgag cttagagaag aagcatgtga ataaaaagca tcagattttt cctccttgta     2700
ttgttactgc taatgattat tttattccca aacattaat agcaagattt agttatactt     2760 tacactttt cccaaaggca aatctaagag attccctgga tcagaacatg gaaataagaa     2820
aaagaagaat tcttcaaagt ggaaccactt tattgctttg tcttatttgg tgcttgcctg     2880
atacaacctt taagccttgc ttacaagaag aaattaaaaa ctggaagcaa attttacaga     2940
gtgaaatatc atatggtaaa ttttgtcaaa tgatagaaaa tgtagaagct ggtcaggacc     3000
ctctgctcaa tattcttatt gaggaagagg gccctgagga aactgaggaa acccaagatt     3060
```

```
ctggtacttt ttctcaataa aggcatctgc ttcatatttc ctgtgtttgt ttttctgggg   3120
cctacttaac tgaataggaa tgcatgaaat aattctcata attgttgtgt ttggctttct   3180
ttttgagagg cctttgagg tcctttcagt ggcgccttgc ccttatcctg ctgattactt    3240
tggaatgtta ctgctgctgg ggcaacagag ggctttgggt aaacagtttt ctcctgccca   3300
aatttatcta aaaatctgac aatatcagga ttaccaggta attgttctga cccctcatat   3360
attctgacct cttctacctg attatctttt ccttccatag gttggcctga cacttttggc   3420
attaagttgc tgaagagtga gtttattaaa ttaactactg ggtaggggtt tttcacccat   3480
attttctca aagtaacatt aaaatatcta ggcaacccat gaagagccat ttttccactg    3540
gttttaaaca gaaaccccac tatgtgtgca cagctaataa ataggccatc tcctttgcat   3600
agagggccca ctccattctc atctaaaagg acagtagtta gagtattact aaattgaaga   3660
actgtaggag tctgagagcc tgtctgaata gacccatagt atctactgtt ttcattttta   3720
gaaggatcag gacaccatac ttctatagga taatttccat ctttatctaa ttttgcttta   3780
gcttgtggat ctaggccctg attttaggt gtcatttttc ttcctaatac agtttcaatt    3840
gtaataggcc caccatttgt agttttggga tactcagtct ggtaatctaa aactaggcct   3900
tgcaaatcca gaggttctcc cccaatggca acatatggt aatttacccc tgacacagga    3960
ataccagcac cataatcatg aactcttttc atgtcccaat aatgaacatt aattaaagaa   4020
cttattccaa ctacttctgt tttaacagat attgcctccc acatctgcaa tgtgtcacag   4080
gtaatatcct catttagcat tggcagagac actcttgcca cactgtaagc tggcaaattt   4140
tccttgatgg gctgatctgg agatgatccc tttggctgca ggtcataagt ataagtatac   4200
cagtttgaag tagtaggaag atcaggggaa ttaactccca ttcttggatt caaatacaac   4260
tcaatttggg taatgctatc ttctccagta accacagata atacttccac tcctcccttta  4320
acaagcagtt ttggaactga ggcaacatta gggcagcatc ccggcttagg tatacattgc   4380
cttttgggtg ttttacaggt ggatgatgct tttcttttg gtgccatctt caattacttg    4440
taattcagga gaaatatatc cactaaggcc tagtaccaga ggaagaagcc aatctggagt   4500
tgctgctgc agagttcctc ctatatgttc aggaattaat atagcctctc ctgataaaag    4560
gccctgattc tgagaagcag ttgtctgaaa gacccaccgg ctatttagta tcagattcac   4620
taggtttgat tgtatctgca gcctagaggt aggagataaa gaattaaaaa tattttgccc   4680
cacagaatgc agcaagctat tttcccactg cagaggatct aggctaaagg ccataagtgc   4740
atgcctcaaa acctcattac tacctaccca cgaaacatcc ctgttacaa gtgacacttg    4800
ctcgcgtgac aacctcaccc ccacagttat tagagagcct ataccactaa cagtttggag   4860
aatgaagcca taagttaaac cttggttaac caaagaagcc actaatgaga aatttgaaaa   4920
ctgttcagct gtgaacccaa gttgagctaa agcctcaatg ccagaaatac cctcaattgt   4980
cattaaactg gagatgtctg cttccaaagc tgctaaagct tctcctgtaa gaatagcttc   5040
caaagttact cctgtggtgg cacttagttc agtagcaatt tcaccaatat tggccagcag   5100
tgtgatgatg cccccatcc tgaaaaataa ataaggatac ttactctttt aatgtcctcc    5160
tcccttgta agagaaaaaa aagcctccgg gcctcccttg ttgaaaaaaa gttaagagtt    5220
ttccgtctcc ctcccaaaca gaaagaaaaa aagttttgtt tatcagtcaa actccgcctc   5280
tccaggaaat gagtcaatgc cagaaaccct gcagcaataa aagttcaatc atgtaaccac   5340
aacttggctg cctaggtgac ttttttttttt caagttggca gaggctt                5387
```

<210> SEQ ID NO 2

<211> LENGTH: 5201
<212> TYPE: DNA
<213> ORGANISM: Merkel Cell Carcinoma Virus
<220> FEATURE:
<221> NAME/KEY: misc_feature
<222> LOCATION: (1)..(5201)
<223> OTHER INFORMATION: MCV_339 Genome

<400> SEQUENCE: 2

| | | | | | |
|---|---|---|---|---|---|
| ggggctccta | gcctccgagg | cctctggaaa | aaaaagagag | aggcctctga | ggcttaagag | 60 |
| gcttaattag | caaaaaaggc | agtatctaag | ggcagatccc | aagggcggga | aactgcagta | 120 |
| taaaaaccac | tccttagtga | ggtagctcat | ttgctcctct | gctctttctg | caaactcctt | 180 |
| ctgcatatag | acaagatgga | tttagtccta | aacaggaaag | aaagagaggc | tctctgcaag | 240 |
| cttttagaga | ttgctcctaa | ttgttatggc | aacatccctc | tgatgaaagc | tgctttcaaa | 300 |
| agaagctgct | aaagcatca | ccctgataaa | ggggaaatc | ctgttataat | gatggaattg | 360 |
| aacacccttt | ggagcaaatt | ccagcaaaat | atccacaagc | tcagaagtga | cttctctatg | 420 |
| tttgatgagg | tcagtacaaa | atttccttgg | gaagaatatg | gaactttaaa | ggattatatg | 480 |
| caaagtggat | ataatgctag | attttgcaga | ggtcctgggt | gcatgcttaa | gcaacttaga | 540 |
| gattctaagt | gcgcttgtat | tagctgtaag | ttgtctcgcc | agcattgtag | tctaaaaact | 600 |
| ttaaagcaaa | aaaactgtct | gacgtgggga | gagtgttttt | gctatcagtg | ctttattctt | 660 |
| tggtttggat | ttcctcctac | ttgggaaagt | tttgactggt | ggcaaaaaac | tttagaagaa | 720 |
| actgactact | gcttactgca | tctgcacctt | ttctagactc | ctacttcctt | cctctgtaag | 780 |
| tattagatat | ggaaaagtct | ataaggcaaa | atatcaaaga | aaggttattt | atgacagatt | 840 |
| ttctgtactt | tcccatctag | gttgacgagg | cccctatata | tgggaccact | aaattcaaag | 900 |
| aatggtggag | atcaggagga | ttcagcttcg | ggaaggcata | cgaatatggg | cccaatccac | 960 |
| acgggaccaa | ctcaagatcc | agaaagcctt | cctccaatgc | atccagggga | gcccccagtg | 1020 |
| gaagctcacc | accccacagc | cagagctctt | cctctgggta | tgggtccttc | tcagcgtccc | 1080 |
| aggcttcaga | ctcccagtcc | agaggacccg | atatacctcc | cgaacaccat | gaggaaccca | 1140 |
| cctcatcctc | tggatccagt | agcagagagg | agaccaccaa | ttcaggaaga | gaatccagca | 1200 |
| caccaaatgg | aaccagtgta | cctagaaatt | cttccagaac | tgatggcacc | tgggaggatc | 1260 |
| tcttctgcga | tgaatcactt | tcctcccctg | agcctccctc | gtcctctgag | gagcctgagg | 1320 |
| agccccctc | ctcaagaagc | tcgccccggc | agccccgtc | ttcctctgcc | gaggaggcct | 1380 |
| cgtcatctca | gtttacagat | gaggaataca | gatcctcctc | cttcaccacc | ccgaagaccc | 1440 |
| ctcctccatt | ctcaagaaag | cgaaaatttg | ggggtcccg | aagctctgca | agctctgcta | 1500 |
| gttcagcaag | ttttacaagc | actccaccaa | agccaaaaaa | gaacagagaa | actcctgttc | 1560 |
| ctactgattt | tcctattgat | ctttctgatt | atcttagcca | tgctgtatat | agtaataaaa | 1620 |
| cagtaagttg | ttttgccatt | tatactactt | ctgataaagc | tatagagtta | tatgataaga | 1680 |
| ttgagaaatt | taaagttgat | tttaaaagca | ggcatgcctg | tgaattagga | tgtatttat | 1740 |
| tgtttataac | tttatcaaag | catagagtat | ctgctattaa | gaatttctgc | tctaccttct | 1800 |
| gcactataag | cttttaatt | tgtaaaggag | tgaataagat | gcctgaaatg | tataataatt | 1860 |
| tatgcaagcc | cccttacaaa | ttactgcaag | agaataagcc | actgtcaat | tatgaatttc | 1920 |
| aagaaaaaga | aaaagaggcc | agctgcaatt | ggaatttagt | tgctgaattt | gcttgtgaat | 1980 |
| atgagctaga | cgaggttaga | gatgctggaa | atgaccagga | cagaaatgct | atgtaagaag | 2040 |
| tttaagaagc | acctagagag | attaagagat | ttagatacaa | tagatctact | gtattatatg | 2100 |

```
ggtggtgtgg cctggtactg ctgcttattt gaagagtttg aaaagaagct gcagaaaatt    2160
attcaattat taacagagaa tatacctaag tatagaaaca tttggtttaa agggcctatt    2220
aacagtggaa aaacaagctt tgctgcagcc ttaatagatt tgctggaagg gaaggccttg    2280
aatataaact gtccatctga taaactacct tttgaactag gatgtgcttt ggataaattt    2340
atggttgttt ttgaggatgt gaaagggcaa aatagcctaa ataaagatct gcaaccaggg    2400
caaggaataa ataaccttga taacttaaga gatcatctag atggtgctgt agctgtaagc    2460
ttagagaaga agcatgtgaa taaaaagcat cagatttttc ctccttgtat tgttactgct    2520
aatgattatt ttattcccaa aacattaata gcaagattta gttatacttt acactttcc    2580 ccaaaggcaa atctaagaga ttccctggat cagaacatgg aaataagaaa agaagaatt    2640 cttcaaagtg gaaccacttt attgctttgt cttatttggt gcttgcctga tacaaccttt    2700
aagccttgct tacaagaaga aattaaaaac tggaagcaaa ttttacagag tgaaatatca    2760
tatggtaaat tttgtcaaat gatagaaaat gtagaagctg tcaggaccc tctgctcaat    2820 attcttattg aggaagaggg ccctgaggaa actgaagaaa cccaagattc tggtactttt    2880
tctcaataaa gacatctgct tcatatttcc tgtgtttgtt tttctgggc ctacttaact    2940 gaataggaat gcatgaaata attctcataa ttcttgtgtt tggctttctt tttgagaggc    3000
cttttgaggt cctttcagtg gcgccttgcc cttatcctgc tgattacttt ggaatgttac    3060
tgctgctggg gcaacagagg gctttgggta acagttttc tcctgcccaa atttatctaa    3120
aaatctgaca atatcaggat caccaggtaa ttgttctgac ccctcatata ttctaacctc    3180
ttctacctga ttatcttttc cttccatagg ttggcctgac acttttggca ttaagttgct    3240
aaagagtgag tttattaaat taactactgg gtaggggttt tcacccatc tttttctcaa    3300 agtaacatta aaatatctag gcaacccatg aagagccatt tttccactgg ttttaaacag    3360
aaaccccact atgtctgcac agctaataaa taggccgtct cctttgcata gagggcccac    3420
tccattctca tctaaaagga cagtagttag agtattacta aattgaagaa ctgtaggagt    3480
ctgagagcct gtctgaatag acccatagta tctactgttt tcatttttag aaggatcagg    3540
acaccatact tctataggat aatttccatc tttatctaat tttgctttag cttgtggatc    3600
taggccctga ttttaggtg tcatttttct tcccaataca gtttcaattg taataggccc    3660
accatttgta gttttggat actgagtctg gtaatctaaa actaggcctt gcaaatctag    3720
aggttctccc ccaatggcaa acatatggta atttacccct gacacaggaa taccagcacc    3780
ataatcatga actctttca tgtcccaata atgaacatta ttaaagaac taattccaac    3840 tacttctgtt ttaacagata ttgcctccca catctgcaat gtgtcacagg taatatcctc    3900
atttagcatt ggcagagaca ctcttgccac actgtaagct ggcaaatttt ccttgatggg    3960
ctgatctgga gatgatccct ttggctgcag gtcataagta taagtatacc agtttgaagt    4020
agtaggaaga tcagggaat taactcccat tcttggattc aaatacaact caatttgggt    4080
aatgctatct tctccagtaa ccacagataa tacttccact cctcctttaa caagcagttt    4140
tggaactgag gcaacattag ggcagcatcc cggcttaggt atacattgcc ttttgggtgt    4200
tttacaggtg gatgatgctt ttcttttttgg tgccatcttc aattacttgt aattcaggag    4260
aaatatatcc actaaggcct agtaccgaag gaagaagcca atctggagtt tgctgctgca    4320
gagttcctcc tatatgttca ggaattaata tagcctctcc tgataaaagg ccctgattct    4380
gagaagcagt tgtctgaaag acccaccggc tatttagtat cagattcact aggttttgatt    4440 gtatctgcag cctagaggta ggagataaag aattaaaaat atcttgcccc acagaatgca    4500
```

```
gcaagctatt ttcccactgc agaggatcta ggctaaaggc cataagtgca tgcctcaaaa    4560
cctcattact acctacccac gaaacatccc tctttacaag tgacacttgc tcgcgtgaca    4620
acctcacccc cacagttatt agagagccta taccactaac agtttggaga atgaagccat    4680
aagttaaacc ttggttaacc aaagaagcca ctaatgagaa atttgaaaac tgttcagctg    4740
tgaacccaag ttgagctaaa gcctcaatgc cagaaatacc ctcaattgtc attaaactgg    4800
agatctctgc ttccaaagct gctaaagctt ctcctgtaag tatagcttcc aaagttactc    4860
ctgtggtggc acttagttca gtagcaattt caccaatatt ggccagcagt gtgatgatgc    4920
cccccatcct gaaaaataaa taaggatact tactctttta atgtcctcct cccttttgtaa   4980 gagaaaaaaa agcctccggg cctcccttgt tgaaaaaaag ttgagttaag agtcttccgt    5040
ctccctccca aacagaaaga aaaaagtttt tgtttatcag tcaaactccg cctctccagg    5100
aaatgagtca atgccagaaa ccctgcagca ataaaagttc aatcatgtaa ccacaacttg    5160
gctgcctagg tgactttttt ttttcaagtt ggcagaggct t                       5201

<210> SEQ ID NO 3
<211> LENGTH: 5185
<212> TYPE: DNA
<213> ORGANISM: Merkel Cell Carcinoma Virus
<220> FEATURE:
<221> NAME/KEY: misc_feature
<222> LOCATION: (1)..(5185)
<223> OTHER INFORMATION: MCV_352 Genome

<400> SEQUENCE: 3
ggggctccta gcctccgagg cctctggaaa aaaagagag aggcctctga ggcttaagag       60
gcttaattag caaaaaaggc agtatctaag ggcagatccc aagggcggga aactgcagta    120
taaaaaccac tccttagtga ggtagctcat ttgctcctct gctctttctg caaactcctt    180
ctgcatatag acaagatgga tttagtccta aataggaaag aaagagaggc tctctgcaag    240
cttttagaga ttgctcctaa ttgttatggc aacatccctc tgatgaaagc tgcttttcaaa   300 agaagctgct taaagcatca ccctgataaa gggggaaatc ctgttataat gatggaattg    360
aacacccttt ggagcaaatt ccagcaaaat atccacaagc tcagaagtga cttctctatg    420
tttgatgagg tcagtacaaa atttccttgg gaagaatatg gaactttaaa ggattatatg    480
caaagtggat ataatgctag attttgcaga ggtcctgggt gcatgcttaa gcaacttaga    540
gattctaagt gcgcttgtat tagctgtaag ttgtctcgcc agcattgtag tctaaaaact    600
ttaaagcaaa aaaactgtct gacgtgggga gagtgttttt gctatcagtg ctttattctt    660
tggtttggat ttcctcctac ttgggaaagt tttgactggt ggcaaaaaac tttagaagaa    720
actgactact gcttactgca tctgcacctt ttctagactc ctacttcctt cctctgtaag    780
tattagatat ggaaaagtct ataaggcaaa atatcaaaga aaggttattt atgacagatt    840
ttctgtactt tccatctag gttgacgagg cccctatata tgggaccact aaattcaaag     900
aatggtggag atcaggagga ttcagcttcg ggaaggcata cgaatatggg cccaatccac     960
acgggaccaa ctcaagatcc agaaagcctt cctccaatgc atccagggga gcccccagtg   1020
gaagctcacc accccacagc cagagctctt cctctgggta tgggtccttc tcagcgtccc   1080
aggcttcaga ctcccagtcc agaggacccg atatacctcc cgaacaccat gaggaaccca   1140
cctcatcctc tggatccagt agcagagagg agaccaccaa ttcaggaaga gaatccagca   1200
cacccaatgg aaccagtgta cctagaaatt cttccagaac ggatggcacc tgggaggatc   1260
tcttctgcga tgaatcactt tcctcccctg agcctccctc gtcctctgag gagcctgagg   1320
```

```
agcccccctc ctcaagaagc tcgccccggc agccccgtc ttcctctgcc gaggaggcct    1380
cgtcatctca gtttacagat gaggaataca gatcctcctc cttcaccacc ccgaagaccc    1440
ctcctccatt ctcaagaaag cgaaaatttg gggggtgccg aagctctgca agctctgcta    1500
gttgagcaag ttttacaagc actccaccaa agccaaaaaa gaacagagaa actcctgttc    1560
ctactgattt tcctattgat ctttctgatt atcttagcca tgctgtatat agtaataaaa    1620
cagtaagttg ttttgccatt tatactactt ctgataaagc tatagagtta tatgataaga    1680
ttgagaaatt taaagttgat tttaaaagca ggcatgcctg tgaattagga tgtattttat    1740
tgtttataac tttatgaaag catagagtat ctgctattaa gaattttgc tctaccttct     1800 gcactataag cttttaatt tgtaaaggag tgaataagat gcctgaaatg tataataatt     1860
tatgcaagcc cccttacaaa ttactgcaag agaataagcc actgctcaat tatgaatttc    1920 aagaaaaga aaagaggcc agctgtaatt ggaatttagt tgctgaattt gcttgtgaat      1980
atgagctaga cgaccacttt attatcttag cccattatct agactttgca aaaccatttc    2040
cttgccaaaa gtgtgaaaac agatctcgcc tcaaacctca caaggctcat gaggctcatc    2100
attctaatgc taagctattt tatgaatcta aatctcagaa aaccatttgc caacaagccg    2160
cagacactgt tctagccaaa aggaggttag agatgctgga aatgaccagg acagaaatgc    2220
tatgtaagaa gtttaagaag cacctagaga gattaagaga tttagataca atagatctac    2280
tgtattatat gggtggtgtg gcctggtact gctgcttatt tgaagagttt gaaagaagc     2340 tgcagaaaat tattcaatta ttaacagaga atatacctaa gtatagaaac atctggttta    2400
aagggcctat taacagtgga aaaacaagct ttgctgcagc cttaatagat ttgctagaag    2460
ggaaggcctt gaatataaac tgtccatctg ataaactgcc ttttgaagta ggatgtgctt    2520
tggataaatt tatggttgtt tttgaggatg tgaaagggca aaatagccta aataaagatc    2580
tgcaaccagg gcaaggaata aataaccttg ataacttaag agatcatcta gatggtgctg    2640
tagctgtaag cttagagaag aagcatgtga ataaaaagca ttagatttt cctccttgta     2700 ttgttactgc taatgattat tttattccca aaacattaat agcaagattt agttatactt    2760 tacactttc cccaaaggca aatctaagag attccctgga tcagaacatg gaaataagaa     2820
aaagaagaat tcttcaaagt ggaaccactt tattgctttg tcttatttgg tgcttgcctg    2880
atacaacctt taagccttgc ttacaagaag aaattaaaaa ctggaagcaa attttacaga    2940
gtgaaatatc atatggtaaa ttttgtcaaa tgatagaaaa tgtagaagct ggtcaggacc    3000
ctctgctcaa tattcttatt gaggaagagg gccctgagga aactgaagaa acccaagatt    3060
ctggtacttt ttctcaataa aggcatctgc ttcatatttc ctgtgtttgt ttttctgggg    3120
cctacttaac tgaataggaa tgcatgaaat aattctcata attcttgtgt ttggctttct    3180
ttttgagagg cctttttgagg tcctttcagt ggcgccttgc ccttatcctg ctgattactt    3240
tggaatgtta ctgctgctgg ggcaacagag ggctttgggt aaacagtttt ctcctgccca    3300
aatttatcta aaaatctgac aatatcagga tcaccaggta attgttctga cccctcatat    3360
attctaacct cttctacctg attatctttt ccttccatag gttggcctga cacttttggc    3420
attaagttgc tgtagttaga gtattactaa attgaagaac tgtaggagtc tgagagcctg    3480
tctgaataga cccatagtat ctactgtttt catttttaga aggatcagga caccatactt    3540
ctataggata atttccatct ttatctaatt ttgctttagc ttgtggatct aggccctgat    3600
ttttaggtgt cattttctt cccaatacag tttcaattgt aataggccca ccatttgtag     3660
tttttggata ctcagtctgg taatctaaaa ctaggccttg caaatccaga ggttctcccc    3720
```

```
caatggcaaa catatggtaa tttacccctg acacaggaat accagcacca taatcatgaa    3780
ctcttttcat gtcccaataa tgaacattaa ttaaagaact tattccaact acttctgttt    3840
taacagatat tgcctcccac atctgcaatg tgtcacaggt aatatcctca tttagcattg    3900
gcagagacac tcttgccaca ctgtaagctg gcaaattttc cttgatgggc tgatctggag    3960
atgatccctt tggctgcagg tcataagtat aagtatacca gtttgaagta gtaggaagat    4020
caggggaatt aactcccatt cttggattca aatacaactc aatttgggta atgctatctt    4080
ctccagtaac cacagataat acttccactc ctcctttaac aagcagtttt ggaactgagg    4140
caacattagg gcagcatccc ggcttaggta tacattgcct tttgggtgtt ttacaggtgg    4200
atgatgcttt tcttttggt gccatcttca attacttgta attcaggaga aatatatcca    4260
ctaaggccta gtaccagagg aagaagccaa tctggagttt gctgctgcag agttcctcct    4320
atatgttcag gaattaatat agcctctcct gataaaaggc cctgattctg agaagcagtt    4380
gtctgaaaga cccaccggct atttagtatc agattcacta ggtttgattg tatctgcagc    4440
ctagaggtag gagataaaga attaaaaata tcttgcccca cagaatgcag caagctattt    4500
tcccactgca gaggatctag gctaaaggcc ataagtgcat gcctcaaaac ctcattacta    4560
cctacccacg aaacatccct ctttacaagt gacacttgct cgcgtgacaa cctcaccccc    4620
acagttatta gagagcctat accactaaca gtttggagaa tgaagccata agttaaacct    4680
tggttaacca agaagccac taatgagaaa tttgaaaact gttcagctgt gaacccaagt    4740
tgagctaaag cctcaatgcc agaaataccc tcaattgtca ttaaactgga gatctctgct    4800
tccaaagctg ctaaagcttc tcctgtaaga atagcttcca aagttactcc tgtggtggca    4860
cttagttcag tagcaatttc accaatattg gccagcagtg tgatgatgcc ccccatcctg    4920
aaaaataaat aaggatactt actcttttaa tgtcctcctc cctttgtaag agaaaaaaaa    4980
gcctccgggc ctcccttgtt gaaaaaaagt taagagtctt ccgtctccct cccaaacaga    5040
aagaaaaaaa gttttgttta tcagtcaaac tccgcctctc caggaaatga gtcaatgcca    5100
gaaaccctgc agcaataaaa gttcaatcat gtaaccacaa cttggctgcc taggtgactt    5160 tttttttttca agttggcaga ggctt                                          5185
```

<210> SEQ ID NO 4
<211> LENGTH: 5341
<212> TYPE: DNA
<213> ORGANISM: Merkel Cell Carcinoma Virus
<220> FEATURE:
<221> NAME/KEY: misc_feature
<222> LOCATION: (1)..(5341)
<223> OTHER INFORMATION: MCV_MKL1 Genome

<400> SEQUENCE: 4

```
ggggctccta gcctccgagg cctctggaaa aaaagagag aggcctctga ggcttaagag      60
gcttaattag caaaaaaggc agtatctaag ggcagatccc aagggcggga aactgcagta    120
taaaaaccac tccttagtga ggtggctcat ttgctcctct gctctttctg caaactcctt    180
ctgcatatag acaagatgga tttagtccta aataggaaag aaagagaggc tctctgcaag    240 ctttttagaga ttgctcctaa ttgttatggc aacatccctc tgatgaaagc tgctttcaaa    300
agaagctgct taaagcatca ccctgataaa ggggaaatc ctgttataat gatggaattg    360
aacacccttt ggagcaaatt ccagcaaaat atccacaagc tcagaagtga cttctctatg    420
tttgatgagg tcagtacaaa atttccttgg gaagaatatg gaactttaaa ggattatatg    480
caaagtggat ataatgctag attttgcaga ggtcctgggt gcatgcttaa gcaacttaga    540
```

```
gattctaagt gcgcttgtat tagctgtaag ttgtctcgcc agcattgtag tctaaaaact    600
ttaaagcaaa aaaactgtct gacgtgggga gagtgttttt gctatcagtg ctttattctt    660
tggtttggat ttcctcctac ttgggaaagt tttgactggt ggcaaaaaac tttagaagaa    720
actgactact gcttactgca tctgcacctt ttctagactc ctacttcctt cctctgtaag    780
tattagatat ggaaaagtct ataaggcaaa atatcaaaga aaggttattt atgacagatt    840
ttctgtactt tcccatctag gttgacgagg cccctatata tgggaccact aaattcaaag    900
aatggtggag atcaggagga ttcagcttcg ggaaggcata cgaatatggg cccaatccac    960
acgggaccaa ctcaagatcc agaaagcctt cctccaatgc atccagggga gcccccagtg   1020
gaagctcacc accccacagc cagagctctt cctctgggta tgggtccttc tcagcgtccc   1080
aggcttcaga ctcccagtcc agaggacccg atatacctcc cgaacaccat gaggaaccca   1140
cctcatcctc tggatccagt agcagagagg agaccaccaa ttcaggaaga gaatccagca   1200
cacccaatgg aaccagtgta cctagaaatt cttccagaac ggatggcacc tgggaggatc   1260
tcttctgcga tgaatcactt tcctcccctg agcctccctc gtcctctgag gagcctgagg   1320 agccccctc ctcaagaagc tcgccccggc agccccgtc ttcctctgcc gaggaggcct   1380
cgtcatctca gtttacagat gaggaataca gatcctcctc cttcaccacc ccgaagaccc   1440
ctcctccatt ctcaagaaag cgaaaatttg ggggtcccg aagctctgca agctctgcta   1500
gttcagcaag ttttacaagc actccaccaa agccaaaaaa gaacagagaa actcctgttc   1560
ctactgattt tcctattgat ctttctgatt atcttagcca tgctgtatat aagctataga   1620
gttatatgat aagattgaga aatttaaagt tgattttaaa agcaggcatg cctgtgaatt   1680
aggatgtatt ttattgttta aactttatc aaagcataga gtatctgcta ttaagaattt   1740
ttgctctacc ttctgcacta taagcttttt aatttgtaaa ggagtgaata agatgcctga   1800
aatgtataat aatttatgca agcccccctta caaattactg caagagaata agccactgct   1860
caattatgaa tttcaagaaa aagaaaaaga ggccagctgt aattggaatt tagttgctga   1920
atttgcttgt gaatatgagc tagacgacca ctttattatc ttagcccatt atctagactt   1980
tgcaaaacca tttccttgcc aaaagtgtga aaacagatct cgcctcaaac ctcacaaggc   2040
tcatgaggct catcattcta atgctaagct attttatgaa tctaaatctc agaaaaccat   2100
ttgccaacaa gccgcagaca ctgttctagc caaaaggagg ttagagatgc tggaaatgac   2160
caggacagaa atgctatgta agaagtttaa gaagcaccta gagagattaa gagatttaga   2220
tacaatagat ctactgtatt atatgggtgg tgtggcctgg tactgctgct tatttgaaga   2280
gtttgaaaag aagctgcaga aaattattca attattaaca gagaatatac ctaagtatag   2340
aaacatttgg tttaaagggc ctattaacag tggaaaaaca agcttgctg cagccttaat   2400 agatttgcta gaagggaagg ccttgaatat aaactgtcca tctgataaac tgccttttga   2460
actaggatgt gctctggata aatttatggt tgttttgag gatgtgaaag ggcaaaatag   2520
cctaaataaa gatctgcaac agggcaagg aataaataac cttgataact aagagatca   2580 tctagatggt gctgtagctg taagcttaga gaagaagcat gtgaataaaa agcatcagat   2640
ttttcctcct tgtattgtta ctgctaatga ttatttatt cccaaaacat aatagcaag   2700 atttagttat acttacact tttccccaaa ggcaaatcta agagattccc tggatcagaa   2760
catggaaata agaaaagaa gaattcttca aagtggaacc actttattgc tttgtcttat   2820
ttggtgcttg cctgatacaa cctttaagcc ttgcttacaa gaagaaatta aaaactggaa   2880 gcaaattta cagagtgaaa tatcatatgg taaattttgt caaatgatag aaaatgtaga   2940
```

-continued

```
agctggtcag gaccctctgc tcaatattct tattgaggaa gagggccctg aggaaactga      3000
agaaacccaa gattctggta ctttttctca ataaaggcat ctgcttcata tttcctgtgt      3060 ttgttttct  ggggcctact taactgaata ggaatgcatg aaataattct cataattctt      3120
gtgtttggct ttcttttga  gaggccttt  gaggtccttt cagtggcgcc ttgcccttat      3180
cctgctgatt actttggaat gttactgctg ctggggcaac agagggcttt gggtaaacag      3240
ttttctcctg cccaaattta tctaaaaatc tgacaatatc aggatcacca ggtaattgtt      3300 ctgaccctc  atatattcta acctcttcta cctgattatc ttttccttcc ataggttggc      3360
ctgacacttt tggcattaag ttgctgaaga gtgagtttat taaattaact actgggtagg      3420 ggttttcac  ccatcttttt ctcaaagtaa cattaaaata tctaggcaac ccatgaagag      3480 ccattttcc  actggtttta aacagaaacc ccactatgtc tgcacagcta ataaataggc      3540
catctccttt gcatagaggg cccactccat tctcatctaa aaggacagta gttagagtat      3600
tactaaattg aagaactgta ggagtctgag agcctgtctg aatagaccca tagtatctac      3660
tgttttcatt tttagaagga tcaggacacc atacttctat aggataattt ccatctttat      3720
ctaattttgc tttagcttgt ggatctaggc cctgattttt aggtgtcatt tttcttccca      3780
atacagtttc aattgtaata ggcccaccat ttgtagtttt tggatactca gtctggtaat      3840
ctaaaactag gccttgcaaa tccagaggtt ctccccaat  ggcaaacata tggtaattta      3900
ctcctgacac aggaatacca gcaccataat catgaactct tttcatgtcc caataatgaa      3960
cattaattaa agaacttatt ccaactactt ctgttttaac agatattgcc tcccacatct      4020
gcaatgtgtc acaggtaata tcctcattta gcattggcag agacactctt gccacactgt      4080
aagctggcaa atttccttg  atgggctgat ctggagatga tcccttggc  tgcaggtcat      4140 aagtataagt ataccagttt gaagtagtag gaagatcagg ggaattaact cccattcttg      4200
gattcaaata caactcaatt tgggtaatgc tatcttctcc agtaaccaca gataatactt      4260
ccactcctcc tttaacaagc agttttggaa ctgaggcaac attagggcag catcccggct      4320
taggtataca ttgccttttg ggtgttttac aggtggatga tgcttttctt tttggtgcca      4380
tcttcaatta cttgtaattc aggagaaata tatccactaa ggcctagtac cagaggaaga      4440
agccaatctg gagtttgctg ctgcagagtt cctcctatat gttcaggaat taatatagcc      4500
tctcctgata aaaggccctg attctgagaa gcagttgtct gaaagaccca ccggctattt      4560
agtatcagat tcactaggtt tgattgtatc tgcagcctag aggtaggaga taagaattaa      4620
aaaatatctt gccccacaga atgcagcaag ctatttccc  actgcagagg atctaggcta      4680
aaggccataa gtgcatgcct caaaacctca ttactaccta cccacgaaac atccctcttt      4740
acaagtgaca cttgctcgcg tgacaacctc acccccacag ttattagaga gcctatacca      4800
ctaacagttt ggagaatgaa gccataagtt aaaccttggt taaccaaaga agccactaat      4860
gagaaatttg aaaactgttc agctgtgaac ccaagttgag ctaaagcctc aatgccagaa      4920
ataccctcaa ttgtcattaa actggagatc tctgcttcca aagctgctaa agcttctcct      4980
gtaagaatag cttccaaagt tactcctgtg gtggcactta gttcagtagc aatttcacca      5040
atattggcca gcagtgtgat gatgcccccc atcctgaaaa ataataagg  atacttactc      5100 ttttaatgtc ctcctccctt tgtaagagaa aaaaagcct  ccgggcctcc cttgttgaaa      5160
aaaagttaag agtcttccgt ctccctccca aacagaaaga aaaaagttt  tgtttatcag      5220 tcaaactccg cctctccagg aaatgagtca atgccagaaa ccctgcagca ataaaagttc      5280
aatcatgtaa ccacaacttg gctgcctagg tgactttttt ttttcaagtt ggcagaggct      5340
```

| | |
|---|---|
| t | 5341 |

<210> SEQ ID NO 5
<211> LENGTH: 1272
<212> TYPE: DNA
<213> ORGANISM: Merkel Cell Carcinoma Virus
<220> FEATURE:
<221> NAME/KEY: misc_feature
<222> LOCATION: (1)..(1272)
<223> OTHER INFORMATION: MCV_350 VP1 gene

<400> SEQUENCE: 5

| | | | | | |
|---|---|---|---|---|---|
| atggcaccaa | aagaaaagc | atcatccacc | tgtaaaacac | ccaaaaggca | atgtatacct | 60 |
| aagccgggat | gctgccctaa | tgttgcctca | gttccaaaac | tgcttgttaa | aggaggagtg | 120 |
| gaagtattat | ctgtggttac | tggagaagat | agcattaccc | aaattgagtt | gtatttgaat | 180 |
| ccaagaatgg | gagttaattc | ccctgatctt | cctactactt | caaactggta | tacttatact | 240 |
| tatgacctgc | agccaaaggg | atcatctcca | gatcagccca | tcaaggaaaa | tttgccagct | 300 |
| tacagtgtgg | caagagtgtc | tctgccaatg | ctaaatgagg | atattacctg | tgacacattg | 360 |
| cagatgtggg | aggcaatatc | tgttaaaaca | gaagtagttg | gaataagttc | tttaattaat | 420 |
| gttcattatt | gggacatgaa | aagagttcat | gattatggtg | ctggtattcc | tgtgtcaggg | 480 |
| gtaaattacc | atatgtttgc | cattggggga | gaacctctgg | atttgcaagg | cctagttta | 540 |
| gattaccaga | ctgagtatcc | aaaaactaca | aatggtgggc | ctattacaat | tgaaactgta | 600 |
| ttaggaagaa | aaatgacacc | taaaaatcag | ggcctagatc | cacaagctaa | agcaaaatta | 660 |
| gataaagatg | gaaattatcc | tatagaagta | tggtgtcctg | atccttctaa | aaatgaaaac | 720 |
| agtagatact | atgggtctat | tcagacaggc | tctcagactc | ctacagttct | tcaatttagt | 780 |
| aatactctaa | ctactgtcct | tttagatgag | aatggagtgg | gccctctatg | caaggagat | 840 |
| ggcctattta | ttagctgtgc | acacatagtg | gggtttctgt | ttaaaaccag | tggaaaaatg | 900 |
| gctcttcatg | ggttgcctag | atattttaat | gttactttga | aaaaatatg | ggtgaaaaac | 960 |
| ccctacccag | tagttaattt | aataaactca | ctcttcagca | acttaatgcc | aaaagtgtca | 1020 |
| ggccaaccta | tggaaggaaa | agataatcag | gtagaagagg | tcagaatata | tgagggtca | 1080 |
| gaacaattac | ctggtaatcc | tgatattgtc | agattttag | ataaatttgg | gcaggagaaa | 1140 |
| actgtttacc | caaagccctc | tgttgcccca | gcagcagtaa | cattccaaag | taatcagcag | 1200 |
| gataagggca | aggcgccact | gaaaggacct | caaaaggcct | ctcaaaaaga | aagccaaaca | 1260 |
| caacaattat | ga | | | | | 1272 |

<210> SEQ ID NO 6
<211> LENGTH: 423
<212> TYPE: PRT
<213> ORGANISM: Merkel Cell Carcinoma Virus
<220> FEATURE:
<221> NAME/KEY: MISC_FEATURE
<222> LOCATION: (1)..(423)
<223> OTHER INFORMATION: MCV_350 VP1 protein

<400> SEQUENCE: 6

Met Ala Pro Lys Arg Lys Ala Ser Ser Thr Cys Lys Thr Pro Lys Arg
1               5                   10                  15

Gln Cys Ile Pro Lys Pro Gly Cys Cys Pro Asn Val Ala Ser Val Pro
            20                  25                  30

Lys Leu Leu Val Lys Gly Gly Val Glu Val Leu Ser Val Val Thr Gly
        35                  40                  45

Glu Asp Ser Ile Thr Gln Ile Glu Leu Tyr Leu Asn Pro Arg Met Gly

```
              50                  55                  60
Val Asn Ser Pro Asp Leu Pro Thr Thr Ser Asn Trp Tyr Thr Tyr Thr
 65                  70                  75                  80

Tyr Asp Leu Gln Pro Lys Gly Ser Ser Pro Asp Gln Pro Ile Lys Glu
                 85                  90                  95

Asn Leu Pro Ala Tyr Ser Val Ala Arg Val Ser Leu Pro Met Leu Asn
                100                 105                 110

Glu Asp Ile Thr Cys Asp Thr Leu Gln Met Trp Glu Ala Ile Ser Val
                115                 120                 125

Lys Thr Glu Val Val Gly Ile Ser Ser Leu Ile Asn Val His Tyr Trp
130                 135                 140

Asp Met Lys Arg Val His Asp Tyr Gly Ala Gly Ile Pro Val Ser Gly
145                 150                 155                 160

Val Asn Tyr His Met Phe Ala Ile Gly Gly Glu Pro Leu Asp Leu Gln
                165                 170                 175

Gly Leu Val Leu Asp Tyr Gln Thr Glu Tyr Pro Lys Thr Thr Asn Gly
                180                 185                 190

Gly Pro Ile Thr Ile Glu Thr Val Leu Gly Arg Lys Met Thr Pro Lys
                195                 200                 205

Asn Gln Gly Leu Asp Pro Gln Ala Lys Ala Lys Leu Asp Lys Asp Gly
210                 215                 220

Asn Tyr Pro Ile Glu Val Trp Cys Pro Asp Pro Ser Lys Asn Glu Asn
225                 230                 235                 240

Ser Arg Tyr Tyr Gly Ser Ile Gln Thr Gly Ser Gln Thr Pro Thr Val
                245                 250                 255

Leu Gln Phe Ser Asn Thr Leu Thr Thr Val Leu Leu Asp Glu Asn Gly
                260                 265                 270

Val Gly Pro Leu Cys Lys Gly Asp Gly Leu Phe Ile Ser Cys Ala His
                275                 280                 285

Ile Val Gly Phe Leu Phe Lys Thr Ser Gly Lys Met Ala Leu His Gly
                290                 295                 300

Leu Pro Arg Tyr Phe Asn Val Thr Leu Arg Lys Ile Trp Val Lys Asn
305                 310                 315                 320

Pro Tyr Pro Val Val Asn Leu Ile Asn Ser Leu Phe Ser Asn Leu Met
                325                 330                 335

Pro Lys Val Ser Gly Gln Pro Met Glu Gly Lys Asp Asn Gln Val Glu
                340                 345                 350

Glu Val Arg Ile Tyr Glu Gly Ser Glu Gln Leu Pro Gly Asn Pro Asp
                355                 360                 365

Ile Val Arg Phe Leu Asp Lys Phe Gly Gln Glu Lys Thr Val Tyr Pro
                370                 375                 380

Lys Pro Ser Val Ala Pro Ala Ala Val Thr Phe Gln Ser Asn Gln Gln
385                 390                 395                 400

Asp Lys Gly Lys Ala Pro Leu Lys Gly Pro Gln Lys Ala Ser Gln Lys
                405                 410                 415

Glu Ser Gln Thr Gln Gln Leu
                420

<210> SEQ ID NO 7
<211> LENGTH: 726
<212> TYPE: DNA
<213> ORGANISM: Merkel Cell Carcinoma Virus
<220> FEATURE:
<221> NAME/KEY: misc_feature
<222> LOCATION: (1)..(726)
<223> OTHER INFORMATION: MCV_350 VP2 gene
```

<400> SEQUENCE: 7

```
atgggggggca tcatcacact gctggccaat attggtgaaa ttgctactga actaagtgcc    60
accacaggag taactttgga agctattctt acaggagaag ctttagcagc tttggaagca   120
gacatctcca gtttaatgac aattgagggt atttctggca ttgaggcttt agctcaactt   180
gggttcacag ctgaacagtt ttcaaatttc tcattagtgg cttctttggt taaccaaggt   240
ttaacttatg gcttcattct ccaaactgtt agtggtatag ctctctaat aactgtgggg   300
gtgaggttgt cacgcgagca agtgtcactt gtaaacaggg atgtttcgtg ggtaggtagt   360
aatgaggttt tgaggcatgc acttatggcc tttagcctag atcctctgca gtgggaaaat   420
agcttgctgc attctgtggg gcaaaatatt tttaattctt tatctcctac ctctaggctg   480
cagatacaat caaacctagt gaatctgata ctaaatagcc ggtgggtctt tcagacaact   540
gcttctcaga atcagggcct tttatcagga gaggctatat taattcctga acatatagga   600
ggaactctgc agcagcaaac tccagattgg cttcttcctc tggtactagg ccttagtgga   660
tatatttctc ctgaattaca agtaattgaa gatggcacca aaagaaaag catcatccac   720
ctgtaa                                                              726
```

<210> SEQ ID NO 8
<211> LENGTH: 241
<212> TYPE: PRT
<213> ORGANISM: Merkel Cell Carcinoma Virus
<220> FEATURE:
<221> NAME/KEY: MISC_FEATURE
<222> LOCATION: (1)..(241)
<223> OTHER INFORMATION: MCV_350 VP2 protein

<400> SEQUENCE: 8

```
Met Gly Gly Ile Ile Thr Leu Leu Ala Asn Ile Gly Glu Ile Ala Thr
1               5                   10                  15
Glu Leu Ser Ala Thr Thr Gly Val Thr Leu Glu Ala Ile Leu Thr Gly
            20                  25                  30
Glu Ala Leu Ala Ala Leu Glu Ala Asp Ile Ser Ser Leu Met Thr Ile
        35                  40                  45
Glu Gly Ile Ser Gly Ile Glu Ala Leu Ala Gln Leu Gly Phe Thr Ala
    50                  55                  60
Glu Gln Phe Ser Asn Phe Ser Leu Val Ala Ser Leu Val Asn Gln Gly
65                  70                  75                  80
Leu Thr Tyr Gly Phe Ile Leu Gln Thr Val Ser Gly Ile Gly Ser Leu
                85                  90                  95
Ile Thr Val Gly Val Arg Leu Ser Arg Glu Gln Val Ser Leu Val Asn
            100                 105                 110
Arg Asp Val Ser Trp Val Gly Ser Asn Glu Val Leu Arg His Ala Leu
        115                 120                 125
Met Ala Phe Ser Leu Asp Pro Leu Gln Trp Glu Asn Ser Leu Leu His
    130                 135                 140
Ser Val Gly Gln Asn Ile Phe Asn Ser Leu Ser Pro Thr Ser Arg Leu
145                 150                 155                 160
Gln Ile Gln Ser Asn Leu Val Asn Leu Ile Leu Asn Ser Arg Trp Val
                165                 170                 175
Phe Gln Thr Thr Ala Ser Gln Asn Gln Gly Leu Leu Ser Gly Glu Ala
            180                 185                 190
Ile Leu Ile Pro Glu His Ile Gly Gly Thr Leu Gln Gln Gln Thr Pro
        195                 200                 205
```

-continued

```
Asp Trp Leu Leu Pro Leu Val Leu Gly Leu Ser Gly Tyr Ile Ser Pro
    210                 215                 220

Glu Leu Gln Val Ile Glu Asp Gly Thr Lys Lys Lys Ser Ile Ile His
225                 230                 235                 240

Leu
```

```
<210> SEQ ID NO 9
<211> LENGTH: 591
<212> TYPE: DNA
<213> ORGANISM: Merkel Cell Carcinoma Virus
<220> FEATURE:
<221> NAME/KEY: misc_feature
<222> LOCATION: (1)..(591)
<223> OTHER INFORMATION: MCV_350 VP3 gene

<400> SEQUENCE: 9
atgacaattg agggtatttc tggcattgag gctttagctc aacttgggtt cacagctgaa    60
cagttttcaa atttctcatt agtggcttct ttggttaacc aaggtttaac ttatggcttc    120
attctccaaa ctgttagtgg tataggctct ctaataactg tgggggtgag gttgtcacgc    180
gagcaagtgt cacttgtaaa cagggatgtt tcgtgggtag gtagtaatga ggttttgagg    240
catgcactta tggcctttag cctagatcct ctgcagtggg aaaatagctt gctgcattct    300
gtggggcaaa atatttttaa ttctttatct cctacctcta ggctgcagat acaatcaaac    360
ctagtgaatc tgatactaaa tagccggtgg gtctttcaga caactgcttc tcagaatcag    420
ggccttttat caggagaggc tatattaatt cctgaacata taggaggaac tctgcagcag    480
caaactccag attggcttct tcctctggta ctaggcctta gtggatatat ttctcctgaa    540
ttacaagtaa ttgaagatgg caccaaaaag aaaagcatca tccacctgta a             591
```

```
<210> SEQ ID NO 10
<211> LENGTH: 196
<212> TYPE: PRT
<213> ORGANISM: Merkel Cell Carcinoma Virus
<220> FEATURE:
<221> NAME/KEY: MISC_FEATURE
<222> LOCATION: (1)..(196)
<223> OTHER INFORMATION: MCV_350 VP3 protein

<400> SEQUENCE: 10

Met Thr Ile Glu Gly Ile Ser Gly Ile Glu Ala Leu Ala Gln Leu Gly
1               5                   10                  15

Phe Thr Ala Glu Gln Phe Ser Asn Phe Ser Leu Val Ala Ser Leu Val
            20                  25                  30

Asn Gln Gly Leu Thr Tyr Gly Phe Ile Leu Gln Thr Val Ser Gly Ile
        35                  40                  45

Gly Ser Leu Ile Thr Val Gly Val Arg Leu Ser Arg Glu Gln Val Ser
    50                  55                  60

Leu Val Asn Arg Asp Val Ser Trp Val Gly Ser Asn Glu Val Leu Arg
65                  70                  75                  80

His Ala Leu Met Ala Phe Ser Leu Asp Pro Leu Gln Trp Glu Asn Ser
                85                  90                  95

Leu Leu His Ser Val Gly Gln Asn Ile Phe Asn Ser Leu Ser Pro Thr
            100                 105                 110

Ser Arg Leu Gln Ile Gln Ser Asn Leu Val Asn Leu Ile Leu Asn Ser
        115                 120                 125

Arg Trp Val Phe Gln Thr Thr Ala Ser Gln Asn Gln Gly Leu Leu Ser
    130                 135                 140

Gly Glu Ala Ile Leu Ile Pro Glu His Ile Gly Gly Thr Leu Gln Gln
```

|  | 145 |  |  |  | 150 |  |  |  |  | 155 |  |  |  | 160 |
|---|---|---|---|---|---|---|---|---|---|---|---|---|---|---|

Gln Thr Pro Asp Trp Leu Leu Pro Leu Val Leu Gly Leu Ser Gly Tyr
                          165                    170                  175

Ile Ser Pro Glu Leu Gln Val Ile Glu Asp Gly Thr Lys Lys Lys Ser
        180                    185                    190

Ile Ile His Leu
    195

<210> SEQ ID NO 11
<211> LENGTH: 2454
<212> TYPE: DNA
<213> ORGANISM: Merkel Cell Carcinoma Virus
<220> FEATURE:
<221> NAME/KEY: misc_feature
<222> LOCATION: (1)..(2454)
<223> OTHER INFORMATION: MCV_350 T-1 gene

<400> SEQUENCE: 11

```
atggatttag tcctaaatag aaagaaaga gaggctctgt gcaagctttt ggagattgct    60
cctaattgtt atggcaacat ccctctgatg aaagctgctt tcaaaagaag ctgcttaaag   120
catcaccctg ataaggggg aaatcctgtt ataatgatgg aattgaacac cctttggagc   180
aaattccagc aaaatatcca caagctcaga agtgacttct ctatgtttga tgaggttgac   240
gaggccccta tatgtgggac cactaaattc aaagaatggt ggagatcagg aggattcagc   300
ttcgggaagg catacgaata tgggcccaat ccacacgggg ccaactcaag atccagaaag   360
ccttcctcca atgcatccag gggagccccc agtggaagct caccacccca cagccagagc   420
tcttcctctg ggtatgggtc cttctcagcg tcccaggctt cagactccca gtccagagga   480
cccgatatac ctcccgaaca ccatgaggaa cccacctcat cctctggatc cagtagcaga   540
gaggagacca ccaattcagg aagagaatcc agcacaccca tggaaccag tgtacctaga   600
aattcttcca gaacgtatgg cacctgggag gatctcttct gcgatgaatc actttcctcc   660
cctgagcctc cctcgtcctc tgaggagcct gaggagcccc cctcctcaag aagctcgccc   720
cggcagcccc cgtgttcctc tgccgaggag gcctcgtcat ctcagtttac agattaggaa   780
tacatatcct cctccttcac caccccgaag accctcctc cattctcaag aaagcgaaaa   840
tttgggggt cccgaagctc tgcaagtctc gctagttcag caagttttac aagcactcca   900
ccaaagctaa aaacaacag agaaactcct gttcctacta atttttcctat tgatgtttct   960
gattatctta gccatgctgt atatagtaat aaaacagtaa gttgttttgc cattatact  1020
acttctgata aagctataga gttatatgat aagattgaga aatttaaagt tgatttaaa  1080
agcaggcatg cctgtgaatt aggatgtatt ttattgttta actttatc aaagcataga   1140
gtatttgcta ttaagaattt tgctctacc ttctgcacta aagcttttt aatttgtaaa   1200
ggagtgaata agatgcctga aatgtataat aatttatgca agcccccta caaattactg   1260
caagagaata agccactgct caattatgaa tttcaagaaa aagaaaaaga ggccagctgt   1320
aattggaatt tagttgctga atttgcttgt gaatatgagc tagacgacca ctttattatc   1380
ttagcccatt atctagactt tgcaaaacca tttccttgcc aaaagtgtga aaacagatct   1440
cgcctcaaac ctcacaaggc tcatgaggct catcattcta atgctaagct attttatgaa   1500
tctaaatctc agaaaaccat tgccaacaa gccgcagaca ctgttctagc caaaggagg   1560
ttagagatgc tggaaatgac caggacagaa atgctatgta agaagtttaa gaagcaccta   1620
gagagattaa gagatttaga tacaatagat ctactgtatt atatgggtgg tgtggcctgg   1680
tactgctgct tatttgaaga gtttgaaaag aagctgcaga aaattattca attattaaca   1740
```

-continued

```
gagaatatac ctaagtatag aaacatttgg tttaaagggc ctattaacag tggaaaaaca    1800
agctttgctg cagccttaat agatttgcta gaagggaagg ccttgaatat aaactgtcca    1860
tctgataaac tgccttttga actaggatgt gcttttggata aatttatggt tgttttttgag  1920 gatgtgaaag ggcaaaatag cctaaataaa gatctgcaac cagggcaagg aataaataac    1980
cttgataact taagagatca tctagatggt gctgtagctg tgagcttaga aagaagcat     2040 gtgaataaaa agcatcagat ttttcctcct tgtattgtta ctgctaatga ttatttatt    2100 cccaaaacat taatagcaag atttagttat actttacact ttttcccaaa ggcaaatcta    2160
agagattccc tggatcagaa catggaaata agaaaaagaa gaattcttca aagtggaacc    2220
actttattgc tttgtcttat ttggtgcttg cctgatacaa cctttaagcc ttgcttacaa    2280
gaagaaatta aaaactggaa gcaaattttta cagagtgaaa tatcatatgg taaattttgt   2340
caaatgatag aaaatgtaga agctggtcag gaccctctgc tcaatattct tattgaggaa    2400
gagggccctg aggaaactga ggaaacccaa gattctggta ctttttctca ataa           2454
```

<210> SEQ ID NO 12
<211> LENGTH: 854
<212> TYPE: PRT
<213> ORGANISM: Merkel Cell Carcinoma Virus
<220> FEATURE:
<221> NAME/KEY: MISC_FEATURE
<222> LOCATION: (1)..(854)
<223> OTHER INFORMATION: MCV_350 T-1 protein
<220> FEATURE:
<221> NAME/KEY: MISC_FEATURE
<222> LOCATION: (259)..(259)
<223> OTHER INFORMATION: Xaa marks site of tumor-derived stop codon that
    is absent in wild-type virus

<400> SEQUENCE: 12

```
Met Asp Leu Val Leu Asn Arg Lys Glu Arg Glu Ala Leu Cys Lys Leu
1               5                   10                  15

Leu Glu Ile Ala Pro Asn Cys Tyr Gly Asn Ile Pro Leu Met Lys Ala
            20                  25                  30

Ala Phe Lys Arg Ser Cys Leu Lys His His Pro Asp Lys Gly Gly Asn
        35                  40                  45

Pro Val Ile Met Met Glu Leu Asn Thr Leu Trp Ser Lys Phe Gln Gln
    50                  55                  60

Asn Ile His Lys Leu Arg Ser Asp Phe Ser Met Phe Asp Glu Val Asp
65                  70                  75                  80

Glu Ala Pro Ile Tyr Gly Thr Thr Lys Phe Lys Glu Trp Trp Arg Ser
                85                  90                  95

Gly Gly Phe Ser Phe Gly Lys Ala Tyr Glu Tyr Gly Pro Asn Pro His
            100                 105                 110

Gly Ala Asn Ser Arg Ser Arg Lys Pro Ser Ser Asn Ala Ser Arg Gly
        115                 120                 125

Ala Pro Ser Gly Ser Ser Pro His Ser Gln Ser Ser Ser Ser Gly
    130                 135                 140

Tyr Gly Ser Phe Ser Ala Ser Gln Ala Ser Asp Ser Gln Ser Arg Gly
145                 150                 155                 160

Pro Asp Ile Pro Pro Glu His His Glu Glu Pro Thr Ser Ser Ser Gly
                165                 170                 175

Ser Ser Ser Arg Glu Glu Thr Thr Asn Ser Gly Arg Glu Ser Ser Thr
            180                 185                 190

Pro Asn Gly Thr Ser Val Pro Arg Asn Ser Ser Arg Thr Tyr Gly Thr
        195                 200                 205
```

-continued

```
Trp Glu Asp Leu Phe Cys Asp Glu Ser Leu Ser Ser Pro Glu Pro Pro
    210                 215                 220
Ser Ser Ser Glu Glu Pro Glu Pro Ser Ser Arg Ser Ser Pro
225                 230                 235                 240
Arg Gln Pro Pro Cys Ser Ser Ala Glu Glu Ala Ser Ser Ser Gln Phe
                245                 250                 255
Thr Asp Xaa Glu Tyr Ile Ser Ser Ser Phe Thr Thr Pro Lys Thr Pro
            260                 265                 270
Pro Pro Phe Ser Arg Lys Arg Lys Phe Gly Gly Ser Arg Ser Ser Ala
        275                 280                 285
Ser Ser Ala Ser Ser Ala Ser Phe Thr Ser Thr Pro Pro Lys Leu Lys
    290                 295                 300
Asn Asn Arg Glu Thr Pro Val Pro Thr Asn Phe Pro Ile Asp Val Ser
305                 310                 315                 320
Asp Tyr Leu Ser His Ala Val Tyr Ser Asn Lys Thr Val Ser Cys Phe
                325                 330                 335
Ala Ile Tyr Thr Thr Ser Asp Lys Ala Ile Glu Leu Tyr Asp Lys Ile
            340                 345                 350
Glu Lys Phe Lys Val Asp Phe Lys Ser Arg His Ala Cys Glu Leu Gly
        355                 360                 365
Cys Ile Leu Leu Phe Ile Thr Leu Ser Lys His Arg Val Phe Ala Ile
    370                 375                 380
Lys Asn Phe Cys Ser Thr Phe Cys Thr Ile Ser Phe Leu Ile Cys Lys
385                 390                 395                 400
Gly Val Asn Lys Met Pro Glu Met Tyr Asn Asn Leu Cys Lys Pro Pro
                405                 410                 415
Tyr Lys Leu Leu Gln Glu Asn Lys Pro Leu Leu Asn Tyr Glu Phe Gln
            420                 425                 430
Glu Lys Glu Lys Glu Ala Ser Cys Asn Trp Asn Leu Val Ala Glu Phe
        435                 440                 445
Ala Cys Glu Tyr Glu Leu Asp Asp His Phe Ile Ile Leu Ala His Tyr
    450                 455                 460
Leu Asp Phe Ala Lys Pro Phe Pro Cys Gln Lys Cys Glu Asn Arg Ser
465                 470                 475                 480
Arg Leu Lys Pro His Lys Ala His Glu Ala His His Ser Asn Ala Lys
                485                 490                 495
Leu Phe Tyr Glu Ser Lys Ser Gln Lys Thr Ile Cys Gln Gln Ala Ala
            500                 505                 510
Asp Thr Val Leu Ala Lys Arg Arg Leu Glu Met Leu Glu Met Thr Arg
        515                 520                 525
Thr Glu Met Leu Cys Lys Lys Phe Lys Lys His Leu Glu Arg Leu Arg
    530                 535                 540
Asp Leu Asp Thr Ile Asp Leu Leu Tyr Tyr Met Gly Gly Val Ala Trp
545                 550                 555                 560
Tyr Cys Cys Leu Phe Glu Glu Phe Glu Lys Lys Leu Gln Lys Ile Ile
                565                 570                 575
Gln Leu Leu Thr Glu Asn Ile Pro Lys Tyr Arg Asn Ile Trp Phe Lys
            580                 585                 590
Gly Pro Ile Asn Ser Gly Lys Thr Ser Phe Ala Ala Ala Leu Ile Asp
        595                 600                 605
Leu Leu Glu Gly Lys Ala Leu Asn Ile Asn Cys Pro Ser Asp Lys Leu
    610                 615                 620
Pro Phe Glu Leu Gly Cys Ala Leu Asp Lys Phe Met Val Val Phe Glu
```

```
                    625                 630                 635                 640
Asp Val Lys Gly Gln Asn Ser Leu Asn Lys Asp Leu Gln Pro Gly Gln
                    645                 650                 655
Gly Ile Asn Asn Leu Asp Asn Leu Arg Asp His Leu Asp Gly Ala Val
                    660                 665                 670
Ala Val Ser Leu Glu Lys Lys His Val Asn Lys His Gln Ile Phe
                    675                 680                 685
Pro Pro Cys Ile Val Thr Ala Asn Asp Tyr Phe Ile Pro Lys Thr Leu
                    690                 695                 700
Ile Ala Arg Phe Ser Tyr Thr Leu His Phe Phe Pro Lys Ala Asn Leu
705                 710                 715                 720
Arg Asp Ser Leu Asp Gln Asn Met Glu Ile Arg Lys Arg Arg Ile Leu
                    725                 730                 735
Gln Ser Gly Thr Thr Leu Leu Leu Cys Leu Ile Trp Cys Leu Pro Asp
                    740                 745                 750
Thr Thr Phe Lys Pro Cys Leu Gln Glu Glu Ile Lys Asn Trp Lys Gln
                    755                 760                 765
Ile Leu Gln Ser Glu Ile Ser Tyr Gly Lys Phe Cys Gln Met Ile Glu
                    770                 775                 780
Asn Val Glu Ala Gly Gln Asp Pro Leu Leu Asn Ile Leu Ile Glu Glu
785                 790                 795                 800
Glu Gly Pro Glu Glu Thr Glu Thr Gln Asp Ser Gly Thr Phe Ser
                    805                 810                 815
Gln Gln Met Ile Glu Asn Val Glu Ala Gly Gln Asp Pro Leu Leu Asn
                    820                 825                 830
Ile Leu Ile Glu Glu Glu Gly Pro Glu Glu Thr Glu Glu Thr Gln Asp
                    835                 840                 845
Ser Gly Thr Phe Ser Gln
    850

<210> SEQ ID NO 13
<211> LENGTH: 1674
<212> TYPE: DNA
<213> ORGANISM: Merkel Cell Carcinoma Virus
<220> FEATURE:
<221> NAME/KEY: misc_feature
<222> LOCATION: (1)..(1674)
<223> OTHER INFORMATION: MCV_350 T-2 gene

<400> SEQUENCE: 13
atggatttag tcctaaatag gaaagaaaga gaggctctgt gcaagctttt ggagattgct      60
cctaattgtt atggcaacat ccctctgatg aaagctgctt tcaaaagaag ctgcttaaag     120
catcaccctg ataaagggg aaatcctgtt ataatgatgg aattgaacac cctttggagc      180
aaattccagc aaaatatcca aagctcaga agtgacttct ctatgtttga tgaggttagt      240
acaaaatttc cttgggaaga atatggaact ttaaaggatt atatgcaaag tggatataat     300
gctagatttt gcagaggtcc tgggtgcatg cttaagcaac ttagagattc taagtgcgct     360
tgtattagct gtaagttgtc tcgccagcat tgtagtctaa aactttaaa gcaaaaaaac      420 tgtctgacgt ggggagagtg ttttttgctat cagtgctta ttctttggtt tggatttcct     480 cctactggg aaagttttga ctggtggcaa aaaactttag aagaaactga ctactgctta      540
ctgcatctgc acctttctc gactcctact tccttcctct gtgttgacga ggcccctata     600
tatgggacca ctaaattcaa agaatggtgg agatcaggag gattcagctt cgggaaggca      660
tacgaatatg ggcccaatcc acacggggcc aactcaagat ccagaaagcc ttcctccaat    720
```

-continued

```
gcatccaggg gagcccccag tggaagctca ccaccccaca gccagagctc ttcctctggg    780
tatgggtcct tctcagcgtc ccaggcttca gactcccagt ccagaggacc cgatatacct    840
cccgaacacc atgaggaacc cacctcatcc tctggatcca gtagcagaga ggagaccacc    900
aattcaggaa gagaatccag cacacccaat ggaaccagtg tacctagaaa ttcttccaga    960
acgtatggca cctggagga tctcttctgc gatgaatcac tttcctcccc tgagcctccc    1020
tcgtcctctg aggagcctga ggagcccccc tcctcaagaa gctcgccccg gcagccccg    1080 tgttcctctg ccgaggaggc ctcgtcatct cagtttacag attaggaata catatcctcc    1140
tccttcacca ccccgaagac ccctcctcca ttctcaagaa agcgaaaatt tgggggtcc    1200 cgaagctctg caagctctgc tagttcagca agttttacaa gcactccacc aaagctaaaa    1260
aacaacagag aaactcctgt tcctactaat tttcctattg atgtttctga ttatcttagc    1320
catgctgtat atagtaataa aacagcaaat ctaagagatt ccctggatca gaacatggaa    1380
ataagaaaaa gaagaattct tcaaagtgga accactttat tgctttgtct tatttggtgc    1440
ttgcctgata caacctttaa gccttgctta caagaagaaa ttaaaaactg gaagcaaatt    1500
ttacagagtg aaatatcata tggtaaattt tgtcaaatga tagaaaatgt agaagctggt    1560
caggaccctc tgctcaatat tcttattgag gaagagggcc ctgaggaaac tgaggaaacc    1620
caagattctg gtacttttc tcaataacaa gattctggta cttttctca ataa           1674
```

<210> SEQ ID NO 14
<211> LENGTH: 548
<212> TYPE: PRT
<213> ORGANISM: Merkel Cell Carcinoma Virus
<220> FEATURE:
<221> NAME/KEY: MISC_FEATURE
<222> LOCATION: (1)..(548)
<223> OTHER INFORMATION: MCV_350 T-2 protein
<220> FEATURE:
<221> NAME/KEY: MISC_FEATURE
<222> LOCATION: (187)..(187)
<223> OTHER INFORMATION: Xaa marks site of tumor-derived stop codon that
    is absent in wild-type virus
<220> FEATURE:
<221> NAME/KEY: MISC_FEATURE
<222> LOCATION: (375)..(375)
<223> OTHER INFORMATION: Xaa marks site of tumor-derived stop codon that
    is absent in wild-type virus

<400> SEQUENCE: 14

```
Met Asp Leu Val Leu Asn Arg Lys Glu Arg Glu Ala Leu Cys Lys Leu
1               5                   10                  15

Leu Glu Ile Ala Pro Asn Cys Tyr Gly Asn Ile Pro Leu Met Lys Ala
            20                  25                  30

Ala Phe Lys Arg Ser Cys Leu Lys His His Pro Asp Lys Gly Gly Asn
        35                  40                  45

Pro Val Ile Met Met Glu Leu Asn Thr Leu Trp Ser Lys Phe Gln Gln
    50                  55                  60

Asn Ile His Lys Leu Arg Ser Asp Phe Ser Met Phe Asp Glu Val Ser
65                  70                  75                  80

Thr Lys Phe Pro Trp Glu Glu Tyr Gly Thr Leu Lys Asp Tyr Met Gln
                85                  90                  95

Ser Gly Tyr Asn Ala Arg Phe Cys Arg Gly Pro Gly Cys Met Leu Lys
            100                 105                 110

Gln Leu Arg Asp Ser Lys Cys Ala Cys Ile Ser Cys Lys Leu Ser Arg
        115                 120                 125

Gln His Cys Ser Leu Lys Thr Leu Lys Gln Lys Asn Cys Leu Thr Trp
    130                 135                 140
```

```
Gly Glu Cys Phe Cys Tyr Gln Cys Phe Ile Leu Trp Phe Gly Phe Pro
145                 150                 155                 160

Pro Thr Trp Glu Ser Phe Asp Trp Trp Gln Lys Thr Leu Glu Glu Thr
                165                 170                 175

Asp Tyr Cys Leu Leu His Leu His Leu Phe Xaa Thr Pro Thr Ser Phe
            180                 185                 190

Leu Cys Val Asp Glu Ala Pro Ile Tyr Gly Thr Thr Lys Phe Lys Glu
        195                 200                 205

Trp Trp Arg Ser Gly Gly Phe Ser Phe Gly Lys Ala Tyr Glu Tyr Gly
    210                 215                 220

Pro Asn Pro His Gly Ala Asn Ser Arg Ser Arg Lys Pro Ser Ser Asn
225                 230                 235                 240

Ala Ser Arg Gly Ala Pro Ser Gly Ser Ser Pro His Ser Gln Ser
                245                 250                 255

Ser Ser Ser Gly Tyr Gly Ser Phe Ser Ala Ser Gln Ala Ser Asp Ser
            260                 265                 270

Gln Ser Arg Gly Pro Asp Ile Pro Pro Glu His His Glu Glu Pro Thr
        275                 280                 285

Ser Ser Ser Gly Ser Ser Ser Arg Glu Glu Thr Thr Asn Ser Gly Arg
    290                 295                 300

Glu Ser Ser Thr Pro Asn Gly Thr Ser Val Pro Arg Asn Ser Ser Arg
305                 310                 315                 320

Thr Tyr Gly Thr Trp Glu Asp Leu Phe Cys Asp Glu Ser Leu Ser Ser
                325                 330                 335

Pro Glu Pro Pro Ser Ser Glu Glu Pro Glu Pro Pro Ser Ser
            340                 345                 350

Arg Ser Ser Pro Arg Gln Pro Pro Cys Ser Ser Ala Glu Glu Ala Ser
        355                 360                 365

Ser Ser Gln Phe Thr Asp Xaa Glu Tyr Ile Ser Ser Phe Thr Thr
    370                 375                 380

Pro Lys Thr Pro Pro Phe Ser Arg Lys Arg Lys Phe Gly Gly Ser
385                 390                 395                 400

Arg Ser Ser Ala Ser Ser Ala Ser Ser Ala Ser Phe Thr Ser Thr Pro
                405                 410                 415

Pro Lys Leu Lys Asn Asn Arg Glu Thr Pro Val Pro Thr Asn Phe Pro
            420                 425                 430

Ile Asp Val Ser Asp Tyr Leu Ser His Ala Val Tyr Ser Asn Lys Thr
        435                 440                 445

Ala Asn Leu Arg Asp Ser Leu Asp Gln Asn Met Glu Ile Arg Lys Arg
    450                 455                 460

Arg Ile Leu Gln Ser Gly Thr Thr Leu Leu Cys Leu Ile Trp Cys
465                 470                 475                 480

Leu Pro Asp Thr Thr Phe Lys Pro Cys Leu Gln Glu Glu Ile Lys Asn
                485                 490                 495

Trp Lys Gln Ile Leu Gln Ser Glu Ile Ser Tyr Gly Lys Phe Cys Gln
            500                 505                 510

Met Ile Glu Asn Val Glu Ala Gly Gln Asp Pro Leu Leu Asn Ile Leu
        515                 520                 525

Ile Glu Glu Glu Gly Pro Glu Thr Glu Thr Gln Asp Ser Gly
    530                 535                 540

Thr Phe Ser Gln
545
```

```
<210> SEQ ID NO 15
<211> LENGTH: 1338
<212> TYPE: DNA
<213> ORGANISM: Merkel Cell Carcinoma Virus
<220> FEATURE:
<221> NAME/KEY: misc_feature
<222> LOCATION: (1)..(1338)
<223> OTHER INFORMATION: MCV_350 T-3 gene

<400> SEQUENCE: 15
atggatttag tcctaaatag gaagaaaga gaggctctgt gcaagctttt ggagattgct      60
cctaattgtt atggcaacat ccctctgatg aaagctgctt tcaaaagaag ctgcttaaag     120
catcaccctg ataaagggg aaatcctgtt ataatgatga aattgaacac cctttggagc     180
aaattccagc aaaatatcca caagctcaga agtgacttct ctatgtttga tgaggttgac     240
gaggccccta tatgggac cactaaattc aagaatgg ggagatcagg aggattcagc       300
ttcgggaagg catacgaata tgggcccaat ccacacgggg ccaactcaag atccagaaag    360
ccttcctcca atgcatccag gggagcccc agtggaagct caccacccca cagccagagc     420
tcttcctctg ggtatgggtc cttctcagcg tcccaggctt cagactccca gtccagagga    480
cccgatatac ctcccgaaca ccatgaggaa ccccacctcat cctctggatc cagtagcaga    540
gaggagacca ccaattcagg aagagaatcc agcacaccca atggaaccag tgtacctaga    600
aattcttcca gaacgtatgg cacctgggag gatctcttct gcgatgaatc acttttcctcc   660 cctgagcctc cctcgtcctc tgaggagcct gaggagcccc cctcctcaag aagctcgccc    720
cggcagcccc cgtgttcctc tgccgaggag gcctcgtcat ctcagtttac agattaggaa    780
tacatatcct cctccttcac cacccccgaag accccctcctc cattctcaag aaagcgaaaa   840
tttggggggt cccgaagctc tgcaagctct gctagttcag caagttttac aagcactcca    900
ccaaagctaa aaacaacag agaaactcct gttcctacta attttcctat tgatgtttct     960
gattatctta gccatgctgt atatagtaat aaaacagcaa atctaagaga ttccctggat   1020
cagaacatgg aaataagaaa aagaagaatt cttcaaagtg gaaccacttt attgctttgt   1080
cttatttggt gcttgcctga tacaaccttt aagccttgct tacaagaaga aattaaaaac   1140
tggaagcaaa ttttacagag tgaaatatca tatggtaaat tttgtcaaat gatagaaaat   1200
gtagaagctg gtcaggaccc tctgctcaat attcttattg aggaagaggg ccctgaggaa   1260
actgaggaaa cccaagattc tggtactttt tctcaataaa ctgaggaaac ccaagattct   1320 ggtactttt ctcaataa                                                  1338

<210> SEQ ID NO 16
<211> LENGTH: 432
<212> TYPE: PRT
<213> ORGANISM: Merkel Cell Carcinoma Virus
<220> FEATURE:
<221> NAME/KEY: MISC_FEATURE
<222> LOCATION: (1)..(432)
<223> OTHER INFORMATION: MCV_350 T-3 protein
<220> FEATURE:
<221> NAME/KEY: MISC_FEATURE
<222> LOCATION: (259)..(259)
<223> OTHER INFORMATION: Xaa marks site of tumor-derived stop codon that
      is absent in wild-type virus

<400> SEQUENCE: 16

Met Asp Leu Val Leu Asn Arg Lys Glu Arg Glu Ala Leu Cys Lys Leu
1               5                   10                  15

Leu Glu Ile Ala Pro Asn Cys Tyr Gly Asn Ile Pro Leu Met Lys Ala
            20                  25                  30
```

```
Ala Phe Lys Arg Ser Cys Leu Lys His His Pro Asp Lys Gly Gly Asn
         35                  40                  45

Pro Val Ile Met Met Glu Leu Asn Thr Leu Trp Ser Lys Phe Gln Gln
 50                  55                  60

Asn Ile His Lys Leu Arg Ser Asp Phe Ser Met Phe Asp Glu Val Asp
 65                  70                  75                  80

Glu Ala Pro Ile Tyr Gly Thr Thr Lys Phe Lys Glu Trp Trp Arg Ser
                 85                  90                  95

Gly Gly Phe Ser Phe Gly Lys Ala Tyr Glu Tyr Gly Pro Asn Pro His
            100                 105                 110

Gly Ala Asn Ser Arg Ser Arg Lys Pro Ser Ser Asn Ala Ser Arg Gly
        115                 120                 125

Ala Pro Ser Gly Ser Ser Pro Pro His Ser Gln Ser Ser Ser Ser Gly
130                 135                 140

Tyr Gly Ser Phe Ser Ala Ser Gln Ala Ser Asp Ser Gln Ser Arg Gly
145                 150                 155                 160

Pro Asp Ile Pro Pro Glu His His Glu Pro Thr Ser Ser Ser Ser Gly
                165                 170                 175

Ser Ser Ser Arg Glu Glu Thr Thr Asn Ser Gly Arg Glu Ser Ser Thr
            180                 185                 190

Pro Asn Gly Thr Ser Val Pro Arg Asn Ser Ser Arg Thr Tyr Gly Thr
        195                 200                 205

Trp Glu Asp Leu Phe Cys Asp Glu Ser Leu Ser Ser Pro Glu Pro Pro
210                 215                 220

Ser Ser Ser Glu Glu Pro Glu Glu Pro Ser Ser Arg Ser Ser Ser Pro
225                 230                 235                 240

Arg Gln Pro Pro Cys Ser Ser Ala Glu Glu Ala Ser Ser Ser Gln Phe
                245                 250                 255

Thr Asp Xaa Glu Tyr Ile Ser Ser Phe Thr Thr Pro Lys Thr Pro
            260                 265                 270

Pro Pro Phe Ser Arg Lys Arg Lys Phe Gly Gly Ser Arg Ser Ser Ala
        275                 280                 285

Ser Ser Ala Ser Ser Ala Ser Phe Thr Ser Thr Pro Pro Lys Leu Lys
290                 295                 300

Asn Asn Arg Glu Thr Pro Val Pro Thr Asn Phe Pro Ile Asp Val Ser
305                 310                 315                 320

Asp Tyr Leu Ser His Ala Val Tyr Ser Asn Lys Thr Ala Asn Leu Arg
                325                 330                 335

Asp Ser Leu Asp Gln Asn Met Glu Ile Arg Lys Arg Ile Leu Gln
        340                 345                 350

Ser Gly Thr Thr Leu Leu Leu Cys Leu Ile Trp Cys Leu Pro Asp Thr
355                 360                 365

Thr Phe Lys Pro Cys Leu Gln Glu Glu Ile Lys Asn Trp Lys Gln Ile
370                 375                 380

Leu Gln Ser Glu Ile Ser Tyr Gly Lys Phe Cys Gln Met Ile Glu Asn
385                 390                 395                 400

Val Glu Ala Gly Gln Asp Pro Leu Leu Asn Ile Leu Ile Glu Glu Glu
                405                 410                 415

Gly Pro Glu Glu Thr Glu Glu Thr Gln Asp Ser Gly Thr Phe Ser Gln
            420                 425                 430

<210> SEQ ID NO 17
<211> LENGTH: 537
<212> TYPE: DNA
<213> ORGANISM: Merkel Cell Carcinoma Virus
```

<220> FEATURE:
<221> NAME/KEY: misc_feature
<222> LOCATION: (1)..(537)
<223> OTHER INFORMATION: MCV_350 T-4 gene

<400> SEQUENCE: 17

```
atggatttag tcctaaatag gaaagaaaga gaggctctgt gcaagctttt ggagattgct      60
cctaattgtt atggcaacat ccctctgatg aaagctgctt tcaaaagaag ctgcttaaag     120
catcaccctg ataaggggg aaatcctgtt ataatgatgg aattgaacac cctttggagc      180
aaattccagc aaaatatcca aagctcaga agtgacttct ctatgtttga tgaggcaaat     240
ctaagagatt ccctggatca aacatggaa ataagaaaaa gaagaattct tcaaagtgga      300
accactttat tgctttgtct tatttggtgc ttgcctgata aacccttaa gccttgctta     360 caagaagaaa ttaaaaactg gaagcaaatt ttacagagtg aaatatcata tggtaaattt     420
tgtcaaatga tagaaaatgt agaagctggt caggaccctc tgctcaatat tcttattgag     480
gaagagggcc ctgaggaaac tgaggaaacc caagattctg gtacttttttc tcaataa      537
```

<210> SEQ ID NO 18
<211> LENGTH: 178
<212> TYPE: PRT
<213> ORGANISM: Merkel Cell Carcinoma Virus
<220> FEATURE:
<221> NAME/KEY: MISC_FEATURE
<222> LOCATION: (1)..(178)
<223> OTHER INFORMATION: MCV_350 T-4 protein

<400> SEQUENCE: 18

```
Met Asp Leu Val Leu Asn Arg Lys Glu Arg Glu Ala Leu Cys Lys Leu
1               5                   10                  15

Leu Glu Ile Ala Pro Asn Cys Tyr Gly Asn Ile Pro Leu Met Lys Ala
            20                  25                  30

Ala Phe Lys Arg Ser Cys Leu Lys His His Pro Asp Lys Gly Gly Asn
        35                  40                  45

Pro Val Ile Met Met Glu Leu Asn Thr Leu Trp Ser Lys Phe Gln Gln
    50                  55                  60

Asn Ile His Lys Leu Arg Ser Asp Phe Ser Met Phe Asp Glu Ala Asn
65                  70                  75                  80

Leu Arg Asp Ser Leu Asp Gln Asn Met Glu Ile Arg Lys Arg Arg Ile
                85                  90                  95

Leu Gln Ser Gly Thr Thr Leu Leu Cys Leu Ile Trp Cys Leu Pro
            100                 105                 110

Asp Thr Thr Phe Lys Pro Cys Leu Gln Glu Glu Ile Lys Asn Trp Lys
        115                 120                 125

Gln Ile Leu Gln Ser Glu Ile Ser Tyr Gly Lys Phe Cys Gln Met Ile
    130                 135                 140

Glu Asn Val Glu Ala Gly Gln Asp Pro Leu Leu Asn Ile Leu Ile Glu
145                 150                 155                 160

Glu Glu Gly Pro Glu Glu Thr Glu Glu Thr Gln Asp Ser Gly Thr Phe
                165                 170                 175

Ser Gln
```

<210> SEQ ID NO 19
<211> LENGTH: 678
<212> TYPE: DNA
<213> ORGANISM: Merkel Cell Carcinoma Virus
<220> FEATURE:
<221> NAME/KEY: misc_feature
<222> LOCATION: (1)..(678)

<223> OTHER INFORMATION: MCV_350 T-5 gene similar to middle T pattern

<400> SEQUENCE: 19

```
atgcatccag gggagccccc agtggaagct caccacccca cagccagagc tcttcctctg    60
ggtatgggtc cttctcagcg tcccaggctt cagactccca gtccagagga cccgatatac   120
ctcccgaaca ccatgaggaa cccacctcat cctctggatc cagtagcaga gaggagacca   180
ccaattcagg aagagaatcc agcacaccca atggaaccag tgtacctaga aattcttcca   240
gaacgtatgg cacctgggag gatctcttct gcgatgaatc actttcctcc cctgagcctc   300
cctcgtcctc tgaggagcct gaggagcccc cctcctcaag aagctcgccc cggcagcccc   360
cgtgttcctc tgccgaggag gcctcgtcat ctcagtttac agattaggaa tacatatcct   420
cctccttcac caccccgaag accccctcctc cattctcaag aaagcgaaaa tttgggggt    480
cccgaagctc tgcaagctct gctagttcag caagttttac aagcactcca ccaaagctaa   540
aaaacaacag agaaactcct gttcctacta attttcctat tgatgtttct gattatctta   600
gccatgctgt atatagtaat aaaacagtaa gttgttttgc catttatact acttctgata   660
aagctataga agctatag                                                  678
```

<210> SEQ ID NO 20
<211> LENGTH: 222
<212> TYPE: PRT
<213> ORGANISM: Merkel Cell Carcinoma Virus
<220> FEATURE:
<221> NAME/KEY: MISC_FEATURE
<222> LOCATION: (1)..(222)
<223> OTHER INFORMATION: MCV_350 T-5 protein similar to middle T pattern
<220> FEATURE:
<221> NAME/KEY: MISC_FEATURE
<222> LOCATION: (180)..(180)
<223> OTHER INFORMATION: Xaa marks site of tumor-derived stop codon that is absent in wild-type virus
<220> FEATURE:
<221> NAME/KEY: MISC_FEATURE
<222> LOCATION: (210)..(210)
<223> OTHER INFORMATION: Xaa marks site of tumor-derived stop codon that is absent in wild-type virus

<400> SEQUENCE: 20

Met His Pro Gly Glu Pro Pro Val Glu Ala His His Pro Thr Ala Arg
1               5                   10                  15

Ala Leu Pro Leu Gly Met Gly Pro Ser Gln Arg Pro Arg Leu Gln Thr
            20                  25                  30

Pro Ser Pro Glu Asp Pro Ile Tyr Leu Pro Asn Thr Met Arg Asn Pro
        35                  40                  45

Pro His Pro Leu Asp Pro Val Ala Glu Arg Arg Pro Pro Ile Gln Glu
    50                  55                  60

Glu Asn Pro Ala His Pro Met Glu Pro Val Tyr Leu Glu Ile Leu Pro
65                  70                  75                  80

Glu Arg Met Ala Pro Gly Arg Ile Ser Ser Ala Met Asn His Phe Pro
                85                  90                  95

Pro Leu Ser Leu Pro Arg Pro Leu Arg Ser Leu Arg Ser Pro Pro Pro
            100                 105                 110

Gln Glu Ala Arg Pro Gly Ser Pro Arg Val Pro Leu Pro Arg Arg Pro
        115                 120                 125

Arg His Leu Ser Leu Gln Ile Arg Asn Thr Tyr Pro Pro Ser Pro
    130                 135                 140

Pro Arg Arg Pro Leu Leu His Ser Gln Glu Ser Glu Asn Leu Gly Gly
145                 150                 155                 160

```
Pro Glu Ala Leu Gln Ala Leu Leu Val Gln Gln Val Leu Gln Ala Leu
                165                 170                 175

His Gln Ser Xaa Lys Thr Thr Glu Lys Leu Leu Phe Leu Leu Ile Phe
            180                 185                 190

Leu Leu Met Phe Leu Ile Ile Leu Ala Met Leu Tyr Ile Val Ile Lys
        195                 200                 205

Gln Xaa Val Val Leu Pro Phe Ile Leu Leu Leu Ile Lys Leu
    210                 215                 220

<210> SEQ ID NO 21
<211> LENGTH: 462
<212> TYPE: DNA
<213> ORGANISM: Merkel Cell Carcinoma Virus
<220> FEATURE:
<221> NAME/KEY: misc_feature
<222> LOCATION: (1)..(462)
<223> OTHER INFORMATION: DNA sequence for MCV isolated from NCI-H69
      cells

<400> SEQUENCE: 21
attcaggaag agaatccagc acaccaaatg gaaccagtgt acctagaaat tcttccagaa       60
ctgatggcac ctgggaggat ctcttctgcg atgaatcact ttcctcccct gagcctccct      120
cgtcctctga ggagcctgag gagccccccc cctcaagaag ctcgcccgg  cagccccgt      180 cttcctctgc cgaggaggcc tcgtcatctc agtttacaga tgaggaatac agatcctcct      240
ccttcaccac cccgaagacc cctcctccat tctcaagaaa gcgaaaattt ggggggtccc      300
gaagctctgc aagctctgct agttcagcaa gttttacaag cactccacca aagccaaaaa      360
agaacagaga aactcctgtt cctactgatt ttcctattga tctttctgat tatcttagcc      420
atgctgtata tagtaataaa acagtaagtt gttttgccat tt                         462

<210> SEQ ID NO 22
<211> LENGTH: 461
<212> TYPE: DNA
<213> ORGANISM: Merkel Cell Carcinoma Virus
<220> FEATURE:
<221> NAME/KEY: misc_feature
<222> LOCATION: (1)..(461)
<223> OTHER INFORMATION: DNA sequence for MCV isolated from NCI-H69
      cells

<400> SEQUENCE: 22
ataatcagaa agatcaatag gaaaatcagt aggaacagga gtttctctgt tctttttggg      60
ctttggtgga gtgcttgtaa aacttgctga actagcagag cttgcagagc ttcgggaccc     120
cccaaatttt cgctttcttg agaatggagg aggggtcttc ggggtggtga aggaggagga     180
tctgtattcc tcatctgtaa actgagatga cgaggcctcc tcggcagagg aagacggggg     240
ctgccggggc gagcttcttg aggaggggg ctcctcaggc tcctcagagg acgagggagg     300
ctcaggggag gaaagtgatt catcgcagaa gagatcctcc caggtgccat cagttctgga     360
agaatttcta ggtacactgg ttccatttgg tgtgctggat tctcttcctg aattggtggt     420
ctcctctctg ctactggatc cagaggatga ggtgggttcc t                         461

<210> SEQ ID NO 23
<211> LENGTH: 510
<212> TYPE: DNA
<213> ORGANISM: Merkel Cell Carcinoma Virus
<220> FEATURE:
<221> NAME/KEY: misc_feature
<222> LOCATION: (1)..(510)
<223> OTHER INFORMATION: DNA sequence for MCV isolated from NCI-H69
      cells
```

<400> SEQUENCE: 23

```
aaatggcaaa acaacttact gttttattac tatatacagc atggctaaga taatcagaaa      60
gatcaatagg aaaatcagta ggaacaggag tttctctgtt cttttttggc tttggtggag     120
tgcttgtaaa acttgctgaa ctagcagagc ttgcagagct tcgggacccc ccaaatttc     180
gctttcttga aatggagga ggggtcttcg ggtggtgaa ggaggaggat ctgtattcct       240
catctgtaaa ctgagatgac gaggcctcct cggcagagga agacggggc tgccggggcg     300
agcttcttga ggagggggc tcctcaggct cctcagagga cgagggaggc tcaggggagg      360
aaagtgattc atcgcagaag agatcctccc aggtgccatc agttctggaa gaatttctag    420
gtacactggt tccatttggt gtgctggatt ctcttcctga attggtggtc tcctctctgc    480
tactggatcc agaggatgag gtgggttcct                                      510
```

<210> SEQ ID NO 24
<211> LENGTH: 509
<212> TYPE: DNA
<213> ORGANISM: Merkel Cell Carcinoma Virus
<220> FEATURE:
<221> NAME/KEY: misc_feature
<222> LOCATION: (1)..(509)
<223> OTHER INFORMATION: DNA sequence for MCV isolated from NCI-H69 cells

<400> SEQUENCE: 24

```
aatggcaaaa caacttactg ttttattact atatacagca tggctaagat aatcagaaag      60
atcaatagga aaatcagtag gaacaggagt ttctctgttc ttttttggct tggtggagt     120
gcttgtaaaa cttgctgaac tagcagagct tgcagagctt cggaccccc caaattttcg    180
cttttcttgag aatggaggag gggtcttcgg ggtggtgaag gaggaggatc tgtattcctc    240
atctgtaaac tgagatgacg aggcctcctc ggcagaggaa gacggggct gccggggcga     300
gcttcttgag gagggggct cctcaggctc tcagaggac gagggaggct caggggagga     360
aagtgattca tcgcagaaga gatcctccca ggtgccatca gttctggaag aatttctagg    420
tacactggtt ccatttggtg tgctggattc tcttcctgaa ttggtggtct cctctctgct    480
actggatcca gaggatgagg tgggttcct                                       509
```

<210> SEQ ID NO 25
<211> LENGTH: 261
<212> TYPE: DNA
<213> ORGANISM: Merkel Cell Carcinoma Virus
<220> FEATURE:
<221> NAME/KEY: misc_feature
<222> LOCATION: (1)..(261)
<223> OTHER INFORMATION: DNA sequence for MCV isolated from NCI-H69 cells

<400> SEQUENCE: 25

```
tatacttagg tatattctct gttaataatt gaataatttt ctgcaccttc ttttcaaact      60
cttcaaataa gcagcagtac caggccacac cacccatata atacagtaga tctattgtat    120
ctaaatctct taatctctct aggtgcttct taaacttctt acatagcatt tctgtcctgg    180
tcatttccag catctctaac ctcgtctagc tcatattcac aagcaaattc agcaactaaa    240
ttccaattac agctggcctc t                                               261
```

<210> SEQ ID NO 26
<211> LENGTH: 313
<212> TYPE: DNA
<213> ORGANISM: Merkel Cell Carcinoma Virus

```
<220> FEATURE:
<221> NAME/KEY: misc_feature
<222> LOCATION: (1)..(313)
<223> OTHER INFORMATION: DNA sequence for MCV isolated from NCI-H69
      cells

<400> SEQUENCE: 26
gcagcaaagc ttgttttccc actgttaata ggcccttaaa ccaaatgtt tctatactta       60 ggtatattct ctgttaataa ttgaataatt ttctgcagct tcttttcaaa ctcttcaaat     120
aagcagcagt accaggccac caacccata taatacagta gatctattgt atctaaatct      180
cttaatctct ctaggtgctt cttaaacttc ttacatagca tttctgtcct ggtcatttcc     240
agcatctcta acctcgtcta gctcatattc acaagcaaat tcagcaacta aattccaatt    300
acagctggcc tct                                                        313

<210> SEQ ID NO 27
<211> LENGTH: 312
<212> TYPE: DNA
<213> ORGANISM: Merkel Cell Carcinoma Virus
<220> FEATURE:
<221> NAME/KEY: misc_feature
<222> LOCATION: (1)..(312)
<223> OTHER INFORMATION: DNA sequence for MCV isolated from NCI-H69
      cells

<400> SEQUENCE: 27
cagcaaagct tgtttttcca ctgttaatag gcccttaaa ccaaatgttt ctatacttag       60
gtatattctc tgttaataat tgaataattt tctgcagctt cttttcaaac tcttcaaata    120
agcagcagta ccaggccaca ccacccatat aatacagtag atctattgta tctaaatctc    180
ttaatctctc taggtgcttc ttaaacttct tacatagcat ttctgtcctg gtcatttcca    240
gcatctctaa cctcgtctag ctcatattca caagcaaatt cagcaactaa attccaatta   300
cagctggcct ct                                                        312

<210> SEQ ID NO 28
<211> LENGTH: 456
<212> TYPE: DNA
<213> ORGANISM: Merkel Cell Carcinoma Virus
<220> FEATURE:
<221> NAME/KEY: misc_feature
<222> LOCATION: (1)..(456)
<223> OTHER INFORMATION: DNA sequence for MCV isolated from NCI-H69
      cells

<400> SEQUENCE: 28
tctaactact gtcctttag atgagaatgg agtgggccct ctatgcaaag gagacagcct      60
atttattagc tgtgcasaca tagtgggggtt tctgtttaaa accagtggaa aaatggctct   120
tcatgggttg cctagatatt ttaatgttac tttgagaaaa atatgggtga aaaccccta    180 cccagtagtt aatttaataa actcactctt yagcaactta atgccaaaag tgtcaggcca   240
acctatggaa ggaaaagata tcaggtaga agaggttaga atatatgagg ggtcagaaca    300
attacctggt gatcctgata ttgtcagatt tttagataaa tttgggcagg agaaaactgt   360
ttacccaaag ccctctgttg ccccagcagc agtaacattc caaagtaatc agcaggataa   420
gggcaaggcg ccactgaaag gacctcaaaa ggcctc                              456

<210> SEQ ID NO 29
<211> LENGTH: 460
<212> TYPE: DNA
<213> ORGANISM: Merkel Cell Carcinoma Virus
<220> FEATURE:
```

```
<221> NAME/KEY: misc_feature
<222> LOCATION: (1)..(460)
<223> OTHER INFORMATION: DNA sequence for MCV isolated from NCI-H69
      cells

<400> SEQUENCE: 29
ctgctgatta ctttggaatg ttactgctgc tggggcaaca gagggctttg ggtaaacagt    60
tttctcctgc ccaaatttat ctaaaaatct gacaatatca ggatcaccag gtaattgttc   120
tgacccctca tatattctaa cctcttctac ctgattatct tttccttcca taggttggcc   180
tgacactttt ggcattaagt tgctraagag tgagtttatt aaattaacta ctgggtaggg   240 gttttttcacc catmttttc tcaaagtaac attaaaatat ctaggcaacc catgaagagc   300
cattttccca ctggttttaa acagaaaccc cactatgtst gcacagctaa taaataggcc   360
gtctcctttg catagagggc ccactccatt ctcatctaaa aggacagtag ttagagtatt   420
actaaattga agaactgtag gagtctgaga gcctgtctga                         460

<210> SEQ ID NO 30
<211> LENGTH: 499
<212> TYPE: DNA
<213> ORGANISM: Merkel Cell Carcinoma Virus
<220> FEATURE:
<221> NAME/KEY: misc_feature
<222> LOCATION: (1)..(499)
<223> OTHER INFORMATION: DNA sequence for MCV isolated from NCI-H69
      cells

<400> SEQUENCE: 30
gaggcctttt gaggtccttt cagtggcgcc ttgcccttat cctgctgatt actttggaat    60
gttactgctg ctggggcaac agagggcttt gggtaaacag ttttctcctg cccaaattta   120
tctaaaaatc tgacaatatc aggatcacca gtaattgtt ctgaccccctc atatattcta   180 acctcttcta cctgattatc ttttccttcc ataggttggc ctgacacttt tggcattaag   240
ttgctgaaga gtgagtttat taaattaact actgggtagg gttttttcac ccatcttttt   300
ctcaaagtaa cattaaaata tctaggcaac ccatgaagag ccattttcc actggttta    360 aacagaaacc ccactatgtc tgcacagcta ataaataggc cgtctccttt gcatagaggg   420
cccactccat tctcatctaa aggacagta gttagagtat tactaaattg aagaactgta   480
ggagtctgag agcctgtct                                                499

<210> SEQ ID NO 31
<211> LENGTH: 499
<212> TYPE: DNA
<213> ORGANISM: Merkel Cell Carcinoma Virus
<220> FEATURE:
<221> NAME/KEY: misc_feature
<222> LOCATION: (1)..(499)
<223> OTHER INFORMATION: DNA sequence for MCV isolated from NCI-H69
      cells

<400> SEQUENCE: 31
gaggcctttt gaggtccttt cagtggcgcc ttgcccttat cctgctgatt actttggaat    60
gttactgctg ctggggcaac agagggcttt gggtaaacag ttttctcctg cccaaattta   120
tctaaaaatc tgacaatatc aggattacca ggtaattgtt ctgaccccctc atatattctg   180 acctcttcta cctgattatc ttttccttcc ataggttggc ctgacacttt tggcattaag   240
ttgctgaaga gtgagtttat taaattaact actgggtagg gttttttcac ccatattttt   300
ctcaaagtaa cattaaaata tctaggcaac ccatgaagag ccattttcc actggttta    360 aacagaaacc ccactatgtg tgcacagcta ataaataggc catctccttt gcatagaggg   420
```

```
cccactccat tctcatctaa aaggacagta gttagagtat tactaaattg aagaactgta      480
ggagtctgag agcctgtct                                                   499
```

<210> SEQ ID NO 32
<211> LENGTH: 462
<212> TYPE: DNA
<213> ORGANISM: Merkel Cell Carcinoma Virus
<220> FEATURE:
<221> NAME/KEY: misc_feature
<222> LOCATION: (1)..(462)
<223> OTHER INFORMATION: DNA sequence for MCV isolated from NCI-H69
      cells

<400> SEQUENCE: 32

```
gggaggcaat atctgttaaa acagaagtag ttggaataag ttctttaatt aatgttcatt       60
attgggacat gaaaagagtt catgattatg gtgctggtat tcctgtgtca ggggtaaatt      120
accatatgtt tgccattggg ggagaacctc tggatttgca aggcctagtt ttagattacc      180
agactsagta tccaaaaact acaaatggtg gcctattac aattgaaact gtattgggaa       240
gaaaaatgac acctaaaaat cagggcctag atccacaagc taaagcaaaa ttagataaag      300
atgsaaatta tcctatagaa gtatggtgtc ctgatccttc taaaaatgaa acagtagat       360 actatgggtc tattcagaca ggctctcaga ctccctacagt tcttcaattt agtaatactc     420
taactactgt cctttagat gagaatggag tgggccctct at                          462
```

<210> SEQ ID NO 33
<211> LENGTH: 466
<212> TYPE: DNA
<213> ORGANISM: Merkel Cell Carcinoma Virus
<220> FEATURE:
<221> NAME/KEY: misc_feature
<222> LOCATION: (1)..(466)
<223> OTHER INFORMATION: DNA sequence for MCV isolated from NCI-H69
      cells

<400> SEQUENCE: 33

```
agtattacta aattgaagaa ctgtaggagt ctgagagcct gtctgaatag acccatagta       60
tctactgttt tcatttttag aaggatcagg acaccatact tctataggat aatttscatc      120
tttatctaat tttgctttag cttgtggatc taggccctga ttttaggtg tcattttct        180 tcccaataca gtttcaattg taataggccc accatttgta gttttggat actsagtctg       240 gtaatctaaa actaggcctt gcaaatccag aggttctccc ccaatggcaa acatatggta      300
atttacccct gacacaggaa taccagcacc ataatcatga actcttttca tgtcccaata      360
atgaacatta ttaaagaac ttattccaac tacttctgtt ttaacagata ttgcctccca       420
catctgcaat gtgtcacagg taatatcctc atttagcatt ggcaga                     466
```

<210> SEQ ID NO 34
<211> LENGTH: 509
<212> TYPE: DNA
<213> ORGANISM: Merkel Cell Carcinoma Virus
<220> FEATURE:
<221> NAME/KEY: misc_feature
<222> LOCATION: (1)..(509)
<223> OTHER INFORMATION: DNA sequence for MCV isolated from NCI-H69
      cells

<400> SEQUENCE: 34

```
atagagggcc cactccattc tcatctaaaa ggacagtagt tagagtatta ctaaattgaa       60
gaactgtagg agtctgagag cctgtctgaa tagacccata gtatctactg ttttcatttt      120
```

```
tagaaggatc aggacaccat acttctatag gataatttgc atctttatct aattttgctt        180
tagcttgtgg atctaggccc tgattttag gtgtcatttt tcttcccaat acagtttcaa         240
ttgtaatagg cccaccattt gtagttttg gatactcagt ctggtaatct aaaactaggc         300
cttgcaaatc cagaggttct cccccaatgg caaacatatg gtaatttacc cctgacacag        360
gaataccagc accataatca tgaactcttt tcatgtccca ataatgaaca ttaattaaag        420
aacttattcc aactacttct gttttaacag atattgcctc ccacatctgc aatgtgtcac        480
aggtaatatc ctcatttagc attggcaga                                         509
```

<210> SEQ ID NO 35
<211> LENGTH: 509
<212> TYPE: DNA
<213> ORGANISM: Merkel Cell Carcinoma Virus
<220> FEATURE:
<221> NAME/KEY: misc_feature
<222> LOCATION: (1)..(509)
<223> OTHER INFORMATION: DNA sequence for MCV isolated from NCI-H69
      cells

<400> SEQUENCE: 35

```
atagagggcc cactccattc tcatctaaaa ggacagtagt tagagtatta ctaaattgaa         60
gaactgtagg agtctgagag cctgtctgaa tagacccata gtatctactg ttttcatttt        120
tagaaggatc aggacaccat acttctatag gataatttcc atctttatct aattttgctt        180
tagcttgtgg atctaggccc tgattttag gtgtcatttt tcttcccaat acagtttcaa         240
ttgtaatagg cccaccattt gtagttttg gatactgagt ctggtaatct aaaactaggc         300
cttgcaaatc cagaggttct cccccaatgg caaacatatg gtaatttacc cctgacacag        360
gaataccagc accataatca tgaactcttt tcatgtccca ataatgaaca ttaattaaag        420
aacttattcc aactacttct gttttaacag atattgcctc ccacatctgc aatgtgtcac        480
aggtaatatc ctcatttagc attggcaga                                         509
```

<210> SEQ ID NO 36
<211> LENGTH: 510
<212> TYPE: DNA
<213> ORGANISM: Merkel Cell Carcinoma Virus
<220> FEATURE:
<221> NAME/KEY: misc_feature
<222> LOCATION: (1)..(510)
<223> OTHER INFORMATION: DNA sequence for MCV isolated from NCI-H146
      cells

<400> SEQUENCE: 36

```
aggaacccac ctcatcctct ggatccagta gcagagagga gaccaccaat tcaggaagag         60
aatccagcac acccaatgga accagtgtac ctagaaattc ttccagaacg tatggcacct        120
gggaggatct cttctgcgat gaatcacttt cctcccctga gcctccctcg tcctctgagg        180
agcctgagga gcccccctcc tcaagaagct cgccccggca gccccgtgt tcctctgccg         240 aggaggcctc gtcatctcag tttacagatt aggaatacat atcctcctcc ttcaccaccc        300
cgaagacccc tcctccattc tcaagaaagc gaaaatttgg ggggtcccga agctctgcaa        360
gctctgctag ttcagcaagt tttacaagca ctccaccaaa gccaaaaaac aacagagaaa        420
ctcctgttcc tactaatttt cctgttgatg tttctgatta tcttagccat gctgtatata        480
gtaataaaac agtaagttgt tttgccattt                                        510
```

<210> SEQ ID NO 37
<211> LENGTH: 510
<212> TYPE: DNA

```
<213> ORGANISM: Merkel Cell Carcinoma Virus
<220> FEATURE:
<221> NAME/KEY: misc_feature
<222> LOCATION: (1)..(510)
<223> OTHER INFORMATION: DNA sequence for MCV isolated from NCI-H146
      cells

<400> SEQUENCE: 37
aaatggcaaa acaacttact gttttattac tatatacagc atggctaaga taatcagaaa      60
gatcaatagg aaaatcagta ggaacaggag tttctctgtt cttttttggc tttggtggag     120
tgcttgtaaa acttgctgaa ctagcagagc ttgcagagct tcggaccccc ccaaattttc     180
gctttcttga aatggagga ggggtcttcg gggtggtgaa ggaggaggat ctgtattcct      240
catctgtaaa ctgagatgac aaggcctcct cggcagagga agacggggc tgccggggcg      300 agcttcttga ggaggggggc tcctcaggct cctcaggag cgaggggagc tcaggggagg      360
aaagtgattc atcgcagaag agatcctccc aggtgccatc agttctggaa gaatttctag     420
gtacactggt tccatttggt gtgctggatt ctcttcctga attggtggtc tcctctctgc     480
tactggatcc agaggatgag gtgggttcct                                      510

<210> SEQ ID NO 38
<211> LENGTH: 313
<212> TYPE: DNA
<213> ORGANISM: Merkel Cell Carcinoma Virus
<220> FEATURE:
<221> NAME/KEY: misc_feature
<222> LOCATION: (1)..(313)
<223> OTHER INFORMATION: DNA sequence for MCV isolated from NCI-H146
      cells

<400> SEQUENCE: 38
gcagcaaagc ttgttttttcc actgttaata ggccctttaa accaaatgtt tctatactta     60
ggtatattct ctgttaataa ttgaataatt ttctgcagct tcttttcaaa ctcttcaaat    120
aagcagcagt accaggccac accacccata taatacagta gatctattgt atctaaatct    180
cttaatctct ctaggtgctt cttaaacttc ttacatagca tttctgtcct ggtcatttcc    240
agcatctcta acctcgtcta gctcatattc acaagcaaat tcagcaacta aattccaatt    300
acagctggcc tct                                                        313

<210> SEQ ID NO 39
<211> LENGTH: 313
<212> TYPE: DNA
<213> ORGANISM: Merkel Cell Carcinoma Virus
<220> FEATURE:
<221> NAME/KEY: misc_feature
<222> LOCATION: (1)..(313)
<223> OTHER INFORMATION: DNA sequence for MCV isolated from NCI-H146
      cells

<400> SEQUENCE: 39
gcagcaaagc ttgttttttcc actgttaata ggccctttaa accaaatgtt tctatactta     60
ggtatattct ctgttaataa ttgaataatt ttctgcagct tcttttcaaa ctcttcaaat    120
aagcagcagt accaggccac accacccata taatacagta gatctattgt atctaaatct    180
cttaatctct ctaggtgctt cttaaacttc ttacatagca tttctgtcct ggtcatttcc    240
agcatctcta acctcgtcta gctcatattc acaagcaaat tcagcaacta aattccaatt    300
acagctggcc tct                                                        313

<210> SEQ ID NO 40
<211> LENGTH: 445
```

```
<212> TYPE: DNA
<213> ORGANISM: Merkel Cell Carcinoma Virus
<220> FEATURE:
<221> NAME/KEY: misc_feature
<222> LOCATION: (1)..(445)
<223> OTHER INFORMATION: DNA sequence for MCV isolated from NCI-H146
      cells

<400> SEQUENCE: 40
tggatgttac tgctgctggg gcaacagagg gctttgggta acagttttc tcctgcccaa      60 atttatctaa aaatctgaca atatcaggat taccaggtaa ttgttctgac ccctcatata    120
ttctgacctc ttctacctga ttatctttc cttccatagg ttggcctgac acctttggca    180
ttaagttgct gaagagtgag tttattaaat taactactgg gtaggggttt ttcacccata    240
tttttctcaa agtaacatta aaatatctag gcaacccatg aagagccatt tttccactgg    300
ttttaaacag aaaccccact atgtgtgcac agctaataaa taggccatct cctttgcata    360
gagggcccac tccattctca tctaaaagga cagtagttag agtattacta aattgaagaa    420
ctgtaggagt ctgagagcct gtctg                                          445

<210> SEQ ID NO 41
<211> LENGTH: 458
<212> TYPE: DNA
<213> ORGANISM: Merkel Cell Carcinoma Virus
<220> FEATURE:
<221> NAME/KEY: misc_feature
<222> LOCATION: (1)..(458)
<223> OTHER INFORMATION: DNA sequence for MCV isolated from NCI-H146
      cells

<400> SEQUENCE: 41
actctaacta ctgtcctttt agatgagaat ggagtgggcc ctctatgcaa aggagatggc      60
ctatttatta gctgtgcaca catagtgggg tttctgttta aaaccagtgg aaaaatggct    120
cttcatgggt tgcctagata ttttaatgtt actttgagaa aatatgggt gaaaaacccc     180 tacccagtag ttaatttaat aaactcactc ttcagcaact taatgccaaa ggtgtcaggc    240
caacctatgg aaggaaaaga taatcaggta gaagaggtca gaatatatga ggggtcagaa    300
caattacctg gtaatcctga tattgtcaga ttttagata aatttgggca ggagaaaact    360
gtttacccaa agccctctgt tgccccagca gcagtaacat tccaaagtaa tcagcaggat    420
aagggcaagg cgccactgaa aggacctcaa aaggcctc                            458

<210> SEQ ID NO 42
<211> LENGTH: 501
<212> TYPE: DNA
<213> ORGANISM: Merkel Cell Carcinoma Virus
<220> FEATURE:
<221> NAME/KEY: misc_feature
<222> LOCATION: (1)..(501)
<223> OTHER INFORMATION: DNA sequence for MCV isolated from NCI-H146
      cells

<400> SEQUENCE: 42
tcagacaggc tctcagactc ctacagttct tcaatttagt aatactctaa ctactgtcct      60
tttagatgag aatggagtgg gccctctatg caaaggagat ggcctatttta ttagctgtgc   120 acacatagtg gggtttctgt ttaaaaccag tggaaaaatg gctcttcatg ggttgcctag    180
atattttaat gttactttga gaaaatatgg gtgaaaaac ccctacccag tagttaattt     240
aataaactca ctcttcagca acttaatgcc aaaggtgtca ggccaaccta tggaaggaaa    300
agataatcag gtagaagagg tcagaatata tgaggggtca gaacaattac ctggtaatcc    360
```

```
tgatattgtc agattttag ataaatttgg gcaggagaaa actgtttacc caaagccctc    420
tgttgcccca gcagcagtaa cattccaaag taatcagcag gataagggca aggcgccact    480
gaaaggacct caaaaggcct c                                              501
```

<210> SEQ ID NO 43
<211> LENGTH: 499
<212> TYPE: DNA
<213> ORGANISM: Merkel Cell Carcinoma Virus
<220> FEATURE:
<221> NAME/KEY: misc_feature
<222> LOCATION: (1)..(499)
<223> OTHER INFORMATION: DNA sequence for MCV isolated from NCI-H146
      cells

<400> SEQUENCE: 43

```
cagacaggct ctcagactcc tacagttctt caatttagta atactctaac tactgtcctt     60
ttagatgaga atggagtggg ccctctatgc aaaggagatg gcctatttat tagctgtgca    120
cacatagtgg ggtttctgtt taaaaccagt ggaaaaatgg ctcttcatgg gttgcctaga    180
tattttaatg ttactttgag aaaaatatgg gtgaaaaacc cctacccagt agttaattta    240
ataaactcac tcttcagcaa cttaatgcca aaggtgtcag gccaacctat ggaaggaaaa    300
gataatcagg tagaagaggt cagaatatat gaggggtcag aacaattacc tggtaatcct    360
gatattgtca gattttaga taaatttggg caggagaaaa ctgtttaccc aaagccctct    420
gttgccccag cagcagtaac attccaaagt aatcagcagg ataagggcaa ggcgccactg    480
aaaggacctc aaaaggcct                                                499
```

<210> SEQ ID NO 44
<211> LENGTH: 461
<212> TYPE: DNA
<213> ORGANISM: Merkel Cell Carcinoma Virus
<220> FEATURE:
<221> NAME/KEY: misc_feature
<222> LOCATION: (1)..(461)
<223> OTHER INFORMATION: DNA sequence for MCV isolated from NCI-H146
      cells

<400> SEQUENCE: 44

```
ggaggcaata tctgttaaaa cagaagtagt tggaataagt tctttaatta atgttcatta     60
ttgggacatg aaaagagttc atgattatgg tgctggtatt cctgtgtcag ggtaaaatta    120
ccatatgttt gccattgggg gagaacctct ggatttgcaa ggcctagttt tagattacca    180
gactgaatat ccaaaaacta caaatggtgg gcctattaca attgaaacag tattgggaag    240
aaaaatgaca cctaaaaatc agggcctaga tccacaagct aaagcaaaat tagataaaga    300
tggaaattat cctatagaag tatggtgtcc tgatccttct aaaaatgaaa acagtagata    360
ctatgggtct attcagacag gttctcagac tcctacagtt cttcaattca gtaatacttt    420
aactactgtc cttttagatk agaatggagt gggccctcta t                       461
```

<210> SEQ ID NO 45
<211> LENGTH: 457
<212> TYPE: DNA
<213> ORGANISM: Merkel Cell Carcinoma Virus
<220> FEATURE:
<221> NAME/KEY: misc_feature
<222> LOCATION: (1)..(457)
<223> OTHER INFORMATION: DNA sequence for MCV isolated from NCI-H146
      cells

<400> SEQUENCE: 45

```
gaattgaaga actgtaggag tctgagaacc tgtctgaata gacccatagt atctactgtt     60
```

```
ttcattttta gaaggatcag gacaccatac ttctatagga taatttccat ctttatctaa      120
ttttgcttta gcttgtggat ctaggccctg atttttaggt gtcatttttc ttcccaatac      180
tgtttcaatt gtaataggcc caccatttgt agtttttgga tattcagtct ggtaatctaa      240
aactaggcct tgcaaatcca gaggttctcc cccaatggca acatatggt aatttacccc      300 tgacacagga ataccagcac cataatcatg aactcttttc atgtcccaat aatgaacatt      360
aattaaagaa cttattccaa ctacttctgt tttaacagat attgcctccc acatctgcaa      420
tgtgtcacag gtaatatcct catttagcat tggcaga                              457
```

```
<210> SEQ ID NO 46
<211> LENGTH: 31
<212> TYPE: DNA
<213> ORGANISM: Artificial Sequence
<220> FEATURE:
<223> OTHER INFORMATION: Primer

<400> SEQUENCE: 46
ttctcttgca gtaatttgta agggacttac                                      31

<210> SEQ ID NO 47
<211> LENGTH: 22
<212> TYPE: DNA
<213> ORGANISM: Artificial Sequence
<220> FEATURE:
<223> OTHER INFORMATION: Primer

<400> SEQUENCE: 47
tttcaggcat cttattcact cc                                              22

<210> SEQ ID NO 48
<211> LENGTH: 28
<212> TYPE: DNA
<213> ORGANISM: Artificial Sequence
<220> FEATURE:
<223> OTHER INFORMATION: Primer

<400> SEQUENCE: 48
agcaggcatg cctgtgaatt aggatgta                                        28

<210> SEQ ID NO 49
<211> LENGTH: 22
<212> TYPE: DNA
<213> ORGANISM: Artificial Sequence
<220> FEATURE:
<223> OTHER INFORMATION: Primer

<400> SEQUENCE: 49
tttttgctct accttctgca ct                                              22

<210> SEQ ID NO 50
<211> LENGTH: 33
<212> TYPE: DNA
<213> ORGANISM: Artificial Sequence
<220> FEATURE:
<223> OTHER INFORMATION: Primer

<400> SEQUENCE: 50
taatacaagc gcacttagaa tctctaagtt gct                                  33

<210> SEQ ID NO 51
<211> LENGTH: 32
<212> TYPE: DNA
<213> ORGANISM: Artificial Sequence
```

```
<220> FEATURE:
<223> OTHER INFORMATION: Primer

<400> SEQUENCE: 51
tttccttggg aagaatatgg aactttaaag ga                              32

<210> SEQ ID NO 52
<211> LENGTH: 22
<212> TYPE: DNA
<213> ORGANISM: Artificial Sequence
<220> FEATURE:
<223> OTHER INFORMATION: Primer

<400> SEQUENCE: 52
gctagatttt gcagaggtcc tg                                         22

<210> SEQ ID NO 53
<211> LENGTH: 23
<212> TYPE: DNA
<213> ORGANISM: Artificial Sequence
<220> FEATURE:
<223> OTHER INFORMATION: Primer

<400> SEQUENCE: 53
ccagacccaa ctarraatga raa                                        23

<210> SEQ ID NO 54
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(17)
<223> OTHER INFORMATION: N can be A, T, G, or C
<220> FEATURE:
<221> NAME/KEY: misc_feature
<222> LOCATION: (23)..(23)
<223> OTHER INFORMATION: N can be A, T, G, or C

<400> SEQUENCE: 54
aacaagagac acaaatnttt ccncc                                      25

<210> SEQ ID NO 55
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (20)..(20)
<223> OTHER INFORMATION: N can be A, T, G, or C
<220> FEATURE:
<221> NAME/KEY: misc_feature
<222> LOCATION: (23)..(23)
<223> OTHER INFORMATION: N can be A, T, G, or C

<400> SEQUENCE: 55
atgaaaatgg ggttggcccn ctntgyaarg                                 30

<210> SEQ ID NO 56
<211> LENGTH: 29
<212> TYPE: DNA
<213> ORGANISM: Artificial Sequence
<220> FEATURE:
<223> OTHER INFORMATION: Primer

<400> SEQUENCE: 56
```
ccctcataaa cccgaacytc ytchacytg                                           29

<210> SEQ ID NO 57
<211> LENGTH: 22
<212> TYPE: DNA
<213> ORGANISM: Artificial Sequence
<220> FEATURE:
<223> OTHER INFORMATION: Primer

<400> SEQUENCE: 57
ggagtgaata agatgcctga aa                                                  22

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
atgggtgaaa aacccctacc                                                     20

<210> SEQ ID NO 59
<211> LENGTH: 27
<212> TYPE: DNA
<213> ORGANISM: Artificial Sequence
<220> FEATURE:
<223> OTHER INFORMATION: Primer

<400> SEQUENCE: 59
ggtagagcaa aaattcttaa tagcaga                                             27

<210> SEQ ID NO 60
<211> LENGTH: 20
<212> TYPE: DNA
<213> ORGANISM: Artificial Sequence
<220> FEATURE:
<223> OTHER INFORMATION: Primer

<400> SEQUENCE: 60
ctaggcaacc catgaagagc                                                     20

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
actcttgcca cactgtaagc                                                     20

<210> SEQ ID NO 62
<211> LENGTH: 19
<212> TYPE: DNA
<213> ORGANISM: Artificial Sequence
<220> FEATURE:
<223> OTHER INFORMATION: Primer

<400> SEQUENCE: 62
caggggagga aagtgattc                                                      19

<210> SEQ ID NO 63
<211> LENGTH: 21
<212> TYPE: DNA
<213> ORGANISM: Artificial Sequence -continued

```
<220> FEATURE:
<223> OTHER INFORMATION: Primer

<400> SEQUENCE: 63
gggtaatgct atcttctcca g                                              21

<210> SEQ ID NO 64
<211> LENGTH: 18
<212> TYPE: DNA
<213> ORGANISM: Artificial Sequence
<220> FEATURE:
<223> OTHER INFORMATION: Primer

<400> SEQUENCE: 64
tattcgtatg ccttcccg                                                  18

<210> SEQ ID NO 65
<211> LENGTH: 24
<212> TYPE: DNA
<213> ORGANISM: Artificial Sequence
<220> FEATURE:
<223> OTHER INFORMATION: Primer

<400> SEQUENCE: 65
cacagataat acttccactc ctcc                                           24

<210> SEQ ID NO 66
<211> LENGTH: 19
<212> TYPE: DNA
<213> ORGANISM: Artificial Sequence
<220> FEATURE:
<223> OTHER INFORMATION: Primer

<400> SEQUENCE: 66
ttatcagtca aactccgcc                                                 19

<210> SEQ ID NO 67
<211> LENGTH: 19
<212> TYPE: DNA
<213> ORGANISM: Artificial Sequence
<220> FEATURE:
<223> OTHER INFORMATION: Primer

<400> SEQUENCE: 67
tcaatgccag aaaccctgc                                                 19

<210> SEQ ID NO 68
<211> LENGTH: 19
<212> TYPE: DNA
<213> ORGANISM: Artificial Sequence
<220> FEATURE:
<223> OTHER INFORMATION: Primer

<400> SEQUENCE: 68
aacagcagag gagcaaatg                                                 19

<210> SEQ ID NO 69
<211> LENGTH: 19
<212> TYPE: DNA
<213> ORGANISM: Artificial Sequence
<220> FEATURE:
<223> OTHER INFORMATION: Primer

<400> SEQUENCE: 69
tctgcccttA gatactgcc                                                 19
```

```
<210> SEQ ID NO 70
<211> LENGTH: 20
<212> TYPE: DNA
<213> ORGANISM: Artificial Sequence
<220> FEATURE:
<223> OTHER INFORMATION: Primer

<400> SEQUENCE: 70
ttggctgcct aggtgacttt                                              20

<210> SEQ ID NO 71
<211> LENGTH: 20
<212> TYPE: DNA
<213> ORGANISM: Artificial Sequence
<220> FEATURE:
<223> OTHER INFORMATION: Primer

<400> SEQUENCE: 71
ccaggacctc tgcaaaatct                                              20

<210> SEQ ID NO 72
<211> LENGTH: 20
<212> TYPE: DNA
<213> ORGANISM: Artificial Sequence
<220> FEATURE:
<223> OTHER INFORMATION: Primer

<400> SEQUENCE: 72
ggaattgaac accctttgga                                              20

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73
atataggggc ctcgtcaacc                                              20

<210> SEQ ID NO 74
<211> LENGTH: 20
<212> TYPE: DNA
<213> ORGANISM: Artificial Sequence
<220> FEATURE:
<223> OTHER INFORMATION: Primer

<400> SEQUENCE: 74
tgcttactgc atctgcacct                                              20

<210> SEQ ID NO 75
<211> LENGTH: 20
<212> TYPE: DNA
<213> ORGANISM: Artificial Sequence
<220> FEATURE:
<223> OTHER INFORMATION: Primer

<400> SEQUENCE: 75
gggaggaaag tgattcatcg                                              20

<210> SEQ ID NO 76
<211> LENGTH: 20
<212> TYPE: DNA
<213> ORGANISM: Artificial Sequence
<220> FEATURE:
<223> OTHER INFORMATION: Primer

<400> SEQUENCE: 76
```
aggaacccac ctcatcctct                                              20

<210> SEQ ID NO 77
<211> LENGTH: 23
<212> TYPE: DNA
<213> ORGANISM: Artificial Sequence
<220> FEATURE:
<223> OTHER INFORMATION: Primer

<400> SEQUENCE: 77
aaatggcaaa acaacttact gtt                                          23

<210> SEQ ID NO 78
<211> LENGTH: 24
<212> TYPE: DNA
<213> ORGANISM: Artificial Sequence
<220> FEATURE:
<223> OTHER INFORMATION: Primer

<400> SEQUENCE: 78
aaacaacaga gaaactcctg ttcc                                         24

<210> SEQ ID NO 79
<211> LENGTH: 20
<212> TYPE: DNA
<213> ORGANISM: Artificial Sequence
<220> FEATURE:
<223> OTHER INFORMATION: Primer

<400> SEQUENCE: 79
gagccttgtg aggtttgagg                                              20

<210> SEQ ID NO 80
<211> LENGTH: 20
<212> TYPE: DNA
<213> ORGANISM: Artificial Sequence
<220> FEATURE:
<223> OTHER INFORMATION: Primer

<400> SEQUENCE: 80
agaggccagc tgtaattgga                                              20

<210> SEQ ID NO 81
<211> LENGTH: 20
<212> TYPE: DNA
<213> ORGANISM: Artificial Sequence
<220> FEATURE:
<223> OTHER INFORMATION: Primer

<400> SEQUENCE: 81
gcagcaaagc ttgttttcc                                               20

<210> SEQ ID NO 82
<211> LENGTH: 22
<212> TYPE: DNA
<213> ORGANISM: Artificial Sequence
<220> FEATURE:
<223> OTHER INFORMATION: Primer

<400> SEQUENCE: 82
tttgaaaaga agctgcagaa aa                                           22

<210> SEQ ID NO 83
<211> LENGTH: 20
<212> TYPE: DNA
<213> ORGANISM: Artificial Sequence

```
<220> FEATURE:
<223> OTHER INFORMATION: Primer

<400> SEQUENCE: 83
tgtatcaggc aagcaccaaa                                              20

<210> SEQ ID NO 84
<211> LENGTH: 21
<212> TYPE: DNA
<213> ORGANISM: Artificial Sequence
<220> FEATURE:
<223> OTHER INFORMATION: Primer

<400> SEQUENCE: 84
cactttttcc caaaggcaaa t                                            21

<210> SEQ ID NO 85
<211> LENGTH: 20
<212> TYPE: DNA
<213> ORGANISM: Artificial Sequence
<220> FEATURE:
<223> OTHER INFORMATION: Primer

<400> SEQUENCE: 85
ttacccaaag ccctctgttg                                              20

<210> SEQ ID NO 86
<211> LENGTH: 20
<212> TYPE: DNA
<213> ORGANISM: Artificial Sequence
<220> FEATURE:
<223> OTHER INFORMATION: Primer

<400> SEQUENCE: 86
gaggcctttt gaggtccttt                                              20

<210> SEQ ID NO 87
<211> LENGTH: 21
<212> TYPE: DNA
<213> ORGANISM: Artificial Sequence
<220> FEATURE:
<223> OTHER INFORMATION: Primer

<400> SEQUENCE: 87
tcagacaggc tctcagactc c                                            21

<210> SEQ ID NO 88
<211> LENGTH: 20
<212> TYPE: DNA
<213> ORGANISM: Artificial Sequence
<220> FEATURE:
<223> OTHER INFORMATION: Primer

<400> SEQUENCE: 88
atagagggcc cactccattc                                              20

<210> SEQ ID NO 89
<211> LENGTH: 20
<212> TYPE: DNA
<213> ORGANISM: Artificial Sequence
<220> FEATURE:
<223> OTHER INFORMATION: Primer

<400> SEQUENCE: 89
tctgccaatg ctaaatgagg                                              20
```

```
<210> SEQ ID NO 90
<211> LENGTH: 21
<212> TYPE: DNA
<213> ORGANISM: Artificial Sequence
<220> FEATURE:
<223> OTHER INFORMATION: Primer

<400> SEQUENCE: 90
cctgacacag gaataccagc a                                              21

<210> SEQ ID NO 91
<211> LENGTH: 20
<212> TYPE: DNA
<213> ORGANISM: Artificial Sequence
<220> FEATURE:
<223> OTHER INFORMATION: Primer

<400> SEQUENCE: 91
gcaaactcca gattggcttc                                                20

<210> SEQ ID NO 92
<211> LENGTH: 21
<212> TYPE: DNA
<213> ORGANISM: Artificial Sequence
<220> FEATURE:
<223> OTHER INFORMATION: Primer

<400> SEQUENCE: 92
ttttggaact gaggcaacat t                                              21

<210> SEQ ID NO 93
<211> LENGTH: 20
<212> TYPE: DNA
<213> ORGANISM: Artificial Sequence
<220> FEATURE:
<223> OTHER INFORMATION: Primer

<400> SEQUENCE: 93
taactgtggg ggtgaggttg                                                20

<210> SEQ ID NO 94
<211> LENGTH: 20
<212> TYPE: DNA
<213> ORGANISM: Artificial Sequence
<220> FEATURE:
<223> OTHER INFORMATION: Primer

<400> SEQUENCE: 94
tacccacgaa acatccctgt                                                20

<210> SEQ ID NO 95
<211> LENGTH: 20
<212> TYPE: DNA
<213> ORGANISM: Artificial Sequence
<220> FEATURE:
<223> OTHER INFORMATION: Primer

<400> SEQUENCE: 95
agcctctgcc aacttgaaaa                                                20

<210> SEQ ID NO 96
<211> LENGTH: 20
<212> TYPE: DNA
<213> ORGANISM: Artificial Sequence
<220> FEATURE:
<223> OTHER INFORMATION: Primer

<400> SEQUENCE: 96
```
tacaagcact ccaccaaagc                                               20

<210> SEQ ID NO 97
<211> LENGTH: 20
<212> TYPE: DNA
<213> ORGANISM: Artificial Sequence
<220> FEATURE:
<223> OTHER INFORMATION: Primer

<400> SEQUENCE: 97
tccaattaca gctggcctct                                               20

<210> SEQ ID NO 98
<211> LENGTH: 20
<212> TYPE: DNA
<213> ORGANISM: Artificial Sequence
<220> FEATURE:
<223> OTHER INFORMATION: Primer

<400> SEQUENCE: 98
ttgtctcgcc agcattgtag                                               20

<210> SEQ ID NO 99
<211> LENGTH: 20
<212> TYPE: DNA
<213> ORGANISM: Artificial Sequence
<220> FEATURE:
<223> OTHER INFORMATION: Primer

<400> SEQUENCE: 99
atataggggc ctcgtcaacc                                               20

<210> SEQ ID NO 100
<211> LENGTH: 20
<212> TYPE: DNA
<213> ORGANISM: Artificial Sequence
<220> FEATURE:
<223> OTHER INFORMATION: Primer

<400> SEQUENCE: 100
tttgccagct tacagtgtgg                                               20

<210> SEQ ID NO 101
<211> LENGTH: 21
<212> TYPE: DNA
<213> ORGANISM: Artificial Sequence
<220> FEATURE:
<223> OTHER INFORMATION: Primer

<400> SEQUENCE: 101
tggatctagg ccctgatttt t                                             21

<210> SEQ ID NO 102
<211> LENGTH: 20
<212> TYPE: DNA
<213> ORGANISM: Artificial Sequence
<220> FEATURE:
<223> OTHER INFORMATION: Primer

<400> SEQUENCE: 102
ggcatgcctg tgaattagga                                               20

<210> SEQ ID NO 103
<211> LENGTH: 23
<212> TYPE: DNA
<213> ORGANISM: Artificial Sequence

```
<220> FEATURE:
<223> OTHER INFORMATION: Primer

<400> SEQUENCE: 103
ttgcagtaat ttgtaagggg act                                             23

<210> SEQ ID NO 104
<211> LENGTH: 22
<212> TYPE: DNA
<213> ORGANISM: Artificial Sequence
<220> FEATURE:
<223> OTHER INFORMATION: Primer

<400> SEQUENCE: 104
gctcctaatt gttatggcaa ca                                              22

<210> SEQ ID NO 105
<211> LENGTH: 24
<212> TYPE: DNA
<213> ORGANISM: Artificial Sequence
<220> FEATURE:
<223> OTHER INFORMATION: Primer

<400> SEQUENCE: 105
tgggaaagta cacaaaatct gtca                                            24

<210> SEQ ID NO 106
<211> LENGTH: 20
<212> TYPE: DNA
<213> ORGANISM: Artificial Sequence
<220> FEATURE:
<223> OTHER INFORMATION: Primer

<400> SEQUENCE: 106
tctgccaatg ctaaatgagg                                                 20

<210> SEQ ID NO 107
<211> LENGTH: 20
<212> TYPE: DNA
<213> ORGANISM: Artificial Sequence
<220> FEATURE:
<223> OTHER INFORMATION: Primer

<400> SEQUENCE: 107
atagagggcc cactccattc                                                 20

<210> SEQ ID NO 108
<211> LENGTH: 20
<212> TYPE: DNA
<213> ORGANISM: Artificial Sequence
<220> FEATURE:
<223> OTHER INFORMATION: Primer

<400> SEQUENCE: 108
ttggctgcct aggtgacttt                                                 20

<210> SEQ ID NO 109
<211> LENGTH: 20
<212> TYPE: DNA
<213> ORGANISM: Artificial Sequence
<220> FEATURE:
<223> OTHER INFORMATION: Primer

<400> SEQUENCE: 109
ccaggacctc tgcaaaatct                                                 20
```

```
<210> SEQ ID NO 110
<211> LENGTH: 20
<212> TYPE: DNA
<213> ORGANISM: Artificial Sequence
<220> FEATURE:
<223> OTHER INFORMATION: Primer

<400> SEQUENCE: 110
tgcttactgc atctgcacct                                              20

<210> SEQ ID NO 111
<211> LENGTH: 20
<212> TYPE: DNA
<213> ORGANISM: Artificial Sequence
<220> FEATURE:
<223> OTHER INFORMATION: Primer

<400> SEQUENCE: 111
gggaggaaag tgattcatcg                                              20

<210> SEQ ID NO 112
<211> LENGTH: 20
<212> TYPE: DNA
<213> ORGANISM: Artificial Sequence
<220> FEATURE:
<223> OTHER INFORMATION: Primer

<400> SEQUENCE: 112
agaggccagc tgtaattgga                                              20

<210> SEQ ID NO 113
<211> LENGTH: 20
<212> TYPE: DNA
<213> ORGANISM: Artificial Sequence
<220> FEATURE:
<223> OTHER INFORMATION: Primer

<400> SEQUENCE: 113
gcagcaaagc ttgttttcc                                               20

<210> SEQ ID NO 114
<211> LENGTH: 20
<212> TYPE: DNA
<213> ORGANISM: Artificial Sequence
<220> FEATURE:
<223> OTHER INFORMATION: Primer

<400> SEQUENCE: 114
gaggcctttt gaggtccttt                                              20

<210> SEQ ID NO 115
<211> LENGTH: 21
<212> TYPE: DNA
<213> ORGANISM: Artificial Sequence
<220> FEATURE:
<223> OTHER INFORMATION: Primer

<400> SEQUENCE: 115
tcagacaggc tctcagactc c                                            21

<210> SEQ ID NO 116
<211> LENGTH: 21
<212> TYPE: DNA
<213> ORGANISM: Artificial Sequence
<220> FEATURE:
<223> OTHER INFORMATION: Primer

<400> SEQUENCE: 116
``` tttggaact gaggcaacat t                                          21

<210> SEQ ID NO 117
<211> LENGTH: 20
<212> TYPE: DNA
<213> ORGANISM: Artificial Sequence
<220> FEATURE:
<223> OTHER INFORMATION: Primer

<400> SEQUENCE: 117
taactgtggg ggtgaggttg                                           20

<210> SEQ ID NO 118
<211> LENGTH: 20
<212> TYPE: DNA
<213> ORGANISM: Artificial Sequence
<220> FEATURE:
<223> OTHER INFORMATION: Primer

<400> SEQUENCE: 118
ctgggtatgg gtccttctca                                           20

<210> SEQ ID NO 119
<211> LENGTH: 20
<212> TYPE: DNA
<213> ORGANISM: Artificial Sequence
<220> FEATURE:
<223> OTHER INFORMATION: Primer

<400> SEQUENCE: 119
tggtgaagga ggaggatctg                                           20

<210> SEQ ID NO 120
<211> LENGTH: 20
<212> TYPE: DNA
<213> ORGANISM: Artificial Sequence
<220> FEATURE:
<223> OTHER INFORMATION: Primer

<400> SEQUENCE: 120
tttcagacgg aagcgaagtt                                           20

<210> SEQ ID NO 121
<211> LENGTH: 20
<212> TYPE: DNA
<213> ORGANISM: Merkel Cell Carcinoma Virus

<400> SEQUENCE: 121
accacgattt ggaaaacagc                                           20

<210> SEQ ID NO 122
<211> LENGTH: 23
<212> TYPE: DNA
<213> ORGANISM: Artificial Sequence
<220> FEATURE:
<223> OTHER INFORMATION: primer

<400> SEQUENCE: 122
cctctgggta tgggtccttc tca                                       23

<210> SEQ ID NO 123
<211> LENGTH: 21
<212> TYPE: DNA
<213> ORGANISM: Artificial Sequence
<220> FEATURE:
<223> OTHER INFORMATION: primer

```
<400> SEQUENCE: 123
atggtgttcg ggaggtatat c                                              21

<210> SEQ ID NO 124
<211> LENGTH: 23
<212> TYPE: DNA
<213> ORGANISM: Artificial Sequence
<220> FEATURE:
<223> OTHER INFORMATION: primer

<400> SEQUENCE: 124
agtaccagag gaagaagcca atc                                            23

<210> SEQ ID NO 125
<211> LENGTH: 30
<212> TYPE: DNA
<213> ORGANISM: Artificial Sequence
<220> FEATURE:
<223> OTHER INFORMATION: primer

<400> SEQUENCE: 125
ggccttttat caggagaggc tatattaatt                                     30

<210> SEQ ID NO 126
<211> LENGTH: 16
<212> TYPE: DNA
<213> ORGANISM: Artificial Sequence
<220> FEATURE:
<223> OTHER INFORMATION: TaqMan probe

<400> SEQUENCE: 126
cccaggcttc agactc                                                    16

<210> SEQ ID NO 127
<211> LENGTH: 12
<212> TYPE: DNA
<213> ORGANISM: Artificial Sequence
<220> FEATURE:
<223> OTHER INFORMATION: TaqMan probe

<400> SEQUENCE: 127
gcagagttcc tc                                                        12

<210> SEQ ID NO 128
<211> LENGTH: 18
<212> TYPE: DNA
<213> ORGANISM: Artificial Sequence
<220> FEATURE:
<223> OTHER INFORMATION: primer

<400> SEQUENCE: 128
cccaagggcg ggaaactg                                                  18

<210> SEQ ID NO 129
<211> LENGTH: 23
<212> TYPE: DNA
<213> ORGANISM: Artificial Sequence
<220> FEATURE:
<223> OTHER INFORMATION: primer

<400> SEQUENCE: 129
gcagaaggag tttgcagaaa cag                                            23

<210> SEQ ID NO 130
<211> LENGTH: 28
```

-continued

```
<212> TYPE: DNA
<213> ORGANISM: Artificial Sequence
<220> FEATURE:
<223> OTHER INFORMATION: probe

<400> SEQUENCE: 130
ccactcctta gtgaggtagc tcatttgc                                    28

<210> SEQ ID NO 131
<211> LENGTH: 20
<212> TYPE: DNA
<213> ORGANISM: Artificial Sequence
<220> FEATURE:
<223> OTHER INFORMATION: primer

<400> SEQUENCE: 131
cactggctcg tgtgacaagg                                             20

<210> SEQ ID NO 132
<211> LENGTH: 24
<212> TYPE: DNA
<213> ORGANISM: Artificial Sequence
<220> FEATURE:
<223> OTHER INFORMATION: primer

<400> SEQUENCE: 132
cagacctact gtgcgcctac ttaa                                        24

<210> SEQ ID NO 133
<211> LENGTH: 26
<212> TYPE: DNA
<213> ORGANISM: Artificial Sequence
<220> FEATURE:
<223> OTHER INFORMATION: probe

<400> SEQUENCE: 133
tggtgtaaag cggccttgga gtgtgt                                      26

<210> SEQ ID NO 134
<211> LENGTH: 14
<212> TYPE: PRT
<213> ORGANISM: Merkel Cell Carcinoma Virus
<220> FEATURE:
<221> NAME/KEY: MISC_FEATURE
<222> LOCATION: (1)..(14)
<223> OTHER INFORMATION: polypeptide epitope for CM2B4 antibody

<400> SEQUENCE: 134

Ser Arg Ser Arg Lys Pro Ser Ser Asn Ala Ser Arg Gly Ala
1               5                   10
```

US 8,524,248 B2

METHODS TO DIAGNOSE AND IMMUNIZE AGAINST THE VIRUS CAUSING HUMAN MERKEL CELL CARCINOMA

CROSS-REFERENCE TO RELATED APPLICATIONS

This patent application is a U.S. National Phase of International Patent Application No. PCT/US08/86895, filed Dec. 15, 2008. This patent application claims the benefit of U.S. Provisional Patent Application No. 61/013,772 filed Dec. 14, 2007, which is incorporated by reference.

STATEMENT REGARDING FEDERALLY SPONSORED RESEARCH AND DEVELOPMENT

This invention was made with Government support under Grant Number NIH R33CA120726 awarded by the National Institutes of Health. The Government has certain rights in this invention.

BRIEF SUMMARY OF THE INVENTION

The present invention provides isolated or substantially purified polypeptides, nucleic acids, and virus-like particles (VLPs) derived from a Merkel cell carcinoma virus (MCV), which is a newly-discovered virus. The invention further provides monoclonal antibody molecules that bind to MCV polypeptides. The invention further provides diagnostic, prophylactic, and therapeutic methods relating to the identification, prevention, and treatment of MCV-related diseases. These aspects, and other inventive features, will be apparent upon reading the following detailed description in conjunction with the accompanying figures and sequence listing.

BRIEF DESCRIPTION OF THE SEVERAL VIEWS OF THE DRAWING(S)

FIG. 1. A) Merkel cell carcinoma (MCC). MCC is an aggressive small, round-cell skin cancer of Merkel mechanoreceptor cells with higher mortality rates than most other skin cancers (Left panel: H&E, Right panel: cytokeratin 20 staining, 40×). B) 3'-RACE mapping of MCV T antigen-human PTPRG fusion transcript. The viral transcript discovered by DTS in MCC347 was extended by 3'-RACE. Three mRNA sequences were isolated, two of which terminate in human PTPRG intron 1 on Chromosome 3p14. The two viral-human transcripts were generated by read-through of a weak polyadenylation signal in the viral T antigen gene.

Figure 2:
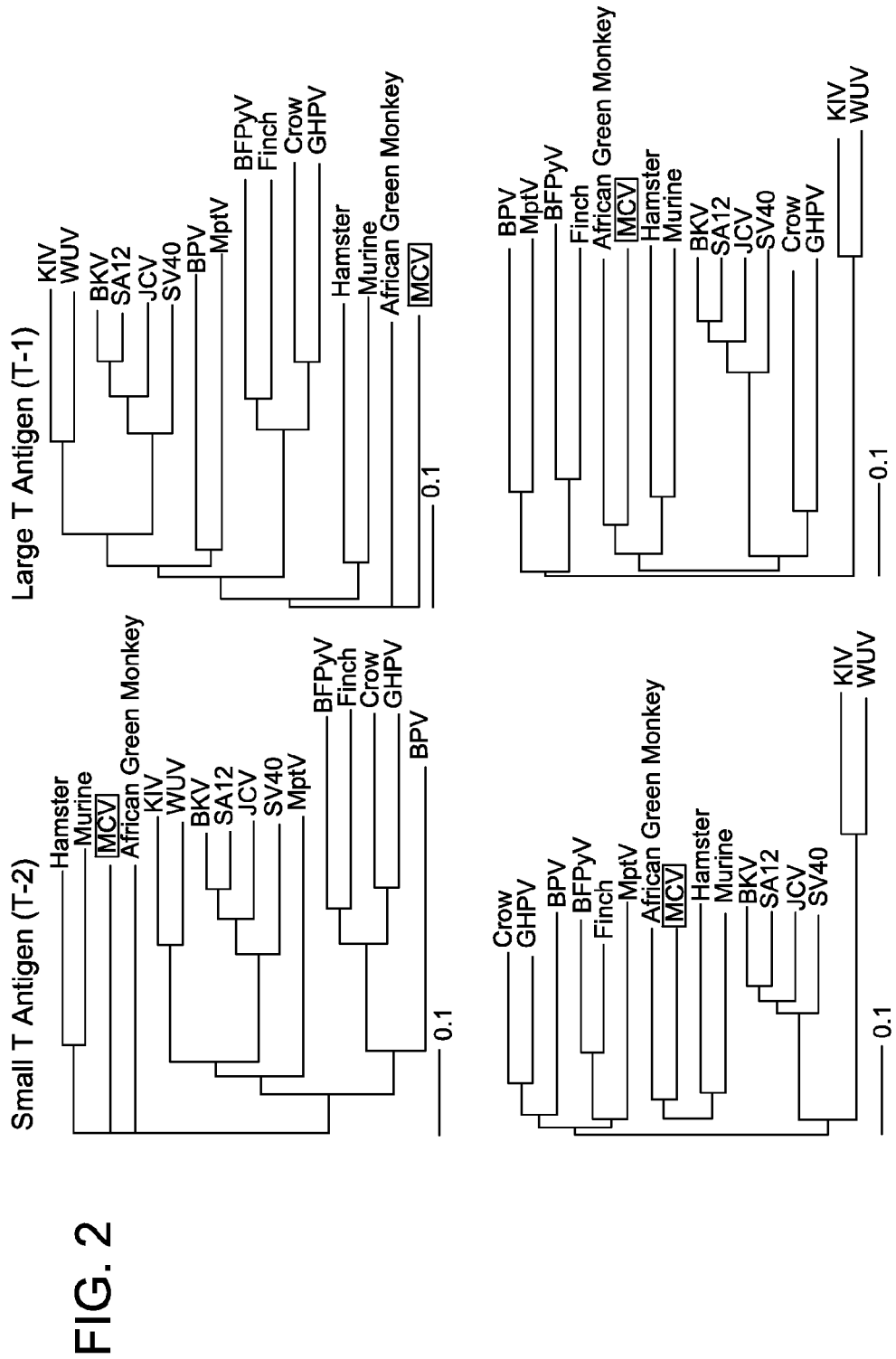

FIG. 2. Neighbor-joining trees for MCV putative large T (T-1, see FIG. 3), small T (T-2), VP1 and VP2 proteins. The four known human polyomaviruses (BK, JC, KI and WU) cluster together in the SV-40 subgroup while MCV is most closely related to MuPyV subgroup viruses. Both subgroups are distinct from the avian polyomavirus subgroup.

Figure 3:
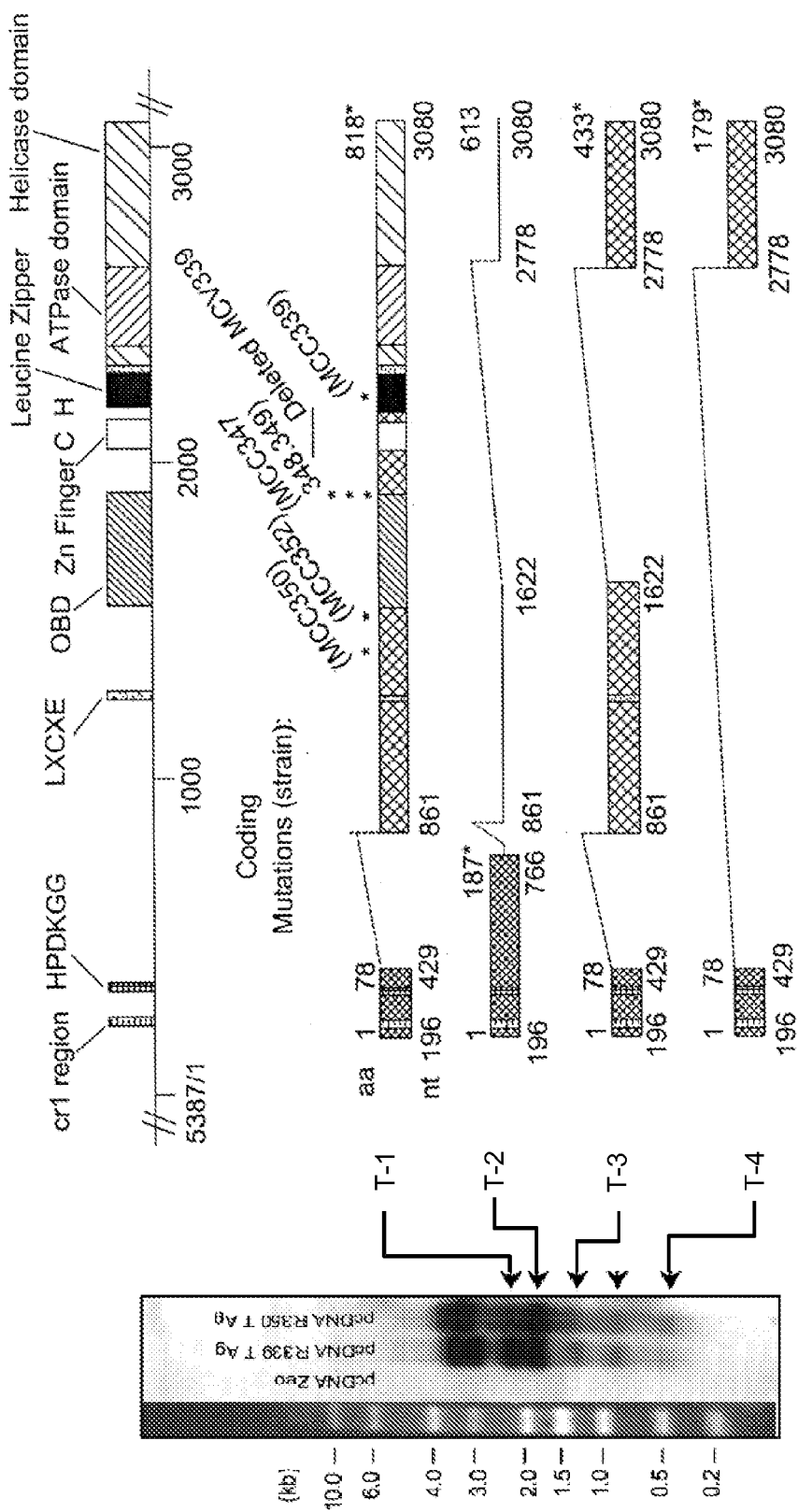

FIG. 3. Northern and 3'-, 5'-RACE mapping of MCV T antigen transcripts in MCC tumors and during expression in 293 cells. Genomic T antigen fragments from MCV350 and 339 were expressed in pcDNA vector in 293 cells. The left panel shows northern blotting of the 293 cell RNAs allowing individual transcripts to be assigned to four distinct bands. Higher molecular weight bands in this northern blot exceed the genome fragment size and are artifactually produced from vector expression (note difference sizes between pcDNA339 and pcDNA350 result from a 201 nt. deletion in MCV339 T antigen sequence). T-1 is similar to polyomavirus large T antigens and possesses highly conserved cr1, DnaJ (HPD-KGG), LXCXE, origin binding domain (OBD) and helicase/ATPase features. Stop codons and deletions prevent full-length large T protein expression in tumor derived viruses. T-2 possesses a large intronic sequence resulting in a protein similar to small T antigens from other polyomaviruses. An additional 0.8 kbase band is expressed in 293 cells but no corresponding tumor RACE product was isolated.

FIG. 4. A) Clonal MCV integration in MCC tumors detected by direct Southern hybridization. DNA digests with BamHI (left) or EcoRI (right) and Southern blotted with seven MCV DNA probes reveals different banding patterns in each tumor, including >5.4 kbase bands. Open arrow shows the expected position for MCV episomal or concatenated-integrated genome (5.4 kbase) with corresponding bands present in tumors MCC344 and 350. Tumors MCC339, 347/348, and 349 have different band sizes and doublet bands (closed arrows) consistent with genomic monoclonal integration. MCC352 has both prominent episomal/concatenated bands (EcoRI), and higher and lower molecular weight integration bands (BamHI). Tumors MCC337, 343 and 346 have no MCV DNA detected by Southern blotting (bands at 1.5 kbase (kidney) and 1.2 kbase (MCC346) are artifacts). B) Viral and cellular monoclonality in MCC347. Tumor MCC347 and its metastasis MCC348 were digested with SacI and NheI, and Southern blotted with unique human flanking sequence probe (Chr3 (red), left panel) or viral probes (LT1 and LT2 (yellow), right panel). The wild-type human allele is present in all samples at 3.1 kbase (left panel). The MCC tumors, however, have an additional 3.9 kbase allelic band from MCV insertion into 3p14. Probing with for MCV T antigen sequence (right panel) generates an identical band.

Figure 5:
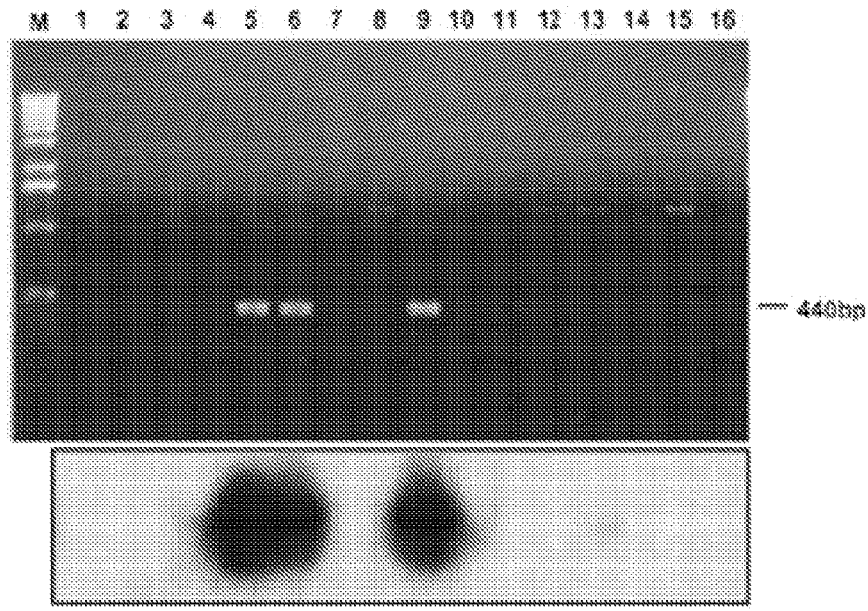

FIG. 5. Representative results of MCC and control tissue PCR-Southern blotting. (Top panel) Agarose gel of amplification products from 16 randomized control and MCC tissue samples using LT1 primers (see Supplementary Table 4) (Bottom panel). Specific hybridization of PCR products to a (α32P) dCTP-labeled M1-M2 internal probe (see Supplementary Table 4) after transfer of DNA to nitrocellulose membrane. Sample identities are as follows: MCC tissue samples in lanes 1 (MCC346), 5 (MCC348), 6 (MCC344), 9 (MCC339), and 15 (MCC343); negative control (H2O) samples in lanes 2, 10 and 11; and surgical control tissue samples in lanes 3, 4, 7, 8, 12, 13, 14 and 16. Weak signal in lane 13 (control gall bladder tissue) is positive only after Southern blotting of the PCR product compared to robust PCR amplification for MCC348, 344, 339 tissues. MCC346 and 343 are negative.

Figure 6:
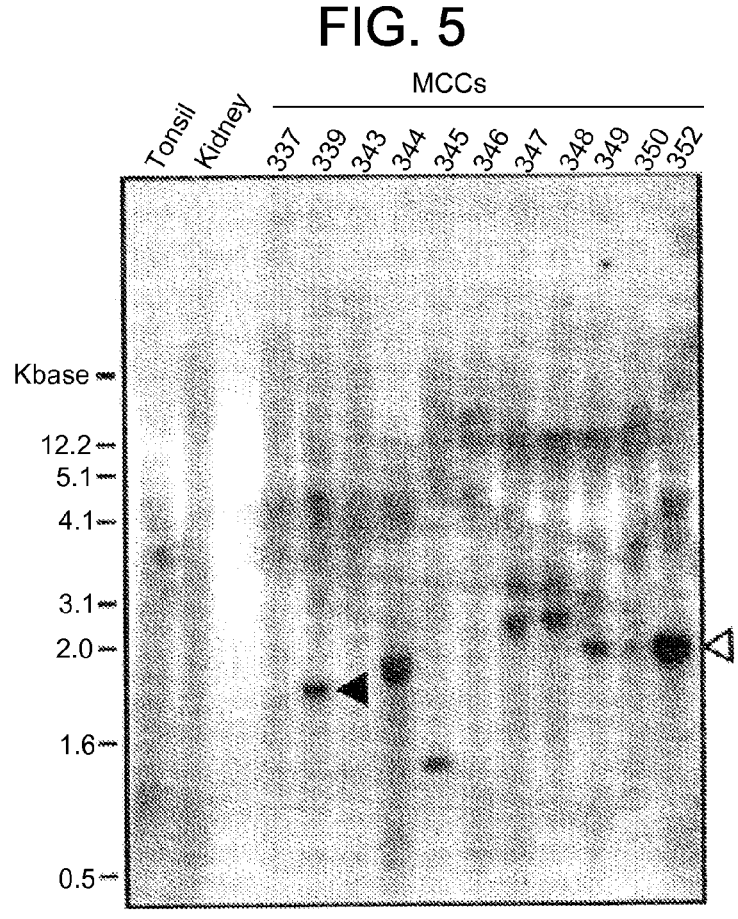

FIG. 6. BamHI-EcoRI double-digestion and Southern hybridization of the MCV T antigen locus. BamHI-EcoRI should generate a single ~1.5-1.7 kbase fragment from T antigen (see FIG. 7) unless genomic integration or deletion occurs in this region. Marked variation in band sizes (MCC339, 344, 345, 347, 348) are consistent with either human genomic integrations or deletions within T antigen locus. Open arrow indicates expected BamHI-EcoRI viral fragment (1.7 kbase) for MCV350 and closed arrow, expected T antigen fragment (1.5 kbase) for MCV 339.

Figure 7:
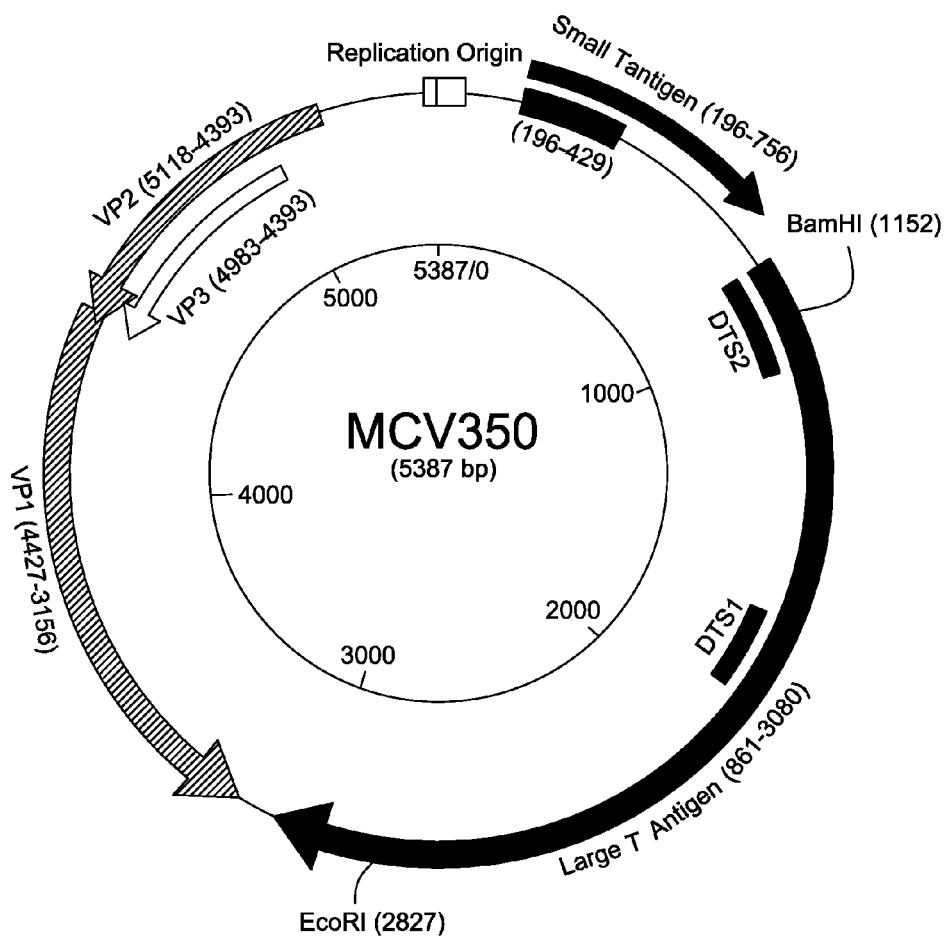

FIG. 7. MCV genome diagram showing large T, small T, VP1, and overlapping VP2 and VP3 genes and DTS1 and DTS2. The former was used to identify MCV and latter is a spliced transcript having low polyomavirus homology.

Figure 8:
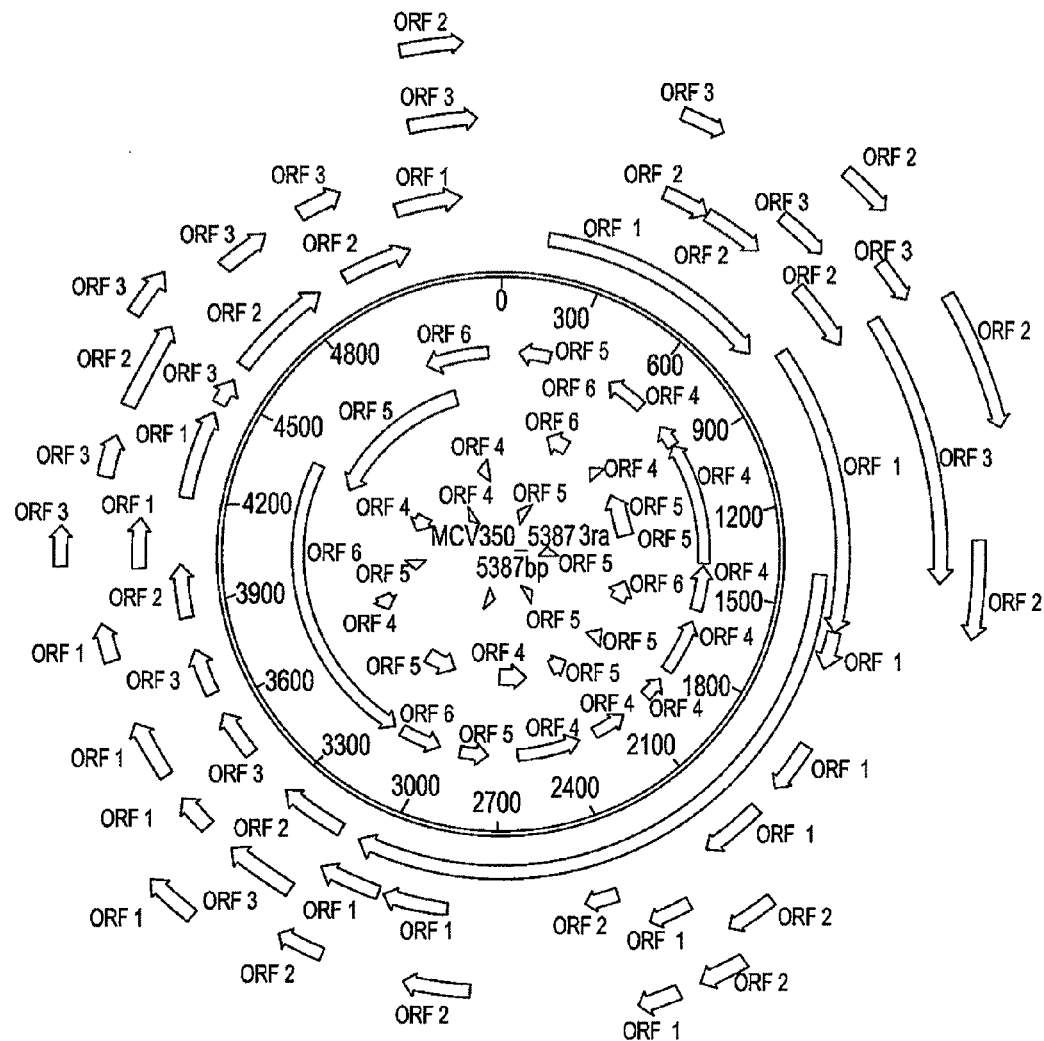

FIG. 8 graphically illustrates the location of the ORFS within the genome of MCV 350.

FIG. 9 presents data showing CM2B4 mAb is specific for MCV LT. (A) A MCV T antigen-EGFP fusion protein colocalizes with CM2B4 staining in 293 cells transfected with pMCV TAg-EGFP or pEGFP, an empty vector. (B) CM2B4 does not react with T antigens of human polyomaviruses belonging to SV40 subgroup. Constructs encoding LT genes for JCV, BKV and MCV were expressed in 293 cells and stained with CM2B4 or PAb416 antibodies. PAb416 cross reacts with JCV and BKV LT proteins but not with MCV LT. (C) Immunoblotting for expressed polyomavirus LT with PAb416 and CM2B4 antibodies in cell lysates described in (B). CM2B4 recognizes an MCV 120 kDa (LT) protein and a shorter 60 kDa T antigen isoform. No cross-reactivity is apparent for PAb416 with MCV LT or CM2B4 with SV40-group polyomavirus proteins. (D) Brain tissue with progressive multifocal leukoenchephalopathy show JCV infection of oligodendroglial cells by JCV specific in situ hybridization (left panel), and CM2B4 shows no reactivity to JCV antigens (right panel). (E) Detection of truncated LT protein by CM2B4 in MCV positive MKL-1 cell line. Proteins from MKL-1 cells and MCV negative UISO, MCC13 and MCC26 cells were immunoblotted with CM2B4. LT antigen bands are only present in MKL-1 cells.

FIG. 10 presents data showing specific and uniform expression of MCV LT protein in MCC. (A) Uniform expression of MCV LT in MKL-1 cell line. Representative sections showing MCV LT and CK20 protein expression in MKL-1 and UISO cells. (B) MCC tissue specific expression of LT protein. Representative sequential sections from MCC showing histological phenotype (H&E) and immunostaining for MCV LT (CM2B4) and CK20 proteins. Expression of MCV LT protein expression is precisely localized in nucleus of MCC cells but not in surrounding tissues including the epidermis, adnexal epithelium (arrow), endothelial cells, or dermal fibroblasts.

FIG. 11 presents data demonstrating the construction of MCV VLPs.

FIG. 12 presents data demonstrating the construction of MCV VLPs. The top panel shows an anti-MCV Western blot of 293TT cells after transfection with the VP1 expression construct shown, together with an appropriate VP2 expression construct. In the far right lane of the Western, 5-fold more cell lysate was applied to the gel. The bottom panel shows a SYPRO Ruby-stained SDS-PAGE gel analysis of Optiprep gradients used to purify VLPs out of cell lysates. For MPyV and MCV399, 2.5 µl each of fractions 6-9 was loaded onto the gel. For MCV350, 12.5 µl each of fractions 6-9 was loaded. Fractions were screened for the presence of encapsidated DNA using Picogreen reagent.

Figure 13:
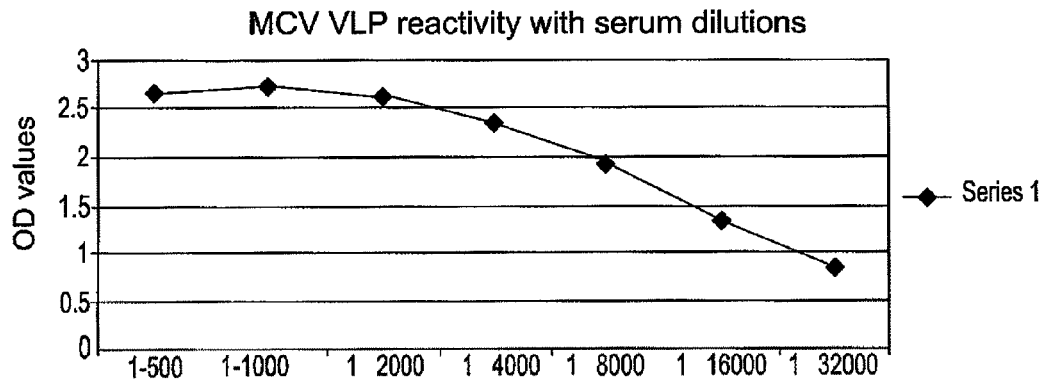

FIG. 13 presents data showing the determination of serum sample working dilution for competitive ELISA for MCV VLP. This figure represents a single experiment with one serum sample. Working dilution was estimated as lowest dilution at which OD was greater than 1.

Figure 14A:
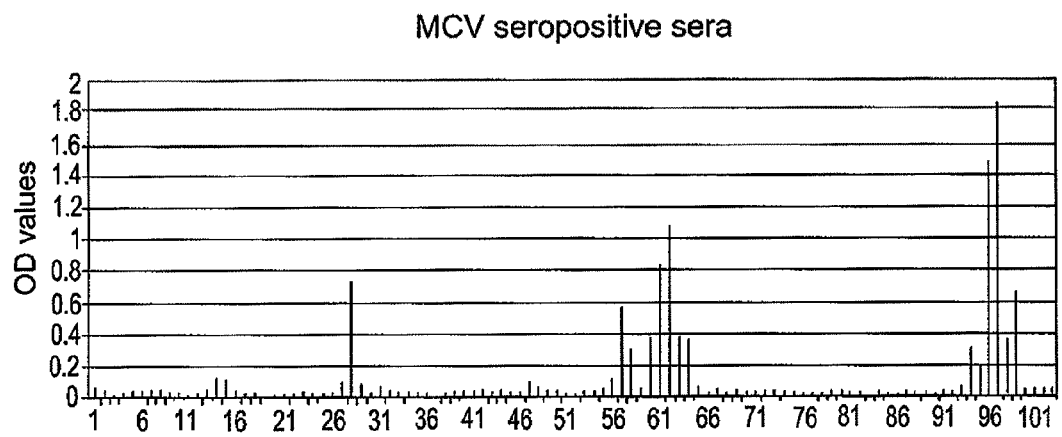
Figure 14B:
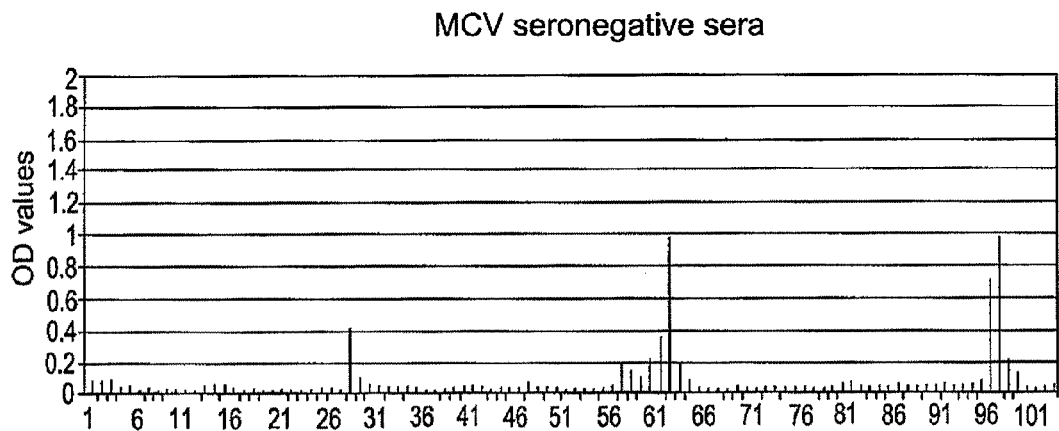

FIG. 14 presents data showing examples of VP1 peptides screen (A-B) of MCV-positive sera (A) and negative sample (B) diluted 1:500.

Figure 15:
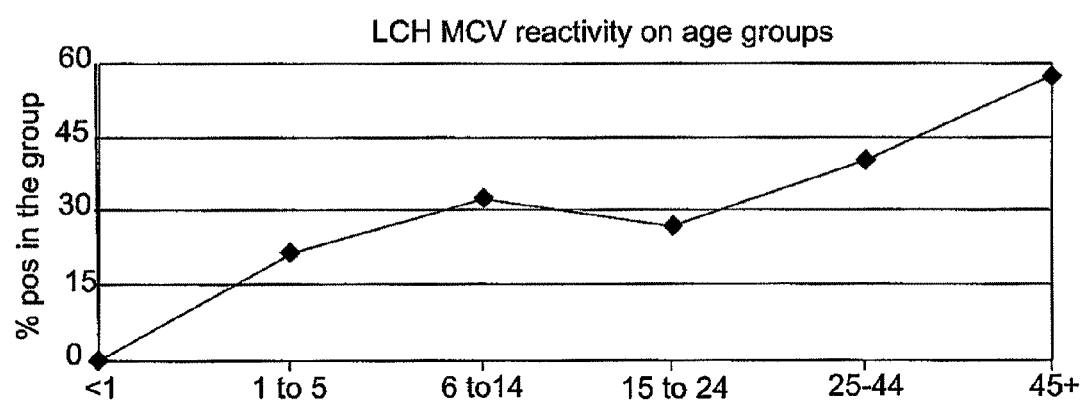

FIG. 15 presents data showing the extent of positive reaction to MCV VLP ELISA among Langerhan's cell histiocytosis patients of various age groups.

Figure 16:
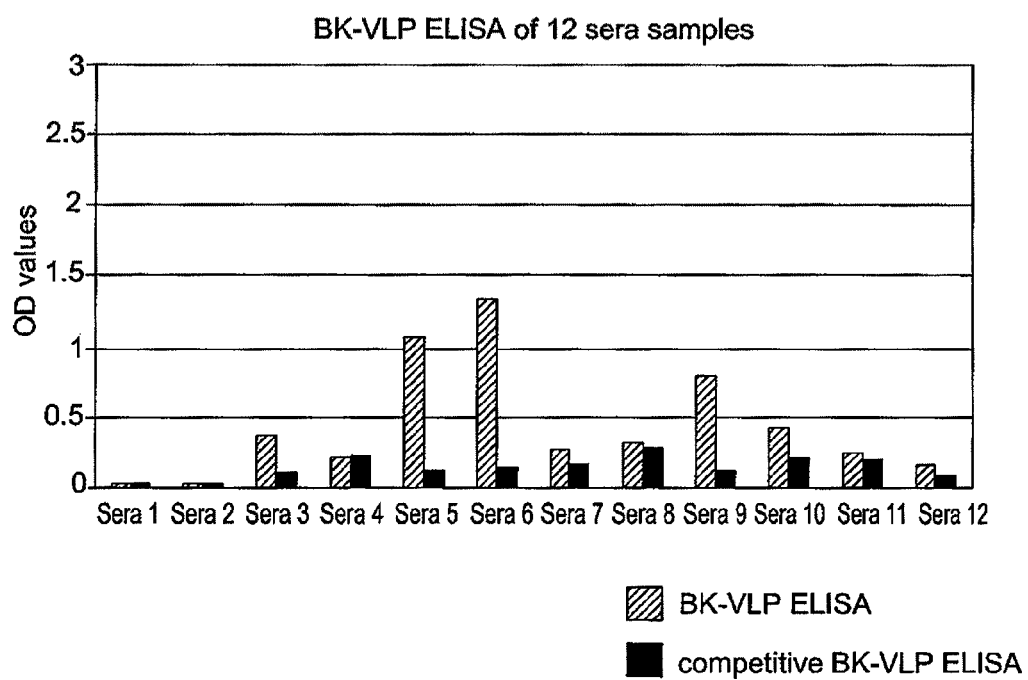

FIG. 16 presents data showing the results of the reactivity (ELISA) of 12 sera samples to BKV VLPs.

Figure 17:
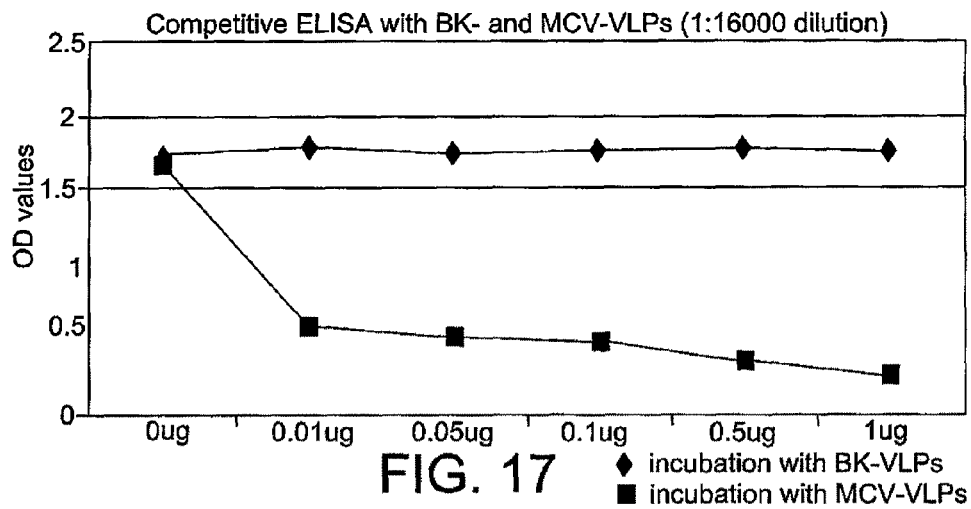

FIG. 17 presents data showing competitive ELISA with BK- and MCV-VLPs. This figure demonstrates results of the typical experiment with MCV-positive serum.

Figure 18A:
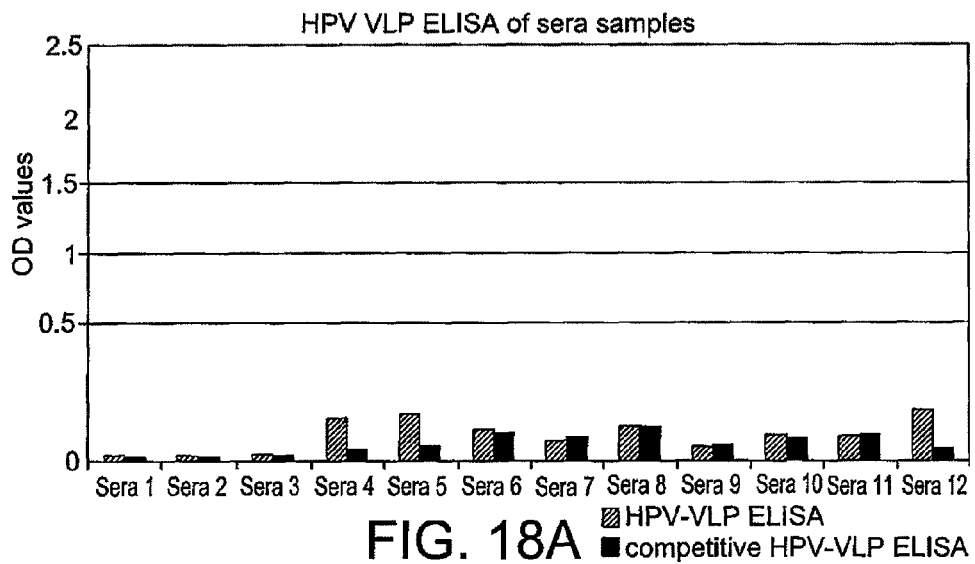
Figure 18B:
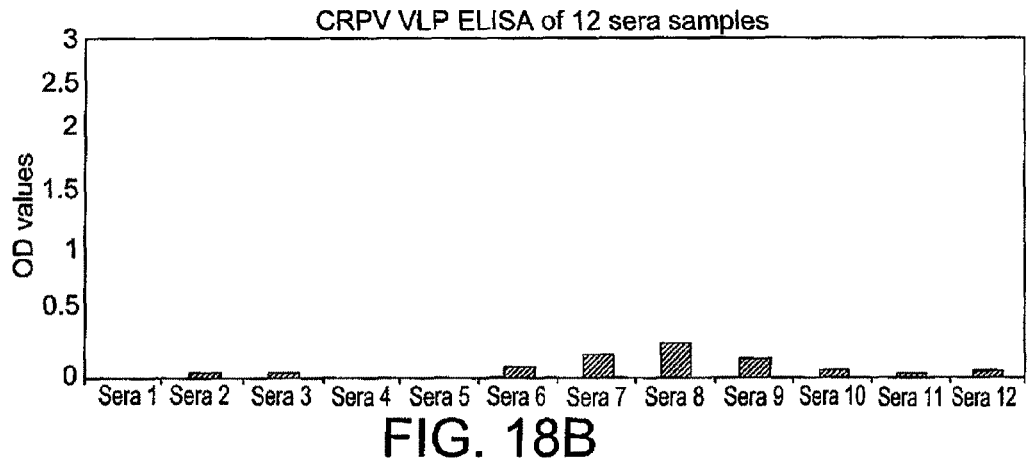

FIG. 18 presents data showing the seroreactivity of 12 serum samples to HPV and CRPV VLPs. A—HPV VLP, B—CRPV VLP ELISA.

Figure 19:
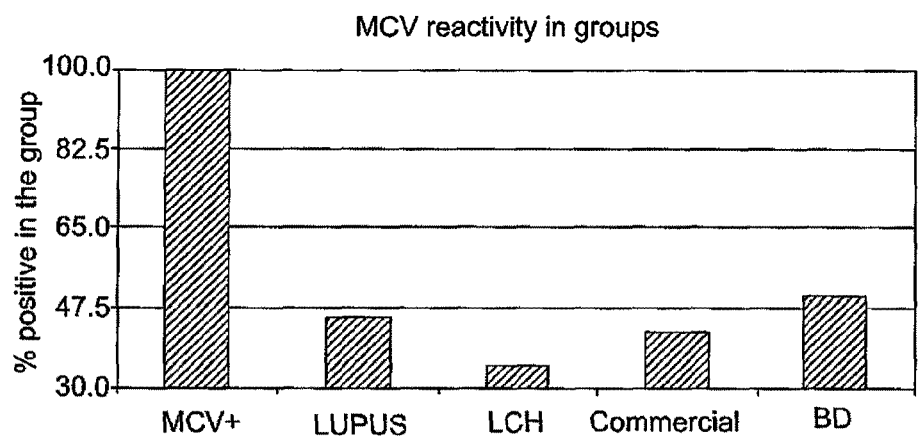

FIG. 19 presents the results of ELISA assays for MCV VLPs in various cohorts (confirmed MCC patients positive with MCV, lupus patients, Langerhan's cell histiocytosis patients, blod from commercial sources, and serum form blood donors).

Figure 20:
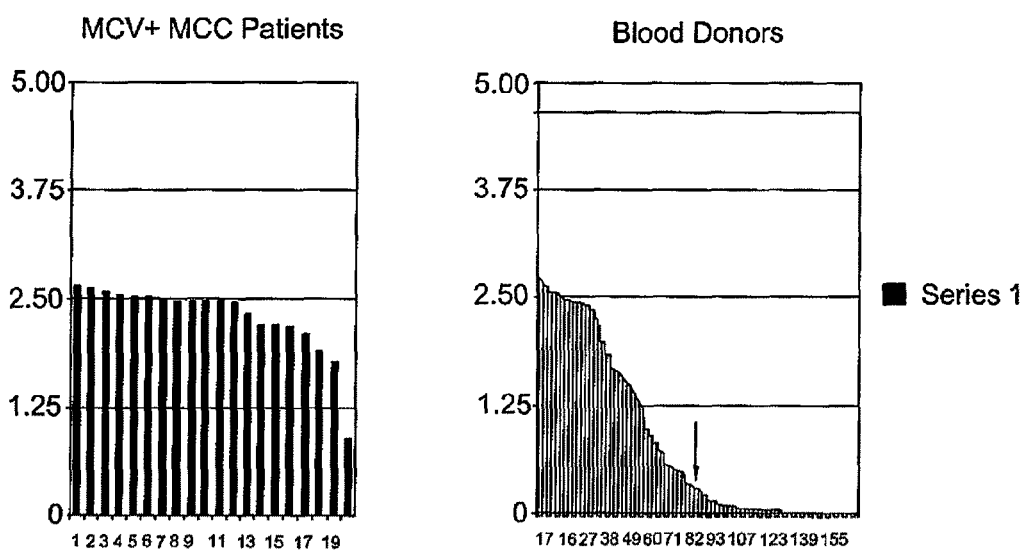

FIG. 20 presents data showing the OD values of 20 confirmed MCC patients positive with MCV (left) and from blood donors.

Figure 21:
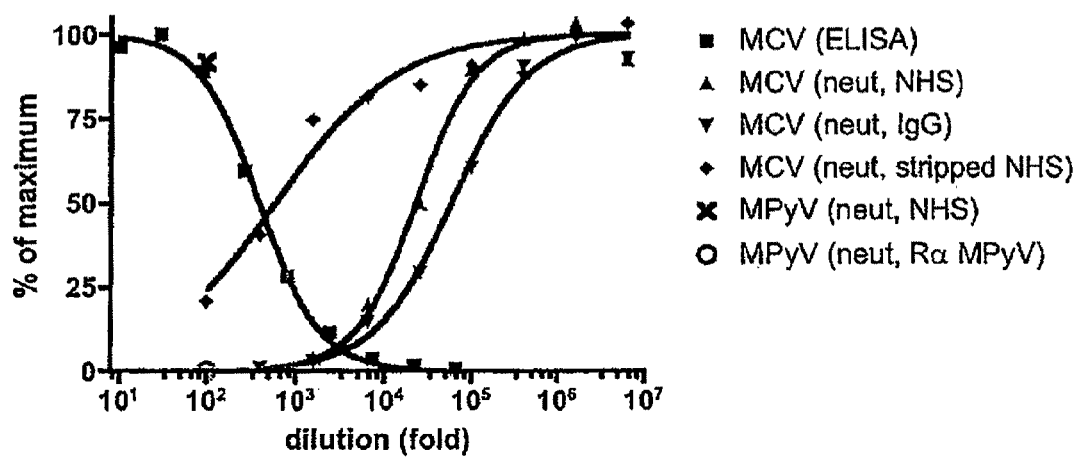

FIG. 21 presents data showing validation of a MCV neutralization assay. The ▼ line shows an MCV neutralization curve for IgG purified out of the pooled human serum using protein G resin (starting concentration 1 mg/ml). The ♦ line shows results using serum after passage over protein G resin. The X and O points display, respectively a general lack of neutralization of an MPyV reporter vector by the pooled human serum and complete neutralization of the MPyV vector by MPyV-specific rabbit serum.

Figure 22:
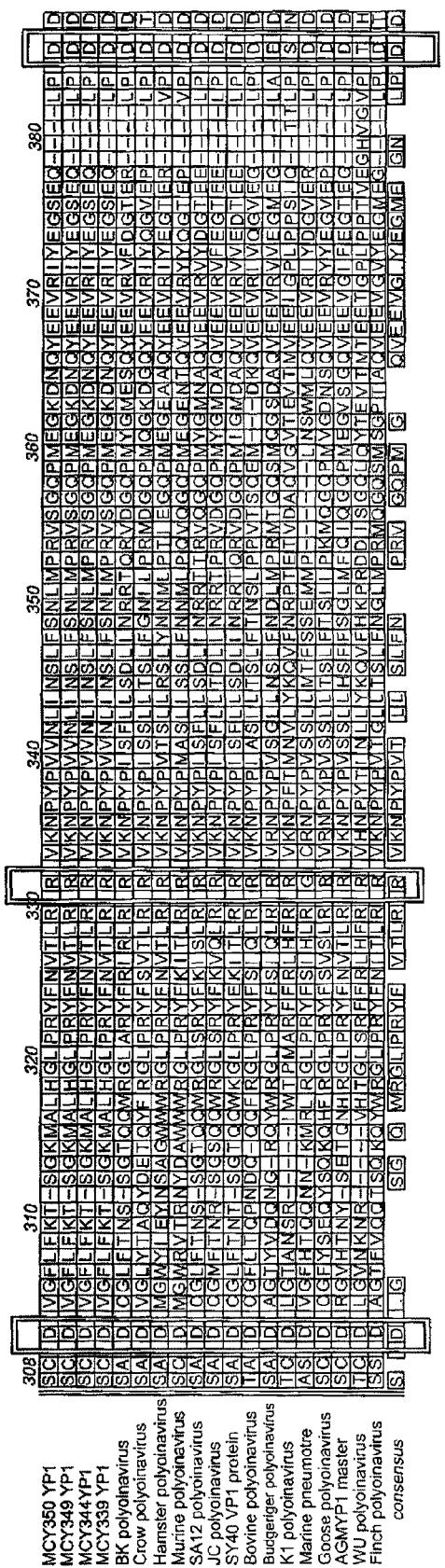

FIG. 22 compares the sequence of VP1 proteins for strains of MCV against a consensus polyomavirus sequence.

FIG. 23 presents sequences discussed herein.

DETAILED DESCRIPTION OF THE INVENTION

Within the context of the present invention, a nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature ($T_m$) of the nucleic acid binding complex or probe. For example, "maximum stringency" typically occurs at about $T_m$–5° C. (5° C. below the $T_m$ of the probe); "high stringency" at about 5-10° C. below the $T_m$; "intermediate stringency" at about 10-20° C. below the $T_m$ of the probe; and "low stringency" at about 20-25° C. below the $T_m$. Functionally, maximum stringency conditions may be used to identify sequences having strict identity or near-strict identity with the hybridization probe; while high stringency conditions are used to identify sequences having about 80% or more sequence identity with the probe. This is especially true for polynucleotides having a minimum of from about 18-22 nucleic acids, but those of ordinary skill in the art are also able to apply these principals to larger or smaller polynucleotides.

Moderate and high stringency hybridization conditions are well known in the art (see, for example, Sambrook et al. Molecular Cloning: A Laboratory Manual (Second Edition), Cold Spring Harbor Press, Plainview, N.Y., 1989, especially chapters 9 and 11; and Ausubel F M et al. Current Protocols in Molecular Biology, John Wiley & Sons, New York, N.Y., 1993). An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

Furthermore, within the context of the present invention, it will be understood that a protein (such as an antibody molecule, but also applicable to other proteins (e.g., in the context of binding other proteins or DNA)) "binds selectively" to a target (e.g., an antigen, target DNA, etc.) if it binds to the target to a significantly higher degree than it binds to another substance (e.g., another protein or a non-specific DNA sequence). Those of ordinary skill will understand this concept as being a hallmark of immunoglobulin-antigen interaction or the interaction between a DNA-binding protein and its target consensus sequence.

One aspect of the present invention relates to proteins and nucleic acids (DNAs or RNAs) derived from the newly-identified MCV. In this respect, one embodiment of the present invention provides an isolated or substantially purified nucleic acid molecule comprising at least about 6 contiguous nucleotides of a MCV genomic DNA sequence. The complete genomic DNA sequence of MCVs from four tissue sources (MCV 350 (SEQ ID NO:1), MCV 339 (SEQ ID NO:2), MCV 352 (SEQ ID NO:3) and MCV MKLI (SEQ ID NO:4) are set forth in the Sequence Listing. Amino acid sequences for the VP1, VP2, VP3, T-1, T-2, T-3, T-4, and T-5 proteins, as well as their coding DNA sequences, are set forth in the Sequence Listing as SEQ ID NOs:5-20. DNA sequences for MCVs isolated from small cell lung carcinomas are set forth as SEQ ID NOs:21-45 in the Sequence Listing. Furthermore, possible ORFs of the MCV 350 genome (SEQ ID NO:1) are displayed in FIGS. 7 and 8. With reference to the genome itself (SEQ ID NO:1), these ORFs are further identified in the following table A:

TABLE A

| Sense Strand | Antisense Strand |
|---|---|
| 124 to 756 length = 633 | C 5386 to 5294 length = 93 |
| 330 to 410 length = 81 | C 5324 to 5064 length = 261 |
| 362 to 469 length = 108 | C 5266 to 5141 length = 126 |
| 470 to 595 length = 126 | C 5148 to 4393 length = 756 |
| 591 to 695 length = 105 | C 5068 to 4973 length = 96 |
| 623 to 715 length = 93 | C 4846 to 4760 length = 87 |
| 716 to 865 length = 150 | C 4718 to 4620 length = 99 |
| 780 to 860 length = 81 | C 4433 to 3156 length = 1278 |
| 835 to 1536 length = 702 | C 4429 to 4250 length = 180 |
| 861 to 1403 length = 543 | C 4249 to 4094 length = 156 |
| 893 to 1132 length = 240 | C 4182 to 4090 length = 93 |
| 1319 to 1501 length = 183 | C 3975 to 3874 length = 102 |
| 1404 to 3080 length = 1677 | C 3742 to 3638 length = 105 |
| 1537 to 1626 length = 90 | C 3222 to 3016 length = 207 |
| 1834 to 1959 length = 126 | C 3205 to 3122 length = 84 |
| 2023 to 2175 length = 153 | C 3125 to 2949 length = 177 |
| 2132 to 2227 length = 96 | C 3073 to 2993 length = 81 |
| 2237 to 2323 length = 87 | C 3006 to 2914 length = 93 |
| 2275 to 2364 length = 90 | C 2965 to 2834 length = 132 |
| 2365 to 2445 length = 81 | C 2862 to 2749 length = 114 |
| 2414 to 2491 length = 78 | C 2735 to 2652 length = 84 |
| 2753 to 2881 length = 129 | C 2703 to 2530 length = 174 |
| 2818 to 2973 length = 156 | C 2623 to 2354 length = 270 |
| 2986 to 3129 length = 144 | C 2529 to 2410 length = 120 |
| 3047 to 3133 length = 87 | C 2441 to 2361 length = 81 |
| 3134 to 3319 length = 186 | C 2349 to 2233 length = 117 |
| 3162 to 3311 length = 150 | C 2284 to 2135 length = 150 |
| 3283 to 3381 length = 99 | C 2232 to 2128 length = 105 |
| 3382 to 3465 length = 84 | C 2114 to 2019 length = 96 |
| 3450 to 3584 length = 135 | C 2014 to 1919 length = 96 |
| 3523 to 3657 length = 135 | C 1998 to 1906 length = 93 |
| 3642 to 3770 length = 129 | C 1905 to 1804 length = 102 |
| 3802 to 3885 length = 84 | C 1873 to 1640 length = 234 |
| 3863 to 4012 length = 150 | C 1667 to 1533 length = 135 |
| 4006 to 4128 length = 123 | C 1588 to 1400 length = 189 |
| 4017 to 4097 length = 81 | C 1392 to 1222 length = 171 |
| 4195 to 4443 length = 249 | C 1387 to 857 length = 531 |
| 4209 to 4301 length = 93 | C 1274 to 1182 length = 93 |
| 4370 to 4567 length = 198 | C 1221 to 922 length = 300 |
| 4467 to 4544 length = 78 | C 911 to 825 length = 87 |
| 4545 to 4646 length = 102 | C 856 to 761 length = 96 |
| 4589 to 4873 length = 285 | C 760 to 677 length = 84 |
| 4737 to 4850 length = 114 | C 725 to 645 length = 81 |
| 4935 to 5030 length = 96 | C 711 to 601 length = 111 |
| 4946 to 5134 length = 189 | C 652 to 560 length = 93 |
| 5131 to 5292 length = 162 | C 641 to 474 length = 168 |
| 5205 to 5336 length = 132 | C 591 to 466 length = 126 |
| 5216 to 5320 length = 105 | C 473 to 318 length = 156 |
| | C 465 to 310 length = 156 |
| | C 309 to 208 length = 102 |
| | C 263 to 147 length = 117 |
| | C 256 to 134 length = 123 |
| | C 201 to 67 length = 135 |
| | C 146 to 63 length = 84 |
| | C 85 to 8 length = 78 |

Exemplary MCV genomic DNA sequences from which the inventive nucleic acid can be derived from include, but are not limited to, SEQ ID NOs: 1-5, 7, 9, 11, 13, 15, 17, 19, and 21-45. Thus, for example, the inventive DNA can include from about 10 to about 20 contiguous nucleotides of such MCV genomic DNA sequences, the majority of contiguous nucleotides of such MCV genomic DNA sequences, substantially all of such MCV genomic DNA sequences, or even including the complete sequence set forth in SEQ ID NOs: 1-5, 7, 9, 11, 13, 15, 17, 19, or 21-45 or other MCV genomic DNA sequence. It will be understood that the invention also includes the complement of such sequences. Furthermore, the invention also includes a nucleic acid that hybridizes under high stringency conditions to such sequences.

As minor differences in sequence are tolerated, so long as they do not impede the function of the nucleic acids, the invention further provides an isolated or substantially purified nucleic acid molecule consisting essentially of at least about 6 contiguous nucleotides of a MCV genomic DNA sequence, such as those discussed herein. Thus, for example, the inventive DNA can consist essentially of from about 10 to about 20 contiguous nucleotides of such MCV genomic DNA sequences, the majority of contiguous nucleotides of such MCV genomic DNA sequences, substantially all of such MCV genomic DNA sequences, or even consisting essentially of the complete sequence set forth in SEQ ID NOs: 1-5, 7, 9, 11, 13, 15, 17, 19, or 21-45 or other MCV genomic DNA sequence. It will be understood that the invention also includes the complement of such sequences as well a nucleic acid that hybridizes under high stringency conditions to such sequences.

In one respect, the inventive isolated or substantially purified nucleic acids can be employed as probes, for example in diagnostic assays for identifying MCV. In this respect, while it has been recited that the inventive nucleic acid can comprise at least about 6 contiguous nucleic acids from an MCV genomic sequence, somewhat shorter contiguous residues can be permitted, if the molecule is nonetheless capable of hybridizing under high stringency to MCV genomic DNA or its complement. Moreover, the length of the probe can vary to be as long as useful for the assay-in-question. Thus, the probe can comprise about 12-15 nucleotides, or can comprise longer sequences, such as about 20 or about 25 nucleotides, if desired. Of course, a probe also can have sequences other than MCV sequences, such as restriction endonuclease consensus recognition sequences to facilitate cloning.

In other respects, the inventive inventive isolated or substantially purified nucleic acids can be employed as agents to interfere with viral replication. Thus, the inventive nucleic acid can be or comprise an oligodeoxynucleotide, siRNA molecule, or other suitable type of polynucleic acid. Such molecules can include standard modifications to structure or employed modified sequences/nucleotides (e.g., generation of hairpins, use of triphosphate modified dNTPs, etc.) to enhance activity or stability of such molecules.

In yet further aspects, certain of the inventive nucleic acids encode MCV proteins and polypeptides, and the invention provides such encoding nucleic acids, as well as nucleic acids which complement such or which hybridize to such under high stringency. Thus, for example, the inventive isolated or substantially purified nucleic acid molecule can encode all or a portion of an MCV polypeptide. Examples of some such polypeptides include SEQ ID NOs: 6, 8, 10, 12, 14, 16, 18, 20, and any open reading frame (ORF) of SEQ ID NOs: 1-4. ORFs of SEQ ID NO:1 are represented in table A, but putative ORFs of SEQ ID NOs: 2-4 can be deduced by those of ordinary skill in the art. Typically, the nucleic acid will encode a polypeptide that includes at least about 4 or about 5 contiguous nucleic acid residues of an MCV protein, and often substantially more contiguous nucleic acids from such proteins (e.g., at least about 10 contiguous nucleic acids or at least about 25 contiguous nucleic acids or even at least about 50 contiguous nucleic acids from such proteins). In some preferred embodiments, the amino acid encodes an MCV protein comprising at least about 4 or about 5 or at least about 10 contiguous amino acids of the amino-terminal 258 sequence of an MCV T-1 polypeptide (one example of which is set forth at SEQ ID NO:12). Of course, the nucleic acid can encode a polypeptide comprising the majority of contiguous amino acids from such proteins, such as all or substantially all of such MCV proteins.

For embodiments in which expression of the inventive nucleic acid is desire, the nucleic acid molecule can be placed into a suitable genetic context to promote expression. Thus, in one embodiment, the invention provides a composition of matter comprising an expression cassette comprising a nucleic acid as herein described in operable linkage to a second nucleic acid having an expression control sequence. An "expression control sequence" is any nucleic acid sequence that promotes, enhances, or controls expression (typically and preferably transcription) of another nucleic acid sequence. Suitable expression control sequences include constitutive promoters, inducible promoters, repressible promoters, and enhancers. Examples of suitable promoters include the human cytomegalovirus (hCMV) promoters, such as the hCMV immediate-early promoter (hCMV IEp), promoters derived from human immunodeficiency virus (HIV), such as the HIV long terminal repeat promoter, the phosphoglycerate kinase (PGK) promoter, Rous sarcoma virus (RSV) promoters, such as the RSV long terminal repeat, mouse mammary tumor virus (MMTV) promoters, or the herpes thymidine kinase promoter, promoters derived from SV40 or Epstein Barr virus, and the like.

The expression cassette can be placed within a larger nucleic acid and can include other elements (e.g., sequences for controlling replication, polyadenylation sequences, restriction endonuclease cleavage cites, IRES sites, other expression cassettes (such as encoding proteins conferring resistance to a toxin or other selectable marker) and the like. The expression cassette can be constructed by any suitable methodology, which is known to ordinary skill in the art. For example, a polynucleotide encoding an MCV protein as herein described can be ligated within a suitable distance of a promoter, and the entire cassette can be further ligated into a desired plasma backbone. Thereafter the construct can be propagated, further engineered, and/or expressed within a suitable expression system as desired.

It will be further understood that the inventive polynucleic acid (including expression cassettes) can be incorporated within gene transfer vector. Such a vector can facilitate transfer of an expression cassette into a cell, for example. Alternatively, the vector can facilitate transfer of an interfering oligonucleotide or siRNA into a cell, in conjunction, for example, with a protocol for inhibition of viral replication or expression. The inventive polynucleotide can be incorporated into any suitable vector system, such as plasmids, cosmids, YACs, viral vector systems (e.g., adenovectors, HSV vectors, retroviral vectors, etc.), which are known to those of ordinary skill in the art. Also, methods of constructing such vectors (e.g., via recombinant DNA technology) and of growing and propagating such vectors (e.g., using suitable host cells) are known to those of ordinary skill in the art.

Another embodiment of the present invention provides isolated or substantially purified MCV proteins and polypeptides. The isolated and substantially purified proteins and polypeptides of the present invention can be employed to develop antibodies, or as reagents in diagnostic assays. Examples of some such polypeptides include SEQ ID NOs: 6, 8, 10, 12, 14, 16, 18, 20, and that encoded any open reading frame (ORF) of SEQ ID NOs: 1-4. ORFs of SEQ ID NO:1 are represented in table A, and encoded proteins are set forth in FIG. 8, but putative ORFs of SEQ ID NOs: 2-4 and their encoded proteins can be deduced by those of ordinary skill in the art. Typically, the inventive polypeptide includes at least about 5 contiguous nucleic acid residues of an MCV protein, and often substantially more contiguous nucleic acids from such proteins (e.g., at least about 10 contiguous nucleic acids or at least about 25 contiguous nucleic acids or even at least about 50 contiguous nucleic acids from such proteins). In some preferred embodiments, the inventive protein comprises at least about 5 or at least about 10 contiguous amino acids of the amino-terminal 258 sequence of an MCV T-1 polypeptide (one example of which is set forth at SEQ ID NO:12). Of course, the polypeptide can comprise the majority of contiguous amino acids from such proteins, such as all or substantially all of such MCV proteins.

The proteins and nucleic acids of the present invention are isolated or substantially purified in the sense that they are separated from cellular components or mature MCV virions. Thus, in one example, isolated proteins and nucleic acids can exist in substantially (e.g., 90% or more) purified form away from other proteins, polypeptides, and/or nucleic acids. However, it is possible for the inventive proteins and polypeptides to be present in a combination other than found in natural cellular infection or as a mature virion. Thus, for example, the inventive proteins and polypeptides can be present in an artificial virus-like particle (VLP).

The proteins/polypeptides and nucleic acids of the present invention can be produced by standard technologies. For example, particularly with shorter sequences, the inventive proteins/polypeptides and nucleic acids can be produced by solid-state synthesis. However, it will be understood than an efficient method of synthesis involves recombinant DNA technology coupled with (in the case of polypeptides) in vitro or in vivo translation technology. In many aspects, it is preferable for the inventive polypeptides and proteins to be synthesized using a eukaryotic synthesis system (e.g., CHO cells), to achieve desirable folding of the amino acid chain and desirable glycoslation patterns.

As noted herein, the MCV proteins and polypeptides can be employed to produce antibody molecules, which are useful regents for diagnostic assays and potential therapeutic agents. Thus, in another aspect, the present invention provides an antibody preparation containing antibody molecules directed against MCV proteins, polypeptides, and virions. The antibody molecule that binds specifically to a polypeptide consisting essentially or comprising an amino acid sequence selected from the group of sequences consisting of SEQ ID NOs: 6, 8, 10, 12, 14, 16, 18, 20, and any open reading frame (ORF) of SEQ ID NOs: 1-4 or otherwise to an MCV virion.

The antibody molecules of the present invention typically are immunoglobulins, and can be of any isotype (e.g., IgA, IgE, IgG, IgI, IgM, and the like) or an active fragment that retains specific binding activity (such as Fab fragments and the like). Both polyclonal preparations and monoclonal antibodies can be prepared by standard techniques. Following production, the antibody molecules can be isolated and/or substantially purified, and the nventino provides such antibodies in isolated or substantially purified form.

While not wishing to be bound by theory, it is believed that the T1 antigen ORF acquires a mutation during integration into the host cell chromosome that may be responsible for carcinogenesis. The same mutation results in a truncation of the encoded T1 protein. Thus, it is sometimes desirable for the antibody to bind specifically to the N-terminal portion of the MCV T-1 protein (e.g., to one or more epitopes contained within the N-terminal-most 258 amino acids or so of the MCV T-1 protein. In other embodiments, it is desirable for the antibody molecule to bind specifically to MCV Large T polypeptide (T-1) without specifically binding to the MCV Small T polypeptide (T-2). For diagnostic assays, it also is desirable for the inventive antibodies not to bind specifically to proteins or polypeptides of other polyomaviruses, such as SV-40 Large T antigen.

In another aspect, the invention provides compositions, which include the inventive nucleic acid, polypeptide, and/or antibody. In one embodiment, such a composition can include the inventive nucleic acid, polypeptide, and/or antibody in lyophilized form. Of course, if desired, such a lyophilized composition can include a lyoprotectant, such as sucrose or other agent known to those of ordinary skill in the art. Also, the invention provides a composition comprising the inventive nucleic acid, polypeptide, and/or antibody and a carrier, diluent, or buffer. Such carriers; diluents, and buffers are known to persons of ordinary skill in the art.

In another aspect, the invention provides a virus-like particle (LVP) comprising one or more polypeptides MCV polypeptides selected from the group of polypeptides consisting of VP1, VP2, and VP3. Such particles can be produced by expressing one or more of the VP1, VP2, and/or VP3 proteins in a suitable cell. The protein(s) thereafter will assemble to form VLPs, which can be purified from the producing cells by methods such as employed with purifying VLPs of other polyomaviruses.

While not wishing to be bound by any particular theory, it is believed that MCV VLPs form more efficiently if they comprise VP1 molecules from a MCC strain that has consensus-like polyomavirus VP1 sequences at 288(Asp), 316(Arg) and/or 366(Asp) (See FIG. 22). In this respect, it has been observed that the MCV 350 strain does not form VLPs as efficiently as the MCV 339 strain (MCV 350 has differences at 288(His), 316(Ile) and 366(Asn)). Also, the presence of MCV339-like residues 185(Gln) and 422(Glu) might also be important for efficient formation of VLPs, although these positions are not broadly conserved among polyomaviruses.

The VLPs can be used as carriers for foreign DNA, for example, to facilitate transfection of cells. Thus, the invention provides a composition of matter comprising a MCV VLP and a non-MCV nucleic acid (e.g., DNA). Such compositions can be made by exposing a VPL to the non-MCV nucleic acid under conditions suitable for the VLP to bind the nucleic acid. The inventive VLPs, and their use as vectors, can be accomplished by methods such as are known in the art in connection to other polyomaviruses (see, e.g., Goldmann et al., *J Viral Methods*. 2000 October; 90(1):85-90, Goldmann et al., *J. Virol*. 1999 May; 73(5):4465-9, Kosukegawa et al., *Biochim Biophys Acta*. 1996 May 21; 1290(1):37-45, Lundstig et al., *Adv Exp Med. Biol*. 2006; 577:96-101, Tegerstedt et al., *Anticancer Res*. 2005 July-August; 25(4):2601-8, Tegerstedt et al., *Cancer Immunol Immunother*. 2007 September; 56(9): 1335-44, Viscidi et al., *Adv Exp Biol*. 2006; 577:73-84, Viscidi et al., *Clin Diagn Lab Immunol*. 2003 March; 10(2): 278-85, Yokoyama et al., *J Biochem* (Tokyo). 2007 February; 141(2):279-86, and Zielonka et al., *Virus Res*. 2006 September; 120(1-2):128-37).

In another aspect, the invention provides a pharmaceutical preparation comprising a composition including the inventive nucleic acid, protein, antibody, and/or VLP and one or more pharmaceutically-acceptable excipient. Suitable preparations can be formulated for delivery by oral, nasal, transdermal, parenteral, or other routes by standard methodology. In this respect, the excipient can include any suitable excipient (e.g., lubricant, diluent, buffer, surfactant, co-solvent, glidant, etc.) known to those of ordinary skill in the art of pharmaceutical compounding (see, e.g., "Handbook of Pharmaceutical Excipients" (Pharmaceutical Press), Rowe et al., 5$^{th}$ Ed. (2006)).

In another embodiment, the invention provides a method of assaying for MCV exposure in a patient, which can be used to assess past exposure, primary infection, or possibly an MCV-associated cancer in the patient. In accordance with this method, a tissue or fluid sample is obtained from the patient. The sample can be, for example, tissue biopsy, blood, plasma, urine, or other fluid. The sample is then assayed for the presence of one or more MCV molecule(s). Such molecules can be MCV DNA, an MCV polypeptide, or an antibody that binds specifically to an MCV polypeptide or VLP. The assay for DNA can be facilitated by Northern or Southern hybridization or PCR. Assaying for an MCV polypeptide, or an antibody that binds specifically to an MCV polypeptide can be facilitated using common immunohistochemical methods. In any event, a positive test for the presence of the MCV molecule within the sample is indicative of exposure of the patient to MCV. Where the test is conducted on tissue obtained from a tumor, the test can facilitate diagnosis of a carcinoma in the patient. Such assays can be used to diagnose patients with MCV-induced cancers or predict which individuals are at greater risk of developing MCV-induced cancers. It is possible that high-level MCV infection causes non-cancer disease symptoms. If so, VLPs might be used as a diagnostic tool for primary MCV disease.

A preferred assay for MCV exposure in a patient is an ELISA, in which the sample from the patient is exposed to one or more purified MCV polypeptides, such as VLPs containing VP1, VP2, and/or VP3. Such assays can be facilitated by high-throughput screening methods employing multi-well places. In this sense, a multi-well place can be coated with MCV protein or VLPs by standard methods, and the invention provides a multi-well (e.g., 96 well) plate coated with MCV protein and/or VLPs.

Another type of assay (a neutralization assay) is facilitated by infectious VLPs. In accordance with such an assay, MCV VLPs are produced such that they encapsulate a reporter construct (e.g., alkaline phosphatase or Gaussia luciferase). It will be observed, that when such VLPs infect cells, the reporter is expressed in the cells and can be readily detected. However, upon exposure of the VLPs to neutralizing antibodies that target MCV prior to exposure to the cells, the titer of VLPs is substantially reduced, leading to the infection of fewer infected cells (and fewer cells expressing the reporter). The neutralization assay can be about 40-fold more sensitive than ELISA for detection of MCV sero-responses. Accordingly, the assay involves producing VLPs that contain a reporter construct, exposing the VLPs to a sample, and then exposing the preparation to cells and assaying for expression of the reporter within the cells. Reduction of reporter expression in comparison to a control indicates the presence of neutralizing antibodies in the sample. In this context, the sample can be obtained from a patient (such as described herein) or a sample of a candidate antibody for clinical use. In this sense, the neutralizing assay can be employed clinically to ascertain patients having immunoreactivity to MCV, or it can be alternatively employed to screen for potential therapeutically-relevant agents targeting MCV (such as immunoglobulins).

In another embodiment, the invention provides a method of identifying an agent that attenuates MCV infection. In this context, attenuation can involve the reduction of likelihood of infection, or reduction in magnitude. In some applications, the reduction can amount to complete prophylaxis. In accordance with this method, target DNA is exposed to an MCV protein (e.g., VP1, VP2, VP3, T-1, T-2, T-3, T-4, and T-5). The target DNA should include a sequence to which the MCV protein can specifically bind relative a negative control DNA. The assay is conducted in the presence of a test agent, which is a putative agent under investigation to assess whether it can attenuate the MCV infection. Thus, the MCV protein and the target DNA are exposed to each other under conditions which, except for the test substance, are suitable for the MCV protein and target DNA to bind. It will be understood that, as a result of this assay, the ability of the test substance to attenuate binding of the MCV protein to the target DNA identifies the test substance as a candidate agent for use as an anti-MCV therapeutic agent. An example of this type of assay is a gel-shift assay, which is known to those of ordinary skill in the art. Also, while the test agent can be identified as a candidate MCV therapeutic agent by this method, other tests likely will be needed to assess whether the agent is safe and effective for clinical use.

In another embodiment, the invention provides a method of identifying an agent that attenuates MCV infection by employing triplex DNA technology. In accordance with this method, a test agent is exposed to MCV DNA, wherein the ability of the test substance to promote the formation of triplex structure within the MCV DNA identifies the test substance as a candidate agent for use as an anti-MCV therapeutic agent. The promotion of triplex DNA can be assessed by standard methods (see, e.g., Havre et al., *J Viral.* 1993 December; 67(12):7324-3). While the test agent can be identified as a candidate MCV therapeutic agent by this method, other tests likely will be needed to assess whether the agent is safe and effective for clinical use.

In other aspects, the invention involves prophylactic and therapeutic methods against MCV diseases. In this context, the MCV disease can be primary MCV infection or a carcinoma (such as Merkel cell carcinoma, small cell lung carcinoma, or other carcinoma associated with MCV infection). For example, the invention provides a method of vaccinating a patient against an MCV disease. In accordance with this method, a patient is vaccinated with MCC DNA and/or a MCV polypeptide under conditions suitable for the patient to generate an immune response to the MCV DNA and/or MCC polypeptide. A preferred agent for serving as the vaccine is a polypeptide comprising at least 10, and preferably at least the majority of, contiguous amino acids from the N terminus of the MCV T1 protein, particularly contiguous amino acids from among the N-terminal approximately 258 amino acids (see SEQ ID NO:12). Another preferred agent is a VLP as herein described. Indeed, rabbits and mice immunized with MCV can exhibit very high anti-MCV antibody responses, with 50% neutralizing titers in the million-fold dilution range. It will be understood that MCV VLPs could be combined with other viral subunit vaccines such as the current vaccines against hepatitis B virus and human papillomavirus, for combined vaccination protocols.

In another aspect, the invention provides a method for treating a patient suffering from an MCV disease involving adoptive immunotherapy. In accordance with this method, a population of T lymphocytes is first obtained from the patient. Thereafter, the population of T lymphocytes is exposed ex vivo to an MCV polypeptide, including a VLP (such as described herein) under conditions suitable to activate and expand the population of T lymphocytes. For example, the T lymphocytes can be exposed to cells in vitro, which express an MCV polypeptide (e.g., having been transfected with an expression cassette encoding the MCV polypeptide). A preferred MCV polypeptide includes at least 10, and preferably at least the majority of, contiguous amino acids from the N terminus of the MCV T1 protein, particularly contiguous amino acids from among the N-terminal approximately 258 amino acids (see SEQ ID NO:12). In other aspects, the method can be practices using standard techniques. (see, e.g., June, *J. Clin. Invest.*, 117(6) 1466-76 (2007)). After they have been activated, at least some of the T lymphocytes are re-introduced into the patient. Such a method can attenuate the severity of the MCV disease within the patient. It should be understood that the method need not eradicate the MCV disease within the patient to be effective as a therapy. The method can be deemed effective if it lessens symptoms, improves prognosis, or augments other modes of therapy if used adjunctively.

It is believed that the newly-discovered MCV should respond to agents that interferes with the replication of other polyomaviruses. Thus, the invention provides a method of treating an MCV disease by administering such an agent to a patient suffering from an MCV disease. As noted, the MCV disease can be primary MCV infection, Merkel cell carcinoma, small cell lung carcinoma, or another carcinoma that is caused by MCV. It is believed that the administration of some such agents can attenuate the severity of the MCV disease within the patient. Examples of such agents are cidofovir and vidarabine, and other agents that interfere with polyomavirus replication known to those of ordinary skill may be useful in treating such conditions as well. Additional agents include interferons and mTOR inhibitors (e.g., sirolimus and tacrolimus).

It will be understood that the diagnostic therapeutic methods described herein to be performed on a patient can include human patients as well as animals. In this respect, the diagnostic and therapeutic methods can be performed in the veterinary context, i.e., on domestic animals, particularly mammals (e.g., dogs, cats, etc.) or agriculturally-important animals (e.g., horses, cows, sheep, goats, etc.) or animals of zoological importance (apes, such as gorillas, chimpanzees, and orangutans, large cats, such as lions, tigers, panthers, etc., antelopes, gazelles, and others).

The following examples further illustrate the invention but, of course, should not be construed as in any way limiting its scope. In summary, they support the possibility that MCV plays a role in MCC tumorigenesis:

1. MCV is integrated into the tumor cell genome. Precisely identical integration sites (confirmed by sequencing) occur in a metastasis (MCC348) and its primary tumor (MCC347). The most likely explanation for this is that the metastatic tumor arose from a single tumor cell already having the virus integration allele.

2. There is an association between MCV and Merkel cell carcinoma. Examination of two different groups of MCC tumors finds them statistically more likely to be positive for virus than control tissues. In our initial analysis, MCV was present in MCC 43-fold more commonly than a convenience sample of tissues from different body sites from different persons. Virus is found only in classic MCC cell lines suggesting that it may be associated with the classic but not variant form of disease. These analyses are based on three independent PCR primers in a blinded and randomized analysis using stringent PCR segregation precautions, and confirmed through two additional qPCR assays.

3. Southern blots can detect MCV in tumors. Direct Southern blotting confirms presence of abundant genome in 8 of 12 tumors and in MCV-positive cell lines. This data indicates that MCV genome is present at sufficient levels to play a biological role in these tumors. Similar data is not available for other polyomaviruses in human cancer. This data is experimentally independent from PCR-based studies and confirms them, demonstrating that the association is not caused by PCR contamination.

4. MCV is monoclonally integrated into MCC genome in 6 of the 8 MCV-positive tumors. Cellular monoclonality is also shown for two tumors (MCC347 and its metastasis MCC348) in which the integration site has been mapped. This suggests MCV infected cells prior to developing into MCC tumors that subsequently underwent monoclonal expansion. This is not consistent with MCV being a passenger virus that secondarily infects MCC tumors.

5. MCV T antigens are expressed in tumor cells. DTS and RACE studies demonstrate viral T antigen gene expression in tumors infected with MCV. Mutations in the T antigen oncoprotein are consistent with animal models of polyomavirus-induced tumors and are not found in non MCC tissues positive for MCV.

EXAMPLE 1

This example demonstrates the identification of a previously-unknown polyomavirus and its integration in Merkel cell carcinoma.

We performed DTS on MCC tissue mRNA and identified T antigen transcripts from a previously undescribed polyomavirus. This virus is closely related to the murine polyoma virus group that includes primate viruses such as the lymphotrophic African green monkey (AGM) polyomavirus (20), and is more distantly related to all known human polyomaviruses including WUV and KIV. The virus is somatically and monoclonally integrated into the human genome, suggesting that it was present prior to tumor cell clonal expansion.

Methods and Materials

Human Tissue Sample Testing:

Human Merkel cell carcinoma tissues were obtained from the Cooperative Human Tissue Network as frozen excess biopsy samples (Supplementary Table 1). All MCC tumors except MCC352 were reconfirmed in our laboratory by H&E and with cytokeratin 20 immunostaining. All MCC tissues except MCC350 were positive for cytokeratin 20. MC350 is MCC metastatic to a lymph node and due to sampling issues we were unable to identify MCC tumor cells the portion of tissue taken for our examination. We relied on the original pathology report as evidence for MCC. Excess surgical tissues used as controls were collected as a consecutive series of anonymized pathology collections from a single operating day (Supplementary Table 1). Confidentiality issues limited the availability of diagnosis for these tissues. Four cases (MCC347, MCC337, MCC343, and MCC346) from 4 men ranging in age from 38 to 84 years were used for DTS.

Generation of cDNA Library for Pyrosequencing:

Total RNA was extracted from MCC tissues using RNE-ASY MIDI kit (Qiagen, Alameda, Calif.) and treated with DNase I (Ambion, Austin, Tex.) to remove genomic DNA. Integrity of tissue RNAs was analyzed by the AGILENT 2100 bioanalyzer (Quantum Analytics, Foster City, Calif.) using the RNA 6000 Nano reagent kit. mRNA was purified with DYNABEADS mRNA purification Kit (Invitrogen). Double strand cDNA was synthesized with oligo (dT) primer using the SUPERSCIRPT™ Double-strand cDNA Synthesis kit (Invitrogen). Five microgram of MCC cDNA was used for pyrosequencing after confirming cDNA quality on an AGILENT bioanalyzer (Quantum Analytics) at 454 Life Sciences (Roche). The cDNA sample was fractionated into small fragments (300-500 bp) and blunted for ligation of two different adaptors at both ends. These two adaptors provide unique priming sequences for both amplification and sequencing, forming the basis of the single-strand template library for pyrosequencing accordingly. Finally, by GENOME SEQUENCER GS20 system (Roche Diagnostic), large scale sequencing was performed on two cDNA libraries from a single (MCC347) and pooled (MCC337, 343 and 346) cases, respectively (M. Margulies et al., Nature 437, 376 (Sep. 15, 2005)).

Digital Transcriptome Subtraction:

The sequences data from large scale library sequencing were first trimmed using Lucy (H. H. Chou, M. H. Holmes, Bioinformatics 17, 1093 (December, 2001)) with similar Phred scores of 20 or higher (−error 0.01 0.01), and long read over 50 bp (−m 50). Only high quality sequences obtained after Lucy trimming were used for further subtraction with SeqClean. First, Poly(A/T), dust (low-complexity), human repeat and primer adaptors sequences were removed to obtain high fidelity (HiFi) datasets. These HiFi sequences were then aligned against human databases, including human Refseq RNA, mitochondrial and assembled chromosomes, and human immunoglobulin variable sequences with a minimum hit length of 30 bp. The remaining sequences were then aligned to online GenBank nonredundant (NR) using BLASTX program in netblast package.

RACE Analysis on MCV Transcripts:

Both rapid amplification of 5' and 3' cDNA ends (RACE) were performed with GENERACER Kit (Invitrogen) according to the manufacturer's instructions. Primers used for RACE are listed in supplementary table 2. To capture the large T antigen, M1-L primer and M3 were used in 5'RACE. M2-L primer and M4 were used as primers in 3'RACE. To capture the small T antigen, small.t.R in intron 1 was used in 5'RACE. Small.t.F and small.t.F.nest were used in 3'RACE. The PCR fragments were isolated from agarose gel and extracted with QIAEX II gel extraction Kit (Qiagen), and ligated in pCR 2.1 vector (Invitrogen) for DNA sequencing.

Consensus PCR for VP1:

Consensus PCR for the VP1 region of Polyomavirus was previously described (R. Johne, D. Enderlein, H. Nieper, H. Muller, J Virol 79, 3883 (March, 2005)). The genomic DNAs from MCC339, MCC344, MCC347, and MCC350 were subjected to PCR amplification by PLATINUM Taq DNA polymerase (Invitrogen) using two sets of VP1 consensus primers, VP1-1 and VP1-2, as in Supplementary Table 2. The cycling conditions for the first PCR was 5 min at 95° C., followed by 45 cycles each of 94° C. for 30 sec, 46° C. for 1 min and 72° C. for 1 min, and final elongation at 72° C. for 10 min. For nested PCR, 4 µl of the first PCR product was used as the template in a similar reaction at 95° C. for 5 min, 45 cycles of 94° C. for 30 sec, 56° C. for 30 min and 72° C. for 30 sec, and 72° C. for 10 min. PCR fragments were recovered from gel, cloned in pCR2.1 cloning vector (Invitrogen) and subjected to nucleotide sequencing. Specific primers (VP1-iF and VP1-iR) for MCV350 VP1 region were designed based on the sequencing results.

MCV Genome Sequencing:

The genome was bidirectionally sequenced with at least 3 fold coverage. Successive outward PCR was performed from the 3' end of the T antigen sequence to a conserved VP1 site with primer M6 and VP1_iR, and 5' end of the T antigen sequences to conserved VP1 site with Primer M5 and VP1_iF. Walking primer set (W1~W10) was used to sequence the long PCR product. Second and third rounds of sequencing used 13 pairs of primers (contig 1~contig 13) designed to encircle the entire genome. All PCR reactions were performed with HIGH FIDELITY PLATINUM Taq DNA polymerase (Invitrogen). Primers for genome sequencing are listed in Supplementary Table 3.

Northern Blotting:

Total RNA from 293 cells transfected with pcDNA R339 or R350 containing large T genomic region, were extracted by the TRIZOL (Invitrogen). Northern blotting was performed using 5 µg of total RNA for each sample. RNAs were electrophoresed through 1.2% formaldehyde-agarose gels and transferred onto nitrocellulose membranes (Amersham) with 10×SSC. DNA probes were generated by random prime labeling of (α32P) dCTP (Amersham) on the P1 MCV DNA fragment which contains the exon-1 sequence of MCV T antigen (Supplementary Table 4). Hybridization was performed at 42° C. in 5×SSC, 50% formamide, 5×Denhardt's solution, 2% SDS, 10% dextran sulfate, and 100 mg/ml of denatured salmon sperm DNA (Stratagene). Final rinse of the blots were conducted in 2×SSC/0.1% SDS at 60° C. for 30 min. RNA ladder marker (Sigma) was used as length control.

MCV Detection by PCR-Southern Blotting:

Genomic DNA was extracted by standard phenol-chloroform technique and the quality of the DNA was ascertained by PCR with β-actin primers. One hundred nanograms of genomic DNA was amplified using Taq DNA polymerase (Invitrogen) in a final volume of 50 µl. The cycling condition was 3 min at 94° C., followed by 31 cycles each of 94° C. for 45 sec, 58° C. for 30 sec and 72° C. for 45 sec, and final elongation of 15 min at 72° C. Three different primer sets for the T antigen locus (LT1 and LT3) and VP1 gene (VP1) and corresponding primers for the internal probes of T antigen (M1-M2 and LT5) and VP1 gene (VP1.3) used in Southern blotting are listed in Supplementary Table 4. To avoid potential contamination of template DNA, PCR mixtures were prepared in an isolated room and template DNA was prepared or added in an UV-irradiated clean hood. Recombinant DNA harboring MCV DNA sequence was not amplified at the same time as tissue samples to avoid cross contamination between PCR samples. Negative controls contained all components except DNA template. Both case and control tissue samples were randomized and blinded to the scientist throughout the PCR-Southern testing for MCV positivity.

Genomic DNA Southern Blotting:

Fifteen microgram of each sample, digested overnight with 60 units of restriction endonucleases, were separated on 0.7% agarose gels at 80 volts. Completion of digestion was checked with ethidium bromide staining. Gels were transferred onto nitrocellulose membrane (Amersham) with 10×SSC and hybridized overnight with (α32P) dCTP-labelled probe (2.7× 10$^7$ d.p.m./ml) at 42° C. Membranes were rinsed in 0.2×SSC/0.5% SDS at 60° C. or 72° C. PCR fragments used for the probe synthesis are listed in Supplementary Table 4. The MCV DNA fragments (LT 1, LT2, P1, P3, P6, P9, and P12), which cover 2.5 kb of non-overlapping MCC 350 genome, were used for Southern blotting in FIG. 4A. For Southern blotting in FIG. 4B, a probe specific for the intron 1 region of the human PTPRG gene (Chr3) was used.

Results and Discussion

Digital Transcriptome Subtraction from Merkel Cell Carcinoma:

To perform DTS, we isolated mRNA from four anonymized MCC tumors from the Cooperative Human Tissue Network (21). One case mRNA (MCC347) was examined separately, while three case mRNAs were pooled (MCC337, 343 and 346) to increase the likelihood for virus discovery (Table S1). We pyrosequenced 216,599 and 179,135 cDNA sequences (~150-200 bp) from these two libraries, respectively. This allowed us to use all high-confidence sequence reads in contrast to our previous DTS analyses with serial analysis of gene expression (SAGE) tags (15). These 395,734 cDNA sequences were trimmed with LUCY stringency equivalent to PHRED scores of 20 or higher (22). Poly(A/T), dust (low-complexity), human repeat and primer adaptor sequences were then removed, leaving 382,747 sequences to form the HiFi dataset. Of these, 380,352 (99.4%) aligned to human Refseq RNA, mitochondrial, assembled chromosomes or immunoglobin NCBI databases. The remaining 2395 sequences were then aligned to GenBank NR using BLASTX.

One transcript (DTS1) from MCC347 aligned over 111 nt. to the DNA binding domain of human BK polyomavirus T antigen [gi:113204635] with 54% identity. The full 201 nt. sequence from this DTS transcript prior to LUCY trimming has highest homology to AGM PyV T antigen [gi:135284] (59% identity over 170 nt., 1×e–12). A second DTS transcript (DTS2) from the T antigen locus was subsequently identified after alignment of candidate HiFi sequences to the full-length viral genome. This fragment corresponds to a unique viral T antigen region with low polyomavirus homology. These two sequences define a new human polyomavirus that we call Merkel cell virus (MCV) because of its close association with Merkel cell carcinoma.

MCV Genome Cloning:

3'-Rapid amplification of cDNA ends (3'-RACE) extended the DTS transcript from case MCC347 to three different cDNAs (FIG. 1B); one transcript terminated at a poly(A) site in the T antigen sequence and two cDNAs read through this poly(A) site to form different length fusions with intron 1 of the human receptor tyrosine phosphatase, type G (PTPRG) gene [gi:18860897] at chromosome 3p14.2. Genomic integration at this site was confirmed by sequencing DNA PCR products from a viral and a PTPRG primer. Identical 3'-RACE cDNA transcripts were independently obtained from MCC348, a metastatic lymph node from MCC347, suggesting that the metastasis was seeded from a clonal tumor cell having the T antigen-PTPRG fusion.

Viral genome walking was successful on DNA from tumor MCC350 (Table S2) providing the complete closed circular genome (5387 bp, prototype) and a second genome, MCV339 (5201 bp), was then cloned and sequenced using specific primers (Table S3). Both viruses have high homology to polyomavirus T antigen, VP1, VP2/3 and the replication origin sequences (FIG. 7). The principal differences between MCV350 and MCV339 being a 201 bp (1994-2184 nt) deletion in T antigen, and a 2 bp (5215-5216 nt) deletion in MCV339 late promoter and a 7 bp deletion (5222-5228 nt.) in the MCV350 late promoter. Excluding these sites, 41 (0.8%) nucleotides differ between MCV350 and 339. In comparison, 1558 HiFi sequences comprising 179,301 nucleotides from the MCC347 dataset were aligned without gaps to known cellular genes in RefSeq RNA database. Only 130 polymorphic nucleotides were found (99.93% concordance), suggesting that high mutation rates are not present in this tumor.

Features of the MCV Genome:

MCV has an early gene expression region (196-3080 nt.) containing the T antigen locus, with large T and small T open reading frames, and a late gene region containing VP1 and VP2/3 open reading frames between 3156 and 5118 nt (FIG. 7). The MCV350 replication origin (5360-69 nt) is highly conserved with seven pentameric T antigen binding sites, including pentanucleotide palindrome and tandem pentanucleotide boxes, a homopolymeric T tract and semiconserved inverted repeats. Comparison of four MCV genes to those of other polyomaviruses show MCV to be highly divergent from known human polyomaviruses and SV40 (FIG. 2). MCV has highest homology to viruses belonging to the MuPyV subgroup and is closely related to AGM PyV (23).

MCV T Antigen Expression:

To examine MCV T antigen transcription, 3'- and 5'-RACE products were sequenced from MCC 339, 347, 348, 349, 350 and 352 RNAs (FIG. 3). These products were compared to results of northern blots and RACE products from 293 cells expressing pcDNA-cloned genomic T antigen (48-3695 nt.) fragments from MCV350 and MCV339. Four T antigen spliced products were identified in tumors that can be assigned to transcripts expressed from the T antigen expression cassettes in 293 cells.

A predicted 2.3 kbase large T transcript (T-1) has near-precise sequence homology to large T domains from SV40 and other polyomaviruses, including pRB1-binding, DnaJ, Bub1-binding and origin-binding domains as well as C-terminal helicase/ATPase A, B1 and B2 motifs (24). Surprisingly, stop codons are present in all large T antigens so far sequenced from tumors (MCV339, 347, 348, 349, 350, 352) that will prematurely terminate this protein at different lengths after the pRB1-binding LXCXE motif (FIG. 3), generally deleting origin-binding and helicase functions. The deletion in MCV339 produces a frameshifted large T antigen, eliminating expression of the highly-conserved helicase/ATPase domain. Given the importance of the origin-binding and helicase domains for replicating episomal virus, these mutations most likely arose after viral integration. This transcript forms the fusion to PTPRG in MCC347/348 but is unlikely to generate a fusion protein due to a stop codon in large T exon 2.

Shorter T antigen proteins are likely to be expressed from other T antigen transcripts that splice out origin-binding and helicase motifs, but all retain the 5' cr1, DnaJ and LXCXE domains. A small T antigen transcript (T-2) reads through the first splice site. Another T transcript (T-3) generates two downstream splice junctions, reminiscent of SV40 17KT (25). Transcripts with obvious, unique homology to rodent virus middle T sequences were not identified. Genomic integration at different sites within the T antigen locus could also be expected to disrupt full-length gene expression but may still allow protein expression from smaller viral transcripts (e.g., T-2, T-3) predicted to target cell cycle regulatory pathways. Defining the actual T antigen proteins expressed in MCC requires specific antibody panels that do not currently exist. But this initial analysis reveals that MCC tumors have an unexpected level of mutational variation affecting T antigen protein expression.

Merkel Cell Virus in Merkel Cell Carcinomas:

To determine whether MCV is commonly found in human tissue, 59 control DNA samples from various body sites were compared to 12 tissues from 10 MCC patients (Tables 1, S1). All case and control samples were randomized and blinded to the scientist testing and scoring two PCR primer sets in the T antigen locus (LT1 and LT3) and one in the VP1 gene (VP1), followed by Southern blotting with internal probes (Table S4). None of these primer sets amplify plasmid cloned human BK or JC genomic DNA (26, 27).

Of 10 MCC tumors, 7 were positive by PCR using one or more primer sets without Southern hybridization to amplify detection (Table 1). One additional tumor was positive only after PCR-Southern hybridization. In comparison, none of the control tissues were positive by PCR alone but 5 of 59 (8.5%) samples tested weakly positive after PCR-Southern hybridization, giving an odds ratio of 43 (95% confidence interval 7 to 261) for detecting MCV in MCC tumors compared to non MCC tissue samples. Both MCC348 (the metastatic lymph node from tumor MCC347) and MCC338 (tumor infiltrating adjacent skin from MCC339) were positive for MCV genome using multiple PCR primer sets.

In addition to patient samples, common cell lines were tested for the presence of MCV genome (Table 2). Of four available MCC cell lines, only one cell line (MLK-1) grows in suspension culture and is positive for MCV genome by PCR. The three negative cell lines (MCC1, MCC13, MCC26) are adherent "variant" cell lines that have been shown to have distinct gene expression profiles from classical, suspension MCC cells (18). None of the nonMCC cells show evidence for MCC infection including COS-7 cells containing SV40 genome.

MCV Genomic Integration:

MCV integration can be expected to destroy transmissible virus replication capacity and thus should be a relatively rare event that does not contribute to viral replication fitness. Integration nonetheless is frequent in polyomavirus-induced tumors, for example (28), suggesting that this biological accident contributes to polyomavirus tumorigenesis—similar to well-characterized papillomavirus integration in cervical cancer (29).

Genomic integration can be exploited to examine the origins of MCV-infected tumor cells. If tumor DNA is digested with single-cutter restriction endonucleases, such as EcoRI or BamHI, and Southern blotted with viral sequence probes, four different patterns can be predicted: 1) If virus exists as closed circular episomes or integrated viral concatemers, then a ~5.4 kbase band will be present, 2) if MCV integrates polyclonally—as might to occur during secondary infection of the tumor—then diffuse hybridization representing different band sizes is expected, 3) if MCV preferentially integrates at one or a few sites, then tumors will have identical or near identical non-5.4 kbase banding patterns, or 4) if MCV integrates at different places in the human genome prior to tumor clonal expansion, distinct bands of different sizes will be present (monoclonal viral integration).

Figure 1B:
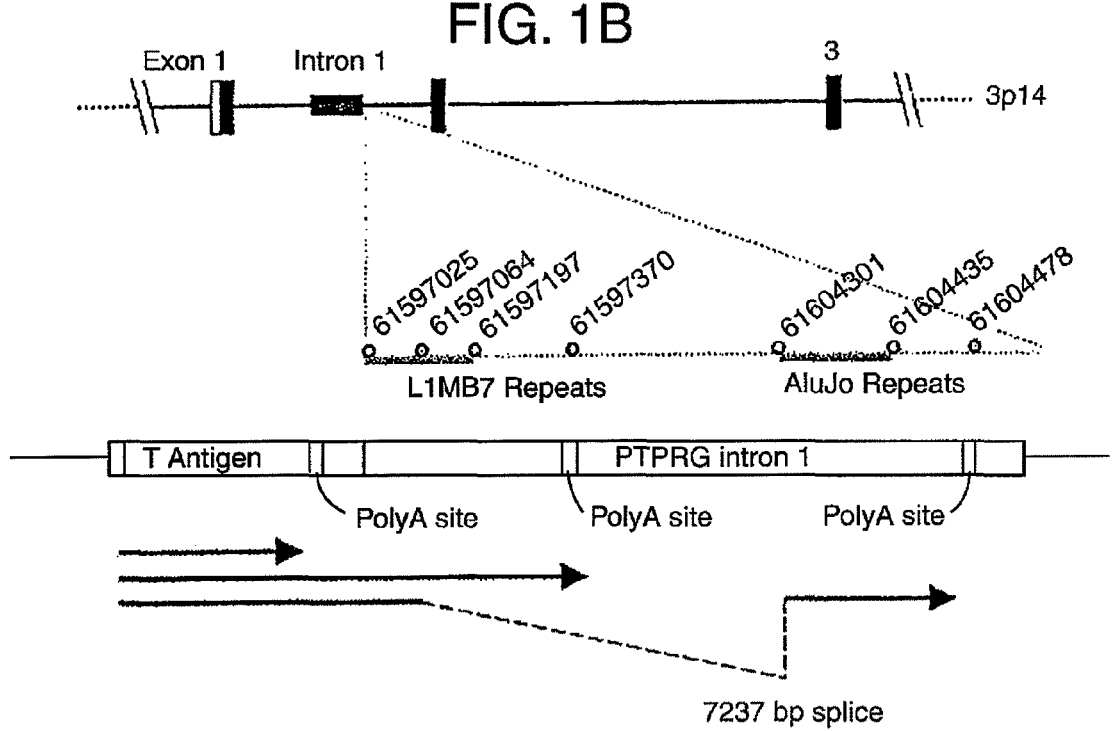

Eight of 11 MCC DNA (including MCC348 metastasis from MCC347) show robust MCV hybridization after BamHI and EcoRI digestion (FIG. 4). These same tumors are also positive by MCV PCR (Table 1). Monoclonal viral integration is evident with one or both enzymes in six tumors: MCC339, 345, 347, 348, 349 and 352 (closed arrows). EcoRI digestion of MCC339, for example, results in two distinct 7.5 and 12.2 kbase bands that can only arise if MCV is integrated at a single site in the bulk of the tumor mass. MCC344 and 350 bands, in contrast, are consistent with episomal virus (open arrow), whereas MCC352 has a predominantly episomal or concatenated-integrated pattern but also clear monoclonal integration bands on BamHI digestion (T antigen sequencing from MCC350, 352 failed to identify a replication-competent T antigen). The banding patterns for MCC347 and its metastasis, MCC348, are identical, consistent with 3'-RACE results (FIG. 1B). Of the three Southern blot negative cases, two were negative by PCR-Southern (MCC343 and 346) and the third was weakly positive with only one PCR primer set (MCC337).

Figure 4A:
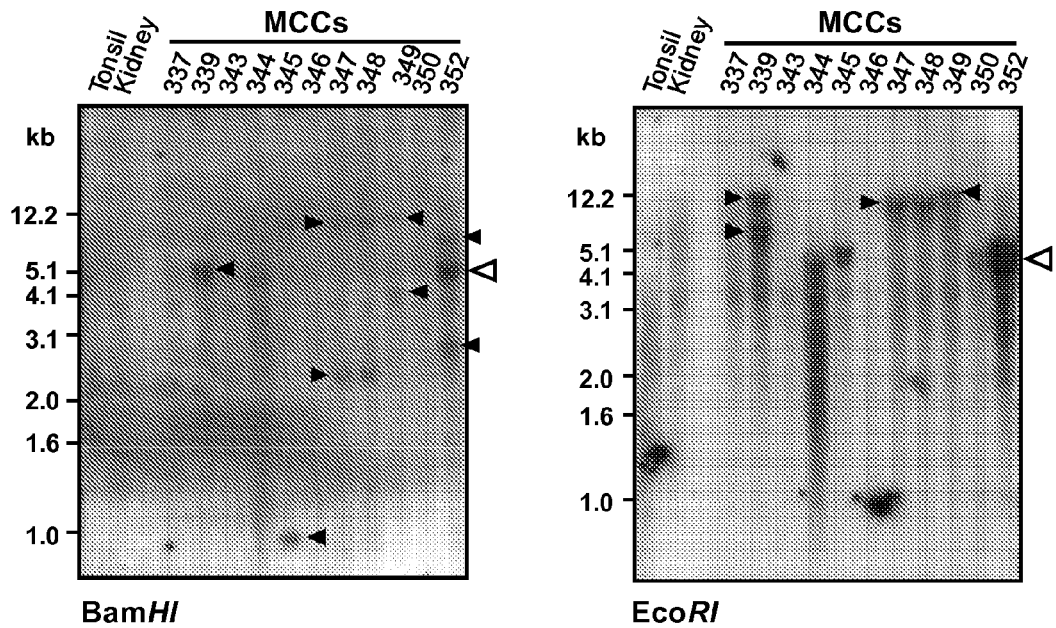
Figure 4B:
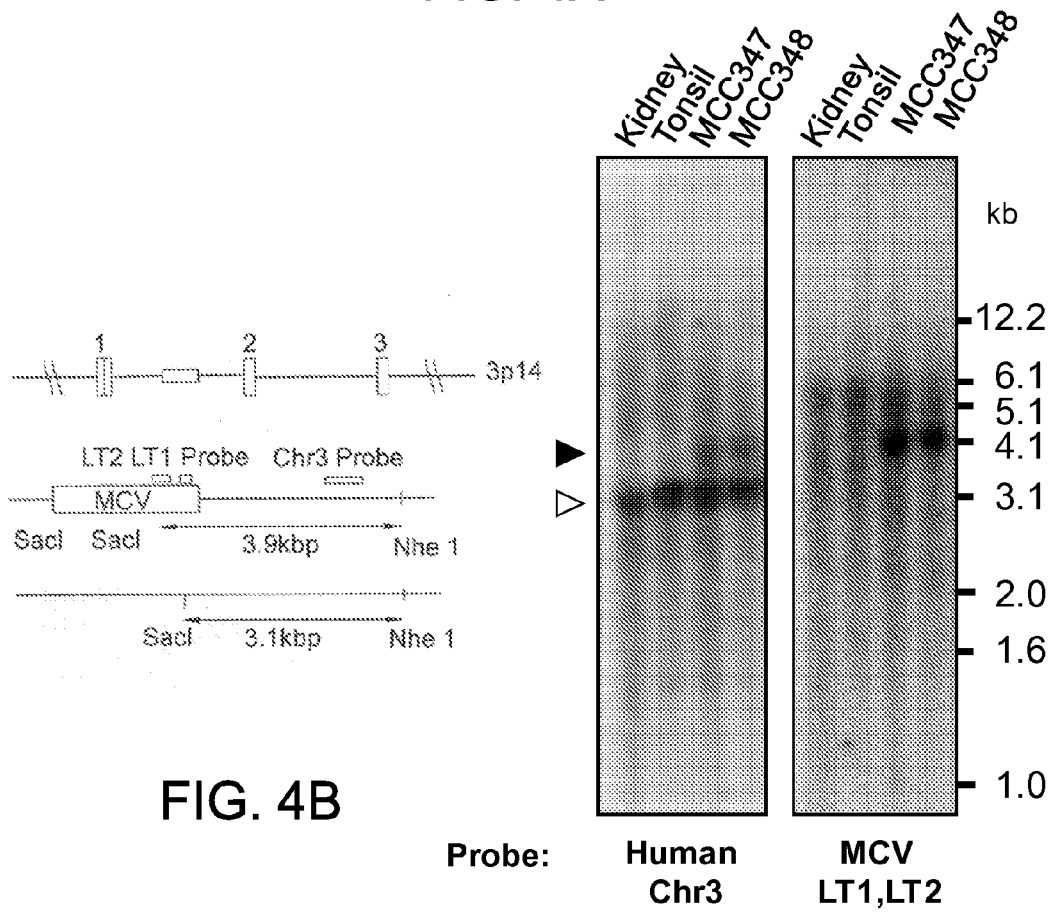

Mapping the human genomic integration site (PTPRG locus on chromosome 3p14) for MCC347 and 348 allows us to directly confirm these results. NheI-SacI digestion of MCC347 is predicted to generate a 3.1 kbase fragment from the wild-type allele and a 3.9 kbase fragment from the MCV-integrated allele. As seen in FIG. 4B, the virus-integrated allele is present in MCC347 and MCC348 DNA, but not control tissues, when probed with a flanking human PTPRG sequence probe. Hybridization with a MCV T antigen sequence probe generates the same 3.9 kbase band in MCC347 and MCC348, consistent with both cellular and viral monclonality in this tumor. These results together with those in FIG. 4A indicate that MCV infection and genome integration often occurs prior to clonal expansion of the MCC tumor.

A Potential Role for MCV in MCC: Our results demonstrate an intimate association between this new human polyomavirus and Merkel cell carcinoma. Determination of causality must await confirmation but our results suggest that MCV is present in most MCC tumors prior to their monoclonal expansion. There are a number of unresolved and interesting questions. If MCV plays a role in MCC tumorigenesis, we do not know whether MCV T antigen expression, insertional mutagenesis or both are contributing to the tumor phenotype. The PTPRG gene is suspected to be a tumor suppressor locus (30) and MCV integration may disrupt its expression. Clonality studies (FIG. 4A) indicate that MCV integration occurs at other sites and it is possible that dysregulation of the PTPRG pathway is one of several complementing mutations that contribute to MCC.

The potential role for MCV T antigen in tumorigenesis is complex but may lead to critical insights into viral carcinogenesis and immunity. Virus-induced tumors are generally rare biological accidents that do not benefit viral transmission (31). We have not yet characterized freely infectious MCV but mutations in tumor-derived MCV paradoxically prevent full-length large T protein from being expressed. This is likely to destroy origin-binding and helicase activities required for free virus replication but unlikely to affect integrated virus. Further, Southern blotting for the viral BamHI-EcoRI fragment spanning the T antigen locus reveals deletions and insertions for several viruses that is also likely to disrupt full large T expression. But these mutations may not affect expression of smaller T antigens (e.g., T-2 and T-3) that retain domains suspected to play a role in cancer cell transformation such as pRB1-interaction and DnaJ domains. These findings demonstrate that tumors strongly select against retention of intact MCV large T antigen. Since polyomavirus T antigens provoke robust cytotoxic immune responses (32), these may represent immune escape mutants selected during tumor evolution.

Identifying a new human tumor virus opens diagnostic, therapeutic and prevention possibilities for tumors like MCC that respond poorly to current therapies. In our study, only eight of 10 MCC tumors had evidence for MCV infection suggesting that MCC may arise from two or more etiologies. This is supported by gene expression and cell culture studies that define MCC into classical and variant types (18). At present, we do not know if this accounts for heterogenous MCV infection in MCC. We also do not know if MCV is a common or uncommon infection of humans. Our PCR analysis only shows that MCV is far more common in MCC tissues than an assortment of nonMCC tissues. Addressing the MCC prevalence in human populations requires development of a sensitive and specific serologic test. Intriguingly, serologic studies led Brade et al. in 1981 to speculate that a virus related to AGM PyV circulates in the human population (23). Caution is needed in interpreting this, however, since polyomavirus serologic cross-reactivity has been a source of confusion (5). PCR contamination has similarly plagued human tumor virology studies. Direct Southern blotting in our study, however, shows that MCV genome is present at high copy numbers in most MCC tumors without amplification (FIGS. 4A-B).

Sequencing technology and databases have matured so that direct high-throughput sequencing now can be used to characterize human viral infections. DTS does not depend on sequence homology and we had no a priori expectation that polyomavirus RNA would be present in MCC. This is only practical for hosts, such as humans, in which validated whole genome sequencing has been accomplished. DTS also has the advantage of placing a quantitative upper limit on the abundance of distinguishable viral transcripts when none are found. This does not rule out all forms of infection but it does help to define the possibilities for infection in a tissue sample.

We chose to study an immune-related tumor based on the concept that direct infectious carcinogens express antigenic viral transcripts in each tumor cell (33). MCC is one of the few tumors significantly elevated, a 13-fold increase, among AIDS patients in population-based database cross-matching for AIDS and cancers (33). DTS is less likely to be useful for tumors caused by chronic inflammation or by viruses that do not generate mRNA.

Of the four tumors we chose to initially study, only one was found retrospectively to have significant MCV virus (Table 1). MCV transcripts in this tumor (MCC347) are present at 9 transcripts per million or approximately 2 transcripts per cell. We and others have found that some latent tumor virus infections retard viral protein synthesis and turnover as a means to evade antigenic peptide processing, with correspondingly reduced mRNA transcription (34, 35). Our experience with MCC illustrates that sequencing to <10 transcript per million level on multiple tissue samples should be used, whenever possible, in searching for new human viruses.

TABLE 1

MCV PCR on human tumor (MCC) and control tissues with LT1, LT3 and VP1 primers, followed by Southern blot hybridization with internal probes

| MCC Cases (n = 10) | | | | | |
|---|---|---|---|---|---|
| Patient | Tissue ID | LT1 | LT3 | VP1 | Summary |
| 1 | MCC337 | +/−* | − | − | +/− |
| 2 | MCC338** | + | + | + | + |
|  | MCC339 | + | + | + | + |
| 3 | MCC343 | − | − | − | − |
| 4 | MCC344 | + | + | + | + |
| 5 | MCC345 | − | + | − | + |
| 6 | MCC346 | − | − | − | − |
| 7 | MCC347 | + | + | − | + |
|  | MCC348*** | + | + | − | + |
| 8 | MCC349 | + | + | +/− | + |
| 9 | MCC350 | + | + | + | + |
| 10 | MCC352 | ND**** | + | + | + |
|  | No. of Positives (%) | 6/9(66.7) | 7/10(70) | 7/10(70) | 8/10(80) |

| Control Cases (n = 59) | | | | |
|---|---|---|---|---|
| Positive Tissues | LT1 | LT3 | VP1 | Summary |
| Appendix | +/− | +/− | +/− | +/− |
| Appendix | − | +/− | +/− | +/− |
| Gall Bladder | +/− | − | − | +/− |
| Bowel | − | +/− | +/− | +/− |
| Hemorrhoid | − | − | +/− | +/− |
| No. of Positives (%) | 2/59(3.4) | 3/59(5.1) | 4/59(6.8) | 5/59(8.5) |

* +/−: Signal positive only after Southern hybridization of PCR products.
** MCC338, non-tumorous skin tissue adjacent to MCC339.
***MCC348 Metastatic lymph node from MCC347.
****ND Not Determined

TABLE 2

MCV PCR detection in various cell lines

| Name | Origin | LT1 | LT3 | VP1 | Summary |
|---|---|---|---|---|---|
| 293 | Human embryonic kidney | − | − | − | − |
| COS7 | SV40-transfected African green monkey kidney | − | − | − | − |
| HT1080 | Human fibrosarcoma | − | − | − | − |
| MCF7 | Human breast cancer | − | − | − | − |
| MCC1 | MCC | − | − | − | − |
| MCC13 | MCC | − | − | − | − |
| MCC26 | MCC | − | − | − | − |
| MKL1 | MCC | + | + | + | + |

SUPPLEMENTARY TABLE 1

Clinicopathological data for MCC patients.

MCC Cases

| Patient | Tissue ID | Age | Sex | Race | Phenotype | Cyto-keratin 20 |
|---|---|---|---|---|---|---|
| 1 | MCC337 | 84 | Male | White | Malignant | — |
| 2 | MCC338* | 79 | Male | White | Normal | — |
|  | MCC339 |  |  |  | Malignant | — |
| 3 | MCC343 | 79 | Male | White | Malignant | — |
| 4 | MCC344 | 57 | Male | White | Malignant | — |
| 5 | MCC345 | 77 | Male | Black | Malignant | — |
| 6 | MCC346 | 38 | Male | Unknown | Malignant | — |
| 7 | MCC347 | 56 | Male | White | Malignant | — |
|  | MCC348** |  |  |  | Malignant | — |
| 8 | MCC349 | 58 | Female | White | Malignant | — |
| 9 | MCC350 | 58 | Male | White | Malignant | — |
| 10 | MCC352 | 58 | Male | White | Malignant | ND*** |

*MCC338 is non-tumorous skin tissue adjacent to MCC339 tumor.
**MCC348: Metastatic lymph node from MCC347.
***ND: Not Determined Control tissue types used in the study (MCV PCR-):

| Colon | 5 |
|---|---|
| Small Bowel | 3 (1) |
| Hemorrhoid | 1 (1) |
| Gall Bladder | 7 (1) |
| Appendix | 9 (2) |
| Mouth | 1 |
| Vein | 2 |
| Heart | 1 |
| Kidney | 1 |
| Skin | 9 |
| Hernia | 2 |

Hematolymphoid tissues

| Lymph node | 1 |
|---|---|
| Tensil | 5 |
| B cell CLL | 1 |
| Myeloid hyperplasia | 1 |
| Posttransplant lymphoma | 1 |
| HIV+ large cell lymphoma | 1 |

Miscellaneous tissues

| Lipoma | 1 |
|---|---|
| Fibrous tissue | 2 |
| Fistula track | 1 |
| Meningioma | 1 |
| Breast cancer | 1 |
| Lung cancer | 1 |
| Prostate | 1 |

SUPPLEMENTARY TABLE 2

Primers used for the MCV cloning.

| Name | Position* | Purpose | Sequence | SEQ ID NO |
|---|---|---|---|---|
| M1L | 1894-1864 | 5'-RACE | TTCTCTTGCAGTAATTTGTAAGGGGACTTAC | 46 |
| M3 | 1848-1827 | 5'-RACE | TTTCAGGCATCTTATTCACTCC | 47 |
| M2L | 1707-1734 | 3'-RACE | AGCAGGCATGCCTGTGAATTAGGATGTA | 48 |
| M4 | 1784-1805 | 3'-RACE | TTTTTGCTCTACCTTCTGCACT | 49 |
| small.t.R | 562-530 | 5'-RACE | TAATACAAGCGCACTTAGAATCTCTAAGTTGCT | 50 |
| small.t.F | 442-473 | 3'-RACE | TTTCCTTGGGAAGAATATGGAACTTTAAAGGA | 51 |
| small.t.F.nest | 496-517 | 3'-RACE | GCTAGATTTTGCAGAGGTCCTG | 52 |
| VP1-1F |  | VP1 Consensus PCR | CCAGACCCAACTARRAATGARAA | 53 |
| VP1-1R |  | VP1 Consensus PCR | AACAAGAGACACAAATNTTTCCNCC | 54 |
| VP1-2F |  | VP1 Consensus PCR | ATGAAAATGGGGTTGGCCCNCTNTGYAARG | 55 |
| VP1-2R |  | VP1 Consensus PCR | CCCTCATAAACCCGAACYTCYTCACYTG | 56 |
| M6 | 1827-1848 | Genome Cloning | GGAGTGAATAAGATGCCTGAAA | 57 |
| VP1iR | 3480-3461 | Genome Cloning | ATGGGTGAAAAACCCCTACC | 58 |
| M5 | 1796-1770 | Genome Cloning | GGTAGAGCAAAATTCTTAATAGCAGA | 59 |
| VP1iF | 3508-3527 | Genome Cloning | CTAGGCAACCCATGAAGAGC | 60 |

*Nucleotide position is based on MCV350 genome

SUPPLEMENTARY TABLE 3

Primers used for genome sequencing

| Name | Position* | Purpose | Sequence | SEQ ID NO |
|---|---|---|---|---|
| W1 | 411-4130 | Primer walking | ACTCTTGCCACACTGTAAGC | 61 |
| W2 | 1290-1272 | Primer walking | CAGGGGAGGAAAGTGATTC | 62 |
| W3 | 4268-4288 | Primer walking | GGGTAATGCTATCTTCTCCAG | 63 |
| W4 | 946-929 | Primer walking | TATTCGTATGCCTTCCCG | 64 |

SUPPLEMENTARY TABLE 3-continued

Primers used for genome sequencing

| Name | Position* | Purpose | Sequence | SEQ ID NO |
|---|---|---|---|---|
| W5 | 4293-4316 | Primer walking | CACAGATAATACTTCCACTCCTCC | 65 |
| W7 | 5260-5278 | Primer walking | TTATCAGTCAAACTCCGCC | 66 |
| W8 | 5294-5312 | Primer walking | TCAATGCCAGAAACCCTGC | 67 |
| W9 | 166-148 | Primer walking | AACAGCAGAGGAGCAAATG | 68 |
| W10 | 96-78 | Primer walking | TCTGCCCTTAGATACTGCC | 69 |
| contig1f | 5344-5363 | overlapping contigs | TTGGCTGCCTAGGTGACTTT | 70 |
| contig1r | 518-499 | overlapping contigs | CCAGGACCTCTGCAAATCT | 71 |
| contig2f | 354-373 | overlapping contigs | GGAATTGAACACCCTTTGGA | 72 |
| contig2r | 879-860 | overlapping contigs | ATATAGGGGCCTCGTCAACC | 73 |
| contig3f | 730-749 | overlapping contigs | TGCTTACTGCATCTGCACCT | 74 |
| contig3r | 1287-1268 | overlapping contigs | GGGAGGAAAGTGATTCATCG | 75 |
| contig4f | 1132-1151 | overlapping contigs | AGGAACCCACCTCATCCTCT | 76 |
| contig4r | 1641-1619 | overlapping contigs | AAATGGCAAAACAACTTACTGTT | 77 |
| contig5f | 1538-1561 | overlapping contigs | AAACAACAGAGAAACTCCTGTTCC | 78 |
| contig5r | 2088-2069 | overlapping contigs | GAGCCTTGTGAGGTTTGAGG | 79 |
| contig6f | 1934-1953 | overlapping contigs | AGAGGCCAGCTGTAATTGGA | 80 |
| contig6r | 2437-2418 | overlapping contigs | GCAGCAAAGCTTGTTTTTCC | 81 |
| contig7f | 2328-2349 | overlapping contigs | TTTGAAAAGAAGCTGCAGAAAA | 82 |
| contig7r | 2885-2866 | overlapping contigs | TGTATCAGGCAAGCACCAAA | 83 |
| contig8f | 2763-2783 | overlapping contigs | CACTTTTTCCCAAAGGCAAAT | 84 |
| contig8r | 3282-3263 | overlapping contigs | TTACCCAAAGCCCTCTGTTG | 85 |
| contig9f | 3187-3206 | overlapping contigs | GAGGCCTTTTGAGGTCCTTT | 86 |
| contig9r | 3687-3667 | overlapping contigs | TCAGACAGGCTCTCAGACTCC | 87 |
| contig10f | 3599-3618 | overlapping contigs | ATAGAGGGCCCACTCCATTC | 88 |
| contig10r | 4107-4088 | overlapping contigs | TCTGCCAATGCTAAATGAGG | 89 |
| contig11f | 3949-3969 | overlapping contigs | CCTGACACAGGAATACCAGCA | 90 |
| contig11r | 4504-4485 | overlapping contigs | GCAAACTCCAGATTGGCTTC | 91 |
| contig12f | 4329-4349 | overlapping contigs | TTTTGGAACTGAGGCAACATT | 92 |
| contig12r | 4829-4810 | overlapping contigs | TAACTGTGGGGGTGAGGTTG | 93 |
| contig13f | 4765-4784 | overlapping contigs | TACCCACGAAACATCCCTGT | 94 |
| contig13r | 5386-5367 | overlapping contigs | AGCCTCTGCCAACTTGAAAA | 95 |

*Nucleotide position is based on MCV350 genome

SUPPLEMENTARY TABLE 4

PCR Primers and Probes used for MCV detection

| Name | Position* | Sense (SEQ ID NO) | Antisense (SEQ ID NO) |
|---|---|---|---|
| Primers for diagnostic PCR | | | |
| LT1 | 1514-1953 | TACAAGCACTCCACCAAAGC (96) | TCCAATTACAGCTGGCCTCT (97) |
| LT3 | 571-879 | TTGTCTCGCCAGCATTGTAG (98) | ATATAGGGGCCTCGTCAACC (99) |
| VP1 | 4137-3786 | TTTGCCAGCTTACAGTGTGG (100) | TGGATCTAGGCCCTGATTTTT (101) |
| PCR Primers for probes in Northern or Southern hybridizations | | | |
| M1-M2 | 1711-1889 | GGCATGCCTGTGAATTAGGA (102) | TTGCAGTAATTTGTAAGGGACT (103) |
| LT5 | 253-855 | GCTCCTAATTGTTATGGCAACA (104) | TGGGAAAGTACACAAAATCTGTCA (105) |
| VP1.3 | 4107-3599 | TCTGCCAATGCTAAATGAGG (106) | ATAGAGGGCCCACTCCATTC (107) |
| P1 | 5344-518 | TTGGCTGCCTAGGTGACTTT (108) | CCAGGACCTCTGCAAATCT (109) |

SUPPLEMENTARY TABLE 4-continued

PCR Primers and Probes used for MCV detection

| Name | Position* | Sense (SEQ ID NO) | Antisense (SEQ ID NO) |
|---|---|---|---|
| P3 | 730-1287 | TGCTTACTGCATCTGCACCT (110) | GGGAGGAAAGTGATTCATCG (111) |
| P6 | 1934-2437 | AGAGGCCAGCTGTAATTGGA (112) | GCAGCAAAGCTTGTTTTTCC (113) |
| P9 | 3187-3687 | GAGGCCTTTTGAGGTCCTTT (114) | TCAGACAGGCTCTCAGACTCC (115) |
| P12 | 4329-4829 | TTTTGGAACTGAGGCAACATT (116) | TAACTGTGGGGGTGAGGTTG (117) |
| LT2 | 1054-1428 | CTGGGTATGGGTCCTTCTCA (118) | TGGTGAAGGAGGAGGATCTG (119) |
| Chr.3 | 61563308-61563830 | TTTCAGACGGAAGCGAAGTT (120) | ACCACGATTTGGAAAACAGC (121) |

*Nucleotide position is based on MCV350 genome
** Nucleotide position is based on NT_022517.17

The publications referenced in this Example are as follows:
1. L. Gross, Proc Soc Exp Biol Med 83, 414 (1953).
2. K. A. Crandall, M. Perez-Losada, R. G. Christensen, D. A. McClellan, R. P. Viscidi, Adv Exp Med Biol 577, 46 (2006).
3. T. Allander et al., J Virol 81, 4130 (2007).
4. A. M. Gaynor et al., PLoS Pathog 3, e64 (2007).
5. D. L. Poulin, J. A. DeCaprio, J Clin Oncol 24, 4356 (2006).
6. J. A. DeCaprio et al., Cell 54, 275 (1988).
7. D. P. Lane, L. V. Crawford, Nature 278, 261 (1979).
8. D. I. Linzer, A. J. Levine, Cell 17, 43 (1979).
9. D. C. Pallas et al., Cell 60, 167 (1990).
10. M. Cotsiki et al., Proc Natl Acad Sci USA 101, 947 (2004).
11. D. R. Kaplan, D. C. Pallas, W. Morgan, B. Schaffhausen, T. M. Roberts, Biochim Biophys Acta 948, 345 (1989).
12. S. M. Dilworth, Nat Rev Cancer 2, 951 (2002).
13. D. Ahuja, M. T. Saenz-Robles, J. M. Pipas, Oncogene 24, 7729 (2005).
14. Y. Chang et al., Science 265, 1865 (1994).
15. H. Feng et al., J Virol 81, 11332 (2007).
16. Y. Xu et al., Genomics 81, 329 (2003).
17. B. Lemos, P. Nghiem, J Invest Dermatol 127, 2100 (2007).
18. M. Van Gele et al., Oncogene 23, 2732 (2004).
19. E. A. Engels, M. Frisch, J. J. Goedert, R. J. Biggar, R. W. Miller, Lancet 359, 497 (2002).
20. M. Pawlita, A. Clad, H. zur Hausen, Virology 143, 196 (1985).
21. V. A. LiVolsi et al., Cancer 71, 1391 (1993).
22. H. H. Chou, M. H. Holmes, Bioinformatics 17, 1093 (2001).
23. L. Brade, N. Muller-Lantzsch, H. zur Hausen, J Med Virol 6, 301 (1981).
24. J. M. Pipas, J Virol 66, 3979 (1992).
25. J. Zerrahn, U. Knippschild, T. Winkler, W. Deppert, Embo J 12, 4739 (1993).
26. P. M. Howley et al., J Virol 36, 878 (1980).
27. I. Seif, G. Khoury, R. Dhar, *Cell* 18, 963 (1979).
28. D. Hollanderova, H. Raslova, D. Blangy, J. Forstova, M. Berebbi, Int J Oncol 23, 333 (2003).
29. M. Durst, A. Kleinheinz, M. Hotz, L. Gissman, Journal of General Virology (1985).
30. D. M. Pitterle, E. M. Jolicoeur, G. Bepler, In Vivo 12, 643 (1998).
31. P. S. Moore, Y. Chang, Annu Rev Microbiol 57, 609 (2003).
32. T. D. Schell et al., J Virol 73, 5981 (1999).
33. J. Parsonnet, in Microbes and Malignancy J. Parsonnet, Ed. (Oxford University Press, New York, 1999) pp. 3-18.
34. Y. Yin, B. Manoury, R. Fahraeus, Science 301, 1371 (2003).
35. H. J. Kwun et al., J Viral 81, 8225 (2007).

EXAMPLE 2

This example demonstrates that MCV is significantly more likely to be present in MCC tumors than in control tissues A second independent set of 8 pathologically-confirmed MCC were randomized and blindly tested; all 8 (100%) were positive for MCV genome, assuring reproducibility of our findings. To examine skin MCV infection, we examined 25 control skin or skin tumor samples from 20 HIV-negative and 5 HIV-positive persons without MCC including another 9 normal skin samples, Kaposi's sarcoma (n=15) and malignant melanoma (n=1). Four tissues (16%, p<0.001) were positive including one normal skin and three KS lesions, all from HIV negative patients. Thus, MCV is significantly more likely to be present in MCC tumors (80-100%) than in control tissues from patients without MCC (8-16%, p<0.001) (see Table 2).

TABLE 3

MCV in MCC and Control Patients by PCR and PCR-Southern

| Test Group | PCR only | PCR-Southen |
|---|---|---|
| 1. MCC (n = 10)* | 7/10 | 8/10 (80%) |
| 2. MCC (n = 8) | 8/8 | 8/8 (100%) |
| 3. Control, various body sites (n = 59) | 0/59 | 4/59 (8%)** |
| 4. Control, skin and skin tumor (n = 25) | 0/25 | 4/25 (16%)*** |

*Two additional metatastatic tumors from these patients were also MCV positive
**p < 0.0001 vs. MCC#1; positive tissues included appendix (2/9), gall bladder (1/7), bowel (1/3), hemorrhoid (1/1). Other tissues (all negative) included 9 skin, 6 other GI, 10 lymphoid, 15 other miscellaneous tissues including organ sites (brain, heart, kidney, lung).
***p < 0.001 vs. MCC#1; positive tissues include KS (3/15), normal skin (1/9). Other negative tissue included malignant melanoma (1).

EXAMPLE 3

This example demonstrates that MCV has a lymphotropic infection in asymptomatic individuals Because of MCV's similarity to African green monkey lymphotropic polyomavirus, we sought to determine if MCV can be detected in peripheral blood from asymptomatic individuals. We have developed qPCR primers that amplify a region of the T antigen and VP1 genes and can be quantified by comparison to cellular RnasP primers.

Using plasmid dilutions, we find precise linearity over a 4-log DNA dilution for these primers (not shown). We performed a pilot study of 29 Multicenter AIDS Cohort Study (MACS) PBMC from HIV-positive participants. Of these 29 PBMC samples, 4 (14%) have >3.5 genome copies/300 ng DNA indicating asymptomatic infection. Sera from these 4 individuals are available in our serum bank and it is evident that additional DNA positive individuals can be readily identified by testing additional individuals with paired PBMC-serum from the MACS repository. A second group of 65 anonymous PBMC collected during routine clinical studies (hence HIV status is unknown) shows that 10 (15%) are MCV positive. Thus, it is likely that MCV is a lymphotropic virus like LPyV. These are initial pilot studies and more detailed and rigorous analysis is needed to determine population rates of infection and possible role of HIV infection in MCV positivity.

EXAMPLE 4

Common cell lines (293, COST, HT1080 and MCF7) were tested and found negative for MCV genome. Five MCC cell lines were tested and two are positive for MCV, providing a renewable source of virus for in vitro studies. Both MCV-positive cell lines have a classic phenotype whereas the three negative MCC cells all belong to the variant phenotype, suggesting the possibility that only classic MCC is infected with MCV (Van Gele et al., *Oncogene* 2004; 23(15):2732-42). This would be analogous to KSHV in Castleman's disease in which plasmacytic multicentric Castleman's disease are KSHV-positive but not hyaline-vascular Castleman's disease (Soulier et al., *Blood* 1995; 86:1276-80), qPCR and Southern blotting reveal monoclonal integration of a single MCV copy into the genome of the MCV positive cell lines. Additional patient studies are needed to confirm a relationship between MCV and classic MCC but this may explain why two MCC tumors were found to be negative in our PCR analysis (Table 3).

EXAMPLE 5

This example demonstrates the construction of MCV VLPs.

To produce MCC VLPs, 293TT cells are co-transfected with expression vectors encoding VP1 and VP2 from either MCV 339 or MCV 350. VLPs are then extracted from the cells and purified by ultracentrifugation through an OPTIPREP density gradient; gradient fractions are collected at the bottom of the tube (See FIG. 11). Fractions 6, 7, and 8, depicted in FIG. 11 were selected for the presence of nuclease-resistant encapsidated DNA detected using QUANT-IT PICOGREEN dsDNA reagent (Invitrogen).

FIG. 12 demonstrates the production of VLPs for MCV 339 relative to MCV 350. The top panel shows an anti-MCV Western blot of 293TT cells after transfection with the VP1 expression construct shown, together with an appropriate VP2 expression construct. In the far right lane of the Western, 5-fold more cell lysate was applied to the gel. The bottom panel shows a SYPRO Ruby-stained SDS-PAGE gel analysis of OPTIPREP gradients used to purify VLPs out of cell lysates. For MPyV and MCV399, 2.5 µl each of fractions 6-9 was loaded onto the gel. For MCV350, 12.5 µl each of fractions 6-9 was loaded. Fractions were screened for the presence of encapsidated DNA using PICOGREEN reagent.

These results reveal the production of MCV VLPs from at least one strain of MCV (MCC 339).

EXAMPLE 6

This example demonstrates the construction of a mouse monoclonal antibody (mAb) specific to the MCV large T (LT) antigen.

Methods

Human Tissue Samples.

DNA samples were obtained from excess clinical specimens. All the DNA samples were obtained from fresh frozen tissues. For reasons of confidentiality, minimal patient identification and demographic data are available for most of these specimens. For Merkel cell carcinoma, fresh frozen tumor samples were obtained from the Cooperative Human Tissue Network (CHTN). An MCC tissue core microarray consisting of 36 MCC specimens was generated from archival paraffin-embedded tissues from the pathology departments at Hospital Universitari del Mar and the Hospital Universitari Germans Trias i Pujol, Barcelona, Spain as previously described (17). Tissue microarrays for lymphoid malignancies and normal controls were purchased commercially (US Biomax, Inc.). Genomic DNA samples from consecutive hematolymphoid tumor tissues were collected and archived by the late Dr. Anne Matsushima, Columbia University, from excess tissue submitted for diagnostic pathology. This was supplemented with additional hematolymphoid tissues obtained from tissue banks at the University of Pittsburgh Department of Pathology. PBMC specimens were obtained from two sources: 1) excess samples submitted to the Division of Molecular Diagnostics, University of Pittsburgh Medical Center for genetic screening, and 2) PBMC collected from HIV-positive persons participating in Kaposi's sarcoma epidemiologic studies (13). None of these study subjects were diagnosed with Merkel cell carcinoma. All specimens were tested under University of Pittsburgh Institutional Review Board-approved guidelines.

Isolation of Genomic DNA.

Genomic DNA was extracted using proteinase K/lysis buffer (0.1 M NaCl, 10 mM Tris-HCl pH 8.0, 25 mM EDTA pH 8.0, SDS 0.5%, 200 µg/ul proteinase K) for up to 3 days at 56° C., followed by phenol-chloroform extraction and ethanol precipitation. DNA amount and quality were determined by spectroscopy followed by PCR amplification for cellular β-actin or RNaseP. Real time quantitative PCR (qPCR). qPCR was performed using primers amplifying the MCV T antigen, TAg (1051 to 1131 nt; forward: 5'-cctctgggtatgggtc-cttctca-3' (SEQ ID NO:122), reverse: 5'-atggtgttcgggagg-tatatc-3' (SEQ ID NO:123)) and VP2 (4563 to 4472 nt, forward: 5'-agtaccagaggaagaagccaatc-3' (SEQ ID NO:124), reverse: 5'-ggccttttatcaggagaggctatattaatt-3' (SEQ ID NO:125)) loci with internal TaqMan probes (TAg: 5'-cccag-gcttcagactc-3' (SEQ ID NO:126), VP2: 5'-gcagagttcctc-3' (SEQ ID NO:127)) labeled with FAM and MGB quencher (Applied Biosystems). For the additional 10 peripheral blood samples with CLL, primers designed against MCV T antigen promoter region (98 to 184 nt forward: 5'-cccaagggcgg-gaaactg-3' (SEQ ID NO:128), reverse: 5'-gcagaaggagtttgca-gaaacag-3' (SEQ ID NO:129)) and internal probe (5'-ccactc-cttagtgaggtagctcatttgc-3' (SEQ ID NO:130)) labeled with FAM and BHQ quencher (Biosearch Technologies) was used. Primers were chosen to maximize specificity to MCV and minimize any cross-reactivity with other polyomaviruses. Copy numbers were established from standard curves of Ct values from serial dilutions of known concentrations of MCV DNA originally amplified by PCR using contig 3 and contig 12 primer sets for TAg and VP2 detections, respectively (1).

Water was used as control to detect template contamination. No evidence of PCR template contamination was observed in the PCR reactions with water control. RNaseP (Applied Biosystems) or 13-actin primer-probe mixtures (forward: 5'-cactggctcgtgtgacaagg-3' (SEQ ID NO:131), reverse: 5'-cagacctactgtgcgcctacttaa-3' (SEQ ID NO:132), probe: 5'-tggtgtaaagcggccttggagtgtgt-3' (SEQ ID NO:133)) (Biosearch Technologies) were used to determine cell genome copy number. qPCR reactions were performed using PRISM 7700 Detection System, PRISM 7900HT Fast Real-Time PCR System (Applied Biosystems) and/or SMART CYCLER 5RX4Z01 (Cepheid) with TaqMan reagents (UNG(+) TaqMan Universal PCR Master Mix). All the primers and probes were aliquoted and stored until in an isolated, clean PCR facility to avoid template DNA contamination. Amplification reactions of all target genes were performed in reaction volumes of 20 µl with following condition: 50° C. for 2 min, denaturing at 95° C. for 10 min, then denaturing at 95° C. for 15 s followed by annealing and extension at 60° C. for 1 min, 40 cycles. Results were expressed as numbers of viral copies per cell calculated from Ct values of viral and cellular gene standards (Table 6-1). Cellular viral DNA copy number below $1.0 \times 10^{-3}$ per cell was considered to be negative.

Cell Lines and Transfection Conditions.

Human embryonic kidney 293 cells (American Type Culture Collection (ATCC)) used for transfection experiment were grown in DMEM medium supplemented with 10% fetal calf serum. For protein expression analysis, cells were transfected with expression constructs using LIPOFECTAMINE 2000 (Invitrogen) following manufacturer's instructions on 90% confluent cells. Cells were harvested 48 h after transfection for analysis.

Plasmids.

To generate the pMCV TAg-EGFP expression constructs, pcDNA6 gLT206 encoding wild type full length genomic T antigen (4) was digested with Nhe I and Sac II and cloned into pEGFP-N1 (Clonetech) in frame to C terminus GFP using same restriction sites. LT expression constructs for JCV and BKV were kindly provided by Dr. James DeCaprio (18). SV40 T antigen cDNA cloned in pCMV vector is described elsewhere (19).

Generation of CM2B4 mAb.

Monoclonal antibody CM2B4 (IgG2b isotype) was generated by standard methods of immunizing mice with KLH-derivatized SRSRKPSSNASRGA (SEQ ID NO: 134) peptide from the MCV T antigen exon 2 with a C-terminal cysteine (Epitope Recognition Immunoreagent Core facility, University of Alabama). Immunofluorescence and immunohistochemistry. For immunofluorescence staining, cells were spotted on glass slides by CYTOSPIN3 (Shandon), fixed with 10% buffered formalin for 20 min, and permeabilized with phosphate-buffered saline (PBS) with 0.1% Triton X-100. After blocking with 10% normal donkey serum (Jackson ImmunoResearch Laboratories), cells were reacted with CM2B4 (1:100 dilution) at 4° C. overnight followed by secondary antibody (Alexa-595-conjugated anti-mouse, 1:1000 Invitrogen) for one hour at room temperature. Stained cells were mounted in aqueous medium containing DAPI (Vector Laboratories, CA). For immunohistochemical staining of paraffin embedded tissues, epitope retrieval was performed using EDTA antigen retrieval buffer (Dako, Glostrup, Denmark) at 126° C. for 3 min after deparaffinization and hydrogen peroxide treatment. After blocking with PROTEIN BLOCK (Dako), samples were reacted to primary antibody for 30 min at room temperature with dilutions described below. After washing, samples were incubated with Mouse ENVISION Polymer (Dako) for 30 min at room temperature for subsequent deaminobenzidine (DAB) reaction. mAbs used for immunohistochemistry were: CM2B4 (1:10-1:50 hybridoma supernatant), CK20 (Dako; 1:50), Chromogranin A (Dako, 1:600), Synaptophysin (Biogenex, San Ramón, Ca, USA; 1:100), and CD56 (Novocastra, Newcastle upon Tine, UK; 1:50).

In-Situ Hybridization.

Tissue sections were deparaffinized, dehydrated, incubated at 95° C. for 20 min, cooled for 5 min at room temperature and reacted over night at 37° C. with JC virus BIOPROBE labeled probe (Enzo Life Sciences) diluted in hybridization buffer. Excess probe was washed with 2×SSC/0.75% BSA followed by PBS. To visualize signal, samples were treated with ABC elite solution (Vector Laboratories, CA) for 30 min, washed twice with PBS and reacted with DAB solution. Samples were counterstained with Shandon hematoxylin.

Immunoblotting.

Transfected cells from 6 well plate were lysed in 120 µl of lysis buffer (10 mM Tris-HCl pH8.0, 0.6% SDS) containing proteinase inhibitor cocktail (Roche). 12.5% of lysate was electrophoresed in 10% SDS-PAGE, transferred to nitrocellulose membrane (Amersham). Membranes were blocked in 5% skim milk for 1 h, reacted with Pab416 (1:10) or CM2B4 mAb (1:10) for overnight at 4° C., followed by anti-mouse IgG-HRP conjugates (Amersham, 1:5000) for 1 h at room temperature. Detection of peroxidase activity was performed by WESTERN LIGHTNING PLUS-ECL reagent (Perkin Elmer).

Cell Sorting.

$5.0 \times 10^6 - 10^7$ PBMC were washed with PBS twice, stained with CD3-FITC, CD20-PE and CD14-PC5 (IOTest) (2 µl/$10 \times 10^6$ cells) and incubated on ice for 20 minutes. The cells were then washed and resuspended in 400 µl of PBS containing 8.0 µg/ml DAPI and sorted by the MOFLOW High Speed Sorter (Cytomation). Single antibody stained and unstained cells were used as controls for compensation purposes. DNA from the sorted cell fractions was extracted using QIAAMP BLOOD MINI KIT (Qiagen).

Results

MCV and T Antigen Expression in Merkel Cell Carcinoma Tumors.

We developed a mouse monoclonal antibody (mAb) (CM2B4) to the peptide epitope (SRSRKPSSNASRGA (SEQ ID NO:134)) in exon 2 of the MCV T antigen. This epitope is N-terminal to an LFCDE motif previously found to bind retinoblastoma protein and is likely to be conserved in viruses from both tumor and nontumor tissues (4). There was precise nuclear colocalization of CM2B4 staining with MCV LT-GFP fusion protein fluorescence when a MCV LT-GFP plasmid was expressed in 293 cells (FIG. 9A).

CM2B4 was highly specific for MCV and did not react to T antigens from JCV or BKV by immunofluorescence (FIG. 9B) or to T antigens from JCV, BKV or SV40 by immunoblotting (FIG. 9C). In contrast, an anti-SV40 T antigen mAb, PAb416, cross-reacts with T antigens from other SV40-group viruses including JCV and BKV, but not with MCV T antigen. We examined 22 other anti-SV40 T antigen mAbs (Table S1), and none showed reactivity to MCV T antigen on immunoblotting (data not shown). CM2B4 also did not react to JCV T antigen in a brain biopsy of JCV-infected progressive multifocal leukoencephalopathy (PML) (FIG. 9D).

The MCV LT protein was detected at 120 kDa on immunoblotting of lysates from cells transfected with the genomic T antigen expression construct (FIG. 9C). An additional 60 kDa band may represent an alternatively spliced T antigen isoform (4, data not shown). Lysates of the MCV positive MKL-1 cell line were positive for T antigen expression while T antigen bands were absent from MCV negative UISO, MCC13, and MCC26 cell lines (4) (FIG. 9E).

Figure 10A:
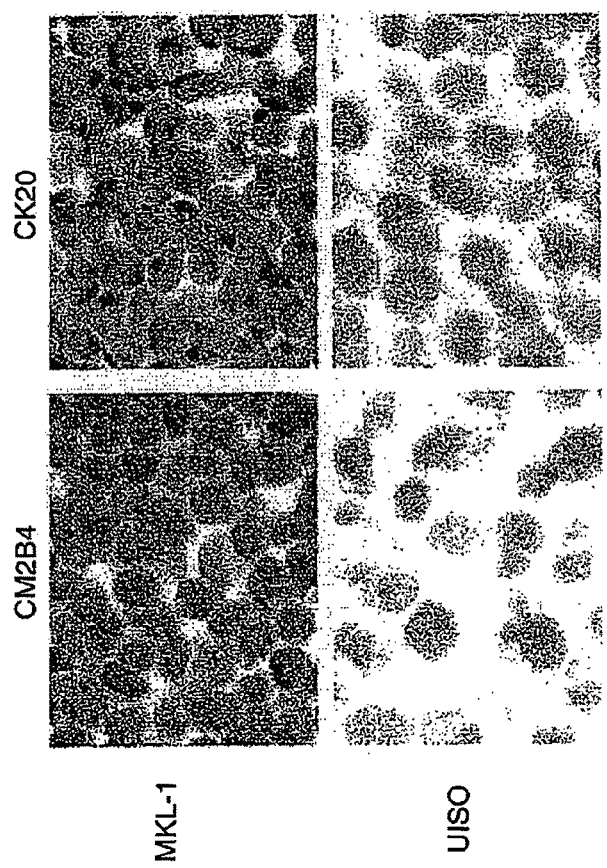
Figure 10B:
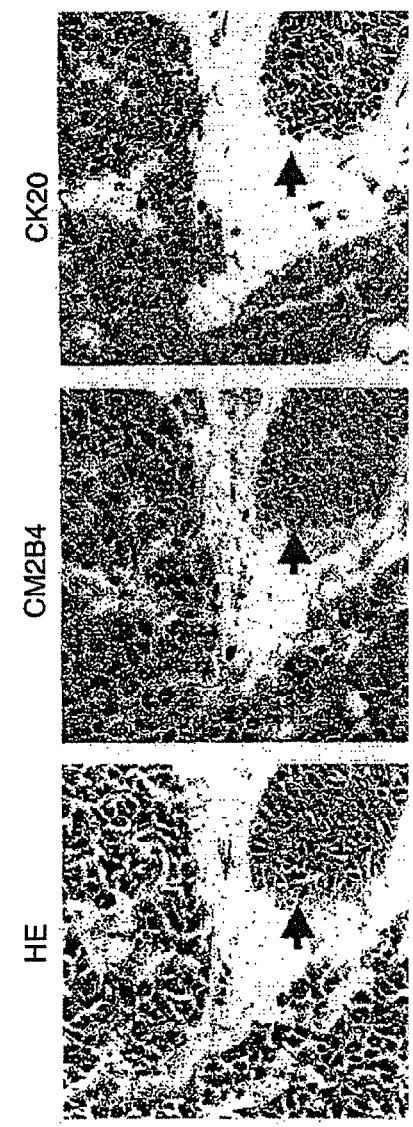

Immunohistochemical staining of MKL-1 cells showed expression of LT protein predominantly in a diffuse nuclear pattern (FIG. 10A). Examination of a MCV positive MCC biopsy (MCC349) showed similar strong reactivity with CM2B4 among tumor cells, but not surrounding tissues including the epidermis, adnexal epithelia, endothelial cells, or dermal fibroblasts (FIG. 10B). CK20, a low molecular weight cytokeratin marker for MCC (9, 10) was present in a characteristic perinuclear dot-like pattern in CM2B4 positive cells (FIGS. 10A and B).

These results were extended by examining a tissue microarray containing 30 CK20-positive MCC, 6 CK20-negative but clinically-suspect MCC and 4 CK20-negative neuroendocrine control tumors (2 small bowel, one bladder and one lung derived). Of the 30 CK20 positive MCC, 21 (70%) were positive for LT protein expression. Of the 6 CK20-negative tumors diagnosed as MCC, none were positive with CM2B4. These six tumors had clinical appearances consistent with MCC and expressed neuroendocrine markers CD56, synaptophysin, or chromogranin (Table 6-1). These results suggest that most CK20-positive MCC express MCV LT in tumor cells.

To screen tissues for MCV infection, we next developed a quantitative real-time PCR (qPCR) assay to determine the burden of virus infection in MCC tumors (Table 6-2). Ten tumors previously examined by PCR and Southern blotting (1) were examined with primers designed to amplify regions of the T antigen and VP2. Seven of these Southern blot positive tumors had an average of 5.2 (range 0.8 to 14) T antigen DNA copies per cell. Consistent results were found using VP2 qPCR except for MCC345 and MCC347. This tumor had robust T antigen qPCR positivity (5 copies per cell) but minimal amplification of the VP2 gene, which may reflect integration and loss of this late viral capsid gene region. These findings were confirmed by CM2B4 staining in CK20+ MCCs, which was concordant with qPCR results for all cases except MCC344 (Table 6-2). This case showed abundant viral DNA but was negative with CM2B4 staining.

PBMC Infection with MCV.

83 whole PBMC DNA samples collected from persons undergoing genetic testing for Factor V Leiden deficiency were tested by qPCR. These samples were collected mainly from adults (average of 60 yrs, range 1-78 yrs) with 73 (88%) samples from persons over 18 years of age. None were positive for viral gene PCR products. Among 21 PBMC collected from adult HIV/AIDS patients without MCC, 2 (9.5%) were positive by either T antigen ($2.8 \times 10^{-3}$ copies per cell) or VP2 ($8.8 \times 10^{-3}$ copies per cell) primers and one (5%) was positive with both primers (T antigen, $7.9 \times 10^{-3}$ copies per cell; VP2, $6.0 \times 10^{-3}$ copies per cell). These levels approach the technical limit of reproducibility of our assay ($>10^{-3}$ copies per cell).

This should not be interpreted as evidence against current infection among these participants. PBMC from two MCV-positive MCC patients and from three healthy blood donors were sorted into CD20+ (B cell), CD3+ (T cell), CD14+ (monocyte) and CD20−/CD3−/CD14− (remainder) fractions and tested for T antigen and VP2 DNA. CD20+ B cell fractions from both MCC patients were positive for both T antigen and VP2 ($2.7-9.8 \times 10^{-3}$ DNA copies per CD20+ cell). In contrast, CD20+ cell fractions from two of three blood donors were only positive for the VP2 locus ($1.2-2.1 \times 10^{-3}$ DNA copies per CD20+ cell) but not MCV T antigen. CD3+ T cells from one MCC patient were positive at lower levels for both viral loci ($1.0-2.0 \times 10^{-3}$ copies per CD3+ cell). Either T antigen or VP2 DNA but not both were also detected in CD14+ cells from one MCC patient (T antigen: $1.2 \times 10^{-3}$ copies per CD14+ cell), CD20+ cells from two blood donors (VP2: $1.2-2.1 \times 10^{-3}$ copies per CD20+ cell). All other fractions from MCC and blood donor patients were either negative or below the threshold value for a positive result. We interpret these results to indicate that mainly B cell fractions from infected persons can harbor low copy MCV but dilution of this fraction in whole PBMC reduces MCV below our reliable threshold for detection.

Survey of Hematolymphoid Malignancies for MCV Infection.

qPCR was performed on DNA from 104 T cell-associated and 161 B cell-associated malignancies, 19 myeloid disorders and 41 other tumors including Hodgkin lymphoma and post-transplant lymphoproliferative disorders (Table 6-3). Of these 325 tumors, 7 (2.2%) were positive for either T antigen or VP2 DNA and two were positive for both. No consistent pattern of virus infection was found among these malignancies: 1 (3%) of 33 chronic lymphocytic leukemia, 1 (7.1%) of 14 non-Hodgkin lymphoma, not otherwise specified (NOS), 2 (3.1%) of 65 diffuse large B cell lymphoma, 1 (11%) of 9 marginal zone lymphoma and 1 (3.3%) of 30 Hodgkin lymphoma (Table 6-3). Copy numbers for these positive hematolymphoid malignancies (Table 6-4), however, were all 2-4 logs lower than MCV-positive MCC tumors (Table 6-2).

These results were confirmed by CM2B4 staining of commercial tissue microarrays of hematolymphoid tumors. Of 122 B cell lymphomas, 17 T cell lymphomas, one myeloid disorder and 2 Hodgkin lymphomas examined, none showed evidence for LT protein expression (Table 6-5). Thirty-one healthy lymphoid control tissues were also negative for MCV T antigen.

MCV and Chronic Lymphocytic Leukemia.

Given the epidemiological relationship between MCC and CLL, we examined additional CLL cases for evidence of MCV infection. Ten peripheral blood samples with CLL (WBC counts ranging from $13.2 \times 10^9$-$84.3 \times 10^9$ cells per L) were harvested and tested for the presence of MCV DNA. One displayed low MCV positivity VP2 ($2.0 \times 10^{-3}$ copies per cell). Twelve additional paraffin-embedded biopsies with CLL were examined by CM2B4 staining. All CLL cases were uniformly negative for MCV T antigen protein expression.

TABLE 6-1

Summary of Merkel cell carcinoma tissue microarray staining

| Case number | CM2B4 | CK20 | CD56 | Chromogranin | Synaptophysin |
|---|---|---|---|---|---|
| 1 | + | + | + | + | + |
| 2 | + | + | + | − | + |
| 3 | + | + | + | + | + |
| 4 | + | + | + | + | + |
| 5 | + | + | ND[4] | ND | ND |
| 6 | + | + | + | − | ND |
| 7 | + | + | + | + | + |
| 8 | + | + | + | + | + |
| 9 | + | + | + | + | + |
| 10 | + | + | + | + | + |
| 11 | + | + | + | + | + |
| 12 | + | + | + | + | + |
| 13 | + | + | + | + | + |
| 14 | + | + | + | + | + |
| 15 | + | + | + | + | + |
| 16 | + | + | − | + | + |
| 17 | + | + | + | + | + |
| 18 | + | + | − | + | + |
| 19 | + | + | + | + | + |
| 20 | + | + | + | − | + |

TABLE 6-1-continued

Summary of Merkel cell carcinoma tissue microarray staining

| Case number | CM2B4 | CK20 | CD56 | Chromogranin | Synaptophysin |
|---|---|---|---|---|---|
| 21 | + | + | + | + | ND |
| 22 | − | + | + | + | + |
| 23 | − | + | + | + | ND |
| 24 | − | + | + | + | + |
| 25 | − | + | + | + | + |
| 26 | − | + | + | + | + |
| 27 | − | + | + | − | + |
| 28 | − | + | + | + | + |
| 29 | − | + | + | − | + |
| 30 | − | + | + | + | + |
| 31 | − | − | − | − | − |
| 32 | − | − | + | + | + |
| 33 | − | − | − | − | − |
| 34 | − | − | − | + | + |
| 35 | − | − | + | − | − |
| 36 | − | − | + | − | + |
| Control: Neuroendocrine small cell carcinoma | | | | | |
| 37 | − | − | − | − | + |
| 38 | − | − | + | − | + |
| 39 | − | − | + | + | + |
| 40 | − | − | + | − | + |

[a]ND, Not determined.

TABLE 6-2 qPCR detection of MCV genome in MCC

| MCC Tissue | MCV genome copies/cell[a] T Ag | MCV genome copies/cell[a] VP2 | Genomic Southern[b] | Immunostaining CM2B4 | Immunostaining CK20[d] |
|---|---|---|---|---|---|
| MCC337 | $<10^{-3}$ | 0 | − | − | + |
| MCC339 | 5.2 | 11.1 | + | + | + |
| MCC343 | 0 | 0 | − | − | + |
| MCC344 | 6.3 | 13.7 | + | − | + |
| MCC345 | 4.9 | $<10^{-3}$ | + | + | + |
| MCC346 | $<10^{-3}$ | 0 | − | − | + |
| MCC347 | 1.6 | 0 | + | + | + |
| MCC349 | 3.3 | 8.0 | + | + | + |
| MCC350 | 0.83 | 3.0 | + | NT[c] | NT |
| MCC352 | 14.3 | 47.5 | + | + | + |

[a]RNaseP copy number was divided by two to determine cellular equivalent of DNA.
[b]MCV positivity was previously examined by Southern blotting (1).
[c]NT, No paraffin embedded MCC tissues to evaluate.
[c]CK20 expression was previously examined by immunostaining (1).

TABLE 6-3 qPCR detection of MCV genome in hematolymphoid malignancies.

| Hematopathological samples studied | No. Tested | No. MCV positive (% MCV Positive) |
|---|---|---|
| B cell-associated lymphomas | | |
| Chronic lymphocytic leukemia | 33 | 1 (3.0) |
| Non-Hodgkin lymphoma, NOS | 14 | 1 (7.1) |
| Diffuse large B cell lymphoma | 65 | 2 (3.1) |
| Follicular lymphoma | 14 | 0 |
| Acute lymphoblastic leukemia | 11 | 0 |
| Primary effusion lymphoma | 2 | 0 |
| Mucosa-associated lymphoid tissue lymphoma | 5 | 0 |
| Mantle cell lymphoma | 8 | 0 |
| Marginal zone lymphoma | 9 | 1 (11) |

TABLE 6-3-continued qPCR detection of MCV genome in hematolymphoid malignancies.

| Hematopathological samples studied | No. Tested | No. MCV positive (% MCV Positive) |
|---|---|---|
| T cell-associated lymphomas | | |
| Acute lymphoblastic leukemia | 10 | 0 |
| Large granular lymphocyte leukemia | 1 | 0 |
| Mycosis fungoides | 11 | 0 |
| T cell lymphoma, unspecified | 82 | 1 (1.2) |
| Myeloid disorders | | |
| Chronic myelogenous leukemia | 5 | 0 |
| Acute myeloid leukemia | 11 | 0 |
| Myelodysplastic syndrome | 3 | 0 |
| Others | | |
| Hodgkin lymphoma | 30 | 1 (3.3) |
| Post transplant lymphoproliferative disorder | 11 | 0 |
| Total | 325 | 7 (2.2%) |

TABLE 6-4 qPCR detection of MCV genome in hematolymphoid malignancies.

| Hematolymphoid malignancies positive for MCV | Copies per cell T Ag | Copies per cell VP2 |
|---|---|---|
| Chronic lymphocytic leukemia (#354[A]) | $1.2 \times 10^{-2}$ | $8.4 \times 10^{-3}$ |
| Non-Hodgkin lymphoma (#351) | $1.5 \times 10^{-3}$ | $<10^{-3}$ |
| Diffuse large B cell lymphoma (#229) | $1.1 \times 10^{-3}$ | 0 |
| Diffuse large B cell lymphoma (#500) | $3.8 \times 10^{-3}$ | $1.1 \times 10^{-3}$ |
| Marginal zone lymphoma (#781) | $5.8 \times 10^{-3}$ | 0 |
| T cell lymphoma (#18) | $3.2 \times 10^{-3}$ | 0 |
| Hodgkin lymphoma (#86) | $1.8 \times 10^{-3}$ | $2.9 \times 10^{-3}$ |

[A]Blinded testing number.

TABLE 6-5

MCV LT protein detection in hematolymphoid malignancies

| | |
|---|---|
| B cell malignancies | 0/122 |
| T cell malignancies | 0/17 |
| Myeloid disorders | 0/1 |
| Hodgkin Lymphoma | 0[2] |
| Normal lymphoid tissues | |
| Normal splenic tissue | 0/18 |
| Normal lymph node | 0/13 |

[A]These cases are derived from tissue microarray slides #SP482t, #LM801t, #NHL801t from BioMax.

TABLE S1

A list of SV40 T antigen specific monoclonal antibodies screened for cross reactivity with MCV T antigen.

| SV40 T antigen Monoclonal Antibodies | Reference(s) |
| --- | --- |
| PAb101, 108 | Gurney, E. G., Tarnowski, S., and Deppert, W. 1986. Antigenic binding sites of monoclonal antibodies specific for simian virus 40 large T antigen.*J Virol* 57: 1168-1172. |
| | Tack, L. C., Wright, J. H., and Gurney, E. G. 1989. Alterations in the structure of new and old forms of simian virus 40 large T antigen (T) defined by age-dependent epitope changes: new T is the same as ATPase-active T.*J Virol* 63: 2352-2356. |
| PAb 204, 210, 211, 216 | Mole, S. E., Gannon. J. V., Ford, M. J., and Lane, D. P. 1987. Structure and function of SV40 large-T antigen.*Philes Trans R Soc Lond B Biol Sci* 317: 455-469. |
| | Gannon, J. V., and Lane, D. P. 1990. Interactions between SV40 T antigen and DNA polymerase alpha. *New Biol* 2: 84-92. |
| PAb 405, 409, 407, 416, 419, 423,430, 431,433, 441, 442 | Harlow, E., Crawford, L. V., Pim, D. C., and Williamson, N. M. 1981. Monoclonal antibodies specific for simian virus 40 tumor antigens.*J Virol* 39: 861-869. |
| PAb 602, 603, 605, 606 | Mole, S. E., Gannon. J. V., Ford, M. J., and Lane. D. P. 1987. Structure and function of SV40 large-T antigen.*Philes Trans R Soc Lond B Biol Sci* 317: 455-469. |
| PAb 901, 902 | Karjalainen, H. E., Tevethia, M. J., and Tevethia, S. S. 1985. Abrogation of simian virus 40 DNA-mediated transformation of primary C57BL/6 mouse embryo fibroblasts by exposure to a simian virus 40-specific cytotoxic T-lymphocyte clone.*J Virol* 56: 373-377. |
| | Thompson, D. L., Kalderon, D., Smith, A. E., and Tevethia, M. J. 1990. Dissociation of Rb-binding and anchorage-independent growth from immortalization and tumorinenicity using SV40 mutants producing N-terminally truncated large T antigens.*Virology* 178: 15-34. |
| | Fu, T. M., Bonneau, R. H., Epler, M., Tevethia, M. J., Alam, S., Verner, K., and Tevethia, S. S. 1996. Induction and persistence of a cytotoxic T lymphocyte (CTL) response against a herpes simplex virus-specific CTL epitope expressed in a cellular protein.*Virology* 222: 269-274. |

The publications referenced in this Example are as follows:

1. Feng, H., Shuda, M., Chang, Y., and Moore, P. S. 2008. Clonal integration of a polyomavirus in human Merkel cell carcinoma. Science 319:1096-1100.
2. Kassem, A., Schöpflin, A., Diaz, C., Weyers, W., Stickeler, E., Werner, M., and Zur Hausen, A. 2008. Frequent Detection of Merkel Cell Polyomavirus in Human Merkel Cell Carcinomas and Identification of a Unique Deletion in the VP1 Gene. Cancer Res 68:5009-5013.
3. Becker, J. C., Houben, R., Ugurel, S., Trefzer, U., Pfohler, C., and Schrama, D. 2008. MC Polyomavirus Is Frequently Present in Merkel Cell Carcinoma of European Patients. J Invest Dermatol. advance online publication PMID: 18633441
4. Shuda, M., Feng, H., Kwun, H. J., Rosen, S. T., Gjoerup, O., Moore, P. S., and Chang, Y. 2008. T antigen mutations are a human tumor-specific signature for Merkel cell polyomavirus. Proc Natl Acad Sci USA 105:16272-16277.
5. Leonard, J. H., Bell, J. R., and Kearsley, J. H. 1993. Characterization of cell lines established from Merkel-cell ("small-cell") carcinoma of the skin. Int J Cancer 55:803-810.
6. Quaglino, D., Di Leonardo, G., Lalli, G., Pasqualoni, E., Di Simone, S., Vecchio, L., and Ventura, T. 1997. Association between chronic lymphocytic leukaemia and secondary tumours: unusual occurrence of a neuroendocrine (Merkell cell) carcinoma. Eur Rev Med Pharmacol Sci 1:11-16.
7. Howard, R. A., Dares, G. M., Curtis, R. E., Anderson, W. F., and Travis, L. B. 2006. Merkel cell carcinoma and multiple primary cancers. Cancer Epidemiol Biomarkers Prey 15:1545-1549.
8. zur Hausen, H., and Gissmann, L. 1979. Lymphotropic papovaviruses isolated from African green monkey and human cells. Med Microbiol Immunol 167:137-153.
9. Moll, R., Schiller, D. L., and Franke, W. W. 1990. Identification of protein IT of the intestinal cytoskeleton as a novel type I cytokeratin with unusual properties and expression patterns. J Cell Biol 111:567-580.
10. Moll, R., Lowe, A., Laufer, J., and Franke, W. W. 1992. Cytokeratin 20 in human carcinomas. A new histodiagnostic marker detected by monoclonal antibodies. Am J Pathol 140:427-447.
11. Pope, J. H., and Rowe, W. P. 1964. Detection of Specific Antigen in Sv40-Transformed Cells by Immunofluorescence. J Exp Med 120:121-128.
12. Diamandopoulos, G. T. 1972. Leukemia, lymphoma, and osteosarcoma induced in the Syrian golden hamster by simian virus 40. Science 176:173-175.
13. Moore, P. S., Kingsley, L. A., Holmberg, S. D., Spira, T., Gupta, P., Hoover, D. R., Parry, J. P., Conley, L. J., Jaffe, H. W., and Chang, Y. 1996. Kaposi's sarcoma-associated herpesvirus infection prior to onset of Kaposi's sarcoma. AIDS 10:175-180.
14. Whitby, D., Howard, M. R., Tenant-Flowers, M., Brink, N. S., Copas, A., Boshoff, C., Hatziouannou, T., Suggett, F. E. A., Aldam, D. M., Denton, A. S., et al. 1995. Detection of Kaposi's sarcoma-associated herpesvirus (KSHV) in peripheral blood of HIV-infected individuals predicts progression to Kaposi's sarcoma. Lancet 364:799-802.
15. Dorries, K., Vogel, E., Gunther, S., and Czub, S. 1994. Infection of human polyomaviruses JC and BK in peripheral blood leukocytes from immunocompetent individuals. Virology 198:59-70.
16. Stolt, A., Sasnauskas, K., Koskela, P., Lehtinen, M., and Dillner, J. 2003. Seroepidemiology of the human polyomaviruses. J Gen Virol 84:1499-1504.
17. Fernandez-Figueras, M. T., Puig, L., Musulen, E., Gilaberte, M., Lerma, E., Serrano, S., Fernandez, C., and Ariza, A. 2007. Expression profiles associated with aggressive behavior in Merkel cell carcinoma. Mod Pathol 20:90-101.
18. Poulin, D. L., Kung, A. L., and DeCaprio, J. A. 2004, p53 targets simian virus 40 large T antigen for acetylation by CBP. J Virol 78:8245-8253.
19. Campbell, K. S., Mullane, K. P., Aksoy, I. A., Stubdal, H., Zalvide, J., Pipas, J. M., Silver, P. A., Roberts, T. M., Schaffhausen, B. S., and DeCaprio, J. A. 1997. DnaJ/hsp40 chaperone domain of SV40 large T antigen promotes efficient viral DNA replication. Genes Dev 11:1098-1110.

EXAMPLE 7

This example demonstrates the use of MCV VLPs as reagents in assays for the detection of MCV infection in human subjects.

Methods

Cases:

22 MCV positive cases were obtained from persons with biopsy-confirmed MCC and qPCR-confirmed MCV infection. Seroprevalence among different age groups was tested using sera from patients with Langerhans Cell Histiocytosis (LCH) (n=151, age of patients: 1 month to 72 years old) were obtained from Dr. Frank Jenkins.

Control:

seroprevalence among adult population was tested using control sera (n=167) were obtained from the New York City Blood Bank (NYCBB) and the Columbia University Blood Bank. All sera were tested for HIV, HCV, HBV, syphilis and were found negative for these infections.

Informed consent from all study participants and IRB approval were received in accordance with the guidelines for human experimentations of the University of Pittsburgh.

ELISA Assay:

an EIA based on purified VLPs was used to detect presence of specific antibodies in sera samples. Sera were tested using 96-well 2HB Immulon plates (Thermo Scientific), coated with codon-optimized MCV VLP, which are based on two major capsid proteins, VP1 and VP2. In addition, 12 sera samples were tested by CRPV-, BK-, and HPV-VLP ELISA.

For all viruses, 100 µl of purified VLPs at concentration of 1 µg/ml were added to the wells. After overnight incubation, plates were washed with PBS and blocked with PBS/0.5% milk for 2 hours at room temperature (see [1] for plate set up).

Serum samples diluted 1:500 were added to 4 wells (2 wells coated with VLP and 2 wells without VLPs) and incubated for 2 hours at room temperature. After one-hour reaction with rabbit anti-human immunoglobulin G horseradish peroxidase (diluted 1:6000, Dako, Carpenteria, Calif.). Following another washing step 3,3',5,5'-tetramethyl-benzidine (Sigma) substrate was added and incubated for 45 minutes in the dark at room temperature. Reaction was stopped adding 2N sulfuric acid. Optical density was measured on a MRX plate reader (Dynex Technologies, Chantilly, Va.) at a 405 nm wavelength with reference at 620 nm.

Quality Control Testing.

For testing each plate included two test sera standards (MCV high- and medium-reactive sera), which were tracked over time. These sera were aliquoted and used through out the testing. If results of these standards were different by greater than 2 standard deviations from the mean optical density, then the results were discarded and the plate was repeated. All sera were tested in duplicates, and average ODs for a given sample were calculated as an average of OD of the wells containing VLPs minus the average of OD of the wells without antigen. Duplicate tests were performed independently, and testing was done in blinded sets.

Competitive ELISA.

12 sera (four high-positive, four-medium, and four negative according to results of MCV-VLP testing) samples were tested by BK-, and HPV-VLP competitive ELISA. Each sera sample was tested by MCV VLP ELISA in serial dilutions: 1:500, 1:1000, 1:2000, 1:4000, 1:8000, 1:16000, and 1:32000. For each sample, working dilutions were determined to perform competitive ELBA (FIG. 13).

BK-Competitive ELISA.

200 µl of sera at working dilutions as determined above were incubated with 2 ug of BK-VLPs for one hour at room temperature. After incubation, sera with VLPs were added to two wells on the plates, previously coated with 100 ng BK-VLPs. Also, two wells were filled with sera without BK-VLPs as a control. After two hours of incubation at room temperature, plates were washed three times with PBS and reacted with 100 ul of rabbit anti-human immunoglobulin G horseradish peroxidase (diluted 1:6000, Dako, Carpenteria, Calif.). Following another washing step 100 ul of 3,3',5,5'-tetramethyl-benzidine (Sigma) substrate was added for a 45 minute incubation in the dark at room temperature. Reaction was stopped by adding 100 ul of 2N sulfuric acid.

HPV-Competitive ELISA.

HPV VLP ELISA was performed the same way as BK-competitive ELISA, except sera samples were incubated with HPV VLPs and added to the plates, precoated with HPV VLPs.

Peptide Mapping of LT-, MT-, and VP1-Antigens.

In total, 183 peptides (LT), 66 peptides (MT), and 103 peptides (VP1) biotinylated (N-terminal SGSK) 17 mer offset by 5 were synthesized by Mimotop (Clayton Victoria, Australia). An ELISA was performed according to the manufacturer's protocol by using a panel of human serum diluted 1:500. 52 samples from LCH patients and 4 positive serum samples were tested for all three antigens peptides in order to identify specific seroreactive linear epitope for MCV infection.

Results

Peptide ELISA.

Analysis of all 352 peptides studied identified 12 potential immunoreactive peptides. An example of the peptide screen by ELISA is shown in FIG. 14. However, when screened against serum from 9 MCC patients, no specific linear epitope was identified.

MCV VLP ELISA.

Total of 340 serum samples were tested by VLP ELISA. Based on results of the test OD value of 0.5 was determined as cutoff. All samples with OD>0.5 were classified as positive.

Among samples derived from MCV-positive individuals 95.5% were positive with OD>2. Only one sera was negative on the test (4.5%) with OD equal to 0.1. To evaluate prevalence among blood donors two groups of sera samples were tested. In the group of NYCBB (n=105) prevalence was 54.3%. Among Columbia University blood donors (n=62) positive results of the test were 27.4% of the samples. Absence of demographic data for these two groups does not allow us to interpret this differences in prevalence.

In order to evaluate prevalence of MCV infection in various age groups we performed testing of 151 serum samples from LCH patients. According to the test results, 29.8% of all samples were positive. Samples were divided in the 5 groups based on age data: group 1—from 0 to 4 years old (y.o.) (n=29), group 2—from 5 to 9 y.o. (n=32), group 3—from 10 to 14 y.o. (n=22), group 4—from 15 to 20 y.o. (n=17), and group 5—from 21 to 72 y.o. (n=51).

These serum studies suggest that approximately one-half of normal blood donors have serum antibodies against MCV, implying that a high proportion of the population has been exposed to MCV. We observed an age-dependent increase in MCV seroprevalence, with about 70% of individuals over age 50 showing detectable MCV antibody responses. The results of testing are presented in FIG. 15.

VLP Competitive ELISA. BK-Competitive ELISA.

Since cross-reactivity between antibodies to SV40, BKV and JCV VLP has been previously reported, we performed testing for BKV VLP ELISA on 12 samples (high-, medium-, and low-positive to MCV VLPs). Results of the testing demonstrate positive reactivity to BKV (FIG. 16).

To determine if MCV VLP reactivity is due to cross-reaction to BKV, BK competitive ELISA was performed. In order to compete out AB to BKV we incubated 100 µl of diluted serum samples with 1 ug of BK VLPs before adding to the plates precoated with MCV VLPs. Results of testing demonstrate that after incubation with BKV VLPs samples were still reactive to MCV (FIG. 17). Serum samples incubated with BK VLPs showed no reactivity on BK precoated plates. This suggests that MCV reactivity is not due to BKV AB.

CRPV and HPV VLP Competitive ELISA.

12 samples were also tested for CRPV and HPV VLP reactivity. Results of the tests are shown in FIG. 18 (A and B).

Prevalence of HPC VLP Positive Reactivity.

As can be seen in FIG. 19, the MCV VLP assay resulted in a nearly 100% positive result for patients who had been diagnosed with MCC. In contrast, patients with unrelated conditions (lupus, Langerhan's cell histiocytosis) and from commercial blood sources as well as blood donors tested positive for MCV VLPs at a rate of about 50%. A comparison between the OD from the Elisa assays for MCV+ MCC patients and blood donors (1:500 dilution) is presented in FIG. 20. The arrow in the right panel represents the mean value for the MCV+ MCC patients (2.3 OD) less 5× the standard deviation for a value of 0.285. While a different threshold can be ascertained, these results suggest that an OD value above 0.285 might be useful diagnostically.

The publication referenced in this Example are as follows:
1. A. S. Laney, J. S. Peters, S. M. Manzi, L. A. Kingsley, Y. Chang, P. S. Moore. 2006 Use of multiantigen detection algorithm for diagnosis of Kaposi's sarcoma-associated herpesvirus infection. J. Clin. Microbiol. 44(10):3734-3741.

EXAMPLE 8

This example demonstrates the development of a neutralizing assay based on MCV VLPs.

Neutralization assays were based on the infection of 293TT cells with MCV and MPyV reporter vectors carrying an expression plasmid encoding Gaussia luciferase, a secreted reporter protein. Using these MCV reporter vectors, a high-sensitivity MCV neutralization assay was developed. The neutralization assay is about 40-fold more sensitive than ELISA for detection of MCV sero-responses. 12 MCC patients' MCV sero-responses are, on average, greater in magnitude than responses found in 35 normal individuals ($p<2.4\times10^{-5}$). A small number of normal individuals were found to exhibit very high MCV sero-responsiveness comparable to the MCC patients. Validation of the assay is shown in FIG. 21 based on titration of MCV-reactive pooled human serum and MPyV-specific rabbit serum. The values for ELISA or neutralizaiton assay (neut) were standardized to calculated maximum optical density (OD) or maximum relative light units (RLUs), respectively.

Hypothetically, these very high sero-responses may be a record of a prior period of sustained high-level MCV replication. Since MCC tumors typically do not express the viral capsid genes, it is likely that this putative episode of high-level virus replication occurred prior to development of the cancer, and may have contributed to the cancer's development. Also is expected that the neutralization assay will be less likely than the ELISA to detect antibody responses to other human polyomavirus types.

EXAMPLE 9

This example demonstrates the development of a neutralizing assay based on MCV VLPs.

It is believed that polyomaviruses require two minor capsid proteins, VP2 and VP3 for full infectivity. In previously-characterized polyomaviruses, VP3 is an internally-initiated, N-truncated isoform of VP2. MCVs do not encode a VP2 methionine codon homologous to the codon that initiates translation of the VP3 ORF of other known polyomaviruses. We therefore produced constructs encoding possible alternative MCV VP3 ORFs initiated from VP2 methionine codons 46 or 129. In pilot experiments, inclusion of expression plasmids encoding MCV VP346 enhanced vector infectious titer yield only very modestly, while inclusion of VP3129 modestly reduced titer yield (data not shown). The putative MCV VP3 genes were therefore omitted from the MCV vector production scheme. For MPyV, an expression plasmid encoding the standard VP3 ORF was incorporated into the reporter vector production process.

A substantial majority of the VLPs used for the ELISA studies above were found to contain ~5 kb fragments of cellular DNA (data not shown). We therefore employed a previously-described procedure for enriching reporter vector stocks for capsids containing reporter plasmids, as opposed to cellular DNA fragments. This strategy resulted in a major improvement in particle to infectivity ratios for the reporter vector stocks (data not shown).

Infection of 293TT cells with an MCV-Glue reporter vector dose of 400 pg/ml (roughly 8 picomolar with respect to VP1 or roughly 100 VLPs per cell) resulted in a robust luminescent signal 72 hours after infection. Typical assay conditions resulted in the appearance of roughly 500,000 relative light units (RLUs) with a background of roughly 500 RLUs in control wells.

To validate the neutralization assay, we tested the ability of pooled human sera (PHS) to neutralize the MCV and MPyV Glue vector stocks. The PHS neutralized the MCV-Glue reporter vector, with 50% neutralization (EC50) occurring at a calculated serum dilution of 1:44,000 (95% CI 1:32,000-1:60,000). In terms of EC50 values, the neutralization assay was >100-fold more sensitive than the ELISA. This improved sensitivity is presumably due to the 2,500-fold lower dose of virions used in the neutralization assay relative to the ELISA.

In an additional set of assay validation experiments, we found that IgG purified out of the PHS neutralized the vector with an EC50 of about 90 ng/ml). Conversely, PHS stripped of IgG using protein G resin neutralized the MCV reporter vector with an EC50 of only 1:600 (data not shown).

PHS diluted 1:100 failed to neutralize the MPyV reporter vector, whereas an MPyV-specific rabbit serum neutralized the MPyV reporter vector titer by >99% at the same dose. The MPyV-specific rabbit serum only partially neutralized the MCV vector at a 1:100 dilution. The results confirm that MCV and MPyV are not serologically cross-reactive and that neutralization is due primarily to virus-specific antibodies in various sera.

We used the MCV neutralization assay to compare serial dilutions of sera from MCV+ MCC patients (age 14+ years) to sera from a subset of the 48 oldest plasma donors (age 47-74 years). We also tested sera from LCH patients age 47-72 years in the neutralization assay. A small number of MCC patients whose tumors were found not to contain MCV were also tested. MCV+ MCC patients displayed very high titer MCV-neutralizing responses that were not typical among control donors. This difference was statistically significant. Although the apparent difference between the neutralizing titers of MCV+ and MCV− MCC patients was not statistically significant, several of the MCV-patients displayed neutralizing titers much lower than titers observed for MCV+ individuals, suggesting that a minority of MCC cases are MCV-independent.

88% (42/48) of the plasma donor sera detectably neutralized the infectivity of the MCV reporter vector at the lowest serum dilution tested (1:100). In contrast, only half (24/48) of this subset of sera scored seropositive in the VLP ELISA, To address this discrepancy, we retested this subset of sera at a more concentrated dilution (1:40) in the VLP ELISAs. For the re-testing, any serum whose raw OD against MCV VLPs was at least three-fold greater than its raw OD against MPyV VLPs was defined as seropositive. By this standard, 75% (36/48) of the plasma donor sera displayed MCV-specific ELISA reactivity, in a pattern generally correlating with neutralizing titers. Taken together, the results suggest that, in addition the roughly 50% of donors who display robust anti-MCV antibody responses, an additional 25% of donor sera have weak, but detectable, MCV-specific reactivity.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of assaying for Merkel cell carcinoma virus (MCV) exposure in a patient, the method comprising:
obtaining a tissue or fluid sample from the patient, and assaying the sample for the presence of at least one MCV molecule,
wherein the assaying comprises a process of exposing the sample to an agent that binds to at least one MCV molecule, and
wherein at least one MCV molecule is selected from the group of MCV molecules consisting of (a) an MCV nucleic acid (b) an MCV polypeptide, and (c) an antibody that binds specifically to an MCV polypeptide,
wherein a positive test for the presence of the MCV molecule within the sample is indicative of exposure of the patient to MCV.

2. The method of claim 1, wherein the assaying comprises an ELISA assay comprising exposing the sample to an MCV polypeptide.

3. The method of claim 2, wherein the MCV polypeptide is VP1, VP2, and/or VP3 and is within a virus-like particle (VLP).

4. A method of assaying for MCV neutralization, the method comprising:
(a) obtaining MCV VLPs that contain a reporter construct,
(b) exposing the VLPs to a sample to produce a preparation,
(c) exposing the preparation to cells amenable to infection by MCV, and
(d) assaying for the expression of the reporter within the cells, wherein a lower level of expression of the reporter in the cells relative to a control indicates the presence of a neutralizing factor within the sample.

5. The method of claim 4, wherein the sample is a fluid or tissue sample obtained from a patient.

6. The method of claim 4, wherein the sample contains a candidate anti-MCV immunoglobulin.

7. The method of claim 1, wherein the patient is human.

8. The method of claim 1, wherein the patient is a non-human animal.

9. The method of claim 1, wherein the sample is a tissue sample and the assay comprises in situ hybridization.

10. The method of claim 1, wherein at least one MCV molecule comprises at least one MCV RNA.

11. The method of claim 1, wherein at least one MCV molecule comprises at least one MCV DNA.

12. The method of claim 1, wherein at least one MCV molecule comprises at least one MCV polypeptide.

13. The method of claim 12, wherein at least one MCV polypeptide is VP1.

14. The method of claim 12, wherein at least one MCV polypeptide is VP2.

15. The method of claim 12, wherein at least one MCV polypeptide is VP3.

16. The method of claim 12, wherein at least one MCV polypeptide is a large T polypeptide.

17. The method of claim 12, wherein at least one MCV polypeptide is a small T polypeptide.

18. The method of claim 12, wherein at least one MCV polypeptide is one or more of T-1, T-2, T-3, T-4, and/or T-5.

19. The method of claim 1, wherein at least one MCV molecule is an antibody that binds specifically to an MCV polypeptide.

20. The method of claim 19, wherein the MCV polypeptide to which the antibody binds is VP1.

21. The method of claim 19, wherein the MCV polypeptide to which the antibody binds is VP2.

22. The method of claim 19, wherein the MCV polypeptide to which the antibody binds is VP3.

23. The method of claim 19, wherein the MCV polypeptide to which the antibody binds is a large T polypeptide.

24. The method of claim 19, wherein the MCV polypeptide to which the antibody binds is a small T polypeptide.

25. The method of claim 19, wherein the MCV polypeptide to which the antibody binds is one or more of T-1, T-2, T-3, T-4, and/or T-5.

* * * * *